(12) United States Patent
Hubert et al.

(10) Patent No.: US 8,597,887 B2
(45) Date of Patent: Dec. 3, 2013

(54) GENETIC MARKER IDENTIFICATION IN ATLANTIC COD

(75) Inventors: Sophie Hubert, Halifax (CA); Brent Higgins, Halifax (CA); Sharen Bowman, Halifax (CA); Tudor Borza, Halifax (CA); Jillian Tarrant Bussey, Halifax (CA); Stewart C. Johnson, Nanaimo (CA); Matthew L. Rise, St. John's (CA); J. Andrew B. Robinson, Guelph (CA); Gary Simpson, Halifax (CA); Amber Garber, St. Andrews (CA); Gordon E. Vander Voort, Guelph (CA); Christina E. Hastings, Guelph (CA); Tiago S. Hori, St. John's (CA); Luis O. Afonso, Campbell River (CA); A. Kurt Gamperl, St. John's (CA)

(73) Assignee: Genome Atlantic, Halifax, NS (CA)

( * ) Notice: Subject to any disclaimer, the term of this patent is extended or adjusted under 35 U.S.C. 154(b) by 0 days.

(21) Appl. No.: 13/263,453

(22) PCT Filed: Apr. 9, 2010

(86) PCT No.: PCT/CA2010/000504
§ 371 (c)(1),
(2), (4) Date: Dec. 22, 2011

(87) PCT Pub. No.: WO2010/115275
PCT Pub. Date: Oct. 14, 2010

(65) Prior Publication Data
US 2012/0100996 A1      Apr. 26, 2012

Related U.S. Application Data

(60) Provisional application No. 61/285,354, filed on Dec. 10, 2009, provisional application No. 61/167,979, filed on Apr. 9, 2009.

(51) Int. Cl.
*C12Q 1/68* (2006.01)

(52) U.S. Cl.
USPC ............... 435/6.11; 435/6.1; 435/6.12

(58) Field of Classification Search
USPC .................................. 506/2; 435/6.1
See application file for complete search history.

(56) References Cited

U.S. PATENT DOCUMENTS

| 2006/0024672 A1 | 2/2006 | Lie et al. |
| 2009/0149641 A1 | 6/2009 | Jorgensen et al. |
| 2009/0165156 A1 | 6/2009 | Rengmark et al. |

FOREIGN PATENT DOCUMENTS

WO   WO2008/074101 A2   6/2008

OTHER PUBLICATIONS

Liu et al., "Generation of genome-scale gene-associated SNPs in catfish for the construction of a high-density SNP array," BMC Genomics 2011, 12:53.*

(Continued)

*Primary Examiner* — Samuel Woolwine
*Assistant Examiner* — Kaijiang Zhang
(74) *Attorney, Agent, or Firm* — Bereskin & Parr LLP/S.E.N.C.R.L., s.r.l.; Micheline Gravelle

(57) ABSTRACT

The present application describes SNPs useful for the genetic analysis of Atlantic cod. Also described are QTLs and SNP marker associations for commercially important traits such as weight, nodavirus resistance, resistance to stress and for determining geographic origin. The application also provides methods and uses of the SNPs for identifying family members and/or estimating relatedness, marker assisted selection, breeding programs, population management, identification of geographic origin and trait-association studies. A SNP-based linkage map for Atlantic cod is also provided.

17 Claims, 8 Drawing Sheets

(56) References Cited

OTHER PUBLICATIONS

Sanchez et al., "Single nucleotide polymorphism discovery in rainbow trout by deep sequencing of a reduced representation library," BMC Genomics 2009, 10:559.*
Z.J. Liu et al. "DNA marker technologies and their applications in aquaculture genetics." Aquaculture, vol. 238, No. 1-4, Sep. 1, 2004, pp. 1-37.
Bowman et al., "Generation of genomics resources for Atlantic cod (*Gadus morhua*): progress and plans." Bulletin of the Aquaculture Association of Canada, 2007, 105, 24-30.
Bricknell et al., "Diseases of gadoid fish in cultivation: a review." ICES Journal of Marine Science, 2006, 63:253-266.
Brown et al., "Larviculture of Atlantic cod (*Gadus morhua*): progress, protocols and problems." Aquaculture, 2003, 227, 357-372.
Delghandi et al., "Simultaneous analysis of six microsatellite markers in Atlantic cod (*Gadus morhua*): a novel multiplex assay system for use in selective breeding studies." Marine Biotechnology, 2003, 5, 141-148.
Delghandi et al., "Development of twenty sequence-tagged microsatellites for the Atlantic cod (*Gadus morhua* L.)." Conservation Genetics, 2008, 9(5):1395-1398. (A).
Delghandi et al., "Twenty-three novel microsatellite markers developed from Atlantic cod (*Gadus morhua* L.) expressed sequence tags." Journal of Fish Biology, 2008, 73(2):444-449. (B).
Fan et al., "Robertsonian polymorphism in plaice, *Pleuronectes platessa* L., and cod, *Gadus morhua* L. (Pisces Pleuronectiformes and Gadiformes)." Journal of Fish Biology, 1991, 38:635-640.
Feng et al., "Identification and analysis of differentially expressed genes in immune tissues of Atlantic cod stimulated with formalin-killed atypical *Aeromonas salmonicida*." Physiological Genomics, 2009, 37:149-163.
Garber et al., "Hormonal induction ovulation and spermiation in Atlantic cod (*Gadus morhua*)." Aquaculture, 2009, 296:179-183.
Gjedrem, T. ,"Genetic improvement of cold-water fish species." Aquaculture Research, 2000, 31, 25-33.
Hayes et al., "An extensive resource of single nucleotide polymorphism markers associated with Atlantic salmon (*Salmo salar*) expressed sequences." Aquaculture, 2007, 265, 82-90.
Herlin et al., "Parentage allocation in a complex situation: A large commercial Atlantic cod (*Gadus morhua*) mass spawning tank." Aquaculture, 2007, 272S1, S195-S203. (A).
Herlin et al., "Analysis of the parental contribution to a group of fry from a single day of spawning from a commercial Atlantic cod (*Gadus morhua*) breeding tank." Aquaculture, 2008, 274, 218-224.
Herlin, M.C.G., "Genetic management of Atlantic cod (*Gadus morhua* L.) hatchery populations." Institute of Aquaculture, University of Stirling, Stirling, Scotland, UK, 2007, pp. 222. (B).
Higgins et al., "Characterization of 155 EST-derived microsatellites from Atlantic cod (*Gadus morhua*) and validation for linkage mapping." Molecular Ecology Resources, 2009, 9(3):733-737.
Hubert et al., "Development of single nucleotide polymorphism markers for Atlantic cod (*Gadus morhua*) using expressed sequences." Aquaculture, 2009, 296(1-2):7-14.
Hubert et al., "Development of a SNP resource and a genetic linkage map for Atlantic cod (*Gadus morhua*)." BMC Genomics, 2010, 11:191.
Jakobsdottir et al., "Nine new polymorphic microsatellite loci for the amplification of archived otolith DNA of Atlantic cod, *Gadus morhua*." L. Molecular Ecology Notes, 2006, 6, 337-339.
Johansen et al., "Large-scale sequence analyses of Atlantic cod." New Biotechnol., 2009, vol. 25, No. 5, 263-271.
Miller et al., "Development of tri- and tetranucleotide repeat microsatellite loci in Atlantic cod (*Gadus morhua*)." Molecular Ecology, 2000, 9, 238-243.
Moen et al., "Identification and characterisation of novel SNP markers in Atlantic cod: evidence for directional selection." BMC Genet, 2008, 9, 18.

Moen et al., "A SNP/microsatellite genetic linkage map of the Atlantic cod (*Gadus morhua*)." Anim Genetics, 2009, 40, 993-996.
Nielsen et al., "Genomic signatures of local directional selection in a high gene flow marine organism; the Atlantic cod (*Gadus morhua*)." BMC Evolutionary Biology, 2009; 9 (276), 11, pages ISSN: 1471-2148.
Ødegard et al., "Heritability of resistance to viral nervous necrosis in Atlantic cod (*Gadus morhua* L.)." Aquaculture, 2010, 300:59-64.
O'Reilly et al., "Isolation of twenty low stutter di- and tetranucleotide microsatellites for population analyses of walleye pollock and other gadoids." Journal of Fish Biology, 2000, 56, 1074-1086.
Pogson et al., "Genetic population structure and gene flow in the Atlantic cod *Gadus morhua*: a comparison of allozyme and nuclear RFLP loci." Genetics, 1995, 139:375-385.
Rise et al., "Functional genomic analysis of the response of Atlantic cod (*Gadus morhua*) spleen to the viral mimic polyriboinosinic polyribocytidylic acid (pIC)." Dev Comp Immunol., 2008, 32(8):916-931.
Ruzzante et al., "Genetic differentiation between inshore and offshore Atlantic cod (*Gadus morhua*) off Newfoundland: Microsatellite DNA variation and antifreeze level." Canadian Journal of Fisheries and Aquatic Sciences, 1996, 53:634-645.
Symonds et al., "Family-based Atlantic cod (*Gadus morhua*) broodstock development." Bulletin of the Aquaculture Association of Canada, 2007, 105, 39-46.
Wesmajervi et al., "Genotyping of Atlantic cod (*Gadus morhua* L.) using five microsatellite markers and a population specific single nucleotide polymorphism." Aquaculture, 2007, 272S1:S317-S318.
Booman et al., "Development and experimental validation of a 20K Atlantic cod (*Gadus morhua*) oligonucleotide microarray based on a collection of over 150,000 ESTs." Marine Biotechnology, 2011, 13(4), 733-750.
Borza et al., "Atlantic cod (*Gadus morhua*) CC chemokines: Diversity and expression analysis." Developmental and Comparative Immunology, 2010, 34 (8), 904-913.
Bowman et al., "An integrated approach to gene discovery and marker development in Atlantic cod (*Gadus morhua*)." Marine Biotechnology, 2011, 13 (2), 242-255.
Bradbury et al., "Parallel adaptive evolution of Atlantic cod on both sides of the Atlantic Ocean in response to temperature." Proceedings of the Royal Society of London Biological Sciences B., 2010, 277: 1701.
Bradbury et al., "Evaluating SNP ascertainment bias and its impact on population assignment in Atlantic Cod, *Gadus morhua*." Molecular Ecology Resources, 2011, 11 (Supplement 1), 218-225.
Campbell et al., "Characterization of 22 novel single nucleotide polymorphism markers in steelhead and rainbow trout." Molecular Ecology Resources, 2009, 9, 318-322.
Feng et al., "Characterization and expression analyses of anti-apoptotic Bcl-2-like genes NIZ-13, Mcl-1, Bcl-X1, and Bcl-X2 in Atlantic cod (*Gadus morhua*)." Molecular Immunology, 2010, 47 (4), 763-784.
Hori et al., "Heat shock-responsive genes identified and validated in Atlantic cod (*Gadus morhua*) liver, head kidney and skeletal muscle using genomic techniques." BMC Genomics, 2010, 11(2), 72.
Hori et al., "Inter-Individual and -Family differences in the cortisol responsiveness of Atlantic cod (*Gadus morhua*)." Aquaculture, 2011, doi:10.1016/j.aquaculture.2011.10.040 (in press). (A).
Hori et al., "The mRNA expression of cortisol axis related genes differs in Atlantic cod (*Gadus morhua*) categorized as high or low responders." General and Comparative Endocrinology, 2011, doi:10.1016/j.ygcen.2011.11.031 (In press). (B).
Rise et al., "Impact of asymptomatic nodavirus carrier state and intraperitoneal viral mimic injection on brain transcript expression in Atlantic cod (*Gadus morhua*)." Physiological Genomics, 2010, 42 (2), 266-280.

* cited by examiner

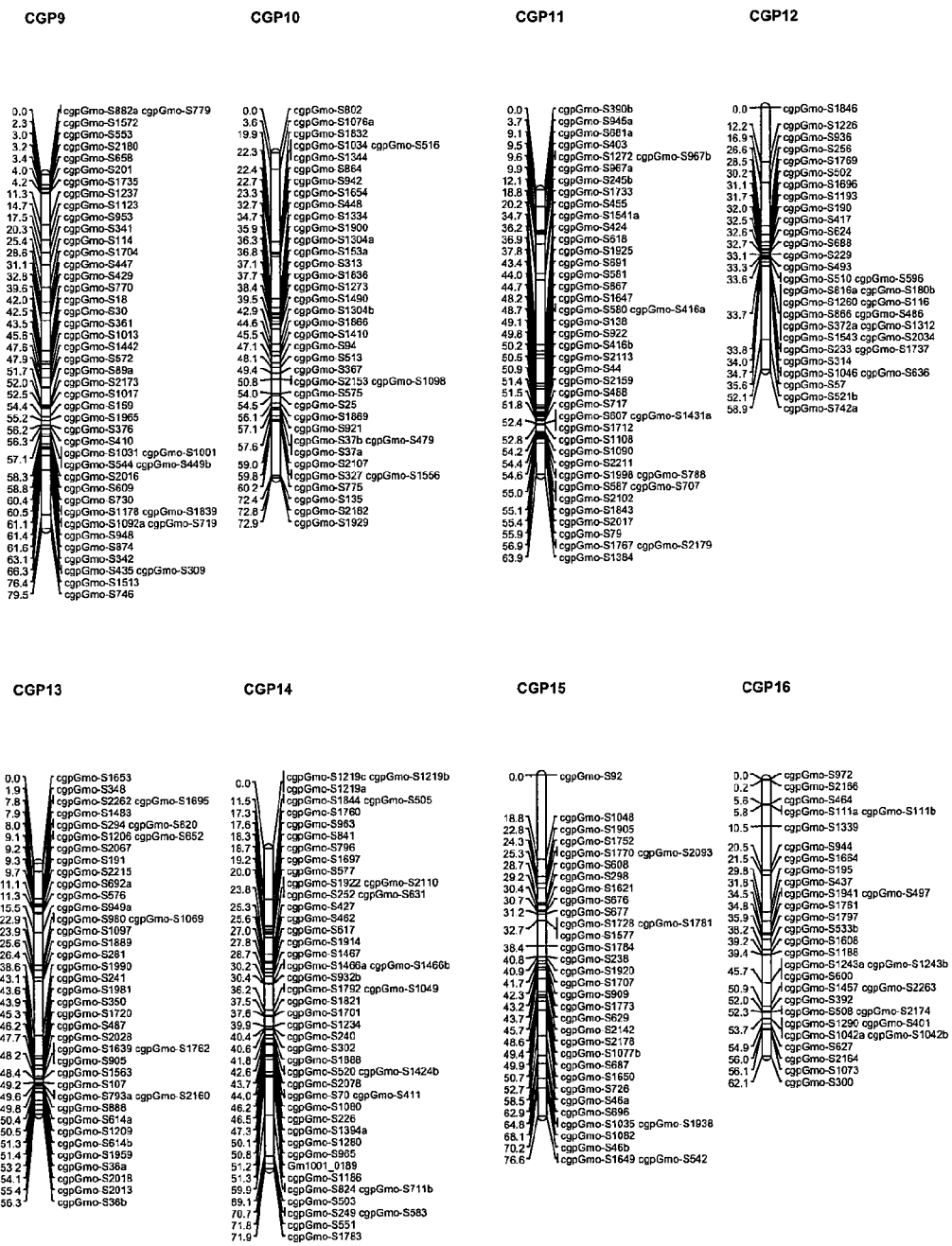
Figure 5 (con't.)

Figure 5 (con't.)
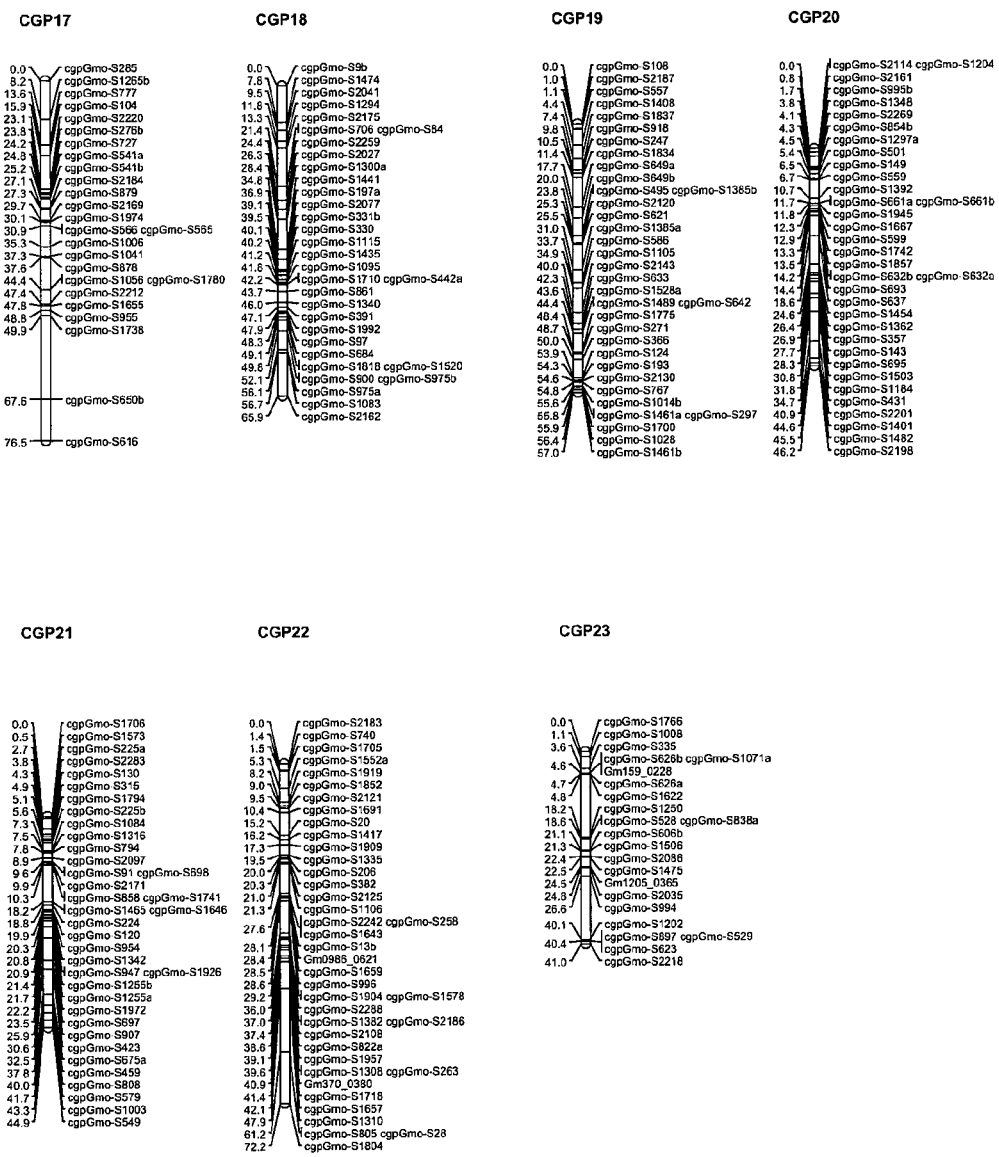

GENETIC MARKER IDENTIFICATION IN ATLANTIC COD

CROSS REFERENCE TO RELATED APPLICATIONS

This application is a U.S. National Phase filing under 35 USC 371 of PCT/CA2010/000504 filed Apr. 9, 2010 claiming priority under 35 USC 119(e) from U.S. Provisional Patent Application No. 61/167,979 filed Apr. 9, 2009, and U.S. Provisional Patent Application No. 61/285,354 filed Dec. 10, 2009 all of which are incorporated herein by reference in their entirety.

INCORPORATION OF SEQUENCE LISTING

A computer readable form of the Sequence Listing "20683-8_SequenceListing.txt" (966,656 bytes), submitted via EFS-WEB and created on Oct. 4, 2011, is herein incorporated by reference.

Please replace the Sequence Listing currently of record with the Sequence Listing provided herewith in text format in computer readable form only.

FIELD

This application relates to single nucleotide polymorphism (SNP) markers and associated methods for the genetic analysis of Atlantic cod (*Gadus morhua*) and more specifically to SNP markers and associated methods for desirable production traits in Atlantic cod.

BACKGROUND

The Atlantic cod (*Gadus morhua*) has a long history as a commercially important species in the North Atlantic and adjacent waters. The decline in the capture fishery has resulted in a shift towards the production of Atlantic cod using aquaculture in a number of countries, including Canada. Selective breeding is a proven, powerful approach in the enhancement of domesticated species for food production. In order to develop an efficient breeding program, it is desirable to generate suitable molecular tools in order to accelerate the selection process. The application of genetic tools in finfish aquaculture breeding programs has only recently become standard practice (De-Santis and Jerry, 2007). Currently, 10 out of 19 major aquaculture species are being produced using selective breeding for improved broodstock selection and new tools are being developed to make selection more precise with the ability to identify and locate quantitative trait loci and then use markers assisted selection to speed the selection process (Hershberger, 2006).

Accordingly, a dense linkage map linked to traits of economic importance would represent one of the most useful genomic tools for application in the selective breeding of Atlantic cod. A variety of different marker types such as amplified fragment length polymorphisms (AFLPs), microsatellite markers or SNP markers can be used for linkage mapping or association mapping. SNPs have become a focus of marker development in many species in recent years due to their abundance and low cost of genotyping allowing the construction of a high density map. In aquaculture species, SNPs are especially important if they cause differences in economic traits or are linked to such a trait. SNPs developed from collections of expressed sequence tags (ESTs) can be particularly valuable as they can be used to identify changes in the amino acid sequence of encoded proteins, also known as non-synonymous SNPs (Kim et al., 2003).

The increased number of ESTs available for fish has facilitated the detection of SNPs for different fish species. Significant numbers of SNPs have been reported in channel catfish (He et al., 2003), salmon (Hayes et al., 2007; Smith et al., 2005) and sea bream (Cenadelli et al., 2007).

With respect to Atlantic cod, Moen et al. (2008) recently developed a large number of SNPs from ESTs based on 5' sequence reads. One SNP has also been identified for the pantophysin (Pan I) locus (Delghandi et al., 2007)

There remains a need for high quality SNP markers and SNP markers associated with traits of commercial importance suitable for the genetic analysis of Atlantic cod.

SUMMARY OF THE DISCLOSURE

The present disclosure provides a large number of single nucleotide polymorphisms (SNPs) useful for the genetic analysis of Atlantic cod. Both a low throughput and a high throughput (automated) SNP detection pipeline were developed and a subset of SNPs identified by these alternate approaches was validated. More specifically, 17,365 putative SNPs were identified through the sequence analysis of 97,964 EST sequence reads assembled into 8,189 contigs. Of the 17,365 putative SNPs, 4,753 SNPs were identified as high quality SNPs based on frequency and quality of sequence data. The 3072 SNPs listed in Table 6 were then hand selected from the 4,753 high quality SNPs based on origin and relevance to project objectives. SEQ ID NOs: 1-3072 provide the flanking sequence with the SNP variant at nucleotide position 61 for each of the 3072 SNPs listed in Table 6.

In addition, the 47 SNPs shown in Table 1 were characterized in 22 Atlantic cod fish from two separate populations of fish from New Brunswick and Newfoundland. Of the 47 SNPs, suitable primer extension assays were developed for the 33 SNPs identified in Table 3. As shown in Table 2, 30 of these SNPs appeared to be polymorphic in the two populations. Further segregation analysis showed that 22 of the SNPs were inherited as expected according to Mendelian segregation (Table 3). Annotation of the sequences shown in Table 5 identified 9 SNPs in specific untranslated gene regions, 2 synonymous coding SNPs and 2 non-synonymous coding SNPs. Table 7 identifies SNPs that overlap between Table 1 and Table 6 and provides corresponding SEQ ID NOS. and SNP nucleotide positions for the SNPs of Table 1.

Accordingly, the disclosure provides for a method of identifying an animal associated with a specific phenotype or trait comprising testing the animal for one or more of the SNPs listed in Table 1 or Table 6, wherein the SNP is associated with a specific phenotype or trait.

The disclosure also provides a method of identifying an association between a SNP and a specific phenotype or trait in an animal comprising comparing the frequency of a SNP allele identified in Table 1 or Table 6 between a control population and a population selected for the specific phenotype or trait.

In a preferred embodiment, the animal is Atlantic cod (*Gadus morhua*), however the SNPs are expected to be useful in the genetic analysis of other 'related' fish species within the family Gadidae.

Genetic analysis using the SNPs described herein provides useful information for breeding programs. Accordingly, one aspect of the disclosure provides a method of selecting a fish for a breeding program comprising testing fish for one or more of the SNPs listed in Table 1 or Table 6 and selecting fish for the breeding program based on the presence or absence of the one or more SNP alleles.

In one aspect, the disclosure provides for determining the parentage of a fish comprising genotyping a sample of fish for one or more SNPs listed in Table 14 wherein the sample includes parent fish (dams/sires) and progeny. In one embodiment, the method includes selecting a fish with unknown parentage and determining the parentage of the fish by comparing the genotypes of the SNP alleles for the parent fish with the genotypes of the SNP alleles for each of the fish genotyped in the sample. In one embodiment, the sample comprises fish that are communally-reared fish. In one embodiment, the method comprises typing at least 16, 20, 24, 30 or 36 of the SNPs listed in Table 14.

The SNPs of the present disclosure are useful for the linkage analysis or association analysis of Atlantic cod. The SNPs are also useful for identifying family members or estimating relatedness of Atlantic cod.

In a further embodiment, the disclosure provides isolated nucleic acid molecules that comprise the SNPs identified herein. In one embodiment, the isolated nucleic acid molecules comprise the SNPs identified in Table 1 or Table 6. In a further embodiment, the disclosure provides the nucleic acid molecules comprising the sequences identified in Table 7.

In another embodiment, the disclosure provides a method of genotyping a sample for a SNP comprising amplifying a nucleic acid molecule from said sample using one of the primer pairs identified in Table 6 and assaying for the SNP using the corresponding interrogation primer identified in Table 6.

The 3072 SNPS identified in Table 6 were tested using two Illumina GoldenGate panels. 1620 of these SNPs were categorised as validated (V) SNPs as set out in Example 2 and identified in Table 6. Validated SNPs were tested for Mendelian segregation in two families and used to create a high-density genetic linkage map useful for the genetic analysis of cod. Accordingly, in one embodiment, the disclosure provides a linkage map for cod as shown in FIG. 5. In another embodiment, the disclosure provides a linkage map for cod as shown in Table 10. In one embodiment, there is provided the validated SNPs identified in Table 6, with the proviso that they are not listed in Table 13.

In one aspect, the SNPs identified herein may be used for determining the geographic origin of cod. The 184 SNPs listed in Table 11 are monomorphic in Eastern Atlantic cod populations (Iceland, Ireland and Norway) and polymorphic in Western Atlantic cod populations. Accordingly, there is provided a method for determining the geographic origin of a codfish comprising genotyping the codfish for one or more of the SNPs listed in Table 11, wherein fish that have homozygous genotypes are from the Eastern Atlantic, and fish that have heterozygous genotypes are from the Western Atlantic.

In one embodiment, the SNPs identified in Table 12 are useful for determining the geographic origin of cod fish, and in particular distinguishing codfish from Northern populations such as Newfoundland and Northern Norway/Barents Sea (which only have distinct 'Northern' genotypes present in populations), from codfish from Ireland and other populations that exhibit a distinct Southern genotype, or a mixed genotype with both Northern and Southern genotypes present in populations. Accordingly, in one embodiment there is provided a method for determining the geographic origin of codfish comprising genotyping one or more of the SNPs in Table 12. In one embodiment, a fish is identified as not from Newfoundland or Northern Norway if it has one or more Southern genotype alleles as set out in Table 12.

In one aspect, there is provided a method for identifying codfish with desirable production traits. In one embodiment, desirable production traits include increased weight, disease resistance, and resistance to stress. In one aspect, a quantitative trait locus (QTL) associated with the weight of codfish has been identified on linkage group 7 (Tables 10 and 20). In another embodiment, QTLs associated with the weight of codfish have been identified on linkage groups 1, 11, 18, 22 and 23 (Tables 10 and 21). Accordingly, in one embodiment, there is provided a method of identifying a codfish with QTL for increased weight, the method comprising genotyping the codfish for one or more of the SNPs listed in Tables 20 or 21, or genotyping a marker in linkage disequilibrium with any one of the SNP marker alleles listed in Tables 20, or 21. In one embodiment, the presence of a marker allele in linkage disequilibrium with the preferred SNP marker allele listed in Tables 20 or 21 indicates the presence of the QTL for increased weight.

In another aspect, markers associated with resistance to nodavirus infection have been identified on linkage groups 8, 19 and 23. Accordingly, in one embodiment there is provided a method of identifying a codfish resistant to nodavirus infection, the method comprising genotyping the codfish for one or more of the SNPs listed in Table 18.

In another aspect, there is provided genetic markers associated with fish that have a QTL for resistance to handling stress. In one embodiment, fish with the preferred alleles shown in Table 24 exhibit lower levels of cortisol in response to handling stress. Accordingly, in one embodiment there is provided a method of identifying a codfish resistant to stress, the method comprising genotyping the codfish for one or more of the SNPs listed in Table 24.

In one aspect, fish may be selected for a plurality of trait-associated markers as described herein. In one embodiment, a fish may be selected for SNP markers for growth, nodavirus resistance, and/or stress resistance as described herein. In one embodiment, there is provided a method for selecting fish with a plurality of genetic markers for desirable production traits such as growth, nodavirus resistance and stress resistance.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION

The present inventors have identified a large number of SNPs useful for the genetic analysis of Atlantic cod presented in Tables 1 and 6.

Figure 1:
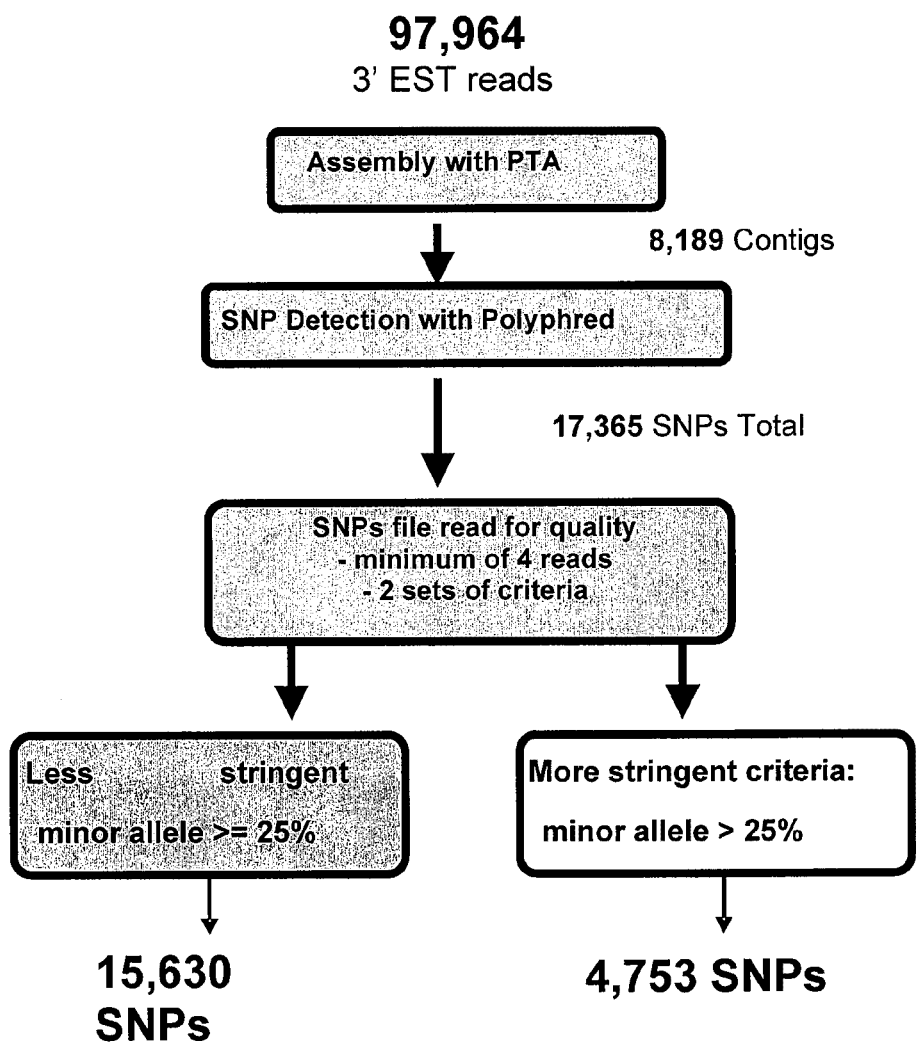
FIG. 1 provides an overview of automated SNP detection. The ESTs are processed using Paracel Transcript Assembler (PTA) to assemble contigs and to remove unwanted sequence. Contigs in ace file format are used as PolyPhred input, to look for SNPs in areas of multi-read coverage. The output of PolyPhred is further refined using a custom perl script that can be adjusted to select various SNP output qualities. Two examples of criteria sets are shown. Both sets require a minimum of 4 read coverage. The less stringent set identifies SNPs that have a minor allele representation equal to or greater than 25%—for example, for a contig region with 4 contributing reads it would detect SNPs with 1 copy of the minor allele and 3 copies of the major allele. The more stringent set requires a minor allele representation greater than 25%, which means that each allele is represented at least twice in contigs containing 4 reads or more.

Referring to FIG. 1, SNP selection was completed as follows: 97,964 3' EST (Expressed Sequence Tag) reads were assembled with PTA (Paracel Transcript Assembler—used for EST cleaning, clustering and assembly) resulting in 8,189 contigs. SNP detection was performed with PolyPhred which is a program that compares sequence information to identify heterozygous sites for single nucleotide substitutions. Analysis outputs included a ranking which indicates quality of the SNPs estimated by bioinformatic analysis (not shown), which was used towards SNP selection. Initial SNP detection yielded 17,365 putative SNPs. This list was trimmed using various criteria to identify 4,753 SNPs that were high quality. Specifically, "predicted frequent" SNPs were selected from contiguous sequences (contigs) which contained 4 or more sequence reads. In addition, from these "predicted frequent" SNPs, for 4,753 of these SNPs, the minor allele was represented in a minimum of 2 of the 4 reads. From these 4,753 SNPs, the 3072 SNPs listed in Table 6 were then hand-selected based on origin and relevance to project objectives.

The 47 SNPs identified in Table 1 were identified and selected for further characterization as set out in Example 1. Primer extension assays for these SNPs were developed and amplification and interrogation primers suitable for the amplification and genotyping of the SNPs are shown in Table 6. The SNPs shown in Table 2 were genotyped and further characterized with respect to segregation in two populations of Atlantic Canadian cod. Sequences containing the SNPs were also annotated with respect to gene location and putative SNP functionality (synonymous vs. nonsynonymous changes).

The term "SNP" as used herein, means a single nucleotide polymorphism which is a single nucleotide position in a nucleic acid sequence for which two or more alternative alleles are present in a given population.

The term "allele" means any one of a series of two or more different gene sequences that occupy the same position or locus on a chromosome.

The term "genotype" means the specification of an allelic composition at one or more loci within an individual organism. In the case of diploid organisms such as codfish, there are two alleles at each locus; a diploid genotype is said to be homozygous when the alleles are the same, and heterozygous when the alleles are different.

As used herein "genotyping" refers to determining the genotype of a organism at a particular locus, such as a SNP.

As used herein, "quantitative trait locus" or "QTL" refers to a genetic locus that contributes, at least in part, to the phenotype of an organism for a trait that can be numerically measured.

SNP Markers and Linkage and Association Studies

In one embodiment, the SNPs of the present disclosure can be used as markers for identifying animals that contain a SNP allele associated with a specific trait or phenotype. In a further embodiment, the SNPs can be used as markers that are associated with a quantitative trait locus (QTL). In a preferred embodiment, the animals are Atlantic cod fish.

The SNPs of the present disclosure may be used in genetic linkage or association studies to identify SNP alleles that are associated with a specific phenotype or QTL. In one embodiment, the linkage maps provided in FIG. 5 or Table 10 are useful for the genetic analysis of Atlantic cod. A person skilled in the art would readily be able to design linkage or association studies using the SNPs of Table 1 or Table 6 in order to identify SNPs that are linked or associated with a specific trait, phenotype or QTL. For example, a SNP associated with a trait or phenotype may be identified by comparing the frequency of a particular SNP allele in a control population and a test population selected for the presence of a specific trait or phenotype. Alleles that are present in a higher frequency in the test population compared to the control population are associated with the specific trait or phenotype. Examples of such traits or phenotypes include rapid growth, disease resistance, tolerance to handling stress, tolerance to thermal stress, high survival rates, low incidence of deformity or other traits of interest which would benefit aquaculture production. Methods of identifying QTL associated with a specific SNP allele are also known in the art. Examples of quantitative traits for which the SNPs of the present disclosure may be associated also include rapid growth, disease resistance, tolerance to handling stress, tolerance to thermal stress, high survival rates, low incidence of deformity or other traits of interest which would benefit aquaculture production.

Marker Assisted Selection

In a further embodiment, the SNP markers of the present disclosure may be used in Marker Assisted Selection (MAS), wherein fish enrolled in a breeding program are checked for the presence or absence of one or more SNP marker alleles. For example, fish having a specific SNP allele associated with a particular trait may be identified and put into a breeding program in order to select for offspring that also carry that marker. In one embodiment, the SNPs alleles or molecular markers identified herein will be associated with fish that perform well or poorly under aquaculture conditions. Accordingly, the SNPs can be used to non-lethally screen potential broodstock for traits of interest. For example, a piece of a fin can be obtained from a fish from a breeding program, and DNA can be extracted and analyzed to determine whether a SNP allele associated with a trait of interest is present. If the SNP allele is present, that fish would be desirable to include in a breeding program. In one embodiment, fish enrolled in a breeding program are checked for the presence or absence of a plurality of SNP markers alleles associated with a trait as described herein.

Identification of Family Members and Estimation of Relatedness

The SNP markers of the present disclosure may also be used to design targeted panels of markers used for the estimation of measures of relatedness. In one embodiment, measures of relatedness derived from the SNPs of the present disclosure may be used to ensure that crosses in breeding programs are not made between individuals that are too closely related.

In another embodiment, the SNPs of the present disclosure may be used to identify family members associated with a particular fish. For example, the SNPs may be used to identify parents of untagged progeny. As set out in Example 3, the present disclosure provides a set of SNPs listed in Table 14 that can be used to determine the parentage of fish, and in particular codfish. In a further embodiment, the SNPs listed in Table 14 can be used to estimate the relatedness of two or more fish. In one embodiment, the methods and SNPs described herein can also be used to identify siblings. In one embodiment, the SNPs identified in Table 14 can be used to identify the parentage of a fish by genotyping as few as 16 SNPs. In other embodiments, more than 16, more than 20 or more than 24 of the SNPs listed in Table 14 can be used to identify the parentage or estimate the relatedness of two or more fish.

Population Management and Analysis—Geographic Origin

The SNPs of the present disclosure may also be used in population management for fisheries, or in population analysis of Atlantic cod stocks. In a further embodiment, the SNPs may be used in forensics/compliance activities, such as determining where fish originated. For example, the SNPs may be used to differentiate between fish caught in different geographic areas that are associated with a specific allele or combinations of alleles.

In one embodiment, there is provided a method for determining the geographic origin of cod based on SNP genotypes. As set out in Example 2 and Tables 11 and 12, codfish from specific geographic areas have been shown to carry a specific set of genotypes which distinguishes fish caught in different areas.

As used herein "Eastern Atlantic Cod" refers to cod fish that are endemic to the European Atlantic seaboard including Iceland, Norway, Ireland and Great Britain. As used herein "Western Atlantic Cod" refers to fish that are endemic to the Canadian Atlantic seaboard including Newfoundland, Nova Scotia and New Brunswick as well as the Atlantic seaboard of the United States of America.

As used herein, a fish with that is not from Newfoundland or Northern Norway (Barents Sea), refers to codfish that are endemic to other areas of the Atlantic such as Ireland, Iceland, Georges Bank, or Cape Sable.

Genetic Markers for Production Traits

The present disclosure also provides genetic markers for production traits for Atlantic cod. Screening codfish for these markers can help identify commercially important breeding stocks or fish with more desirable production traits suitable for use in commercial aquaculture.

As set out in Example 4 and Table 18, SNP alleles that are associated with resistance to nodavirus infection in codfish have been identified. Identifying fish harboring the alleles identified in Table 18 can therefore be used to select cod fish suitable for breeding stocks or acquaculture that are less susceptible to nodavirus infection.

SNPs and specific alleles associated with growth and/or weight in Atlantic cod have also been identified as set out in Example 5. Identifying fish that harbour these QTLs for growth and/or weight can allow the selection of fish for use as parents in breeding programs, or the selection of fish at a young age that are more likely to develop into adult fish with desirable traits such as increased weight or size. Accordingly, in one embodiment fish harbouring growth and/or weight QTLs can be identified by screening for the SNPs alleles associated with increased weight or growth identified in Tables 20 or 21.

In another embodiment, SNPs and specific alleles associated with resistance to stress have been identified as set out in Example 7 and Table 24. Fish that are resistant to stress are better suited for breeding stocks and commercial aquaculture.

A person of skill in the art will appreciate that a fish can be identified that have a particular trait by genotyping the fish for one of the SNPs identified herein and determining whether they have one of the alleles shown to be associated with the trait as described herein, it is also possible to identify fish that have a particular trait by genotyping for markers that are in linkage disequilibrium (LD) wherein one of the alleles of that marker is in LD with one of the alleles shown to be associated with the trait as described herein. As used herein "linkage disequilibrium" refers to the co-segregation of alleles at different loci on a chromosome such that the presence of one allele is indicative of the presence of the other allele. Furthermore, a person of skill in the art would readily be able to identify markers and alleles in linkage disequilibrium on a common halpotype with the SNPs shown to be associated with particular traits identified herein.

A person of skill in the art will also appreciate that the methods and genetic markers described herein can be used to select fish for multiple markers. For example, in one embodiment the fish are selected for genetic markers associated with growth, nodavirus resistance and/or resistance to handling stress. When applying marker assisted selection (MAS) to breeding programs, single trait selection is not necessarily a desirable method to apply in production systems. It is possible, for example that selecting only for one beneficial trait could have the unexpected and undesirable result of selecting for a linked undesirable trait if precautions are not taken. For example, selecting only for improved growth when developing a breeding population for animal production could result in fast growing, and immune susceptible animals. When using MAS, best practices in development of broodstock for production include selection for multiple traits, where possible, such as improved growth, disease resistant and stress tolerance.

Isolated SNP-Containing Nucleic Acid Molecules

Table 6 identifies the corresponding SEQ ID NO. for each of the 3,072 SNPs identified in the present disclosure. Table 7 identifies the corresponding SEQ ID NO: for each of the SNPs of Table 1. Accordingly, one embodiment provides a nucleic acid sequence identified in Table 6 or 7 that comprises either one of the SNP alleles. In a further embodiment, the disclosure provides isolated nucleic acid molecules that comprise one or more of the SNPs identified in Tables 6 or 7. A further embodiment includes amplification primers and interrogation primers for the sequences and SNPs identified in Tables 6 or 7. A person skilled in the art would readily identify suitable amplification primers and interrogation primers based on the sequences identified in Tables 6 or 7 and common general knowledge in the art.

The term "isolated nucleic acid" refers to a nucleic acid substantially free of cellular material or culture medium, for example, when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

Detecting SNP Variants

A person skilled in the art will appreciate that a number of methods can be used to measure or detect the presence of the SNPs identified in the present disclosure. For example a variety of techniques are known in the art for detecting a SNP within a sample, including genotyping, microarrays, Restriction Fragment Length Polymorphism, Southern Blots, SSCP, dHPLC, single nucleotide primer extension, allele-specific hybridization, allele-specific primer extension, oligonucleotide ligation assay, and invasive signal amplification, Matrix-assisted laser desorption/ionization time-of-flight (MALDI-TOF) mass spectrometry, and Fluorescence polarization (FP). Such methods optionally employ the isolated nucleic acid molecules of the disclosure.

Accordingly, the SNPs are detected in one embodiment by genotyping. Methods of genotyping are well known in the art. In one method, primers flanking the SNP are selected and used to amplify the region comprising the SNP. The amplified region is then sequenced using DNA sequencing techniques known in the art and analyzed for the presence of the SNP alleles.

In another embodiment, the method of detecting a SNP comprises using a probe. For example, in one embodiment an amplified region comprising the SNP is hybridized using a composition comprising a probe specific for the SNP allele under stringent hybridization conditions.

Accordingly, one aspect of the disclosure includes isolated nucleic acids that bind to SNP alleles at high stringency that are used as probes to determine the presence of the allele. In a particular embodiment, the nucleic acids are labeled with a detectable marker. The marker or label is typically capable of producing, either directly or indirectly, a detectable signal.

For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The term "probe" refers to a nucleic acid sequence that will hybridize to a nucleic acid target sequence. In one example, the probe hybridizes to a sequence comprising a specific SNP allele or its complement under stringent conditions, but will not to the corresponding alternative allele or its complement. The length of probe depends on the hybridization conditions and the sequences of the probe and nucleic acid target sequence. In one embodiment, the probe is 8-100, 8-200 or 8-500 nucleotides in length, such as 1-7, 8-10, 11-15, 16-20, 21-25, 26-50, 51-75, 76-100, 101-150 or 151-200 nucleotides in length or at least 200, 250, 400, 500 or more nucleotides in length. In other embodiments, 10, 15, 20 or 25 nucleotides provide a lower end for the aforementioned nucleotide ranges.

In a further embodiment, the SNPs are detected using a primer extension assay. Briefly, an interrogation primer is hybridized to the sequence nucleotides immediately upstream of the SNP nucleotide. A DNA polymerase then extends the hybridized interrogation primer by adding a base that is complementary to the SNP. The primer sequence containing the incorporated base is then detected using methods known in the art. In one embodiment, the added base is a fluorescently labeled nucleotide. In another embodiment, the added base is a hapten-labelled nucleotide recognized by antibodies.

The SNPs described herein are optionally detected using restriction enzymes. For example, amplified products can be digested with a restriction enzyme that specifically recognizes sequence comprising one of the SNP alleles, but does not recognize the other allele. In one embodiment PCR is used to amplify DNA comprising a SNP, amplified PCR products are subjected to restriction enzyme digestion under suitable conditions and restriction products are assessed. If for example a specific SNP allele corresponds to a sequence digested by the restriction enzyme, digestion is indicative of detecting that particular SNP allele. Restriction products may be assayed electrophoretically as is common is the art.

SNP alleles can also be detected by a variety of other methods known in the art. For example, PCR and RT-PCR and primers flanking the SNP can be employed to amplify sequences and transcripts respectively in a sample comprising DNA (for PCR) or RNA (for RT-PCR). The amplified products are optionally sequenced to determine which of the SNP alleles is present in the sample.

Accordingly, the disclosure provides in one aspect, methods and nucleic acid molecules useful for detecting SNPs. In one embodiment, a sample comprising genomic DNA is obtained and primers flanking the SNP are used to amplify the region comprising the mutation. Sequencing is optionally employed to determine which SNP allele is present in the sample. In another embodiment, a sample comprising RNA is reverse transcribed, primers flanking the SNP are used to amplify the region comprising the SNP, and sequencing is employed to determine which SNP allele is present in the sample. In another embodiment the SNP is detected using a composition comprising a probe specific for the mutated sequence.

Alternatively SNP alleles are optionally detected by a variety of other techniques known in the art including microarrays, hybridization assays, PCR based assays, molecular beacons, Dynamic allele-specific hybridization (DASH) and/or combinations of these.

In one embodiment, the disclosure includes isolated nucleic acid molecules that selectively hybridize under stringent conditions to one of the sequences listed in Tables 7 or 8. A further embodiment includes an isolated nucleic acid molecule that selectively hybridizes to a nucleic acid comprising a SNP allele or its complement.

The phrase "specifically hybridizes to a SNP allele or its complement" means that under the same conditions, the isolated nucleic acid sequence will preferentially hybridizes to one of the SNPs alleles or its complement, as compared to the other allele.

The term "hybridize" refers to the sequence specific non-covalent binding interaction with a complementary nucleic acid. In a preferred embodiment, the hybridization is under high stringency conditions.

By "high stringency conditions" it is meant that conditions are selected which promote selective hybridization between two complementary nucleic acid molecules in solution. Hybridization may occur to all or a portion of a nucleic acid sequence molecule. The hybridizing portion is typically at least 5-14, 15-20, 21-25, 26-30, 31-40, 41-50 or 50, 50-100, 100-200 or 200 or more or more nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5× Denhardt's solution/1.0% SDS at Tm-5° C. for 15 minutes based on the above equation, followed by a wash of 0.2×SSC/0.1% SDS at 60° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Nucleic acid sequences that are primers are useful to amplify DNA or RNA sequences containing a SNP of the present disclosure. Accordingly, in one embodiment, the disclosure provides a composition comprising at least one isolated nucleic acid sequence that is a specific primer able to amplify a sequence comprising a SNP identified in Table 1 or Table 6. A person skilled in the art would understand how to identify and test primers that are useful for amplifying sequences containing the SNPs identified in Table 6.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Development of Single Nucleotide Polymorphism Markers for Atlantic Cod (*Gadus morhua*) Using Expressed Sequences Materials and Methods
EST Sequencing and Analysis
Information provided for this example is also described in Hubert et al. 2009. Tissue samples and methods used for RNA extraction, construction of normalized cDNA libraries, DNA sequencing and EST clustering have been described in detail previously (Bowman et al., 2007). In brief, directionally-cloned, normalized cDNA libraries were constructed using the Creator Smart cDNA kit (Clontech). Sequences were generated from the 3' direction and basecalling was performed using Phred. After trimming to remove vector and other sequence contaminants and masking in regions of low quality, ESTs were clustered using Paracel Transcript Assembler (PTA), with the cluster threshold parameter set to a value of 100, a match score of 1, a mismatch score of −3 and a hit length of 75 bp which lead to a minimum similarity of 98%. PTA initially groups similar sequences together within clusters, then attempts to assemble sequences within each cluster. Thus, PTA generates a set of sequence clusters and singlets, where clusters can contain one or more contigs (where sequences within clusters have been successfully assembled) and/or associated singlets. The PTA transcriptview function supports a variety of different graphical displays for subsequent sequence analysis, and this contig-viewing tool was used for manual detection of SNPs.

SNP Detection: Manual Identification
Alignments containing at least 5 reads were visually scanned for putative SNPs, with basecalls in the region of interest confirmed by viewing each sequence trace. SNPs identified were grouped into two categories: "predicted frequent" SNPs were defined as those with a minimum of two independent sequence reads representing the minor allele, whereas "predicted rare" SNPs were those where the minor allele was represented by a single sequence read. The "predicted rare" category of SNPs is more likely to represent artifacts caused by errors in PCR amplification.

SNP Detection: Automatic Identification
The automated process for SNP identification used PolyPhred, which requires Ace-format files as input (Nickerson et al., 1997). Although PTA produces output in the form of Ace files, these proved to be incompatible with PolyPhred. Thus, each PTA contig containing 4 or more reads was processed via a pipeline using both Phrap and PolyPhred. Output files for each contig generated by PolyPhred were parsed using a custom perl script to extract information regarding contig coverage, predicted SNPs, and the proportion of contributing sequences harboring each sequence variant. Again, SNPs were grouped into "predicted frequent" and "predicted rare" categories, based on the minor allele frequency, with a small subset of the "predicted frequent" group selected for further analysis.

SNP validation: Primer Design and Generation of PCR Amplicons
A small subset of SNPs identified by both methods were selected for further validation. Genomic DNA was extracted from fin clip samples by Proteinase K lysis, followed by high-speed centrifugation, and eluted in a low-salt buffer (DNeasy® Blood and Tissue Kit, Qiagen). DNA was quantified spectrophotometrically using a NanoDrop (NanoDrop Technologies). Regions of cod genomic DNA containing SNPs of interest were amplified using the polymerase chain reaction (PCR). Flanking primers for SNP amplification were designed using Primer 3 (Rozen and Skaletsky, 2000). The primers selected were between 18-22 nucleotides in length with a G+C content ranging from 45-55%. Each DNA sample (20 ng) was amplified in the following 20 ml reaction: 0.4 U Phusion taq polymerase (Finnzymes, New England Biolabs), 800 mM dNTPs (GE Healthcare), 0.5 mM forward 5' primer, 0.5 mM reverse 3' primer and 1×HF Phusion buffer (Finnzymes, New England Biolabs). Each sample was denatured for 30 seconds at 98° C., cycled 35 times at 98° C. (10 sec), 63° C. (20 sec), 72° C. (20 sec) with a final extension at 72° C. for 4 minutes. Amplified samples were confirmed by gel electrophoresis (1% agarose in 1×TBE, 100V for 90 minutes) and purified using both 10 U of exonuclease I (New England Biolabs) and 2 U of shrimp alkaline phosphatase (SAP) (MBI Fermentas) with incubation at 15 minutes at 37° C. followed by 85° C. for 15 minutes. For high throughput preparation and analysis, multiple samples were amplified and purified in 96 well PCR plates (Axygen).

SNP Genotyping

The purified PCR products were used as the template in a single-base extension reaction with fluorescent dye labeled terminators and an unlabeled locus interrogation primer using the GenomeLab™ SNPStart Primer Extension Kit (Beckman Coulter). The interrogation primer was designed with its 3' end immediately upstream from a predicted SNP. In most cases, the interrogation primer was 30 bp in length, with a G+C composition of around 50+/−10% and a $T_m$ of approximately 60° C. Seven interrogation primers have a different size, ranging from 36 bp to 52 bp to test multiplexing. Samples were cycled 25 times at 90° C. for 10 s, followed by 45° C. for 20 s. The resulting reaction was purified using 0.25 U SAP (MBI Fermentas) with incubation at 37° C. for 30 minutes followed by 65° C. for 15 minutes. Samples were resuspended in formamide together with 0.5 ml GenomeLab™ DNA Size Standard 80 (Beckman Coulter) and separated electrokinetically using a Beckman CEQ 8000 capillary sequencer (Beckman Coulter). The resulting primer peaks were then analysed to determine the identity of the fluorescently-labeled single-base extension, and the resulting genotype called either automatically or manually.

Genotyping of Parents and F1 Progeny

SNPs, detected either manually or automatically, were initially validated and assessed for variability using genomic DNA extracted from adult Atlantic cod fin clips. These fin clips were taken from individual fish enrolled as parents in the two Cod Genome Project (CGP) selective breeding programs in New Brunswick (NB) and Newfoundland (NL). F1 progeny generated from crosses using these adult fish were also available within the breeding programs, and were used in further analysis involving the segregation of variable SNPs.

SNPs were first tested on genomic DNA isolated from two adult Atlantic cod parents in the NB program to ensure the successful amplification of the template PCR product and a successful primer extension step. Putative SNPs which passed this initial screening were then assessed for genetic variability using a parent panel of 22 wild broodstock fish. This parent panel comprised 8 adult fish from NL and 14 fish from NB. Mendelian segregation was then tested using 46 F1 progeny from each of 3 families generated by CGP breeding projects. Genotypes were analysed using the Microsatellite Microsoft excel package (Park, 2001). Allelic frequency, allelic absolute values and observed heterozygosity have been calculated for both NB and NL populations, and in total. Departures from Mendelian segregation have been tested in 46 progeny from at least one of the three families created by the CGP breeding project. Segregation at each locus was tested using the $c^2$ test, with the significance of the individual tests adjusted for multiple testing as shown in Table 3 (Bonferroni correction; Rice (1989)). The adjustment for multiple testing was performed within types of segregation, depending on whether crosses were of the type homozygous×heterozygous or heterozygous×heterozygous.

Analysis of Synonymous/Non-Synonymous SNPs

Each contig consensus was compared against the NCBI protein database using BLASTX (Altschul et al., 1977). SNP positions which fell within regions of similarity were noted, together with the corresponding reading frame and strand. The EMBOSS utility transeq, together with coordinates defining the appropriate region, strand and frame information, was then used to translate the consensus sequence for each version of a SNP. The resulting amino acid sequences were then compared to determine whether the SNP was synonymous or non-synonymous.

Sequence Annotation

For sequences where SNPs were detected, contig consensus was processed using autoFACT (Koski et al., 2005) using default parameters. Databases used in autoFACT analysis included UniProt's UniRef90, NCBI's nr, KEGG, COG, PFAM, LSU and SSU BLAST. Only BLAST hits with a bit score higher than 40 were considered significant.

Results

Manual Detection of SNPs Using PTA

Initially, few contigs had enough depth of coverage to allow identification of SNPs defined as "predicted frequent". Manual scanning of a small number of these contigs was performed to identify potential SNPs, which were used to develop a low throughput SNP validation pipeline. Using the PTA transcriptview tool, 115 putative SNPs were manually identified from a randomly-selected set of contigs with 5 or more contributing sequences. The Applicants selected a small set of SNPs, principally based on the primers design possibilities. Most of the SNPs in the manually-curated set were detected in contigs having 6-10 component sequences, with an average of 8.25 sequences For "frequent SNPs", the minor allele was observed in at least in two reads but the number of sequences in which the major allele was observed varied from 5-12 (50% to 81.1%).

A total of 30 putative SNPs identified using PTA were selected for validation (Table 1). Initially DNA samples from two NB parents were used for assay development. Of these, one failed to amplify in the first stage of testing. A further 5 failed at the primer extension stage, so in total, assays for 24 of these SNP were successfully developed. These 24 SNPs were then assayed to test their variability on a panel consisting of 14 parental fish from the NB breeding program and eight from the NL breeding program (Table 2). Twenty-one SNPs appeared to be polymorphic with the two predicted alleles detected within the set of individuals tested, and three were monomorphic. SNPs were generally polymorphic in both populations, with values for observed heterozygosity ranging from 0.14 to 1.0 in NB, 0.12 to 1.0 in NL and 0.14 to 1.0 overall (Table 2). These data show that SNPs could be selected within the CGP EST data which were highly variable in both of the populations used for family generation within the broodstock programs.

Automated SNP Detection Using PolyPhred

Manual prediction of SNPs was carried out at an early stage of sequence generation within the project. As additional sequences were generated and incorporated into sequence clusters, more contigs were produced with sufficient depth of coverage for detection of "predicted frequent" SNPs and a manual approach becomes untenable. The Applicants developed an automated pipeline using the sequence variation detection tool PolyPhred (Nickerson et al., 1997), which was first used to analyse the output from early stage clustering. A small subset of the SNPs generated by PolyPhred using the SNP validation process (Table 1), were tested and the automated output was analyzed to determine whether the SNPs identified by manual annotation were also detected by the automated process.

Initially 10 SNPs selected from the automated pipeline were tested, with a further seven SNPs added to the analysis where the interrogation primers were synthesized at different lengths to allow multiplexing of the genotyping reaction. The SNPs were selected based on the possibilities of primer design. Of the 17 SNPs tested, two failed at the first amplification step. Additionally, two of the amplification products exceeded the recommended length in the genotyping reaction, presumably because the amplification product included a large intron (or multiple introns) present in the genomic DNA template but not in the original EST sequence. A further four assays failed at the primer extension stage. However, all of the remaining nine predicted SNPs tested as polymorphic against the panel of 22 parental fish (Table 2).

Comparison Between PTA and PolyPhred SNP Identification Methods

The SNPs detected manually using Paracel Transcript Assembler (PTA) software were compared with SNPs detected automatically using PolyPhred (PP) software, to determine whether the automated pipeline was successful in detecting SNPs that would have been called by a manual annotator. The consensus sequences of the equivalent SNP-containing contigs selected from both PTA and PP were aligned using clustalW (Thompson et al., 1994). For both pipelines, the location of the SNP, the number of contributing reads and the allele ratio were confirmed. The success of the automated pipeline in identifying the same SNPs as the manual pipeline was assessed using two sets of criteria. When using the more stringent criteria in PP (allele ratio 30:70; at least four contributing reads), 11 of the 30 manually-annotated SNPs were not detected. However, this number decreased to six when using less stringent criteria (allele ratio 25:75; at least four contributing reads).

Only two of the six manually-annotated SNPs which were not detected by the automated pipeline were successfully validated experimentally (PTA_179.c1 and PTA_153.c1). These SNPs were not identified by the automated pipeline because they fell out of the criteria range since PP eliminated some sequences based on quality criteria. The remaining four SNPs were not identified automatically for several reasons. Two failed on sequence quality criteria (PTA_056.c1, PTA_463.c2), one failed because the PP pipeline generated a contig which did not successfully align with that produced by PTA (PTA_263.C1), and one failed because the minor allele was only represented by one sequence (PTA_079.C1) in the automated assembly.

The Applicants also tested a small number of "rare SNPs" (3) selected from both the manual and the automated pipelines to determine their utility (minor alleles comprising less than 25% of the sequences), for example, PTA_079.C1, PP_161.C1 and PP_134.C1. None of the "predicted rare" SNPs gave good results, although a very small number were analysed. When tested on the parent panel, PTA_079.C1 was monomorphic in all fish tested, with PP_134.C1 and PP_161.C1 appearing to represent gene duplications.

SNP Analysis

Almost all PCR primers (42/47) amplified a product, except for those primers for SNPs PTA_263.C1, PP1062.C1, PP1159.C1, PP1301.C1 and PP127.C1 (Table 1) which did not generate products. When tested on a panel of 22 wild fish, the 33 SNPs shown in Table 2 gave a good primer extension assay. Thirty of the SNPs tested appeared to show polymorphism in the 22 wild fish tested, with a further three SNPs being monomorphic in the small number of individuals assayed. The experimentally detected alleles agreed with those predicted in all cases. Allelic frequencies were compared using a $c^2$ test to see if there was a variation between populations. Overall, no significant differences were observed between the NB and NL populations. SNPs predicted using either method appeared highly variable in both populations (Table 2).

Family Informativeness

SNPs are less informative for linkage mapping because they are almost always biallelic. The 22 wild fish tested to assess SNP variability had been used to create 13 cod families within the CGP breeding programs. These families were assessed to select a small number of crosses in which to assess SNP segregation patterns. The number of informative loci for these 13 families ranged from 25% to 60%, with an average of 42.2%. For the 30 polymorphic SNPs identified, it was necessary to test only three of these families to have informative loci to be tested for linkage analysis.

Of the 30 SNPs tested for their patterns of inheritance, one SNP (PTA_1522.c1) was only tested on a small number of progeny since both parents were homozygous with a different allele, so the resulting progeny are all heterozygous and therefore segregation could not be tested. However, this SNP was inherited as expected. For the remaining 29 SNPs, 22 showed Mendelian inheritance patterns. Of these, four showed a distortion of segregation (PP_1657.C1, PTA_657.c2, PTA_179.c1, PTA_912.c1), but when correcting for multiple tests, none remained significantly different. In order to get genotypes usable to mapping purposes, it is necessary to have one homozygote and one heterozygote for each SNP as parents in a cross. Only these 22 SNPs (out of the 33 successful assays) are suitable for placement on a map using these three families i.e. they are present as homozygote/heterozygote in one of the three crosses tested, and they show correct Mendelian segregation (Table 3).

A further seven SNPs amplified correctly in the parent panel, but when testing allelic segregation in the progeny the parental alleles did not segregate as expected. One SNP, PP_134.C1, is likely to represent gene duplication, or two very similar members of a gene family, rather than different alleles of the same gene, since both parents and their progeny appear to be heterozygotes. A further SNP, PP_161.C1, also appears to result from a gene duplication as three variants were observed, with inheritance patterns suggesting two genes, with one being homozygous (G) and a second having two alleles (C/T). For this SNP, both parents and progeny can be scored as having three genotypes for this SNP in a single individual (G, C and T).

For the other five SNPs no clear pattern to the irregular segregation observed could be discerned, and these "SNPs" may in fact represent evidence of copy number variants, which have recently been identified as occurring frequently in the human genome (Redon et al., 2006). For these 5 SNPs a significant variation in signal strength was also observed for each allele, making scoring difficult, and indicating that there may be underlying copy number changes.

Annotation of Contigs Containing SNPs

Contigs containing each of the SNPs tested were compared with 9 databases, including UniProt's UniRef90, NCBI's nr, KEGG, COG, PFAM, LSU and SSU BLAST with the results analysed using autoFACT. Out of the 23 polymorphic SNPs with Mendelian inheritance patterns and the three monomorphic SNPs, 14 had a significant hit with cutoff BLAST score>40 (Table 4). The Applicants also used BLAST to determine if these SNPs resulted in synonymous or non synonymous amino acid substitutions (Table 5). This could only be determined for four SNPs, with the remaining SNPs either located in non-coding regions (9) or showing no similarity within the databases searched (13). Of the four SNPs present in the coding region, two were synonymous (PTA_1153.C1; PTA_1473.C1) and two were non synonymous (PTA_1090.C1; PTA_624.C1).

Discussion

The Applicant developed both a low throughput (manual) and a high throughput (automated) SNP identification pipeline, together with a set of experimental SNP validation methods in order to validate SNPs detected within cod EST contigs generated using an automated pipeline. As shown in Table 2, for the 47 SNPs tested, 70% (33) amplified correctly and gave a successful primer extension, on a small panel of 22 wild fish. However, when testing for segregation, unusual, non-Mendelian patterns of segregation were observed for 15% (7) of the SNPs tested (Table 3). This Example shows the importance of validating markers for Mendelian segregation. It is possible that these putative SNPs actually represent copy number variants residing on duplicated genome segments. These anomalous SNPs can be identified by analyzing patterns of segregation (Gut and Lathrop, 2004) with, in obvious cases, all progeny appearing heterozygous, but in other cases an excess of heterozygotes is observed, as seen in salmon (Hayes et al., 2007). From the segregation study, we estimated that 15% of putative SNPs are likely to represent gene duplications, which is similar to than in salmon where 14% of putative SNPs have been identified as being located in duplicated regions (Hayes et al., 2007), but much higher than that observed by Moen et al. (2008) who predicted that 2% of SNPs represent duplicated genes. These discrepancies may indicate differences in the clustering parameters used between different groups, and will be resolved on analysis of a larger SNP set.

The criteria used in the present application for SNP identification is biased against the detection of rare SNPs. It was necessary to select SNPs from contigs with a large number of contributing sequence reads to reduce the likelihood that putative SNPs represent artifacts arising from errors in amplification or sequencing. Each different SNP version is required to be represented by a minimum of two confirmatory reads.

It is also important to know if SNPs identified in coding sequence are synonymous/non-synonymous as non-synonymous substitutions will alter the amino acid composition of the resulting protein.

Large-scale SNP discovery is a first step towards developing a dense genetic map for Atlantic cod. Developing SNPs from ESTs is of particular value, since all should be associated with transcribed genes, and can therefore be used to anchor comparative genomic analyses.

The present disclosure presents and validates a set of SNP markers for Atlantic cod. The low throughput study for SNP described here validated manual and automated SNP detection, and estimated genetic variability and segregation. These SNPs represent a valuable resource for genetic mapping and QTL analysis, but also for genetic studies in wild populations of Atlantic cod.

Example 2

Development of a SNP Resource and a Genetic Linkage Map for Atlantic Cod

Background

Information provided for this example is also described in Hubert et al. 2010. With wild Atlantic cod (*Gadus morhua*) stocks declining dramatically over the last few decades (Rose, 2007), aquaculture is becoming increasingly important as a means of maintaining a market supply for this species. Cod aquaculture is currently being developed in several countries (Rosenlund et al., 2006), but has not yet reached a sustainable commercial scale (Brown et al., 2003). Applying genomics tools in the selection of elite broodstock has the potential to enhance the productivity and value of commercial production for this species (Gjedrem, 2000).

Genetic marker discovery is a necessary first step in the application of genomics to improve broodstock as these markers can be used for the creation of linkage maps and subsequent QTL identification. Marker assisted selection (MAS) can then be employed by selecting broodstock based on genotypes at QTL that are relevant to economically important traits such as rapid growth, disease resistance and the control of early maturation. Currently, a limited collection of genetic markers is available for Atlantic cod, including restriction fragment length polymorphisms (RFLP), microsatellites and single nucleotide polymorphisms (SNPs) (Pogson et al., 1995; Delghandi et al., 2008a; Delghandi et al., 2008b; and Higgins et al., 2009). Most of the studies describing genetic markers in Atlantic cod have employed microsatellite markers (Wesmajervi et al., 2007; Ruzzante, 1996). In total, 352 microsatellites have been published to date for this species, including a large, new collection of expressed sequence tag (EST) derived microsatellites (Higgins et al., 2009). However, SNPs are the most abundant type of DNA sequence polymorphism, are suitable for high-throughput genotyping, and provide enhanced possibilities for genetic and breeding applications, linkage map development, assessment of genetic variability and marker assisted breeding. As a result, SNP discovery pipelines have been recently developed for many species including fishes (Hayes et al., 2007; Cenadelli et al., 2007; He et al., 2003; Stickney et al., 2002; and Ryynanen et al., 2006). To date, a collection of 318 SNPs has been identified for Atlantic cod using 17,056 ESTs generated from a North-East Atlantic cod population, and these SNPs have been tested on several additional Norwegian cod populations (Moen et al., 2008). In total, 174 of these SNPs, together with 33 microsatellites, have been used to generate a genetic linkage map for Atlantic cod. This map comprises 25 linkage groups with an overall length of 1225 cM, and represents the first reported linkage map for this species (Moen et al., 2009).

As set out in Example 1, SNPs have been identified from sequence data generated by a large-scale expressed sequence tag (EST) program focusing on fish originating from Canadian waters. A subset (3072) of these SNPs (listed in Table 6) have been tested for polymorphism across a number of different wild stocks and has also been used to generate a preliminary linkage map for this species. The EST set was designed to provide an excellent resource for SNP marker discovery, since it is generated from several cDNA libraries representing different tissues, with three to 340 individuals contributing to each library. Furthermore, many of the SNPs developed were identified from sequence data with functional annotation potentially allowing the identification of genes contributing directly to a phenotype.

Putative SNPs identified in this study were subsequently validated for polymorphism across a number of geographically diverse Atlantic cod populations, ranging from Canada to the North-East Atlantic (Iceland, Norway and Ireland). These SNPs were also tested for Mendelian segregation in two families, and used to create a high-density genetic linkage map that can be applied in QTL analysis to facilitate cod broodstock selection.

Materials and Methods

Validation of Putative SNPs on Panel

In total, 5×96 well plates of selected DNA samples were genotyped using the two Illumina GoldenGate panels. Two plates consisted of two references families, B33 and B87 with two parents and 91 progeny. The three remaining plates consisted of wild cod populations. In total, seven populations of Atlantic cod were genotyped for this study, with an average of 23 fish genotyped per population. The geographic location of collections covers the North Atlantic with a more detailed sampling for Atlantic Canadian populations. DNA extraction methods have been described previously. In summary, fin clips or muscle tissue samples were taken and placed in 95% ethanol. DNA was extracted using the Qiagen DNAeasy 96 extraction kit (Qiagen, Mississauga, ON). The kit protocol utilizes a buffer containing proteinase K to lyse the tissue. The lysate is loaded onto a plate where the DNA binds to a silica membrane in the presence of chaotropic salt. Proteins and other contaminants are washed from the bound DNA using wash buffers and centrifugation. DNA is then eluted in water. High-throughput genotyping was performed using the GoldenGate assay.

SNP Annotation

For sequences where SNPs were detected, the consensus sequence for each contig was compared to the NCBI nr database using BLASTX (Altschul et al., 1990), with a value of $1 \times e^{-05}$ used as the cutoff to determine significance. All SNPs that were determined to be polymorphic after testing have been deposited in the GenBank SNP database under accession numbers ss131570222 to ss131571915. Sequences, and their associated annotation using both BLASTX and AutoFACT (Koski et al., 2005), can also be accessed via the CGP database (http://ri.imb.nrc.ca/codgene).

Identification of Synonymous and Non-Synonymous SNPs

The procedure for determining a SNP as synonymous or non-synonymous is as outlined in Example 1. Briefly, each contig consensus was compared against the NCBI protein database using BLASTX to establish a reading frame in which to assess synonymous or non-synonymous status. For those SNPs within regions of similarity, the consensus sequence was translated for each SNP allele and the resulting amino acid sequences were then compared to determine whether the SNP was synonymous or non-synonymous.

Analysis of Atlantic Cod Populations

Loci deviating from Hardy-Weinberg equilibrium (HWE) were identified in each of four Canadian populations of Atlantic cod. This was assessed separately in each population using Hardy-Weinberg exact tests calculated using GenePop v4.0 (Rousset, 2008). The 64 loci that failed Hardy-Weinberg exact tests in four Canadian populations were excluded from data used to generate the linkage map.

Genetic Linkage Map Construction

The genetic linkage map was constructed using JoinMap®4. Genotypes for progeny generated through the Illumina GoldenGate platform were converted to CP codes based on parental genotypes. Each cross was examined separately, with segregation ratios analysed for all loci, and those which showed abnormal segregation as determined using a chi-square goodness of fit test were removed (P<0.005). Markers were then associated within linkage groups using the group function of JoinMap®4, using a LOD cut-off value of 5.0 or greater. Marker orders within linkage groups were determined and map distances calculated using Haldane's mapping function. Maps generated independently for the two families were compared, and a 1:1 correspondence between linkage groups confirmed. The corresponding groups from the two families were combined using the JoinMap®4 merge function, and a consensus map generated.

Results

SUMMARY

Figure 5:
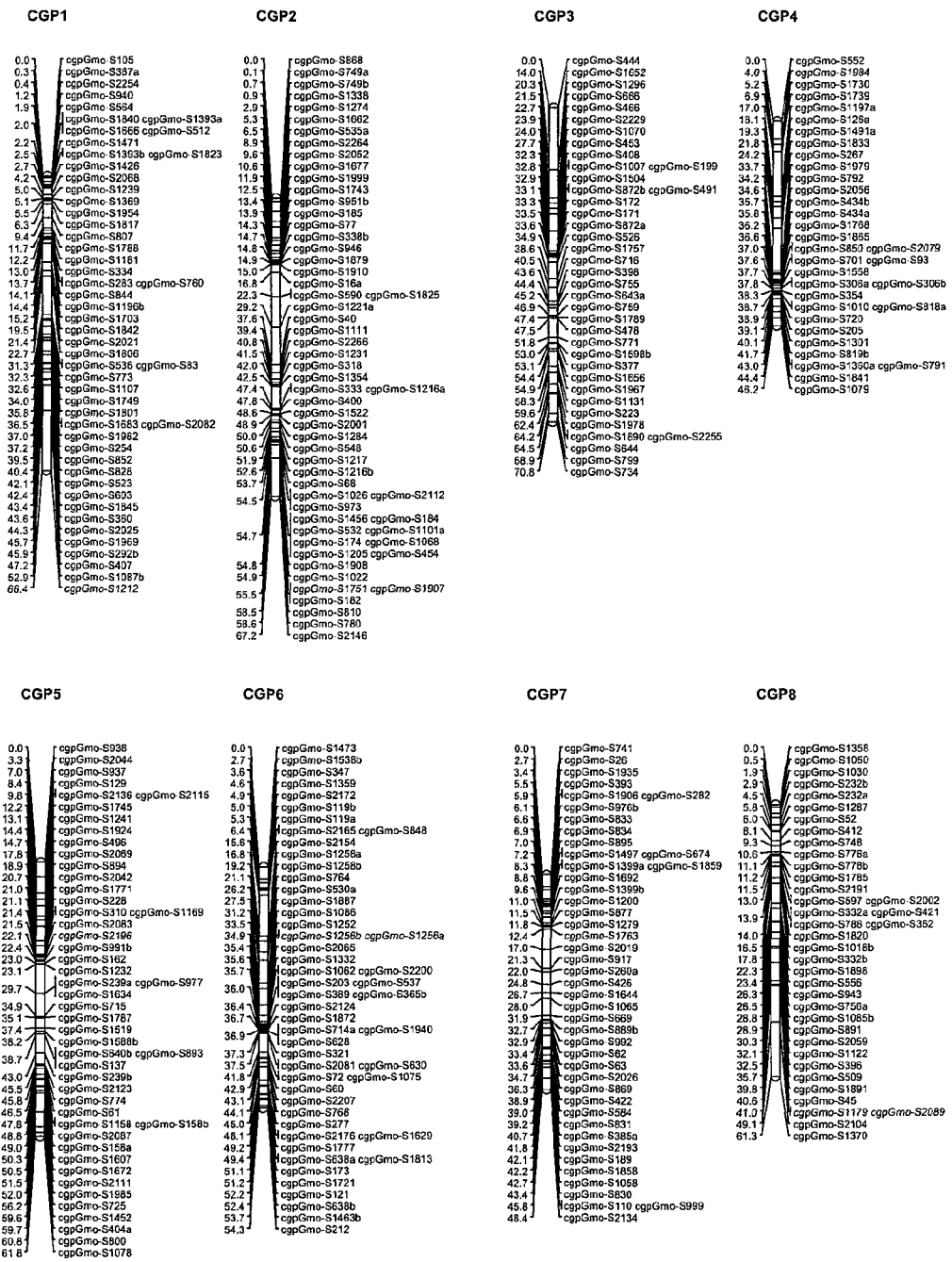
FIG. 5 is a genetic linkage map for Atlantic cod. The 23 major linkage groups are shown. These have been arbitrarily numbered CGP1-23 based on the order generated by JoinMap[4], and to distinguish them from the linkage groups generated by Moen and colleagues (Moen, 2009). Distances in centimorgans are indicated on the left of each linkage group, with SNP identifiers on the right. A revised version of the genetic linkage map used for QTL analyses is provided in Table 10.

A total of 97976 ESTs were assembled to generate 13448 contigs. 4753 SNPs were detected that met our selection criteria, which included a depth of coverage of at least 4 reads with a minor allele frequency higher than 25%. From the 4753 SNPs identified, the 3072 SNPs listed in Table 6 were selected for testing using two Illumina GoldenGate panels. The percentage of successful assays was 75% for these panels, with 2291 SNPs amplifying correctly. From the successful assays, 607 (26%) of the SNPs were found to be monomorphic for all populations tested. In total, 64 (4%) of SNP assays that scored as polymorphic are likely to represent duplicated genes or highly similar members of gene families, rather than alternative alleles of the same gene, since they showed a high frequency of heterozygosity in the samples tested. The remaining polymorphic SNPs (1620) were categorised as validated SNPs and are also identified in Table 6. The mean minor allele frequency among the validated loci was 0.258 (+−0.141). The ratio of transition to transversion types of substitution was 1.11:1 for validated SNPs. Of the 1514 contigs from which validated SNPs were selected, 31% have a significant blast hit. Of the 141 of these SNPs that are predicted to occur in coding regions, we determined that 64% (90) are synonymous. When comparing different populations, including those from North America and Europe, a large number of loci (1033 SNPs; 64%) are polymorphic for all populations originating from the North Atlantic. However a small number of SNPs (184), shown in Table 11 that were shown to be polymorphic in the Western Atlantic were monomorphic in all fish tested from three European populations. The large set of validated, polymorphic SNPs has been used to construct a preliminary linkage map using two families, with two parents and 91 progeny genotyped in each case (FIG. 5). This map has 23 major linkage groups and 924 mapped SNPs.

In addition, a set of associated SNPs was also found to distinguish some Northern and Southern populations of cod. It was noted that linkage group 7 (Table 10) had characteristics that can be associated with low recombination. A set of 21 SNPs (identified on 20 contigs) were found to co-segregate on the linkage map. This was the largest set of co-segregating SNPs on the linkage map. Genotypes for different individuals included in the population analysis were obtained. Individuals from the most extreme populations, Norway and Ireland, were used to identify the "North" and the "South" genotype respectively. Then genotypes for other populations were identified using homozygotes with North or South-type genotypes (Table 12). For the Canadian population tested, it is noteworthy that fish from populations near New Brunswick harboured the South and the North-type genotype, but fish from populations near Newfoundland harboured only the north-type genotype for all fish tested.

Validation of Putative SNPs on Panel

Out of the pool of 4753 predicted good quality SNPs, 3677 SNPs satisfied the criteria for the Illumina Golden Gate platform in that they appeared to be bi-allelic, with 100 bp of flanking sequence and less than 60 bp from a selected neighbouring SNP, and these SNPs were scored for primer design. Two Golden Gate panels, each comprising 1536 SNPs (3072 SNPs total; listed in Table 6), were created from the best-scoring SNPs (CGP Panel 1 and CGP Panel 2) and these were tested against a large number of Atlantic cod sampled from a number of sites (multiple populations from Canada, and single collections from Iceland, Ireland and Norway). Parents and progeny from two reference families selected from the CGP breeding program in New Brunswick were also genotyped to test for non-Mendelian segregation and for the creation of a genetic linkage map (Table 9).

Figure 2:
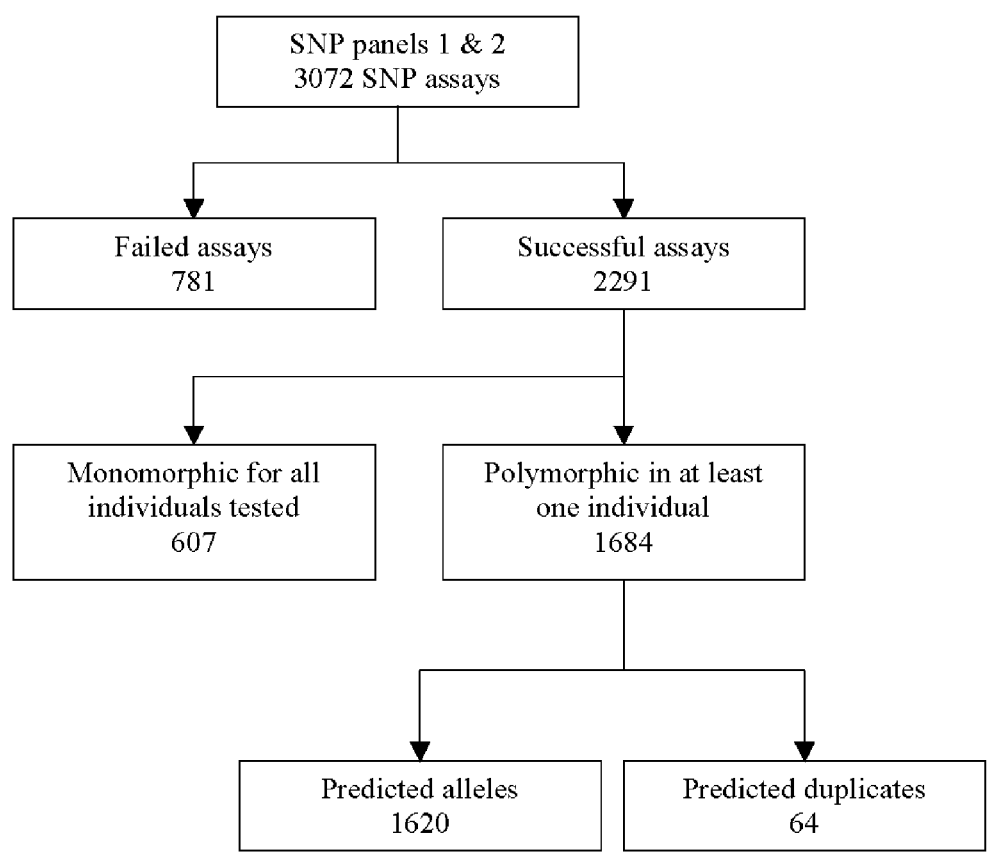
FIG. 2 is a flowchart showing the output resulting from testing of the 3072 selected SNPs. The 1620 "predicted alleles" correspond to the set of validated SNPs.
Figure 3:
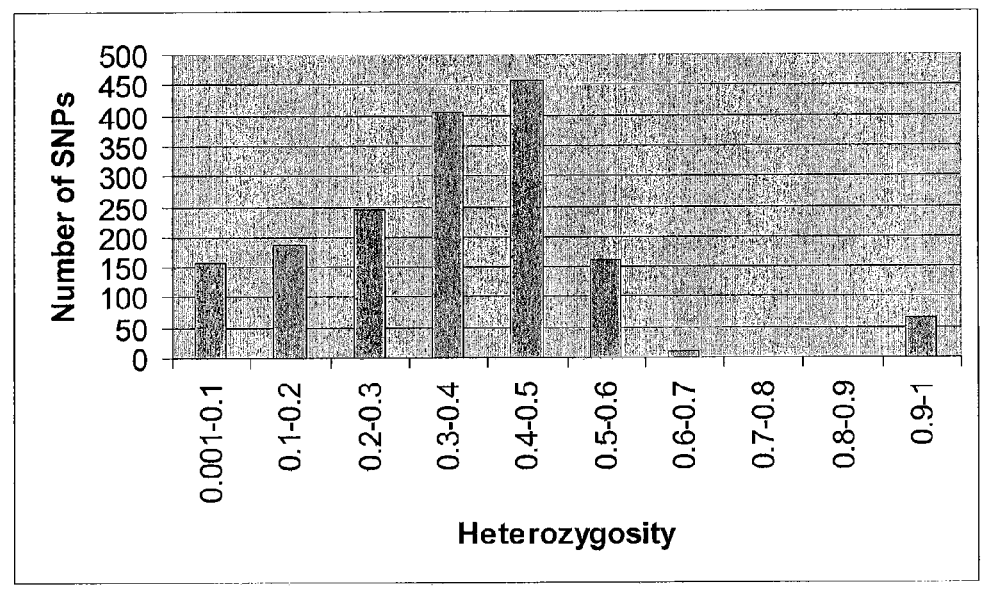
FIG. 3 shows the observed heterozygosity for polymorphic SNPs in four Canadian populations. SNPs were grouped into categories based on their values for observed heterozygosity averaged across four Canadian populations. All polymorphic SNPs were analysed, including those with high values for observed heterozygosity (predicted duplicates). The number of SNPs falling into each category is shown.
Figure 4:
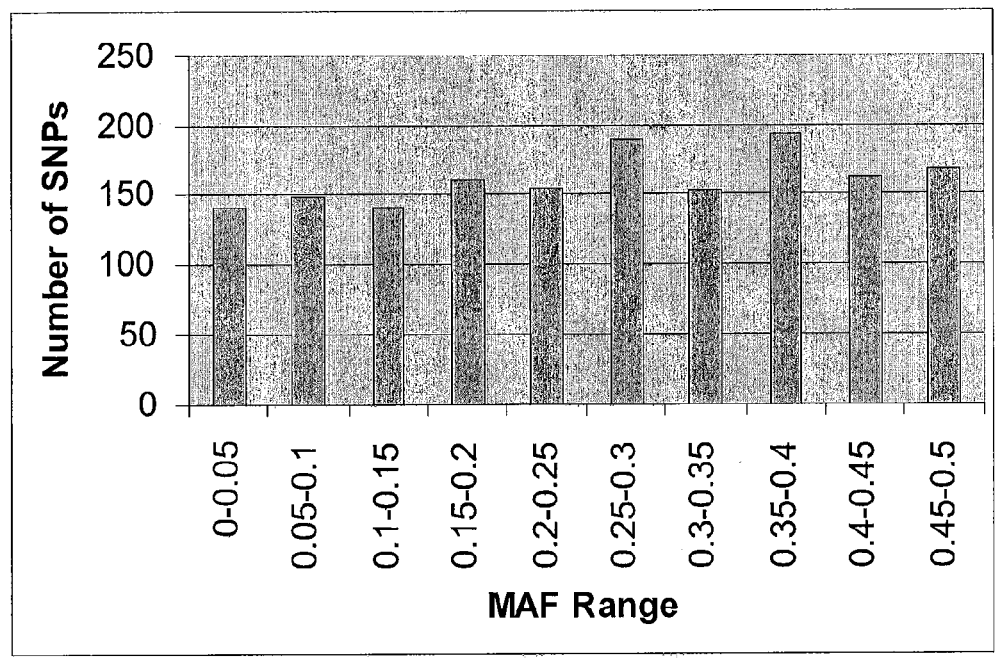
FIG. 4 shows the minor allele frequency of validated SNPs in four Canadian populations. SNPs were grouped into categories based on their minor allele frequency (MAF) averaged across four Canadian populations. Only the validated SNPs have been included in this analysis, with the number of SNPs falling into each MAF category shown.

The success rate for SNP assays was 75% for the two panels tested, with a total of 781 assays that failed to give good quality genotypes (FIG. 2). From the 2291 successful assays, 607 SNPs (26%) were monomorphic (i.e. only one SNP variant was identified) in all individuals from four Canadian populations that were tested (Table 8), and therefore are either incorrectly identified as SNPs, or are rare SNPs within the populations analysed. The majority of these have a minor allele represented by two sequences, the minimum allowed by our selection criteria; only a small number of monomorphic SNPs have more than 2 reads representing the minor allele. In total, 1684 SNP assays identified both SNP variants, with at least one individual tested carrying the predicted minor allele. However, 64 of these SNPs showed a high proportion of heterozygotes in all individuals tested (FIG. 3), indicating that they might represent sequence variation between duplicated genes, or members of closely related gene families, rather than different alleles from the same gene; the total number of SNPs predicted as corresponding to bi-allelic loci was 1620 (FIG. 2; identified in Table 6). For the purpose of this study, we define validated SNPs as those having a value for observed heterozygosity greater than zero but lower than 0.9. Therefore this study has identified 1684 polymorphic SNPs, with 1620 of these being validated SNPs as we predict they correspond to a base change at a single locus. The average observed heterozygosity for these validated SNPs was 0.332 (+/−0.148) and ranged from 0.01 to 0.69. The mean minor allele frequency among the validated SNPs was 0.258 (+/−0.141) and ranged from 0.005 to 0.5. The number of SNPs observed with varying MAFs in the four Canadian populations enrolled in the CGP breeding programs is shown in FIG. 4. The number of SNPs in different MAF ranges from 0.05 to 0.5 is relatively consistent for these populations, with 141 validated SNPs having a MAF lower than 0.05, and 169 SNPs with a MAF from 0.45 to 0.5 for example.

SNPs for CGP panel 1 (1536 SNPs) were chosen such that only one SNP per contig was included. The second panel selection consisted of various categories of SNPs chosen based on a prioritized strategy. Initially, SNPs from remaining contigs not represented on the first panel were selected. The panel was then completed by selecting SNPs that are neighbours on the same contig to SNPs that failed, or were monomorphic, on panel 1, and also SNPs that are neighbours to successful SNPs on panel 1 (or a small number of SNPs included on panel 2 which had not yet been tested) but having a different haplotype. A few SNPs were selected manually based on contig annotations, with some of these identified on SSH EST contigs. Thus the final set of validated SNPs (1620) were selected from 1514 contigs, with several contigs having multiple validated SNPs. These can be identified in the SNP set as they have an identical number, but a different suffix, as in cgpGmo-S177a and S177b for example.

SNPs neighbouring failed panel 1 SNPs had slightly lower success rate (69%) when compared to other SNP categories, which ranged from 72 to 79%. Analysis of the polymorphism of successful panel 2 SNPs showed that SNPs neighbouring panel 1 failures have a higher number of polymorphic SNPs (78%) when compared to the "unique SNPs/contig" category (71%). Two categories showing the smallest number of polymorphic loci are the manually picked SNPs (35%) and the neighbours of monomorphic panel 1 SNPs (47%). Some of the manually picked SNPs were selected from SSH libraries which had each been generated from a single family, and thus this subset may contain a greater proportion of SNPs which are rare within the population as a whole.

The ratio of transition substitutions (A/G and C/T) to transversions among predicted alleles of the 3072 putative SNPs chosen for inclusion on the two Illumina panels was examined. The base substitution frequency was compared with that seen in the validated SNPs. Little variation was found between the ratio of transition:transversion substitution types for the different SNP categories (putative SNPs and validated SNPs), with a ratio of 1.18:1 for the SNPs selected for validation, which decreased slightly to 1.11:1 for validated SNPs (Table 10).

Functional Annotation of SNPs

The SNPs described herein are particularly valuable as they are linked to expressed sequences. However, because a large fraction of the 3' sequence in which the SNPs were detected is likely to originate from the 3' UTR of each transcript, most SNPs were expected to fall in non-coding regions. This resulted in a relatively low percentage of sequences for which a function could be inferred based on sequence similarity. Of the 1514 contigs from which at least one validated SNP was selected, 474 (31%) had a significant blast hit (e value$<=1e^{-05}$) in the NCBI non-redundant dataset. In total, 514 SNPs (32%) were associated with sequences having significant similarity to an entry in the NCBI nr database.

After analysis based on sequence homology, a subset of the SNPs identified was found to fall within coding regions; these SNPs were analysed to determine if substitutions encoded by the two allelic variants would result in an amino acid change, i.e., if the substitutions are non-synonymous or synonymous. Only 9% of validated SNPs occur on a known reading frame within coding regions (i.e. they have similarity with a protein sequence present in public databanks). Of these 141 SNPs, 90 (64%) were predicted to generate synonymous substitutions, while 51 (36%) were non synonymous.

Population Comparison

Provided herein is a description of SNP characteristics in several populations of Atlantic cod shown in Table 9. From our analysis, the number of monomorphic loci varied greatly between the Canadian populations and more distant populations such as Ireland and Norway. A large number of loci (1033) are polymorphic in all populations. As anticipated, the greatest number of monomorphic loci from this SNP set is seen in the East Atlantic populations (Iceland, Ireland and Norway). This is likely to be due to ascertainment bias rather than a real underlying difference in variability between West and East Atlantic populations, as SNPs were selected based on their frequent occurrence in Cape Sable and Bay Bulls fish. A number of SNPs (184; listed in Table 11) have been identified as diagnostic SNPs as they can be used to distinguish between Western and Eastern Atlantic cod populations, being monomorphic in fish tested from the Eastern Atlantic cod populations (Iceland, Ireland and Norway) but polymorphic in Western Atlantic cod populations. In addition, a set of associated SNPs were also identified that can be used to distinguish some Northern and Southern Atlantic populations (see Table 12).

A few of the polymorphic SNPs were not in Hardy Weinberg equilibrium (HWE) in one or more of the four Canadian populations tested. We determined that 65 of the total collection of polymorphic SNPs significantly deviate from HWE in all four populations ($P<=0.05$), and the vast majority of these (64) were screened out from the set of validated SNPs as they had values for observed heterozygosity greater than 0.9. An additional 136 SNPs show significant deviations from HWE in one population only, and this is also true for 19 SNPs in two of the four populations and two SNPs in three of the four populations tested.

Mendelian Inheritance and Informativeness of SNPs for Linkage Mapping

Segregation patterns of SNPs (Mendelian/non-Mendelian) were tested by genotyping the parents and progeny from 2 CGP families, to ensure that SNPs can be used reliably for linkage analysis. In each case, patterns of segregation were assessed in the 91 progeny genotyped for each family. Most of the SNPs that were predicted to represent differences between genes (paralogs or members of gene families) were removed prior to analysis of segregation patterns, although a small number were included in the initial analysis, and all of these demonstrated non-Mendelian inheritance patterns. Additional SNPs also showing non-Mendelian inheritance were screened out prior to generating the linkage groups used for map generation. Different, overlapping sets of SNPs could be assessed for segregation in each of the two families. In family B33 it was possible to examine the inheritance for 858 SNPs, whereas 832 SNPs were informative in family B87. A total of 19 SNPs in family B33 showed a significant departure from Mendelian segregation ($P<=0.005$) however nine of these are predicted to represent gene duplications/multigene families rather than real SNPs since both parents and all progeny are heterozygous. For family B87, 38 SNPs showed significant departure from the Mendelian expectation, with 12 SNPs predicted to arise from duplications rather than segregating alleles in this family. Combining the results from the two families, a total of 46 SNPs show non-Mendelian segregation, with 14 of these giving results indicative of gene duplication in at least one family.

On comparison, 64 of the 65 SNPs that deviate from HWE in all four of the Canadian populations tested in this study were either screened out as potential duplicates prior to analysis, or showed non Mendalian inheritance ($P<=0.005$) in one or both of those crosses. It was possible to map a single SNP, cgpGmo-S89a, from this category. Of the 157 SNPs that deviated from HWE in one, two or three Canadian populations, two failed the test for Mendelian segregation in both families used for mapping (cgpGmo-S1835 and S1962), with a further three SNPs showing departure from Mendelian segregation in family B33 but segregating correctly (within the parameters allowed for Mendelian inheritance) in B87 (cgpGmo-S1219b, S626a and S2232). However, the majority of the SNPs in this second category could be successfully placed on the linkage map.

Generation of a Preliminary Genetic Linkage Map for Atlantic Cod

The generation of genomics resources as described herein is tightly integrated with family-based selective breeding programs based in New Brunswick and Newfoundland. As part of these programs, individual crosses are generated with known parental contribution, with the progeny from these crosses reared in separate tanks until they reach a suitable size for surgical implantation of a passive integrated transponder tag. Parents and 91 progeny from each of two independent crosses, families B33 and B87, were genotyped using the two Illumina GoldenGate panels described in this study (Table 8) with the aim of generating a SNP-based genetic linkage map.

After removal of the loci with highly skewed segregation ratios ($P<0.005$) described earlier, JoinMap®4 (Van Ooijen, 2006) was used to generate linkage groups of associated loci for each family independently, and to order loci within linkage groups to create a preliminary map. For both families, 23 major linkage groups were generated using an LOD threshold value of 5.0, which is in good agreement with the haploid chromosome number of 23 usually reported for Atlantic cod (Fan et al., 1991). A small number of SNPs that failed to be assigned to these 23 linkage groups, as well as a few additional linkage groups generated by JoinMap®4 containing 2-3 loci, were not incorporated in further analyses. Marker content of linkage groups, and marker order within those groups, was in good agreement when the maps for the two families were compared. Therefore, the family maps were combined to generate a consensus map using the merge function of JoinMap®4. The consensus map produced is shown in FIG. 5, and contains 924 loci on 23 linkage groups, ranging from to 41 to 79.5 cM in length, and a total map length of 1421.92 cM. The number of markers per linkage group ranges from 23 to 58, with an average of 40.2.

Discussion

The present description provides a large collection of SNP markers suitable for the genetic analysis of cod. After screening 13448 contigs generated from 97976 ESTs, 4753 SNPs were identified using the criteria of 4 reads minimum and a MAF>25%. Assays have been developed for 3072 SNPs using 465 fish, which were genotyped using a GoldenGate assay. The success rate for this set of SNP assays was 75%. The SNPs were assessed for polymorphism by testing against Canadian and European populations and it was determined that 26% of SNPs were monomorphic. Table 6 lists the 3072 SNPs for which assays were developed, and also identifies the 1620 SNPs that were validated according to the present Example. However, on analysis, a small number of the SNPs were found to be identical to SNPs identified independently in a previous study (Moen et al., 2008). The SNPs of the present disclosure that overlap with those described by Moen et al. are listed in Table 13.

The frequency of the present set of selected SNPs in Atlantic cod is 1/516 bp, which is similar to the frequency reported in Atlantic salmon of 1/614 bp (Hayes et al., 2007). It is somewhat lower than the frequency observed in *Oncorhynchus keta* (chum salmon; 1/175 bp) or in *Oncorhynchus tshawytscha* (Chinook salmon; 1/301 bp) (Smith et al., 2005). SNP selection strategy is likely to play a large role in the observed frequency of SNPs within the genome, but it also might reflect the fact than in case of Atlantic cod and Atlantic salmon SNPs have been detected in fish originating from a limited number of populations.

To maximize the detection of real SNPs, stringent criteria were used to reduce the likelihood of selection of false or rare SNPs. It was postulated that selecting SNPs having the minor allele represented in at least two reads will generate a set of markers that are useful for gene mapping and parental assignment. However, the present SNP set has been selected based on SNPs that are expected to be frequent within populations being used for selective breeding in Atlantic Canada and in related populations located in the area surrounding Atlantic Canada. Therefore, this set of SNPs is likely to be less useful for the estimation of genetic variation in populations with different geographical distribution, such as populations originating in North-East Atlantic The present SNP collection likely contains few rare SNPs because of the selection criteria employed. These rare alleles can be useful for the analysis of certain populations since they may prove to be specific to, and thus diagnostic for, these populations. The fact that 184 SNPs were found that are polymorphic in Canadian populations but monomorphic in North-East Atlantic populations is a clear indication that, due to the ascertainment bias intrinsic within the selection procedure, the present collection of SNPs might be regarded as less useful resource for characterizing the genetic structure of European populations.

The ratio of transition (A/G, C/T) to transversion (interchange of purine for pyrimidine bases) substitutions among validated SNPs was 1.11:1. This is lower than the values obtained in Atlantic salmon, (1.37:1) (Hayes et al., 2007) and for *O. tshawystsha* (1.49:1) (Smith et al., 2005). These values are both slightly higher than that reported for zebrafish of 1.20:1 (Stickney et al., 2002). It was also observed that the ratio is slightly different between predicted SNPs and validated SNPs, which are 1.18:1 and 1.11:1 respectively, showing that the success rate of validation for transition substitutions is marginally lower.

The SNPs developed in the present study add significantly to the total number of validated SNPs for Atlantic cod. In a previous study, Moen and colleagues identified and validated 318 SNPs (Moen et al., 2008), however only 7 SNPs were common between the two studies and these have been listed previously in this section. The SNPs described in both analyses have been detected from EST assemblies and thus are associated with transcripts. One third of the SNPs were detected on annotated sequences in the present analysis as the ESTs on which they were detected have a high proportion of non-coding sequence, whereas in the Norwegian study 87% of the SNPs had a significant BLAST hit. Validation success was similar in both studies, with the percentage of failed assays at 29% for Moen et al. (Moen et al., 2008) and 25% for the present study. The number of polymorphic SNPs as a percentage of all putative SNPs tested was found to be 54% by Moen et al. (Moen et al., 2008) and 55% in the present study (53% for validated SNPs). The number of monomorphic loci was slightly higher in the present study than found by Moen et al. (Moen et al., 2008). The majority (91%) of predicted SNPs that were found to be monomorphic in the present study have their minor allele represented by 2 reads only. These likely fall into two categories; 1) SNPs that are rare within the populations tested, and therefore polymorphism at these loci exists but was not observed in the sample set tested, and 2) incorrect SNP predictions. This emphasizes the need for stringent selection criteria and also that validation of SNPs is a necessary step to establish the accuracy of markers.

The libraries from which the sequences used in the assembly were generated, and thus from which SNPs were identified, were created using tissue from fish originating from collections from Nova Scotia (Cape Sable) and Newfoundland (Bay Bulls), Canada. By testing these SNPs against more eastern populations such as Ireland, Iceland and Norway, we have shown that they are also informative as markers across more geographic distant populations. Some SNPs (184) were found to be polymorphic only in all Canadian populations, and therefore have the potential for use as traceability markers.

By genotyping, two reference families, SNP were checked for Mendelian segregation. A numbers of SNPs showed a significant departure from Mendelian segregation but in fact they were more likely paralogous genes coding for 2 SNPs since both parents and progeny were heterozygous. This is not uncommon when identifying SNPs in fish. In most studies around 2-4% of validated SNPs are assumed to be duplicated SNPs (Moen et al., 2008) except for salmon where 14% of SNPs were scored as heterozygotes in all individuals tested (Hayes et al., 2007). However, in addition to the set of SNPs predicted to occur on duplicated genome segments, several additional SNPs show non-Mendelian segregation patterns in the two families tested. Also, four SNP, two in family B33 and two in B87 appear to be duplicates in that family, but segregate in the other family, which could be indicative of either selective forces acting differently upon those families or, more likely, complex patterns of gene duplication and divergence.

Most of the SNPs described herein are predicted to fall within non-coding sequence. This is expected in the present dataset as all of the ESTs used in SNP identification were sequenced from the 3' direction, and thus the majority of each sequence is likely to represent the 3' untranslated region. Nevertheless, a minority of the SNPs identified herein are predicted to occur in coding regions. The remaining SNPs are either in non-coding sequence, or on contigs with no significant sequence similarity. For the SNPs found in coding regions, only a subset of the polymorphism, i.e., the non-synonymous substitutions will result in a variation in the amino acid sequence of the encoded protein. SNP studies have reported a higher number of synonymous SNPs (sSNPs) when compared to non-synonymous SNPs (nsSNPs); the variation at non-synonymous sites has the potential to be associated with deleterious mutations. A higher number of sSNPs is usually observed, and this is likely to be the result of evolutionary constraints preferentially eliminating variation at non-synonymous sites. For example, 80% of SNPs identified in coding regions in chicken (Kim et al., 2003) are synonymous compared to 71% for *Schistosoma mansoni* (Simoes et al., 2007), 68% for *Anopheles funestus* (Wondji et al., 2007), 60% for zebrafish (Guryev et al., 2006), and 55% for rat (Guryev et al., 2004). An even higher frequency of sSNPs has been detected in *Salmo salar* (82%). The frequency of sSNP observed in Atlantic cod is intermediate (64%) to that reported for other species.

A preliminary linkage map has been constructed using the SNPs presented herein. This map has been generated using the cross-pollination (CP) parameter set of JoinMap4® (Van Ooijen, 2006), which is applicable to crosses generated from wild individuals taken from an outbred population, and has also been used to generate maps from a small number of crosses in other species (Spigler et al., 2008; Tani et al., 2003). Independent maps were created from the two families B33 and B87, which gave the same number of major linkage groups (23) and a similar overall marker order. Maps generated from these two families were merged to give the consensus map shown in FIG. 5. Preliminary analysis of additional families on a second-generation SNP panel gives additional support to this consensus map. The second generation map shown in Table 10 has been constructed using three families and comprises 23 linkage groups with 1298 mapped markers.

It is possible to generate separate male and female maps for most of the genome of Atlantic cod using the two families genotyped on the two SNP panels described here. The majority of the linkage groups in the consensus map could be identified in sex-specific maps, however these maps are less dense and, due to their bi-allelic nature, only a few informative SNPs are common between maps created with a single individual, making the merging of maps problematic. However, although there appears to be a significant difference in the recombination rates between male and female Atlantic cod (Moen et al., 2009), this has not prevented construction of an integrated map both here and in the previous study (Moen et al., 2009).

The large collection of SNPs described herein for Atlantic cod are of great utility for both the aquaculture industry, and for the management of wild fisheries. As improved automated genotyping systems have been developed, SNPs have become important markers for commercial diagnostics and parental genotyping applications. Due to lower individual information content, a higher number of SNPs is required for parental assignment (Werner et al., 2004) when compared to the microsatellite marker approach that is the current industry standard. In pigs, comparable parental exclusion probabilities have been achieved when using a panel of 60 SNPs or a 10 microsatellite marker panel, but the SNP panel was more sensitive for individual identification (Rohrer et al., 2007). In cattle, panels of 32 and 37 highly informative SNPs were powerful enough to distinguish progeny from multibreed composite populations (Werner et al., 2004; Heaton et al., 2002). In order to develop a powerful SNP panel for cod parental assignment, SNPs must have a high minor allele frequency within the population under study (Werner et al., 2004), and it is also useful if information of linkage between the marker set chosen is available. In total, 332 SNPs markers described herein have a minor allele frequency higher than 0.4 (FIG. 4). This SNP panel may also be used in product traceability applications. It is also possible to apply this large marker set to increase the resolution of population structuring within wild populations of Atlantic cod, and to better monitor the genetic diversity within populations that are being actively fished.

The SNP collection presented here is useful for the genetic analysis of cod fish which may lead to the association of features showing interesting transcriptional responses with QTL intervals, potentially providing useful tools for marker assisted selection. For example, cgpGmo-S1123 is located in the sequence coding for 3-oxo-5-beta-steroid 4-dehydrogenase (AKR1D1). This gene belongs to the Aldo-keto reductase family 1, member D1 and catalyzes the reduction of progesterone, androstenedione, 17-alpha-hydroxyprogesterone and testosterone to 5-beta-reduced metabolites, as well as playing a role in bile acid biosynthesis (Palermo et al., 2008). This gene is of great interest for its role in sexual maturation, and this SNP can be used for marker assisted selection of selected variants.

The SNPs described here have been derived from ESTs, and thus can provide anchor points for more extensive comparative genomic analyses.

The present description provides an extensive resource of SNP markers for Atlantic cod, *Gadus morhua*. The SNPs have been validated across a panel comprising several populations of wild cod, and using two family crosses. This large collection of SNPs is valuable for developing diagnostic assays to distinguish between cod populations, as well as producing tools useful for the aquaculture industry. The genetic linkage map provided is also a valuable resource for QTL discovery and marker assisted selection.

Example 3

Development of a SNP Marker Panel for use in Parentage Analysis of Atlantic Cod (*Gadus morhua*)

Introduction

Single nucleotide polymorphism (SNP) markers have great potential for accelerating studies in the analysis of aquatic species with commercial value. Here, we describe a SNP panel for use in parentage assignment of communally reared Atlantic cod (*Gadus morhua*). SNPs were initially selected from a larger set based on their high minor allele frequency in fish collected from multiple diverse geographic locations throughout the North Atlantic. The 145 SNPs in this initial set were tested to determine their ability to correctly assign parents to progeny from two cod families for which genotyping data was available. SNPs that ranked highly in initial analysis were further tested to determine their performance in assigning parents to a large set of simulated progeny. A medium throughput assay was developed for 48 SNPs, and this SNP panel was analyzed experimentally for its ability to assign parents to a set of communally grown progeny. These progeny had been pre-assigned to parents using a set of six microsatellite markers as part of a more extensive program in selective breeding. The 48 SNP panel performed well on testing, assigning all progeny correctly. However, a panel comprising 30 SNPs, selected from the original 48 on the basis of performance and predicted informativeness, showed the best overall performance, assigning all progeny correctly while allowing for fewer genotyping errors. Panels comprising 24 SNPs or fewer showed deteriorating performance, generating increasing numbers of ambiguous or incorrect assignments. The SNP panel described here is suitable for aquaculture and food traceability applications, and could be improved further with the inclusion of additional SNPs on linkage groups not represented in the current panel.

Molecular traceability tools for economically important aquaculture species, such as Atlantic cod (*Gadus morhua*), can be used both to accelerate the development of elite broodstock suitable for commercial production and to efficiently manage aquaculture stocks. Detection of the parental genetic contribution to successful broodstock can be particularly challenging, since land-based aquaculture production of cod progeny frequently involves mass spawning of numerous parental fish in multiple large breeding tanks (Herlin, et al., 2007), but is essential within a family-based selective breeding program. The alternative to this approach involves growing the progeny of known crosses in individual tanks until they achieve a sufficient size to allow the surgical implantation of a passive integrated transponder tag, before pooling into a large communal tank (Symonds, et al., 2007). The additional infrastructure and fish husbandry costs associated with this alternative approach can be prohibitive.

Although SNP markers have been developed for Atlantic cod (Moen, et al., 2008), a panel of microsatellites (Delghandi, et al., 2003) is still being used for applications such as relatedness testing and parental assignment that are now routinely used in breeding program management. The present Example describes a subset of SNPs from the larger collection of SNPs described in Examples 1 and 2 to develop a marker panel suitable for use in the parental assignment of Atlantic cod.

Materials and Methods

Generation and Maintenance of Atlantic Cod Families

Atlantic cod from the collections used to generate four different year classes from the CGP breeding program (New Brunswick Year Class 1 (NB YC1), New Brunswick Year Class 2 (NB YC2), Newfoundland Year Class 2 (NL YC2) and Newfoundland Year Class 3 (NL YC3) were used in this study, and have been previously described by Bowman et al. (2007). Wild fish to initiate the CGP selective breeding program were collected from Cape Sable, Nova Scotia (NB YC1), Georges Bank and Cape Sable (NB YC2), Bay Bulls, NL (NL YC2) and Smith Sound (NL YC3). Fish were collected in excess of those used as parents in the breeding programs; these are referred to as non-parents, but originate from the same collections as the fish used as parents in those year classes. Fin clips were taken from all wild-caught fish prior to mating. F1 progeny fish for NB YC1 were generated by hand stripping or paired mating of wild-caught adult fish. Progeny fish from NB YC1 were pooled at the larval stage and grown in communal tanks at the St. Andrews Biological Station before transfer to sea cages. A harvest assessment of 2000 progeny from NB YC1 was carried out in fall 2008, at which time fin clip samples were taken for DNA extraction.

DNA Extraction

Briefly, for SNP genotyping (both for Illumina Golden Gate and KBiosciences KASPar assays) fin clip samples were stored in 95% ethanol at room temperature until DNA was extracted using a QIAGEN DNeasy 96 extraction kit (Bowman, et al., 2007) according to the manufacturers instructions. With respect to MS genotyping, fin clip DNA extraction from NB YC1 parents and 2000 NB YC1 progeny was performed by the Research and Productivity Council, Fredericton, New Brunswick, Canada and formed part of a more extensive harvest assessment exercise.

Selection of SNPs for Parental Assignment Testing

Figure 6:
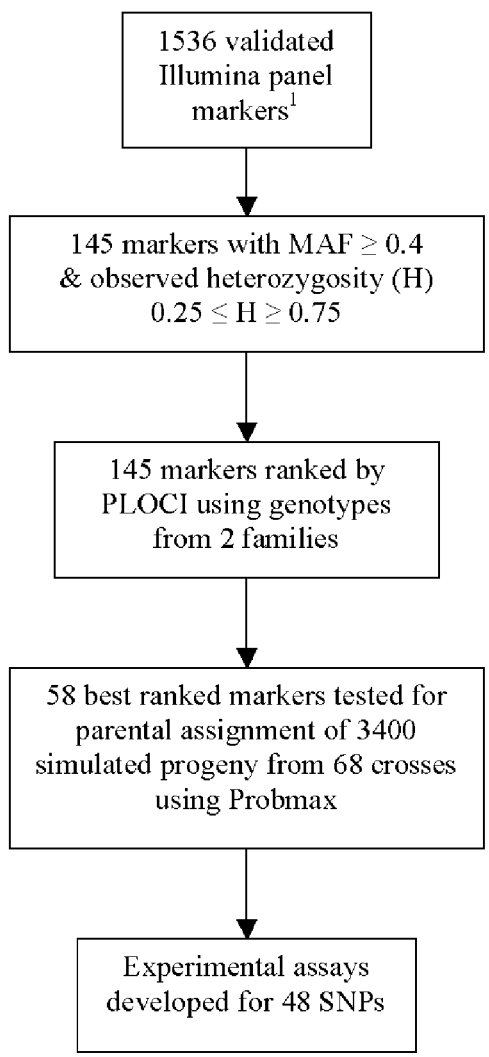
FIG. 6 provides a schematic showing the selection process for SNPs for the parentage panel as described in Example 3.

A set of SNPs suitable for parental assignment was selected from a larger panel of 1536 SNPs were developed and validated using the Illumina GoldenGate Assay as described in Examples 1 and 2. The selection criteria that were used included SNPs having a minor allele frequency (MAF) ≥0.4 (Table 14) and an observed heterozygosity value between 0.25 and 0.75. The initial set of selected SNP markers were ranked using P-LOCI, a parental assignment loci choice software program (Matson, et al., 2008), using genotyping data from the GoldenGate platform for 2 families of NB YC1 (2 parents and 91 progeny), with the genotypes for an additional 64 non-parent fish taken from the four different cod year classes used to populate the cross matrix for assignment. A schematic view of the selection process is shown in FIG. 6. Efforts were made to include SNPs that were located on different linkage groups, or that were not closely linked within groups, although only a preliminary genetic linkage map was available at the time when SNPs were chosen for assay development. Some properties of the 48 SNPs chosen for experimental testing are shown in Table 14.

Generation of Simulated Crosses

Figure 7:
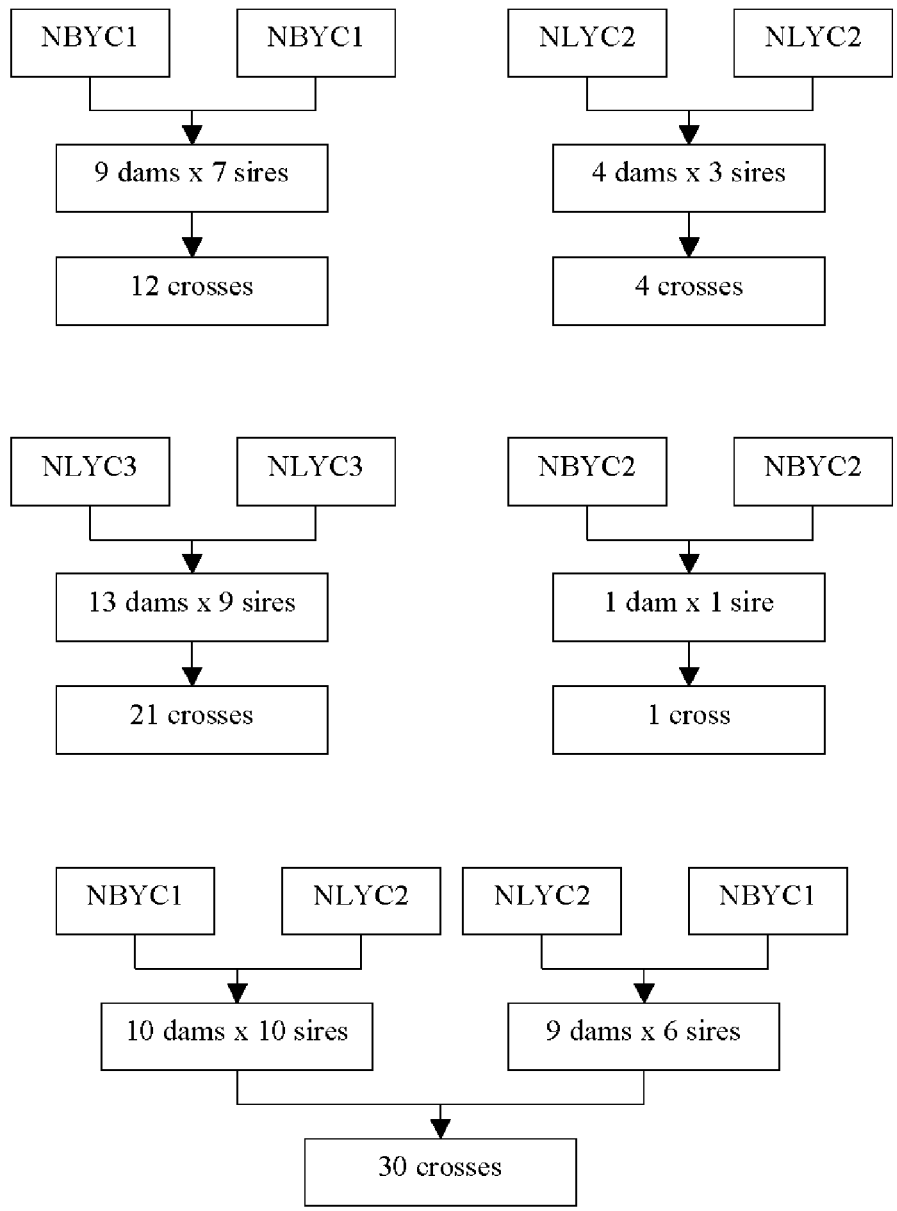
FIG. 7 shows crosses used to generate simulated progeny for in silico parental assignment testing of selected SNPs as described in Example 3. PLOCI was used to randomly generate a set of crosses using genotyping data for 58 SNPs generated from a population study of fish from collections used to generate NB YC1, NB YC2, NL YC2 and NL YC3 families. Fifty simulated progeny were generated per cross.

P-LOCI was used to simulate 3400 progeny genotypes from 4 different year classes (NB YC1, NB YC2, NL YC2 and NL YC3). Genotypes from the same fish used for SNP selection were used to generate simulated crosses. Crosses (68) with 50 progeny per cross were generated (FIG. 7). These crosses were chosen at random for 62 fish for which genotyping data was available from the Illumina GoldenGate platform, with the following two exceptions: a) progeny were generated for two crosses which had been produced experimentally during the course of family generation from NBYC1 (NB2×NB13 and NB291×NB265) and b) one simulated cross was selected to allow testing of parental assignment of a mating between two different regional populations of fish (NBYC2×NLYC2).

Microsatellite Genotyping

A multiplex of six microsatellites was used, which included Gmo8, Gmo19, Gmo37 (Miller, et al., 2000), Tch5, Tch11 (O'Reilly, et al., 2000) and PGmo38 (Jakobsdottir, et al., 2006). Genomic DNA was prepared from finclips using the Wizard SV 96 genomic DNA purification kit (Promega) according to manufacturers instructions. Microsatellite sequences were amplified from individual DNA preps using PCR, with final primer concentrations of 0.05 µM for PGmo38, 0.1 µM for Gmo8, Gmo19 and Tch11, 0.2 µM for Tch5 and 0.4 µM for Gmo37. Cycling conditions were as follows; an initial denaturation step of 95° C. for 15 mins, 35 cycles of 94° C. for 30 s, 55° C. for 90 s and 72° C. for 60 s, with a final elongation step at 60° C. for 30 min. Amplicons were analyzed following electrophoresis using a ABI Prism® 3100 Genetic Analyzer (Applied Biosystems) and alleles were identified after comparison to internal fluorescent size standards (Genescan 500LIZ, Applied Biosystems). Microsatellite genotyping was performed at the Research and Productivity Council, Fredericton, New Brunswick, Canada.

SNP Genotyping of Selected Markers Using KASPar Genotyping Assays

For experimental testing of the parental assignment panel, genomic DNA samples were genotyped using KBiosciences' KASPar homogenous fluorescent endpoint SNP genotyping system. SNP genotyping primers were designed using KBiosciences Primer Picker software. Briefly, DNA (25 ng) was genotyped in the following 8 ml reaction: 0.165 mM allele specific primer 1, 0.165 mM allele specific primer 2, 0.330 mM common reverse primer and 1.5-2.2 mM $MgCl_2$. The samples were thermally cycled on an Applied Biosystems 9600 GeneAmp PCR System in 384 well reaction plates under the following conditions: 94° C. for 15 minutes followed by 20 cycles of 94° C. for 10 seconds, 57-60° C. for 5 seconds, 72° C. for 10 seconds, followed by an additional 18 cycles of 94° C. for 10 seconds, 57° C. for 20 seconds, 72° C. for 40 seconds. The plate was allowed to cool to room temperature before being read using the StepOne System fluorescent plate reader (Applied Biosystems). Genotypes were automatically called and clustered using the StepOne with the Autocaller software provided (Applied Biosystems).

Parental Assignment of Progeny

Parental assignment for both simulated and real progeny was carried out using the exclusion-based parentage assignment program Probmax (Danzmann, 1997). Genotype data from the Illumina GoldenGate Assay for selected SNP markers was used to assign 91 progeny from each of 2 families of NB YC1 cod. Probmax was also used in the assignment of simulated progeny, with tests run allowing 0, 1, 2, 3, 4 and 5 genotyping errors per cross. The maximum number of mismatch alleles was set to 0, 1 or 2 when testing the experimental panel of SNPs. Parentage was determined using ProbMax which calculates the maximum probability of progeny assignments to a mixture of possible contributing parents using genotype data from parents and progeny at several loci (Danzmann 1997). ProbMax can also be used to identify siblings in that sibling fish will have the same parent set identified. Other methods known in the art for determining relatedness or parentage based on genotype data may also be used with the SNPs identified herein.

Results

Selection of SNPs for Parental Assignment

A set of 1536 validated polymorphic SNPs were analyzed to determine their observed heterozygosity values and minor allele frequencies for a set of samples collected from multiple locations across the North Atlantic. These SNPs had originally been selected from a larger set for inclusion on an Illumina GoldenGate panel that was designed for use in QTL analysis as described in Example 2. In total, 145 SNPs had both a MAF of ≥0.4 and an observed heterozygosity falling between 0.25 and 0.75 (FIG. 6). These SNPs were selected for further analysis.

Initially, the genotype data for these 145 SNPs from two families of NB YC1 cod were used to rank the parental assignment value of SNP markers by P-LOCI, with 2 parents and 91 progeny analyzed for each cross. The 58 highest ranked SNPs having parental assignment values of 25% or greater were subjected to additional testing using simulated crosses prior to experimental assay development.

Validation of SNP Panel Using P-LOCI Simulated Progeny and KASPar Genotyping Assays P-LOCI was used to simulate the genotype data for 50 progeny fish generated from each of 68 crosses (FIG. 7). The 62 fish used as virtual parents in the simulated crosses had been genotyped for the 58 selected SNPs using the Illumina GoldenGate assay, and originated from populations that had been used in multiple year classes from each of the two breeding programs, including NB YC1, NB YC2, NL YC2 and NL YC3 and four parent fish from NB YC1 (FIG. 7). Simulated crosses included same year class/same breeding program, same year class/different breeding program, and different year class/different breeding program. These crosses also included many half-sib crosses, where the same dam or sire had been crossed with different individuals, to mimic the cross structure used by the breeding programs.

Progeny simulated for 2 NB YC1 families (13×1002 and 291×1265) are real broodstock crosses used in the CGP breeding programs, but progeny genotype data was simulated in PLOCI for this parental assignment exercise. Probmax was used to assign parentage to 3400 simulated progeny genotypes in several rounds of analysis, allowing 0, 1, 2, 3, 4 or 5 genotyping errors, and tested how many markers were necessary for correct parental assignment. These tests showed that 48 markers correctly assigned 99.99% of simulated progeny after allowing for 1 genotyping error.

Comparison of Selected SNPs with Microsatellite Markers for Parental Assignment

As part of selective breeding programs, a set of progeny fish from different families were mixed prior to tagging, and had been grown to harvest weight in a common environment. These fish were assigned to families using a panel of six microsatellite markers in order to develop an experimental SNP panel using the markers tested in silico and to use this for parental assignment of cod progeny using an experimental design that approximated a commercial breeding setting. Individual SNP assays were developed for 48 of the selected SNPs using the KASPar SNP genotyping chemistry. Using the 48 SNP assays, 42 NB YC1 parental DNA samples, and also 93 NB YC1 cod progeny that had previously been genotyped and assigned to parents using the MS marker set were genotyped. Data from SNP genotyping was used to assess the parental assignment properties of the selected SNP panel.

Progeny were chosen for analysis that assigned to parents with no mismatches using the multiplex of six microsatellite markers. The microsatellite-assigned parents were considered to be the correct parents for the purpose of this study. SNP genotypes were generated for the 93 cod progeny and Probmax was used to assign parents allowing zero, one, two and three genotyping mismatches, at which point all progeny were assigned. In all cases, the parents identified were identical to those identified using the microsatellite study. Fifty progeny (53.8%) assigned with no mismatches, with a further 31 (33.3%), 10 (10.7%) and 2 (2.2%) assigning with one, two and three mismatches respectively. In total, 57 out of 4416 genotypes (1.3%) were considered to be inconsistent between parent and progeny pairs (Table 15).

Of the SNPs generating errors, 23 (40.4%) arise from a single SNP, S1001 (Table 15). When examining the cluster plot from this SNP using the KASPar assay, one allele appears over-represented. After analysis of the data generated by the Illumina GoldenGate platform, this SNP scored as having a high minor allele frequency (0.49). However, primers used for the KASPar assay are not necessarily identical to those used by the GoldenGate assay, i.e. they may be of different length and therefore could have different properties. It is most likely that the KASPar assay failed to amplify one of the two alleles for S1001, resulting in the high incidence of genotyping miscalls seen for this SNP. When examining the incidence of SNP failures with respect to family, three families (B21, B23 and B24) dominate, harboring 10 (17.5%), 9 (15.8%) and 6 (10.5%) of the problem genotypes (Table 16). Two individuals contributing to these families, M1330 (sire for B21 and B24) and F182 (dam for B21 and B24) are associated with 28% and 26.3% of the miscalled SNPs respectively (Table 16).

Linkage Analysis

As set out in Example 2, a genetic linkage map has been generated for Atlantic cod. This map was created using the two NB YC1 families described earlier, and has 23 major linkage groups, with 924 mapped SNPs. The current version of the map contains 1298 SNPs. It was thus possible to locate the majority of the SNPs chosen for inclusion in this analysis, and to identify SNPs that are closely linked (Table 14). In total, SNPs from the final set used for experimental parental assignment were mapped to 18 of the 23 linkage groups. It was not possible to locate six SNPs on the current linkage map; S1168, S1440, S1498, S1593, S1606 and S1631. In addition, five linkage groups, CGP 1, 7, 13, 21 and 23 do not contain a mapped SNP that is part of the current panel. The number of SNPs per linkage group ranges from one (CGP 3, 6, 10, 14, 15, 16, 18, 20 and 22) to six (CGP 19).

Tests Using a Smaller SNP Set for Parental Assignment

The cost-effectiveness of a SNP panel is dependant on the number of SNPs required. To determine the minimum number of SNPs necessary for correct, unambiguous parental assignment we removed SNPs sequentially from the set, and used Probmax to test the smaller SNP panel for its ability to correctly assign progeny. SNPs were removed selectively from the original panel, starting with the SNPs that had generated inconsistent genotyping results, followed by SNPs that were closely linked to other SNPs included in the panel. Due to the removal of SNPs that were responsible for genotyping errors, the stringency of the assignment criteria could be increased, with the number of mismatches necessary to allow assignment of parents to all progeny reduced from three for the 48 SNP panel, to two for a 36 SNP panel and one for 30, 24, 20 and 16 SNP panels. A 30 SNP panel proved to be the best performing SNP set, with all progeny correctly and unambiguously assigned, allowing for one genotyping mismatch (Table 17). However, using SNP panels of 24 SNPs and below resulted in a progressive increase in ambiguous and incorrect assignments. The smallest panel tested comprised 16 SNPs, achieving 79 correct, 12 multiple and two incorrect family assignments (Table 17).

Discussion

The present Example identifies a set of SNPs that are highly polymorphic in the populations of Atlantic cod that had been used to set up breeding programs based in NB and NL. A set of 145 SNPs with high MAF and high (but not extreme) levels of heterozygosity (between 0.4-0.5 and 0.25-0.75 respectively) were selected for further analysis. These SNPs were ranked using two families for which genotyping data was available, and the top 58 SNPs tested using a larger set of families that were simulated using genotyping data (FIG. 6). During this testing, a panel of 48 SNPs was sufficient to correctly assign 100% of the 3400 simulated progeny.

Experimental assays for 48 selected SNPs (Table 14) using KASPar chemistry were developed and used to genotype a set of parents and progeny that had been generated experimentally as part of the NB-based program in selective breeding. KASPar SNP genotyping cannot be highly multiplexed, but is very flexible, relatively inexpensive, and can be used in low, medium and high throughput applications. However, the choice of chemistry means that the multiplexing capabilities of this panel have only been assessed as part of the larger GoldenGate panel.

This 48 SNP panel was successful in unambiguously assigning all progeny to their correct parents. However, a few of the selected SNPs showed a relatively high number of errors, including one problem SNP (S1001) where allele drop out appeared to occur i.e. a single allele was over-represented in the KASPar dataset (Table 15). This SNP originally tested as having a high minor allele frequency using the GoldenGate assay (Table 14), indicating that assay transferability between SNP genotyping platforms is not always successful. Three parents contributing to two families also had a high incidence of SNP miscalling (Table 16). It was necessary to relax the criteria for parental assignment to allow for these sporadic genotyping failures; however all tested progeny assigned unambiguously to their correct parents after allowing for three genotyping failures per assignment (Table 17).

It was possible to position 42 of the SNPs on the genetic linkage map for Atlantic cod. To maximize the informativeness of the SNP panel, it is necessary to select SNPs that are not closely linked. Ideally each SNP would segregate independently, i.e. each SNP would be located on a unique linkage group. However, this would limit the number of useable SNPs to 23 for Atlantic cod, the haploid chromosome number in this species. Therefore, it is necessary to include SNPs that map to the same linkage group, but are not closely linked, as assessed from their location on that group in centimorgans (Cm). Several SNPs in our set of 48 mapped to the same linkage group, with CGP 19 harboring six SNPs (Table 14). Also, five linkage groups were not represented on the current SNP panel (Table 14). Therefore, straightforward measures to improve the current panel include removing SNPs which are closely linked to others, whilst selecting additional SNPs from the original set of 145 highly variable SNPs for inclusion that are located on new linkage groups.

The set of SNPs was tested to determine the minimum number required for parental assignment using data generated experimentally. SNPs were removed sequentially from the set of 48, with the SNPs removed from the set either having a higher incidence of genotyping failure or being located close to others on the same linkage group. A set of 30 SNPs was found to show the best overall performance, assigning all parents correctly and unambiguously (Table 17). It was also possible to use more stringent assignment criteria for this set of SNPs, i.e. allowing for only one genotyping mismatch, as most of the SNPs responsible for genotyping errors had been removed from the set. Panels of 24 SNPs or less were not sufficient to correctly assign all parents (Table 17). The addition of SNPs from linkage groups that were not included in this set may make it possible to further reduce the number of SNPs required for assignment, and thus reduce the cost of the panel.

This first generation SNP panel has identified a set of experimentally robust SNPs, which have been validated in genotyping assays using two chemistries. These SNPs are compatible in a multiplex using GoldenGate technology; KASPar chemistry does not support a high level of multiplexing. This SNP set has the capacity to assign a large number of simulated progeny in an extensive cross structure, and its ability to correctly assign parents to progeny in a smaller number of crosses has been tested experimentally. This panel can discriminate between half-sib crosses, where the same sire has been used with different dams, or vice versa. The present SNP parentage panel can be used in breeding programs for different populations, as many of the SNPs identified as part of the CGP have proved to be highly variable in multiple European populations.

The SNP panel described here is suitable for use in family assignment of communally reared fish, to determine parental contribution n mass spawning, or for genetic analysis as part of a selective breeding program. It would be straightforward to enhance the power of this panel by adding SNPs that are present on the linkage groups not currently represented.

Example 4

SNPs Associated with Resistance to Nodavirus in Atlantic Cod

Introduction

Nodavirus has been identified as a potential disease risk associated with the development of cod aquaculture and one of the greatest threats in this development (Bricknell et al. 2006). Worldwide, this disease has been reported to cause high mortalities in more than 20 marine fish species and with the same viral strains causing disease across species. Nodavirus is referred to as VER (viral encephalopathy and retinopathy) or VNN (viral nervous necrosis as the disease targets the neural tissues and retina. This importance has led Norwegian researchers to identify this disease as one of interest for further research in their cod breeding program (Odegard et al. 2010). Nodavirus can result in high mortalities in juvenile fish and to a lesser extent in adult fish.

Material and Methods

Broodstock

Wild Atlantic cod were obtained from three sites off North America in late 2006 for ambient spawning in 2007. Broodstock were caught off Georges Bank (Northwest Atlantic Fisheries Organization division 5Z) and Cape Sable, Nova Scotia (NAFO Division 4x). Cod broodstock were transported to the Department of Fisheries and Oceans, St. Andrews Biological Station, Canada (SABS). A third site was located off New Hampshire (NAFO division 5Y) and cod broodstock were transported to Great Bay Aquaculture (GBA), New Hampshire, United States. All broodstock were maintained in tanks on a mixed ration of Atlantic mackerel (*Scomber scombrus*) and northern shortfin squid (*Illex illecebrosus*) with vitamin and mineral supplement twice weekly. Prior to spawning, broodstock were tagged with Passive Integrated Transponders (PIT, Sokymat, Switzerland) and fin clip tissue was collected.

Progeny Production and Sampling

Broodstock handling and fertilization of eggs followed that described in Garber et al. (2009). From 12 Jan. 2007 to 15 Feb. 2007, 40 crosses were generated from 27 female and 24 male broodstock (full and half sibling families, 33 at SABS and 7 at GBA). Thirty-three of the 40 crosses were produced and maintained at SABS. Seven of the 40 crosses were produced at GBA and shipped to SABS 6-10 days post fertilization at which time eggs were stocked in incubators at SABS. Progeny from each cross were stocked into individual 80 l incubators followed by stocking into individual 500 l larval tanks—one family per rearing unit.

The number of fish in each tank was standardized to a constant quantity twice to reduce tank 'density' effects caused by variable numbers of progeny per family tank. The initial standardization occurred at ~123 days post fertilization and all family numbers were decreased to 1500 fish per tank. During the second standardization from 1500 to 450 fish per tank at ~176 days post fertilization, 50 fish from each of 40 families were PIT tagged and stocked into two tanks. On 25 Oct. 2007 (~267 days post fertilization), fish were anaesthetized with 20 mg/l tricaine methane sulphonate (MS-222; Finquel®; Argent Laboratories, Redmond, Wash., USA), PIT tags were scanned, weights were recorded on each fish, fish were injected with 0.1 ml of nodavirus (titer $1\times10^{9.25} TCID_{50}$/ml) for a total challenge dose of $1\times10^{8.25} TCID_{50}$, and each fish was fin clipped prior to stocking into one of two tanks.

Tanks were checked twice daily for dead or moribund fish. Dead fish were removed from the tank, PIT tags were scanned, date recorded and weights or genders were recorded if fish were completely intact. Fish were considered moribund if they were floating toward the surface, flashing, spinning in circles and having an overall pink hue and/or with hemorrhaging in the tail, eye or brain areas and sometimes with exopthalmus of the eye. Moribund fish were removed, placed into a holding container, anaesthetized with MS-222, PIT tags were scanned, weight was recorded and blood was collected. Fish were then killed by pithing and tissue from brain, spleen and head kidney was collected for microarray analysis. Gender of each fish was also recorded at time of sampling.

Data was recorded on 1626 fish from 40 families as they became moribund or 70 days after the study was initiated when all remaining fish were terminated. Of the 1626 fish, 232 fish from 30 families were included in the QTL analysis. Families were selected for the QTL analysis based on their relatedness (half siblings) and susceptibility to nodavirus. Approximately 10 fish per family were selected (five of the most susceptible and five of the least susceptible individuals in each family).

DNA was isolated from fin clip tissue. A selective genotyping approach was used to maximize the probability of detecting QTL segregating in the population. The DNA isolation and genotyping process to identify SNPs were as described in Examples 1 and 2.

Quantitative Trait Loci Analysis

Of the 332 Noda challenged fish 185 died at a mean weight of 29.2 gm (9.7-71.3) were given a death status of 1. The balance of the fish alive at the end of the test period with a mean weight of 50.85(16-102.6) were given a death status of 0.

A generalized linear mixed model was fitted to test the association between death status and each individual SNP assuming a binomial distribution of errors (SAS 9.1, GLIMMIX macro). A covariate of death weight along with classification effects including family and gender with family fitted as random death status were also fitted. A linkage group-wise multiple test adjustment for Type I error rate (Benjamini and Hochberg, 1995) was used assuming each linkage group segregating independently and is therefore a unique experimental unit.

Results

As shown in Table 18, on linkage group 8 and 19 two SNPs were significantly associated with nodavirus and remaining significant with a false discovery rate<0.1. In addition, on linkage group 23 there were two SNPs significantly associated with nodavirus and remaining significant with a false discovery rate<0.1.

Example 5

Genetic Markers Associated With Growth in Atlantic Cod

Introduction

Many practical breeding situations exist in which trait-based selection index is inefficient or impractical, such as traits that cannot be scored on all individuals (carcass composition) or with low heritability (fertility traits and disease resistance). In these instances marker-based selection can create a significant gain (Weller, 2001). This Example provides SNP markers suitable for use in trait-based selection for growth in cod.

Materials and Methods

Fish

Progeny for this study were obtained from wild-caught founders from three eastern North American regions caught in 2005 for ambient spawning in 2006. All broodstock were maintained in tanks on a mixed ration of Atlantic mackerel (*Scomber scombrus*) and northern shortfin squid (*Illex illecebrosus*) with vitamin and mineral supplement twice weekly. Broodstock handling and fertilization of eggs followed that described in Garber et al. (2009). This study includes progeny from 19 families that were reared at the New Brunswick and New Hampshire facilities from 2006 to 2009.

Full-sib families were reared separately until the family reached an average weight of 15 grams, which occurred at an average of 220 days post fertilization (DPF). Families were then implanted with Passive Integrated Transponder (PIT) tags, used to mark and identify individual fish, and then moved to a single 1008 m³ sea cage in New Brunswick. Family performance related to growth, survival and overall health was recorded. Fish were harvested from the sea cages at an average of 990 DPF (s.d. 10.6) and 968 (s.d. 11.1) days post hatch (DPH).

Post-Mortem Measurements and Genotyping

Standard length (SL) was defined as the length from the tip of the upper jaw to the posterior end of the hypural plate. Weight (Wt) was taken on unconscious individuals. For bled weight (BledWt) the gills were slit and the fish were allowed to bleed out for approximately 4 hours before the carcass was weighed. Gutted weight (HOGWt) is the weight of an eviscerated carcass with the head attached. Gonad weight (GonadWt) and liver weight (LiverWt) are the weights of the respective organs. Skin on fillet (SOnWt) and skin off fillet (SOffWt) weights are the weight of a standard commercial fillet with the skin intact or removed, respectively, left and right fillets weighed together for a total weight of marker product per fish.

Atlantic Cod are a diploid species with 46 chromosomes (Johansen et al, 2009). A total of 1,298 single nucleotide polymorphisms (SNPs) were tested for association with a number of growth and carcass composition traits.

Fin clip tissue was taken at harvest in the processing facility. A selective genotyping approach was used to maximize the probability of detecting QTL segregating in the population. Individuals for genotyping for this study were selected based on Wt; the 10 heaviest and 10 lightest progeny for each family were chosen, regardless of fish gender.

Statistical Analyses

Growth traits were analysed using the Mixed procedure in SAS (SAS 9.1) fitted using linear model assuming a normal distribution of errors (SAS 9.1, mixed macro). Classification effects included sire, dam and gender with sire and dam effects fitted as random. A linkage group-wise adjustment for error rate was used assuming each linkage group (chromosome) was independent and that loci on different linkage groups segregated independently.

The model for Wt and BledWt is as follows:

$$Y_i = \mu + Sire + Dam + Gender + Gender \times GonadWt + GonadWt + e \quad [1]$$

Where Y is the Wt or BledWt phenotype of the animal i, sire, dam and gender are as described above, and e is the residual error. The model for HOGWt was [1] with the inclusion of SL as a covariate to account for the size of the fish. The model for SL was the same as [1] but included BledWt as a covariate to account for the weight of the fish. The possibility that maturity might have an impact was accounted for through the inclusion of the Gender by GonadWt interaction and GonadWt alone as a covariate.

The model for SOnFWt, SOffFWt and GonadWt was as follows:

$$Y_i = \mu + sire + dam + gender + BledWt + SL + DPH + e \quad [2]$$

Where Y is the phenotype of the animal i, sire, dam and gender are as described above, DPH is described above and e is the residual error. The model for LiverWt was the same as [2] but did not include DPH because it was not found to significantly affect LiverWt. Variables were identified as significant factors to include in the various models through backwards elimination at p<0.05.

Results

The eight growth and carcass composition traits were recorded for 351 fish, of which 159 were male and 192 were female.

On linkage group 7, there were 15 SNPs associated with Wt, 14 associated with BledWt, and 17 associated with HOGWt (Table 20). Seventeen of the 19 SNPs that were significantly associated with growth and carcass composition traits were found within a very tight region around 19.147cM into the linkage group. The Pearson product-moments correlations between Wt, BledWt and HOGWt were above 98% indicating that these traits were essentially equivalent. When the weight of the fish was accounted for, no SNPs were found to be associated with SL.

In addition to the large cluster of SNPs associated with the weight traits on Linkage Group 7, some associations were found in other linkage groups as shown in Table 21. Two SNPs were found to be significantly associated with each of SOnFWt, SOffFWt, GonadWt and LiverWt. Linkage group 23 had two SNPs with significant associations, one with LiverWt and one shared by SOnWt and SOffWt. Four other linkage groups (1, 18, 22 and 23) had significant SNP associations, two SNPs associated with GonadWt on linkage groups 18 and 22, one shared association with HOGwt and two SNPs associated with LiverWt on linkage groups 1 and 23. Table 21 identifies the preferred alleles associated with increased weight (SOnFWt, SOffFWt) as well as the preferred alleles associated with a reduction in weight (GonadWt and LiverWt).

The fillet traits had a Pearson product-moment correlation of 0.996 indicating that phenotypically they are the same trait. SOffWt and SOnWt respectively had a correlation of 0.284 and 0.300 with GonadWt and 0.875 and 0.882 for LiverWt. The fillet traits had correlations with BledWt, Wt, and HOGWt increasing from 0.943 to 0.974 respectively. LiverWt had a correlation of 0.425 with GonadWt, and ranged from 0.894 to 0.928 with GuttedWt, Wt and BledWt respectively. GonadWt had a correlation that ranged from 0.352 to 0.493 for GuttedWt, Wt and BledWt.

Discussion

Twelve out of 20 SNPs associated with the QTL on linkage group 7 were associated with all three measures of weight of the fish as they showed associations with Wt, BledWt and HOGWt. This is consistent with a QTL or region influencing overall growth as each measure of weight has a component of the overall weight of the fish. All of these SNPs with significant associations are located in a very tightly spaced region of linkage group 7 and therefore one would suspect that a single QTL with a large effect on growth is segregating in this region. In this circumstance, the single SNP that is most significantly associated with all three growth traits is probably sufficient to use for marker assisted selection for increased growth.

These associations will enable marker-assisted selection within Atlantic cod breeding programs, leading to rapid enhancement of cod broodstock.

Example 6

A Sex Determining Region in Atlantic Cod

Introduction

Vertebrates employ diverse mechanisms to produce progeny of different sex, including systems that can be environmental, genetic or both (Peichel et al 2004). Even when genetic gender determination is established, the precise mechanism by which this occurs can vary, since the genes or chromosomal systems involved can differ depending on the species. The XY system of sex determination, employed by humans and other mammals, involves cytogenetically distinct chromosomes that are so divergent in sequence that no genetic recombination occurs between the Y and X chromosomes. Other systems of sex determination include the WZ system common in avian species whereby females are the heterogametic sex, morphologically similar sex chromosomes, or the use of several genes on multiple autosomes. Atlantic cod are a diploid species with 46 chromosomes (Johansen et al, 2009). As with many fish species, there are no cytogenetically obvious sex chromosomes with Atlantic cod but beyond that, the mechanism of sex determination in cod is unknown.

Atlantic cod (*Gadus morhua*) inhabit benthopelagic environments in the North Atlantic Ocean where they contribute to the economy and cultural identity of people living in the coastal areas (Johansen et al, 2009). A high consumer demand coupled with a general decline in cod stocks has stimulated the development of cod aquaculture in several countries including Norway, the United States and Canada (Garber et al., 2009).

Materials and Methods

Fish

Broodstock for this experiment were wild-caught founder stock from three eastern North American regions. This study includes the progeny of 19 families that were part of the New Brunswick and New Hampshire stock reared at St. Andrews Biological Station, St. Andrews, New Brunswick, Canada in 2005/2006. All broodstock were maintained in tanks with ambient water temperature and photoperiod and fed a mixed ration of Atlantic mackerel (*Scomber scombrus*) and northern shortfin squid (*Illex illecebrosus*) with vitamin and mineral supplement twice weekly.

Full-sib families were reared separately until the family reached an average weight of 15 grams, which occurred at an average of 220 days post fertilization (DPF). Fish were then fitted with Passive Integrated Transponder (PIT) tags to identify individual fish, and moved to a single 1008 $m^3$ sea cage in New Brunswick coastal waters. Family performance related to growth, survival and overall health was recorded. Individuals for this study on gender determination were the same subset of the fish harvested for growth and carcass characteristic studies, as gender was being determined during carcass composition dissection. These fish were primarily selected based on the 10 largest and 10 smallest progeny for each family, regardless of fish gender at time of harvest which occurred an average of 990 DPF (std 10.6) and 968 (std 11.1) days post hatch (DPH). Gender balance in the subset was determined before further analysis to avoid a gender bias due to the primary interest in growth rate.

Gender Determination and Genotyping

Gender was confirmed at harvest by direct observation of the gonads during carcass dissection. Finclips were taken at harvest for genotyping. DNA extracted from these finclips was genotyped using an Illumina Golden Gate panel consisting of 1532 single nucleotide polymorphisms as described in Example 2. Groups of SNPs from individual linkage group were used for analysis, with each linkage group representing a separate experiment; these were extracted from a linkage map comprising 1298 mapped SNPs.

The generalized linear mixed model was fitted using straight association analysis assuming a binomial distribution of errors (SAS 9.1, GLIMMIX macro). Classification effects included sire, dam and gender with sire and dam fitted as random and gender fitted as the dependent variable. A chromosome-wise adjustment for error rate was used assuming each chromosome is segregating independently and is therefore a unique experimental unit.

Results

A total of 159 males and 192 females were genotyped. Twenty SNPs were found to be significant on linkage group 11 and one on linkage group 15 (Table 22). The SNPs with significant associations with gender on linkage group 11 were spread over a distance of 23.744 cM with 14 of those SNPs having a false discovery rate (FDR) adjusted p-value of less than 1%, indicating that linkage group 11 is a putative sex chromosome in Atlantic cod.

Some interesting patterns emerge when considering a few families and looking at one SNP at a time. In these cases, when the female is heterozygous and the male is homozygous at specific SNPs, the alleles from the female are relatively evenly distributed to both males and females. However, in the cases where the male is a heterozygote and the female is a homozygote, male alleles tend to be distributed with one going to the male progeny and the other going to the female progeny. These two cases were consistent with an XY system and the male being the heterogametic sex. There are a few SNPs that do not fit this overall pattern. With these SNPs, the patterns are mostly consistent with a dropout of one allele in particular lineages, which might again be consistent with cod Y chromosome losing genetic information on the way to becoming similar to the Y chromosome found in humans.

Example 7

SNPs Associated With Cortisol Responsiveness in Stressed Atlantic Cod

Introduction

The present Example identifies SNPs associated with a reduced a cortisol response in fish exposed to handling stress. Fish that exhibit reduced level of cortisol in response to stress are better suited to acquaculture.

Materials and Methods

Fish

All broodstock were maintained in tanks with ambient water temperature and photoperiod and fed on a mixed ration of Atlantic mackerel (*Scomber scombrus*) and northern shortfin squid (*Illex illecebrosus*) with vitamin and mineral supplement twice weekly.

Full-sib families were reared separately until the families reached an average mass of 15 grams, which occurred at an average of 220 days post-fertilization (DPF). Families were then implanted with Passive Integrated Transponder (PIT) tags to mark and identify individual fish.

Thirty fish from each of nine full-sib families were transported to the National Research Council of Canada—Marine Research Station in Ketch Harbor, NS. Fish were first acclimated for a month in 2 500-L flow-through sea-water tanks (at 10° C. with DO above 90%). After the initial acclimation period, the fish were sorted according to family ID into 9 different tanks (150-L flow-through sea-water tanks with the same conditions as the holding tanks. Briefly, after one month of acclimation to the family tanks, fish were lightly anesthetized in TMS (tricaine methanesulfonate; 100 mg/L) and had blood immediately sampled (~100 µl) from the caudal vein. Plasma was separated by centrifugation and stored at −80° C. until cortisol analysis of resting cortisol levels (RCortisol). Thereafter, fish were submitted to 5 stress events, these events separated by ~one month. For each event, fish were submitted to a 30 seconds net-stress (i.e. being exposed to air in a net for 30 seconds) and were allowed one hour to elicit the cortisol response under holding conditions. After this one-hour period had elapsed, blood was sampled and processed as before. Resulting plasma was used to assess post-stress plasma cortisol levels (MCortisol).

Plasma cortisol levels were quantified using an Enzyme-Linked Immunosorbent Assay (ELISA) (Neogen Corp., Lexington, Ky.) previously validated for cod. For this analysis, thirty µl of plasma were diluted in 270 µl of the provided EIA buffer, and quantification was performed in duplicate following the manufacturer's instructions.

Z-scores were calculated for the fish involved in the experiment using all 5 stress sampling points as $Z=(cortisol_{ind}-avg\_cortisol_{allind})/SD_{allind}$, where $cortisol_{ind}$ is the value for a given individual, $avg\_cortisol_{allind}$ is the average cortisol of all individual at a given sampling point and $SD_{allind}$ is the standard deviation of all individuals at a given sampling point. A given individual had 5 Z-scores, each representing its cortisol responsiveness at one sampling point. Total Z-score (Zt) was calculated as the sum of all Z-scores for a given individual. For genotyping fish with the 5 highest (i.e. consistent high cortisol response) and lowest (i.e. consistent low cortisol response) Zt within each family were selected.

Post-Mortem Measurements and Genotyping

A total of 1298 single nucleotide polymorphisms (SNPs) were tested for association with cortisol levels.

The difference (DCortisol) between the resting cortisol level (RCortisol) and the average of the 5 post-stress cortisol levels (MCortisol) was fitted using straight association analysis assuming a normal distribution of errors (SAS 9.1, mixed macro). Classification effects were Sire and Dam fitted as random. A chromosome wise adjustment for error rate was used assuming each chromosome is independent and a unique experiment unto itself.

The model for DCortisol=(MCortisol−Rcortisol) was:

$$Y_i = \mu + Sire + Dam + Zt + Weight + e$$

Where Y was the phenotype of animal i, Zt was the average Z score over 5 months (March-July), Weight was the average live weight over 5 months and e was the residual error.

Results

Cortisol levels and live weight were recorded for 90 fish as set out in Table 23. The SNPs identified in Table 24 are associated with fish with reduced cortisol levels in response to stress. High cortisol levels are associated with stress conditions in fish. Fish that are highly stressed that exhibit high levels or cortisol in response to stress exhibit reduced growth and reduced immune robustness.

Accordingly, marker-assisted selection of Atlantic cod with the preferred alleles listed in Table 24 allows for the selection of fish resistant to stress and enhancement of broodstock.

While the present disclosure has been described with reference to what are presently considered to be the preferred examples, it is to be understood that the application is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

SNP detection in manual (PTA) and automated (PolyPhred) pipelines [1]

| Contig name | NCBI_SS | Clustering software | Length | nbre seq | location | substitution | n 1st | n 2nd |
|---|---|---|---|---|---|---|---|---|
| PTA_1803.c1 | #N/A | PTA | 819 | 8 | 322 | T/C | 2 | 6 |
| PTA_1473.c1 | 105434840 | PTA | 713 | 6 | 429 | G/A | 4 | 2 |
| PTA_1153.c1 | 105434836 | PTA | 898 | 9 | 541 | G/A | 6 | 3 |
| PTA_233.C1 | #N/A | PTA | 862 | 12 | 485 | C/T | 5 | 7 |
| PTA_703.C2 | 105434856 | PTA | 784 | 6 | 462 | C/T | 4 | 2 |
| PTA_624.C1 | 105434854 | PTA | 687 | 11 | 184 | C/G | 8 | 3 |
| PTA_1764.c1 | 105434844 | PTA | 881 | 10 | 528 | G/A | 7 | 3 |
| PTA_1641.c1 | 105434841 | PTA | 958 | 10 | 397 | A/T | 6 | 4 |
| PTA_1090.c1 | 105434839 | PTA | 775 | 8 | 204 | G/A | 2 | 6 |
| PTA_179.c1 | 105434845 | PTA | 758 | 9 | 546 | C/T | 7 | 2 |
| PTA_912.c1 | 105434858 | PTA | 1110 | 5 | 273 | G/A | 3 | 2 |
| PTA_423.c1 | 105434851 | PTA | 1136 | 7 | 728 | C/T | 4 | 3 |
| PTA_056.c1 | #N/A | PTA | 789 | 10 | 594 | C/A | 5 | 5 |
| PTA_685.c1 | #N/A | PTA | 844 | 9 | 549 | C/A | 5 | 4 |
| PTA_657.c2 | 105434855 | PTA | 780 | 5 | 461 | C/G | 2 | 3 |
| PTA_463.c2 | 105434853 | PTA | 975 | 5 | 458 | A/G | 3 | 2 |
| PTA_854.c1 | 105434857 | PTA | 1016 | 9 | 700 | G/T | 4 | 5 |
| PTA_028.c1 | #N/A | PTA | 692 | 6 | 178 | G/C | 3 | 3 |
| PTA_449.c1 | 105434852 | PTA | 1001 | 8 | 685 | T/A | 3 | 5 |
| PTA_2675.c1 | 105434847 | PTA | 816 | 8 | 458 | A/G | 6 | 2 |
| PTA_153.c1 | 105434843 | PTA | 789 | 6 | 255 | A/G | 2 | 4 |
| PTA_1435.C1 | 105434837 | PTA | 1057 | 10 | 697 | G/A | 5 | 5 |
| PTA_263.C1 | #N/A | PTA | 1324 | 11 | 666 | T/G | 9 | 2 |
| PTA_1522.c1 | 105434838 | PTA | 783 | 8 | 561 | C/T | 4 | 4 |
| PTA_286.c1 | 105434850 | PTA | 997 | 8 | 317 | T/G | 6 | 2 |
| PTA_276.c1 | 105434849 | PTA | 740 | 6 | 193 | C/A | 4 | 2 |
| PTA_2083.c2 | 105434846 | PTA | 1144 | 6 | 328 | G/A | 3 | 3 |
| PTA_018.C2 | #N/A | PTA | 1143 | 11 | 803 | A/G | 8 | 3 |
| PTA_275.c2 | 105434848 | PTA | 814 | 7 | 421 | C/G | 4 | 3 |
| PTA_079.C1 | 105434835 | PTA | 884 | 12 | 370 | A/G | 1 | 11 |
| PP_1060.c1 | 105434834 | Polyphred | 1077 | 9 | 274 | A/T | 4 | 5 |
| PP_1062.c1 | #N/A | Polyphred | 1189 | 16 | 338 | A/C | 10 | 6 |
| PP_1063.c1 | #N/A | Polyphred | 859 | 10 | 345 | C/T | 6 | 4 |
| PP_1072.C1 | 105434859 | Polyphred | 846 | 11 | 296 | A/C | 6 | 5 |
| PP_1092.C1 | 105434860 | Polyphred | 868 | 14 | 200 | A/G | 7 | 7 |
| PP_1108.C1 | 105434861 | Polyphred | 806 | 6 | 649 | A/T | 2 | 4 |
| PP_1120.C1 | 105434862 | Polyphred | 1062 | 8 | 514 | C/T | 5 | 3 |
| PP_1159.C1 | #N/A | Polyphred | 453 | 6 | 310 | A/G | 3 | 3 |
| PP_1164.C1 | #N/A | Polyphred | 822 | 6 | 158 | A/C | 2 | 4 |
| PP_1206.C1 | 105434863 | Polyphred | 845 | 10 | 528 | A/G | 6 | 4 |
| PP_1657.C1 | 105434866 | Polyphred | 859 | 7 | 247 | C/T | 5 | 2 |
| PP_161.C1 | 105434865 | Polyphred | 1291 | 4 | 296 | C/G | 1 | 3 |
| PP_147.C1 | #N/A | Polyphred | 764 | 10 | 333 | G/T | 3 | 7 |
| PP_1301.C1 | #N/A | Polyphred | 859 | 7 | 112 | A/G | 2 | 5 |
| PP_127.C1 | #N/A | Polyphred | 848 | 8 | 440 | A/G | 5 | 3 |
| PP_134.C1 | 105434864 | Polyphred | 1248 | 4 | 709 | C/T | 1 | 3 |
| PP_1480.C3 | #N/A | Polyphred | 885 | 6 | 502 | A/G | 4 | 2 |

[1] For each SNP, the accession number in SNPdb, the origin of the consensus sequence used to design the primer (PTA or polyphred software), the length of the contig (Length), the number of reads in that contig (nbre), the coordinates of the SNP within the consensus sequences (location), the allele substitution (substitution), the number of reads with the first allele (n 1$^{st}$) and the number of read with the second allele (n 2$^{nd}$) is indicated.

TABLE 2

Low throughput SNP genotyping in Atlantic cod for two Canadian populations [2]

| SNP ID | Base | N | % b1 | | % b2 | | hetero. | | N | % b1 | | % b2 |
|---|---|---|---|---|---|---|---|---|---|---|---|---|
| | | | | | | NL | | | | | NB | |
| PTA_079.C1 | A/G | 8 | 0 | (0) | 1 | (16) | 0.00 | (0) | 10 | 0 | (0) | 1 |
| PTA_1090.c1 | G/A | 8 | 0.81 | (13) | 0.19 | (3) | 0.38 | (3) | 10 | 0.93 | (26) | 0.07 |
| PTA_1153.c1 | G/A | 8 | 0.44 | (7) | 0.56 | (9) | 0.38 | (3) | 14 | 0.21 | (6) | 0.79 |
| PTA_1435.C1 | A/G | 8 | 0.19 | (3) | 0.81 | (13) | 0.38 | (3) | 14 | 0.39 | (11) | 0.61 |
| PTA_1473.c1 | G/A | 8 | 0.25 | (4) | 0.75 | (12) | 0.50 | (4) | 14 | 0.46 | (13) | 0.54 |
| PTA_1522.c1 | C/T | 8 | 0.81 | (13) | 0.19 | (3) | 0.13 | (1) | 14 | 0.79 | (22) | 0.21 |
| PTA_153.c1 | A/G | 8 | 0.5 | (8) | 0.5 | (8) | 0.25 | (2) | 14 | 0.36 | (10) | 0.64 |
| PTA_1641.c1 | A/T | 8 | 0.75 | (12) | 0.25 | (4) | 0.50 | (4) | 14 | 0.71 | (20) | 0.29 |
| PTA_1764.c1 | A/G | 8 | 0.63 | (10) | 0.38 | (6) | 0.25 | (2) | 14 | 0.75 | (21) | 0.25 |
| PTA_179.c1 | C/T | 8 | 0.69 | (11) | 0.31 | (5) | 0.63 | (5) | 14 | 0.86 | (24) | 0.14 |
| PTA_18.C2 | A/G | 8 | 0.88 | (14) | 0.13 | (2) | 0.25 | (2) | 13 | 0.88 | (23) | 0.12 |
| PTA_2083.c2 | A/G | 8 | 0.69 | (11) | 0.31 | (5) | 0.63 | (5) | 14 | 0.71 | (20) | 0.29 |
| PTA_2675.c1 | A/G | 8 | 0.56 | (9) | 0.44 | (7) | 0.63 | (5) | 13 | 0.42 | (11) | 0.58 |

TABLE 2-continued

Low throughput SNP genotyping in Atlantic cod for two Canadian populations [2]

| | | | | | | | | | | | |
|---|---|---|---|---|---|---|---|---|---|---|---|
| PTA_275.c2 | G/C | 8 | 0.69 | (11) | 0.31 | (5) | 0.50 | (4) | 9 | 0.86 | (24) | 0.14 |
| PTA_276.c1 | C/A | 8 | 0.56 | (9) | 0.44 | (7) | 0.38 | (3) | 14 | 0.61 | (17) | 0.39 |
| PTA_286.c1 | G/T | 8 | 0.25 | (4) | 0.75 | (12) | 0.25 | (2) | 14 | 0.21 | (6) | 0.79 |
| PTA_423.c1 | C/T | 8 | 0.06 | (1) | 0.94 | (15) | 0.13 | (1) | 14 | 0.18 | (5) | 0.82 |
| PTA_449.c1 | T/A | 8 | 0.63 | (10) | 0.38 | (6) | 0.25 | (2) | 14 | 0.61 | (17) | 0.39 |
| PTA_463.c2 | A/G | 8 | 1 | (16) | 0 | (0) | 0.00 | (0) | 10 | 1 | (20) | 0 |
| PTA_624.C1 | G/C | 8 | 0.44 | (7) | 0.56 | (9) | 0.38 | (3) | 12 | 0.25 | (6) | 0.75 |
| PTA_657.c2 | C/G | 8 | 0.19 | (3) | 0.81 | (13) | 0.38 | (3) | 10 | 0.07 | (2) | 0.93 |
| PTA_703.C2 | C/T | 6 | 0 | (0) | 1 | (12) | 0.00 | (0) | 8 | 0 | (0) | 1 |
| PTA_854.c1 | G/T | 8 | 0.63 | (10) | 0.38 | (6) | 0.75 | (6) | 14 | 0.86 | (24) | 0.14 |
| PTA_912.c1 | G/A | 7 | 0.29 | (4) | 0.71 | (10) | 0.29 | (2) | 14 | 0.36 | (10) | 0.64 |
| PP_1060.c1 | A/T | 8 | 0.5 | (8) | 0.5 | (8) | 0.25 | (2) | 12 | 0.38 | (9) | 0.63 |
| PP_1072.C1 | A/C | 8 | 0.25 | (4) | 0.75 | (12) | 0.00 | (0) | 14 | 0.43 | (12) | 0.57 |
| PP_1092.C1 | A/G | 7 | 0.07 | (1) | 0.93 | (13) | 0.14 | (1) | 14 | 0.29 | (8) | 0.71 |
| PP_1108.C1 | A/T | 7 | 0.57 | (8) | 0.43 | (6) | 0.86 | (6) | 11 | 0.54 | (13) | 0.46 |
| PP_1120.C1 | T/C | 8 | 0 | (0) | 1 | (16) | 0.00 | (0) | 13 | 0.88 | (3) | 0.12 |
| PP_1206.C1 | A/G | 8 | 0.5 | (8) | 0.5 | (8) | 1.00 | (8) | 14 | 0.46 | (13) | 0.54 |
| PP_134.C1 | C/T | 7 | 0.5 | (7) | 0.5 | (7) | 1.00 | (7) | 10 | 0.5 | (10) | 0.5 |
| PP_161.C1 | C/G | 3 | 0.17 | (1) | 0.83 | (5) | 0.33 | (1) | 8 | 0.38 | (6) | 0.63 |
| PP_1657.C1 | C/T | 8 | 0.25 | (4) | 0.75 | (12) | 0.50 | (4) | 10 | 0.35 | (7) | 0.65 |

| | NB | Total | | | | | |
|---|---|---|---|---|---|---|---|
| SNP ID | hetero. | N | % b1 | | % b2 | | hetero. |
| PTA_079.C1 | (20) 0.00 (0) | 18 | 0 | (0) | 1 | (36) | 0.00 (0) |
| PTA_1090.c1 | (2) 0.20 (2) | 22 | 0.89 | (39) | 0.11 | (5) | 0.23 (5) |
| PTA_1153.c1 | (22) 0.43 (6) | 22 | 0.3 | (13) | 0.7 | (31) | 0.41 (9) |
| PTA_1435.C1 | (17) 0.64 (9) | 22 | 0.32 | (14) | 0.68 | (30) | 0.55 (12) |
| PTA_1473.c1 | (15) 0.64 (9) | 18 | 0.39 | (17) | 0.61 | (27) | 0.72 (13) |
| PTA_1522.c1 | (6) 0.14 (2) | 22 | 0.8 | (35) | 0.2 | (9) | 0.14 (3) |
| PTA_153.c1 | (18) 0.71 (10) | 22 | 0.41 | (18) | 0.59 | (26) | 0.55 (12) |
| PTA_1641.c1 | (8) 0.43 (6) | 22 | 0.73 | (32) | 0.27 | (12) | 0.45 (10) |
| PTA_1764.c1 | (7) 0.21 (3) | 22 | 0.7 | (31) | 0.3 | (13) | 0.23 (5) |
| PTA_179.c1 | (4) 0.29 (4) | 22 | 0.8 | (35) | 0.2 | (9) | 0.41 (9) |
| PTA_18.C2 | (3) 0.23 (3) | 21 | 0.88 | (37) | 0.12 | (5) | 0.24 (5) |
| PTA_2083.c2 | (8) 0.43 (6) | 22 | 0.7 | (31) | 0.3 | (13) | 0.50 (11) |
| PTA_2675.c1 | (15) 0.69 (9) | 21 | 0.48 | (20) | 0.52 | (22) | 0.67 (14) |
| PTA_275.c2 | (4) 0.44 (4) | 22 | 0.8 | (35) | 0.2 | (9) | 0.36 (8) |
| PTA_276.c1 | (11) 0.21 (3) | 22 | 0.59 | (26) | 0.41 | (18) | 0.27 (6) |
| PTA_286.c1 | (22) 0.29 (4) | 22 | 0.23 | (10) | 0.77 | (34) | 0.27 (6) |
| PTA_423.c1 | (23) 0.21 (3) | 22 | 0.14 | (6) | 0.86 | (38) | 0.18 (4) |
| PTA_449.c1 | (11) 0.21 (3) | 22 | 0.61 | (27) | 0.39 | (17) | 0.23 (5) |
| PTA_463.c2 | (0) 0.00 (0) | 18 | 1 | (36) | 0 | (0) | 0.00 (0) |
| PTA_624.C1 | (18) 0.50 (6) | 20 | 0.33 | (13) | 0.68 | (27) | 0.45 (9) |
| PTA_657.c2 | (26) 0.20 (2) | 22 | 0.11 | (5) | 0.89 | (39) | 0.23 (5) |
| PTA_703.C2 | (20) 0.00 (0) | 14 | 0 | (0) | 1 | (32) | 0.00 (0) |
| PTA_854.c1 | (4) 0.14 (2) | 22 | 0.77 | (34) | 0.23 | (10) | 0.36 (8) |
| PTA_912.c1 | (18) 0.43 (6) | 21 | 0.33 | (14) | 0.67 | (28) | 0.38 (8) |
| PP_1060.c1 | (15) 0.58 (7) | 20 | 0.43 | (17) | 0.58 | (23) | 0.45 (9) |
| PP_1072.C1 | (16) 0.29 (4) | 22 | 0.36 | (16) | 0.64 | (28) | 0.18 (4) |
| PP_1092.C1 | (20) 0.29 (4) | 21 | 0.21 | (9) | 0.79 | (33) | 0.24 (5) |
| PP_1108.C1 | (11) 0.82 (9) | 18 | 0.55 | (21) | 0.45 | (17) | 0.83 (15) |
| PP_1120.C1 | (23) 0.23 (3) | 21 | 0.07 | (3) | 0.93 | (39) | 0.14 (3) |
| PP_1206.C1 | (15) 0.64 (9) | 22 | 0.48 | (21) | 0.52 | (23) | 0.77 (17) |
| PP_134.C1 | (10) 1.00 (10) | 17 | 0.5 | (17) | 0.5 | (17) | 1.00 (17) |
| PP_161.C1 | (10) 0.50 (4) | 11 | 0.32 | (7) | 0.68 | (15) | 0.45 (5) |
| PP_1657.C1 | (13) 0.50 (5) | 18 | 0.31 | (11) | 0.69 | (25) | 0.50 (9) |

[2] Genotyping results from predicted SNPs is shown, using DNA isolated from NB YC1 and NL YC2 parents. The number of individuals tested (N), proportion of allelic diversity for base 1 and base 2 (% b1 and % b2 respectively) with number of alleles observed indicated in bold, and the observed heterozygosity (hetero. = number of heterozygotes detected, divided by number of individuals typed) at each locus is shown with the number of individuals analysed is indicated in parentheses. Statistics were generated for each of the two populations, NL and NB, and overall.

TABLE 3

Segregation analysis for cod SNPs.[3]

| SNP ID | segregation | N | p (chi2) |
|---|---|---|---|
| PTA_276.C1 | irregular | | |
| PTA_423.C1 | irregular | | |
| PTA_275.C2 | irregular | | |
| PTA_449.C1 | irregular | | |
| PP_1108.C1* | irregular | | |
| PP_134.C1* | duplicated | | |
| PP_161.C1* | duplicated | | |
| PTA_463.C2 | monomorphic | | |
| PTA_703.C2 | monomorphic | | |
| PTA_079.C1 | monomorphic | | |
| PTA_1522.C1 | not informative | 6 | 1 |
| PP_1060.C1* | Yes | 44 | 0.132 |
| PP_1072.C1* | Yes | 43 | 0.010 |
| PP_1092.C1* | Yes | 44 | 0.768 |

TABLE 3-continued

Segregation analysis for cod SNPs.[3]

| SNP ID | segregation | N | p (chi2) |
|---|---|---|---|
| PP__1120.C1* | Yes | 36 | 0.739 |
| PP__1206.C1* | Yes | 45 | 0.881 |
| PP__1657.C1* | Yes | 44 | 0.035 |
| PTA__1090.C1 | Yes | 34 | 0.17 |
| PTA__1153.C1 | Yes | 46 | 0.404 |
| PTA__1435.C1 | Yes | 42 | 0.67 |
| PTA__1473.C1 | Yes | 38 | 0.746 |
| PTA__153.C1 | Yes | 43 | 0.093 |
| PTA__1641.C1 | Yes | 44 | 0.546 |
| PTA__1764.C1 | Yes | 43 | 0.286 |
| PTA__179.C1 | Yes | 46 | 0.003 |
| PTA__18.C2 | Yes | 39 | 0.872 |
| PTA__2083.C2 | Yes | 46 | 0.376 |
| PTA__2675.C1 | Yes | 46 | 0.768 |
| PTA__286.C1 | Yes | 44 | 0.763 |
| PTA__624.C1 | Yes | 44 | 0.366 |
| PTA__657.C2 | Yes | 31 | 0.048 |
| PTA__854.C1 | Yes | 40 | 0.343 |
| PTA__912.C1 | Yes | 42 | 0.03 |

[3]"Irregular" indicated that the SNPs did not segregated as expected, "duplicated" indicated that these putative SNPs are most likely to represent a gene duplication. "Not informative" indicates that for this SNP both parents were homozygous for a different allele therefore segregation could not be tested. For SNPs that segregated as expected ("yes'), the number of progeny tested (N), and the probability of $\chi^2$ test of a distortion (p (chi2)) are indicated.

TABLE 4

Annotation of validated SNP-containing sequences.[4]

| SNP ID | length | accession | annotation | Bit score | e-value | identity |
|---|---|---|---|---|---|---|
| PP__1657.C1* | 1194 | BAE45262 | anserinase | 804 | 8e-84 | 82% (148/180) |
| PP__1092.C1* | 1525 | NP__997853 | Cathepsin H; | 1206 | 1e-130 | 67% (216/322) |
| PP__1072.C1* | 1612 | tpe|CAK26786.1| | Transposase domain-containing protein | 641 | 3e-79 | 37% (149/396) |
| PP__1120.C1* | 1431 | NP__001002169 | spermidine/spermine N1-acetyltransferase | 748 | 3e-77 | 83% (141/169) |
| PTA__624.C1 | 689 | AAT45249.1 | unknown [*Sparus aurata*] | 64 | 8e-09 | 45% (30/66) |
| PTA__1473.C1 | 699 | BAF45896 | ribosomal protein S8 [*Solea senegalensis*] | 974 | 1e-104 | 87% (182/208) |
| PTA__1153.C1 | 863 | ABD60150 | interferon stimulated gene 15 | 675 | 2e-69 | 99% (134/135) |
| PTA__2083.C2 | 1694 | NP__956144 | c20orf24 homolog | 605 | 2e-60 | 86% (110/127) |
| PTA__179.C1 | 823 | NP__001072618 | cystinosis, nephropathic [*Xenopus tropicalis*] | 623 | 4e-63 | 70% (117/167) |
| PTA__18.C2 | 1325 | NP__956394 | putative growth hormone like protein-1, yghl1 | 372 | 1e-33 | 81% (70/86) |
| PTA__1764.C1 | 854 | NP__775331 | epididymal secretory protein E1 | 593 | 1e-59 | 70% (105/149) |
| PTA__1090.C1 | 1683 | XP__513647 | to WWFQ154 isoform 8 | 656 | 2e-66 | 50% (126/250) |
| PTA__854.C1 | 1522 | NP__999939 | tetraspanin 7 | 783 | 2e-92 | 69% (154/223) |
| PTA__703.C2 | 909 | AAW29025 | Superoxide dismutase [Cu—Zn]; | 699 | 8e-72 | 83% (127/152) |

[4]Length of the contig from which the SNPs was identified, accession number, bit score, e-value and percentage identity for the BLAST hit are indicated.
*indicates SNPs which were detected by the automated pipeline.

TABLE 5

SNPs location in the gene region and putative SNP functionality (non synonymous or synonymous change).[5]

| SNP ID | Region | SNP effect |
|---|---|---|
| PP__1060.C1* | untranslated region | |
| PP__1072.C1* | untranslated region | |
| PP__1092.C1* | untranslated region | |
| PP__1120.C1* | untranslated region | |
| PTA__1764.C1 | untranslated region | |
| PTA__179.C1 | untranslated region | |
| PTA__463.C2 | untranslated region | |
| PTA__703.C2 | untranslated region | |
| PTA__854.C1 | untranslated region | |
| PTA__1153.C1 | protein coding region | syn |
| PTA__1473.C1 | protein coding region | syn |
| PTA__1090.C1 | protein coding region | non-syn |
| PTA__624.C1 | protein coding region | non-syn |

[5]*indicates SNPs detected by the automated pipeline

TABLE 6

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP__Name | New name | V | P | Score |
|---|---|---|---|---|---|
| 1 | 7438C1CO1.456 | cgpGmo-S10 | | 1 | 0.767 |
| 2 | 6146C1CO1.803 | cgpGmo-S100 | | 1 | 0.571 |
| 3 | 8175C1CO1.190 | cgpGmo-S1000 | | 1 | 0.91 |
| 4 | 8198C1CO1.675 | cgpGmo-S1001 | V | 1 | 0.747 |
| 5 | 8200C1CO1.691 | cgpGmo-S1002 | | 1 | 0.707 |
| 6 | 8211C1CO1.404 | cgpGmo-S1003 | V | 1 | 0.628 |
| 7 | 8217C1CO1.286 | cgpGmo-S1004 | | 1 | 0.827 |
| 8 | 821C1CO1.206 | cgpGmo-S1005 | V | 1 | 0.634 |
| 9 | 8237C1CO1.655 | cgpGmo-S1006 | V | 1 | 0.823 |
| 10 | 8243C1CO1.596 | cgpGmo-S1007 | V | 1 | 0.776 |
| 11 | 8248C1CO1.563 | cgpGmo-S1008 | V | 1 | 0.811 |
| 12 | 8254C1CO1.838 | cgpGmo-S1009 | V | 1 | 0.897 |
| 13 | 7089C1CO1.567 | cgpGmo-S101 | | 1 | 0.898 |
| 14 | 825C2CO1.632 | cgpGmo-S1010 | V | 1 | 0.907 |
| 15 | 829C1CO1.285 | cgpGmo-S1011a | V | 2 | 0.9 |
| 16 | 829C1CO1.716 | cgpGmo-S1011b | V | 1 | 0.8 |
| 17 | 8319C1CO1.383 | cgpGmo-S1012 | | 1 | 0.875 |
| 18 | 832C1CO1.98 | cgpGmo-S1013 | V | 1 | 0.794 |
| 19 | 8332C1CO1.229 | cgpGmo-S1014a | V | 2 | 0.94 |
| 20 | 8332C1CO1.325 | cgpGmo-S1014b | V | 1 | 0.596 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 21 | 834C1CO1.125 | cgpGmo-S1015 | | 1 | 0.828 |
| 22 | 8355C1CO1.403 | cgpGmo-S1016 | V | 1 | 0.707 |
| 23 | 8362C1CO1.579 | cgpGmo-S1017 | V | 1 | 0.883 |
| 24 | 8377C1CO1.271 | cgpGmo-S1018a | V | 2 | 0.95 |
| 25 | 8377C1CO1.540 | cgpGmo-S1018b | V | 1 | 0.805 |
| 26 | 8394C1CO1.538 | cgpGmo-S1019 | | 1 | 0.827 |
| 27 | 7113C2CO1.617 | cgpGmo-S102 | V | 1 | 0.739 |
| 28 | 8436C1CO1.307 | cgpGmo-S1020 | | 1 | 0.713 |
| 29 | 843C1CO1.468 | cgpGmo-S1022 | V | 1 | 0.524 |
| 30 | 8462C1CO1.261 | cgpGmo-S1023 | | 1 | 0.781 |
| 31 | 8467C1CO1.305 | cgpGmo-S1024 | V | 1 | 0.733 |
| 32 | 8473C1CO1.538 | cgpGmo-S1025 | V | 1 | 0.718 |
| 33 | 849C1CO1.1197 | cgpGmo-S1026 | V | 1 | 0.698 |
| 34 | 852C1CO1.135 | cgpGmo-S1027 | V | 1 | 0.683 |
| 35 | 8542C1CO1.578 | cgpGmo-S1028 | V | 1 | 0.795 |
| 36 | 8544C1CO1.224 | cgpGmo-S1029 | V | 1 | 0.823 |
| 37 | 727C1CO1.856 | cgpGmo-S103 | V | 1 | 0.875 |
| 38 | 8558C1CO1.691 | cgpGmo-S1030 | V | 1 | 0.734 |
| 39 | 8574C1CO1.147 | cgpGmo-S1031 | V | 1 | 0.761 |
| 40 | 8590C1CO1.487 | cgpGmo-S1032 | V | 1 | 0.731 |
| 41 | 859C1CO1.398 | cgpGmo-S1033a | | 1 | 0.906 |
| 42 | 859C1CO1.587 | cgpGmo-S1033b | | 2 | 0.98 |
| 43 | 85C1CO1.261 | cgpGmo-S1034 | V | 1 | 0.571 |
| 44 | 8612C1CO1.416 | cgpGmo-S1035 | V | 1 | 0.669 |
| 45 | 8660C1CO1.346 | cgpGmo-S1036 | V | 1 | 0.787 |
| 46 | 8671C1CO1.75 | cgpGmo-S1037 | | 1 | 0.68 |
| 47 | 867C2CO1.568 | cgpGmo-S1038 | V | 1 | 0.667 |
| 48 | 8727C1CO1.363 | cgpGmo-S1039a | V | 2 | 0.88 |
| 49 | 8727C1CO1.443 | cgpGmo-S1039b | V | 1 | 0.567 |
| 50 | 7295C1CO1.177 | cgpGmo-S104 | V | 1 | 0.652 |
| 51 | 8760C1CO1.282 | cgpGmo-S1040 | | 1 | 0.613 |
| 52 | 8812C1CO1.226 | cgpGmo-S1041 | V | 1 | 0.817 |
| 53 | 8813C1CO1.178 | cgpGmo-S1042a | V | 2 | 0.98 |
| 54 | 8813C1CO1.456 | cgpGmo-S1042b | V | 1 | 0.774 |
| 55 | 8822C1CO1.155 | cgpGmo-S1043 | | 1 | 0.428 |
| 56 | 8831C1CO1.119 | cgpGmo-S1044 | V | 1 | 0.893 |
| 57 | 8852C2CO1.180 | cgpGmo-S1045 | V | 1 | 0.844 |
| 58 | 8858C1CO1.415 | cgpGmo-S1046 | V | 1 | 0.804 |
| 59 | 8868C1CO1.320 | cgpGmo-S1047 | V | 1 | 0.86 |
| 60 | 886C1CO1.713 | cgpGmo-S1048 | V | 1 | 0.788 |
| 61 | 8876C1CO1.97 | cgpGmo-S1049 | V | 1 | 0.914 |
| 62 | 7360C1CO1.276 | cgpGmo-S105 | V | 1 | 0.761 |
| 63 | 8898C1CO1.316 | cgpGmo-S1050 | V | 1 | 0.732 |
| 64 | 8907C1CO1.624 | cgpGmo-S1051 | V | 1 | 0.416 |
| 65 | 8916C1CO1.482 | cgpGmo-S1052 | | 1 | 0.901 |
| 66 | 896C1CO1.240 | cgpGmo-S1053 | | 1 | 0.871 |
| 67 | 8982C1CO1.388 | cgpGmo-S1054 | | 1 | 0.902 |
| 68 | 898C1CO1.194 | cgpGmo-S1055a | V | 1 | 0.851 |
| 69 | 898C1CO1.501 | cgpGmo-S1055b | V | 2 | 0.97 |
| 70 | 9008C1CO1.522 | cgpGmo-S1056 | | 1 | 0.884 |
| 71 | 9043C1CO1.444 | cgpGmo-S1057a | V | 2 | 1 |
| 72 | 9043C1CO1.620 | cgpGmo-S1057b | | 1 | 0.81 |
| 73 | 9048C1CO1.568 | cgpGmo-S1058 | V | 1 | 0.852 |
| 74 | 9055C1CO1.289 | cgpGmo-S1059 | | 1 | 0.775 |
| 75 | 9106C1CO1.388 | cgpGmo-S1060 | | 1 | 0.823 |
| 76 | 910C1CO1.632 | cgpGmo-S1061 | | 1 | 0.724 |
| 77 | 913C2CO1.505 | cgpGmo-S1062 | V | 1 | 0.639 |
| 78 | 9143C1CO1.292 | cgpGmo-S1063 | V | 1 | 0.862 |
| 79 | 9148C1CO1.367 | cgpGmo-S1064 | | 1 | 0.816 |
| 80 | 915C1CO1.601 | cgpGmo-S1065 | V | 1 | 0.814 |
| 81 | 917C1CO1.115 | cgpGmo-S1066 | V | 1 | 0.718 |
| 82 | 9216C1CO1.189 | cgpGmo-S1067 | | 1 | 0.818 |
| 83 | 9225C1CO1.510 | cgpGmo-S1068 | V | 1 | 0.883 |
| 84 | 922C1CO1.257 | cgpGmo-S1069 | | 1 | 0.901 |
| 85 | 7514C1CO1.267 | cgpGmo-S107 | V | 1 | 0.732 |
| 86 | 9239C1CO1.594 | cgpGmo-S1070 | V | 1 | 0.893 |
| 87 | 9244C1CO1.298 | cgpGmo-S1071a | | 1 | 0.821 |
| 88 | 9244C1CO1.505 | cgpGmo-S1071b | | 2 | 0.86 |
| 89 | 9304C1CO1.479 | cgpGmo-S1072 | | 1 | 0.741 |
| 90 | 9355C1CO1.388 | cgpGmo-S1073 | V | 1 | 0.876 |
| 91 | 9356C1CO1.1059 | cgpGmo-S1074 | V | 1 | 0.857 |
| 92 | 935C1CO1.464 | cgpGmo-S1075 | V | 1 | 0.797 |
| 93 | 9379C1CO1.272 | cgpGmo-S1076a | V | 1 | 0.775 |
| 94 | 9379C1CO1.565 | cgpGmo-S1076b | V | 2 | 0.95 |
| 95 | 943C2CO1.170 | cgpGmo-S1077a | | 2 | 0.87 |
| 96 | 943C2CO1.474 | cgpGmo-S1077b | V | 1 | 0.615 |
| 97 | 947C3CO1.272 | cgpGmo-S1078 | V | 1 | 0.694 |
| 98 | 9484C1CO1.708 | cgpGmo-S1079 | V | 1 | 0.712 |
| 99 | 7521C1CO1.633 | cgpGmo-S108 | V | 1 | 0.794 |
| 100 | 9490C1CO1.438 | cgpGmo-S1080 | V | 1 | 0.619 |
| 101 | 949C1CO1.904 | cgpGmo-S1081 | V | 1 | 0.768 |
| 102 | 9502C1CO1.395 | cgpGmo-S1082 | V | 1 | 0.873 |
| 103 | 9503C1CO1.249 | cgpGmo-S1083 | V | 1 | 0.802 |
| 104 | 9504C1CO1.397 | cgpGmo-S1084 | V | 1 | 0.697 |
| 105 | 952C1CO1.176 | cgpGmo-S1085a | V | 1 | 0.816 |
| 106 | 952C1CO1.299 | cgpGmo-S1085b | V | 2 | 0.89 |
| 107 | 9543C1CO1.323 | cgpGmo-S1086 | V | 1 | 0.76 |
| 108 | 95C1CO1.158 | cgpGmo-S1087a | | 2 | 0.86 |
| 109 | 95C1CO1.548 | cgpGmo-S1087b | V | 1 | 0.679 |
| 110 | 9612C1CO1.594 | cgpGmo-S1088 | | 1 | 0.725 |
| 111 | 9615C1CO1.381 | cgpGmo-S1089 | V | 1 | 0.771 |
| 112 | 7616C1CO1.612 | cgpGmo-S109 | V | 1 | 0.646 |
| 113 | 962C3CO1.584 | cgpGmo-S1090 | V | 1 | 0.786 |
| 114 | 9642C1CO1.154 | cgpGmo-S1091 | V | 1 | 0.914 |
| 115 | 9671C1CO1.293 | cgpGmo-S1092a | V | 2 | 0.96 |
| 116 | 9671C1CO1.624 | cgpGmo-S1092b | | 1 | 0.738 |
| 117 | 9682C1CO1.765 | cgpGmo-S1093 | V | 1 | 0.895 |
| 118 | 9683C2CO1.587 | cgpGmo-S1094 | V | 1 | 0.864 |
| 119 | 968C1CO1.536 | cgpGmo-S1095 | V | 1 | 0.878 |
| 120 | 9710C1CO1.403 | cgpGmo-S1096 | V | 1 | 0.671 |
| 121 | 9732C1CO1.311 | cgpGmo-S1097 | V | 1 | 0.52 |
| 122 | 9755C1CO1.874 | cgpGmo-S1098 | V | 1 | 0.78 |
| 123 | 7696C1CO1.426 | cgpGmo-S110 | V | 1 | 0.647 |
| 124 | 9801C1CO1.287 | cgpGmo-S1101a | V | 1 | 0.865 |
| 125 | 9801C1CO1.431 | cgpGmo-S1101b | | 2 | 0.96 |
| 126 | 985C1CO1.97 | cgpGmo-S1102a | | 2 | 0.78 |
| 127 | 985C1CO1.521 | cgpGmo-S1102b | | 1 | 0.458 |
| 128 | 9860C1CO1.509 | cgpGmo-S1103 | V | 1 | 0.91 |
| 129 | 988C2CO1.100 | cgpGmo-S1104 | V | 1 | 0.84 |
| 130 | 9900C2CO1.72 | cgpGmo-S1105 | V | 1 | 0.789 |
| 131 | 990C1CO1.966 | cgpGmo-S1106 | V | 1 | 0.836 |
| 132 | 9924C1CO1.329 | cgpGmo-S1107 | V | 1 | 0.874 |
| 133 | 993C1CO1.498 | cgpGmo-S1108 | V | 1 | 0.908 |
| 134 | 996C1CO1.70 | cgpGmo-S1109 | | 1 | 0.907 |
| 135 | 9977C1CO1.83 | cgpGmo-S1110 | V | 1 | 0.811 |
| 136 | 1beta1139 | cgpGmo-S1111 | V | 2 | 0.625 |
| 137 | 1beta68 | cgpGmo-S1112 | V | 2 | 0.787 |
| 138 | 1beta787 | cgpGmo-S1113 | V | 2 | 0.703 |
| 139 | 3beta115 | cgpGmo-S1114 | | 2 | 0.535 |
| 140 | 3beta369 | cgpGmo-S1115 | V | 2 | 0.839 |
| 141 | 3beta431 | cgpGmo-S1116 | V | 2 | 0.623 |
| 142 | 3beta670 | cgpGmo-S1117 | V | 2 | 0.722 |
| 143 | all_v2.10471.C1.580 | cgpGmo-S1118 | | 2 | 0.922 |
| 144 | all_v2.10472.C1.668 | cgpGmo-S1119 | | 2 | 0.552 |
| 145 | 7699C1CO1.486 | cgpGmo-S111a | V | 1 | 0.701 |
| 146 | 7699C1CO1.588 | cgpGmo-S111b | V | 2 | 0.73 |
| 147 | 7875C1CO1.273 | cgpGmo-S112 | | 1 | 0.51 |
| 148 | all_v2.10762.C1.327 | cgpGmo-S1120 | | 2 | 0.835 |
| 149 | all_v2.1182.C3.404 | cgpGmo-S1121 | V | 2 | 0.902 |
| 150 | all_v2.1240.C2.204 | cgpGmo-S1122 | V | 2 | 0.84 |
| 151 | all_v2.12584.C1.552 | cgpGmo-S1123 | V | 2 | 0.957 |
| 152 | all_v2.12816.C1.280 | cgpGmo-S1124 | | 2 | 0.894 |
| 153 | all_v2.14.C3.218 | cgpGmo-S1125 | | 2 | 0.981 |
| 154 | all_v2.14470.C1.513 | cgpGmo-S1126 | V | 2 | 0.597 |
| 155 | all_v2.1580.C2.665 | cgpGmo-S1127 | V | 2 | 0.98 |
| 156 | all_v2.16284.C1.608 | cgpGmo-S1128 | | 2 | 0.83 |
| 157 | all_v2.1631.C3.376 | cgpGmo-S1129 | | 2 | 0.958 |
| 158 | 7910C1CO1.596 | cgpGmo-S113 | V | 1 | 0.815 |
| 159 | all_v2.17178.C1.707 | cgpGmo-S1130 | V | 2 | 0.888 |
| 160 | all_v2.1745.C2.198 | cgpGmo-S1131 | V | 2 | 0.935 |
| 161 | all_v2.1778.C1.1202 | cgpGmo-S1132 | | 2 | 0.829 |
| 162 | all_v2.1873.C1.764 | cgpGmo-S1133 | | 2 | 0.901 |
| 163 | all_v2.2218.C1.642 | cgpGmo-S1134 | | 2 | 0.933 |
| 164 | all_v2.2386.C1.119 | cgpGmo-S1135 | | 2 | 0.984 |
| 165 | all_v2.2387.C4.359 | cgpGmo-S1136 | | 2 | 0.958 |
| 166 | all_v2.2487.C3.177 | cgpGmo-S1137 | | 2 | 0.956 |
| 167 | all_v2.269.C1.748 | cgpGmo-S1138 | | 2 | 0.939 |
| 168 | all_v2.3115.C1.694 | cgpGmo-S1139 | | 2 | 0.812 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 169 | 8067C1CO1.557 | cgpGmo-S114 | V | 1 | 0.889 |
| 170 | all_v2.3403.C1.693 | cgpGmo-S1140 | V | 2 | 0.762 |
| 171 | all_v2.37.C2.558 | cgpGmo-S1141 |  | 2 | 0.97 |
| 172 | all_v2.4.C42.1238 | cgpGmo-S1142 | V | 2 | 0.66 |
| 173 | all_v2.4620.C1.743 | cgpGmo-S1143 |  | 2 | 0.688 |
| 174 | all_v2.486.C40.439 | cgpGmo-S1144 |  | 2 | 0.847 |
| 175 | all_v2.495.C1.1115 | cgpGmo-S1145 |  | 2 | 0.738 |
| 176 | all_v2.5424.C1.660 | cgpGmo-S1146 |  | 2 | 0.832 |
| 177 | all_v2.5532.C1.215 | cgpGmo-S1147 |  | 2 | 0.789 |
| 178 | all_v2.6979.C2.795 | cgpGmo-S1148 |  | 2 | 0.753 |
| 179 | all_v2.838.C3.137 | cgpGmo-S1149 |  | 2 | 0.913 |
| 180 | 8428C1CO1.521 | cgpGmo-S115 | V | 1 | 0.517 |
| 181 | all_v2.8471.C1.373 | cgpGmo-S1150 |  | 2 | 0.477 |
| 182 | all_v2.8613.C2.690 | cgpGmo-S1151 |  | 2 | 0.888 |
| 183 | all_v2.8695.C1.117 | cgpGmo-S1152 |  | 2 | 0.726 |
| 184 | all_v2.871.C1.415 | cgpGmo-S1153 |  | 2 | 0.972 |
| 185 | all_v2.8751.C1.210 | cgpGmo-S1154 |  | 2 | 0.929 |
| 186 | all_v2.9258.C1.246 | cgpGmo-S1155 |  | 2 | 0.764 |
| 187 | all_v2.93.C4.268 | cgpGmo-S1156 |  | 2 | 0.708 |
| 188 | all_v2.9521.C1.369 | cgpGmo-S1157 | V | 2 | 0.882 |
| 189 | all_v2.9596.C1.244 | cgpGmo-S1158 | V | 2 | 0.899 |
| 190 | all_v2.9973.C2.356 | cgpGmo-S1159 |  | 2 | 0.346 |
| 191 | 919C1CO1.212 | cgpGmo-S116 | V | 1 | 0.876 |
| 192 | 101C1CO1.258 | cgpGmo-S1162 | V | 2 | 0.92 |
| 193 | 1023C3CO1.295 | cgpGmo-S1163 | V | 2 | 0.94 |
| 194 | 10303C1CO1.348 | cgpGmo-S1164 |  | 2 | 0.89 |
| 195 | 1038C1CO1.319 | cgpGmo-S1166 | V | 2 | 0.75 |
| 196 | 10392C1CO2.1102 | cgpGmo-S1167 | V | 2 | 0.94 |
| 197 | 10574C1CO1.258 | cgpGmo-S1169 | V | 2 | 0.67 |
| 198 | 9346C1CO1.100 | cgpGmo-S117 |  | 1 | 0.785 |
| 199 | 10591C2CO1.420 | cgpGmo-S1170 |  | 2 | 0.62 |
| 200 | 10639C1CO1.217 | cgpGmo-S1171 |  | 2 | 0.92 |
| 201 | 1093C1CO1.226 | cgpGmo-S1172 | V | 2 | 0.67 |
| 202 | 1105C1CO1.668 | cgpGmo-S1175 |  | 2 | 0.79 |
| 203 | 110C1CO1.986 | cgpGmo-S1176 |  | 2 | 0.9 |
| 204 | 1125C1CO1.153 | cgpGmo-S1178 | V | 2 | 0.93 |
| 205 | 11264C1CO1.589 | cgpGmo-S1179 | V | 2 | 0.89 |
| 206 | 9565C1CO1.422 | cgpGmo-S118 |  | 1 | 0.76 |
| 207 | 11275C1CO1.351 | cgpGmo-S1180a |  | 2 | 0.86 |
| 208 | 11275C1CO1.463 | cgpGmo-S1180b |  | 2 | 0.83 |
| 209 | 1140C1CO1.1290 | cgpGmo-S1181 | V | 2 | 0.88 |
| 210 | 1158C1CO1.535 | cgpGmo-S1183 | V | 2 | 0.9 |
| 211 | 1160C1CO1.270 | cgpGmo-S1184 | V | 2 | 0.69 |
| 212 | 1163C1CO1.148 | cgpGmo-S1185 |  | 2 | 0.99 |
| 213 | 1170C1CO1.461 | cgpGmo-S1186 | V | 2 | 0.75 |
| 214 | 11840C1CO1.475 | cgpGmo-S1188 | V | 2 | 0.96 |
| 215 | 1213C1CO1.742 | cgpGmo-S1190 |  | 2 | 0.94 |
| 216 | 1257C1CO1.412 | cgpGmo-S1192 |  | 2 | 0.97 |
| 217 | 1259C2CO1.765 | cgpGmo-S1193 | V | 2 | 0.95 |
| 218 | 1274C3CO1.192 | cgpGmo-S1196a | V | 2 | 0.97 |
| 219 | 1274C3CO1.269 | cgpGmo-S1196b | V | 2 | 0.99 |
| 220 | 1275C1CO1.99 | cgpGmo-S1197a | V | 2 | 0.76 |
| 221 | 1275C1CO1.229 | cgpGmo-S1197b |  | 2 | 0.7 |
| 222 | 972C1CO1.421 | cgpGmo-S119a | V | 1 | 0.649 |
| 223 | 972C1CO1.540 | cgpGmo-S119b | V | 2 | 0.88 |
| 224 | 10001C1CO1.183 | cgpGmo-S120 | V | 1 | 0.629 |
| 225 | 1310C1CO1.339 | cgpGmo-S1200 |  | 2 | 0.97 |
| 226 | 1413C1CO1.696 | cgpGmo-S1201 |  | 2 | 0.95 |
| 227 | 1419C1CO1.602 | cgpGmo-S1202 |  | 2 | 0.96 |
| 228 | 1452C3CO1.125 | cgpGmo-S1204 | V | 2 | 0.98 |
| 229 | 1461C1CO1.559 | cgpGmo-S1205 | V | 2 | 0.93 |
| 230 | 1467C2CO1.417 | cgpGmo-S1206 |  | 2 | 0.94 |
| 231 | 1494C1CO1.446 | cgpGmo-S1208 |  | 2 | 0.92 |
| 232 | 1497C1CO1.102 | cgpGmo-S1209 | V | 2 | 0.96 |
| 233 | 1000C1CO1.595 | cgpGmo-S121 | V | 1 | 0.868 |
| 234 | 1555C1CO1.1236 | cgpGmo-S1212 |  | 2 | 0.98 |
| 235 | 1557C1CO1.474 | cgpGmo-S1213a |  | 2 | 0.94 |
| 236 | 1557C1CO1.325 | cgpGmo-S1213b |  | 1 | 0.847 |
| 237 | 1557C1CO1.255 | cgpGmo-S1213c | V | 2 | 0.94 |
| 238 | 157C2CO1.576 | cgpGmo-S1216a | V | 2 | 0.9 |
| 239 | 157C2CO1.849 | cgpGmo-S1216b |  | 2 | 0.98 |
| 240 | 157C3CO1.630 | cgpGmo-S1217 |  | 2 | 0.96 |
| 241 | 1583C1CO1.958 | cgpGmo-S1218 | V | 2 | 0.97 |
| 242 | 1589C1CO1.67 | cgpGmo-S1219a | V | 2 | 0.6 |
| 243 | 1589C1CO1.147 | cgpGmo-S1219b | V | 2 | 0.7 |
| 244 | 1589C1CO1.288 | cgpGmo-S1219c | V | 1 | 0.503 |
| 245 | 10037C1CO1.421 | cgpGmo-S122 | V | 1 | 0.639 |
| 246 | 1598C1CO1.204 | cgpGmo-S1221a | V | 2 | 0.97 |
| 247 | 1598C1CO1.273 | cgpGmo-S1221b | V | 2 | 0.93 |
| 248 | 1601C1CO1.574 | cgpGmo-S1222 | V | 2 | 0.92 |
| 249 | 1618C1CO1.292 | cgpGmo-S1224 | V | 2 | 0.92 |
| 250 | 1645C1CO1.315 | cgpGmo-S1225 | V | 2 | 0.97 |
| 251 | 1649C4CO1.991 | cgpGmo-S1226 | V | 2 | 0.95 |
| 252 | 1681C2CO1.275 | cgpGmo-S1230a | V | 1 | 0.893 |
| 253 | 1681C2CO1.506 | cgpGmo-S1230b |  | 2 | 0.95 |
| 254 | 172C1CO1.454 | cgpGmo-S1231 | V | 2 | 0.67 |
| 255 | 1741C1CO1.290 | cgpGmo-S1232 | V | 2 | 0.85 |
| 256 | 1790C1CO1.552 | cgpGmo-S1234 | V | 2 | 0.81 |
| 257 | 1802C1CO1.342 | cgpGmo-S1235 | V | 2 | 0.83 |
| 258 | 1808C1CO1.373 | cgpGmo-S1236a |  | 2 | 0.99 |
| 259 | 1808C1CO1.602 | cgpGmo-S1236b |  | 2 | 0.96 |
| 260 | 1824C1CO1.199 | cgpGmo-S1237 | V | 2 | 0.91 |
| 261 | 1860C1CO1.159 | cgpGmo-S1239 | V | 2 | 0.91 |
| 262 | 10053C1CO1.358 | cgpGmo-S123a |  | 2 | 0.68 |
| 263 | 10053C1CO1.491 | cgpGmo-S123b |  | 1 | 0.603 |
| 264 | 10078C1CO1.320 | cgpGmo-S124 | V | 1 | 0.903 |
| 265 | 1890C1CO1.700 | cgpGmo-S1241 | V | 2 | 0.98 |
| 266 | 1898C1CO1.530 | cgpGmo-S1242 | V | 2 | 0.59 |
| 267 | 1933C2CO1.182 | cgpGmo-S1243a | V | 2 | 0.89 |
| 268 | 1933C2CO1.246 | cgpGmo-S1243b | V | 2 | 0.86 |
| 269 | 1008C1CO1.620 | cgpGmo-S125 |  | 1 | 0.591 |
| 270 | 2058C1CO1.325 | cgpGmo-S1250 |  | 2 | 0.93 |
| 271 | 2067C1CO1.438 | cgpGmo-S1251 | V | 2 | 0.83 |
| 272 | 2091C2CO1.488 | cgpGmo-S1252 | V | 2 | 0.98 |
| 273 | 2107C2CO1.395 | cgpGmo-S1255a | V | 2 | 0.8 |
| 274 | 2107C2CO1.110 | cgpGmo-S1255b | V | 2 | 0.94 |
| 275 | 2125C2CO1.134 | cgpGmo-S1256a | V | 2 | 0.93 |
| 276 | 2125C2CO1.377 | cgpGmo-S1256b | V | 2 | 0.95 |
| 277 | 2143C1CO1.182 | cgpGmo-S1258a | V | 2 | 0.92 |
| 278 | 2143C1CO1.548 | cgpGmo-S1258b | V | 2 | 0.93 |
| 279 | 2161C1CO1.347 | cgpGmo-S1260 | V | 2 | 0.71 |
| 280 | 220C1CO1.497 | cgpGmo-S1263 | V | 2 | 0.91 |
| 281 | 2244C1CO1.338 | cgpGmo-S1265a | V | 1 | 0.528 |
| 282 | 2244C1CO1.460 | cgpGmo-S1265b | V | 2 | 0.87 |
| 283 | 2244C1CO1.658 | cgpGmo-S1265c | V | 2 | 0.96 |
| 284 | 2261C1CO1.466 | cgpGmo-S1267 |  | 2 | 0.96 |
| 285 | 2282C1CO1.237 | cgpGmo-S1268 | V | 2 | 0.9 |
| 286 | 2293C1CO1.596 | cgpGmo-S1269 | V | 2 | 0.97 |
| 287 | 1011C1CO1.158 | cgpGmo-S126a | V | 2 | 0.97 |
| 288 | 1011C1CO1.430 | cgpGmo-S126b | V | 1 | 0.821 |
| 289 | 10152C1CO1.625 | cgpGmo-S127 | V | 1 | 0.896 |
| 290 | 2311C1CO1.190 | cgpGmo-S1270 |  | 2 | 0.91 |
| 291 | 2330C1CO1.269 | cgpGmo-S1272 | V | 2 | 0.88 |
| 292 | 2337C1CO1.284 | cgpGmo-S1273 | V | 2 | 0.84 |
| 293 | 2357C2CO1.233 | cgpGmo-S1274 |  | 2 | 0.73 |
| 294 | 2380C1CO1.258 | cgpGmo-S1276a | V | 2 | 0.69 |
| 295 | 2380C1CO1.675 | cgpGmo-S1276b |  | 1 | 0.662 |
| 296 | 2432C1CO1.213 | cgpGmo-S1278 | V | 2 | 0.92 |
| 297 | 2442C1CO1.490 | cgpGmo-S1279 | V | 2 | 0.48 |
| 298 | 2463C3CO1.462 | cgpGmo-S1280 | V | 2 | 0.93 |
| 299 | 2471C2CO1.537 | cgpGmo-S1281 | V | 2 | 0.74 |
| 300 | 2523C1CO1.535 | cgpGmo-S1283 |  | 2 | 0.93 |
| 301 | 252C1CO1.574 | cgpGmo-S1284 | V | 2 | 0.98 |
| 302 | 2568C2CO1.388 | cgpGmo-S1287 | V | 2 | 1 |
| 303 | 2577C1CO1.355 | cgpGmo-S1288 |  | 2 | 0.81 |
| 304 | 101C3CO1.99 | cgpGmo-S129 | V | 1 | 0.823 |
| 305 | 2581C2CO1.625 | cgpGmo-S1290 | V | 2 | 0.79 |
| 306 | 262C1CO1.163 | cgpGmo-S1291 | V | 2 | 0.93 |
| 307 | 2660C1CO1.418 | cgpGmo-S1294 | V | 2 | 0.8 |
| 308 | 268C3CO2.464 | cgpGmo-S1295a |  | 2 | 0.98 |
| 309 | 268C3CO2.740 | cgpGmo-S1295b |  | 2 | 0.94 |
| 310 | 271C1CO1.267 | cgpGmo-S1296 | V | 2 | 0.92 |
| 311 | 2722C1CO1.439 | cgpGmo-S1297a | V | 2 | 0.84 |
| 312 | 2722C2CO1.598 | cgpGmo-S1297b |  | 2 | 0.72 |
| 313 | 2726C1CO1.534 | cgpGmo-S1298 |  | 2 | 0.87 |
| 314 | 10247C1CO1.416 | cgpGmo-S130 | V | 1 | 0.865 |
| 315 | 2744C1CO1.261 | cgpGmo-S1300a | V | 2 | 0.95 |
| 316 | 2744C1CO1.767 | cgpGmo-S1300b |  | 2 | 0.72 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 317 | 2756C2CO1.571 | cgpGmo-S1301 | V | 2 | 0.94 |
| 318 | 2756C4CO1.469 | cgpGmo-S1302 | V | 2 | 0.77 |
| 319 | 2758C1CO1.580 | cgpGmo-S1303 |  | 2 | 0.93 |
| 320 | 276C2CO1.434 | cgpGmo-S1304a | V | 2 | 0.97 |
| 321 | 276C2CO1.504 | cgpGmo-S1304b | V | 2 | 0.92 |
| 322 | 2780C1CO1.510 | cgpGmo-S1305 |  | 2 | 0.85 |
| 323 | 2797C1CO1.633 | cgpGmo-S1306 |  | 2 | 0.91 |
| 324 | 281C2CO1.562 | cgpGmo-S1308 | V | 2 | 0.98 |
| 325 | 1026C2CO1.273 | cgpGmo-S131 |  | 1 | 0.882 |
| 326 | 2881C2CO1.159 | cgpGmo-S1310 | V | 2 | 0.84 |
| 327 | 2898C1CO1.336 | cgpGmo-S1312 | V | 2 | 0.59 |
| 328 | 2929C1CO1.64 | cgpGmo-S1315 | V | 2 | 0.96 |
| 329 | 2940C1CO1.576 | cgpGmo-S1316 | V | 2 | 0.95 |
| 330 | 2952C2CO1.192 | cgpGmo-S1317 |  | 2 | 0.81 |
| 331 | 2988C1CO1.305 | cgpGmo-S1319 |  | 2 | 0.94 |
| 332 | 10285C1CO1.215 | cgpGmo-S132 |  | 1 | 0.815 |
| 333 | 2993C1CO1.495 | cgpGmo-S1320 | V | 2 | 0.91 |
| 334 | 299C1CO1.223 | cgpGmo-S1321 | V | 2 | 0.97 |
| 335 | 3024C2CO1.304 | cgpGmo-S1323 | V | 2 | 0.96 |
| 336 | 3031C1CO1.530 | cgpGmo-S1324 |  | 2 | 0.8 |
| 337 | 3041C3CO1.141 | cgpGmo-S1325a |  | 2 | 0.58 |
| 338 | 3041C3CO1.661 | cgpGmo-S1325b |  | 2 | 0.64 |
| 339 | 3042C1CO1.551 | cgpGmo-S1326 | V | 2 | 0.92 |
| 340 | 3057C1CO1.850 | cgpGmo-S1327a | V | 2 | 0.82 |
| 341 | 3057C1CO1.928 | cgpGmo-S1327b |  | 2 | 0.98 |
| 342 | 3081C1CO1.312 | cgpGmo-S1328 | V | 2 | 0.78 |
| 343 | 3088C1CO1.794 | cgpGmo-S1329 | V | 2 | 0.7 |
| 344 | 10293C1CO1.650 | cgpGmo-S133 | V | 1 | 0.912 |
| 345 | 3099C1CO1.204 | cgpGmo-S1330 |  | 2 | 0.73 |
| 346 | 311C1CO1.517 | cgpGmo-S1331 |  | 2 | 0.91 |
| 347 | 3172C1CO1.116 | cgpGmo-S1332 | V | 2 | 0.93 |
| 348 | 3174C1CO1.162 | cgpGmo-S1333 |  | 2 | 0.89 |
| 349 | 3176C2CO1.333 | cgpGmo-S1334 | V | 2 | 0.72 |
| 350 | 3191C1CO1.397 | cgpGmo-S1335 | V | 2 | 0.92 |
| 351 | 3214C1CO1.85 | cgpGmo-S1336 | V | 2 | 0.93 |
| 352 | 3239C1CO1.514 | cgpGmo-S1337 | V | 2 | 0.92 |
| 353 | 3252C1CO1.148 | cgpGmo-S1338 | V | 2 | 0.76 |
| 354 | 3295C1CO1.390 | cgpGmo-S1339 | V | 2 | 0.84 |
| 355 | 10330C1CO1.584 | cgpGmo-S134 | V | 1 | 0.624 |
| 356 | 3327C1CO1.588 | cgpGmo-S1340 | V | 2 | 0.84 |
| 357 | 3341C1CO1.610 | cgpGmo-S1341 |  | 2 | 0.8 |
| 358 | 3357C1CO1.542 | cgpGmo-S1342 | V | 2 | 0.95 |
| 359 | 33C1CO1.476 | cgpGmo-S1344 | V | 2 | 0.93 |
| 360 | 3411C1CO1.411 | cgpGmo-S1346 | V | 2 | 0.57 |
| 361 | 3418C1CO1.504 | cgpGmo-S1347 | V | 2 | 0.95 |
| 362 | 3420C1CO1.616 | cgpGmo-S1348 |  | 2 | 0.77 |
| 363 | 10340C1CO1.574 | cgpGmo-S135 | V | 1 | 0.604 |
| 364 | 3433C1CO1.513 | cgpGmo-S1350 | V | 2 | 0.65 |
| 365 | 3539C1CO1.797 | cgpGmo-S1354 | V | 2 | 0.91 |
| 366 | 3556C1CO1.522 | cgpGmo-S1355 |  | 2 | 0.84 |
| 367 | 3580C1CO1.179 | cgpGmo-S1357a |  | 2 | 0.92 |
| 368 | 3580C1CO1.451 | cgpGmo-S1357b |  | 2 | 0.43 |
| 369 | 3582C1CO1.307 | cgpGmo-S1358 | V | 2 | 0.96 |
| 370 | 3602C1CO1.568 | cgpGmo-S1359 | V | 2 | 0.87 |
| 371 | 10343C1CO1.545 | cgpGmo-S136 | V | 1 | 0.894 |
| 372 | 3603C1CO1.207 | cgpGmo-S1360a |  | 2 | 0.78 |
| 373 | 3603C1CO1.319 | cgpGmo-S1360b |  | 2 | 0.99 |
| 374 | 3607C2CO1.557 | cgpGmo-S1362 |  | 2 | 0.86 |
| 375 | 3632C1CO1.143 | cgpGmo-S1363 | V | 2 | 0.93 |
| 376 | 3652C2CO1.370 | cgpGmo-S1365a | V | 2 | 0.9 |
| 377 | 3652C2CO1.494 | cgpGmo-S1365b | V | 2 | 0.89 |
| 378 | 3657C2CO1.358 | cgpGmo-S1367a | V | 2 | 0.95 |
| 379 | 3657C2CO1.469 | cgpGmo-S1367b |  | 2 | 0.94 |
| 380 | 3673C1CO1.486 | cgpGmo-S1368 |  | 2 | 0.59 |
| 381 | 3696C1CO1.1386 | cgpGmo-S1369 | V | 2 | 0.96 |
| 382 | 1036C1CO1.238 | cgpGmo-S137 | V | 1 | 0.728 |
| 383 | 3699C2CO1.734 | cgpGmo-S1370 | V | 2 | 0.63 |
| 384 | 36C3CO1.351 | cgpGmo-S1372 |  | 2 | 0.83 |
| 385 | 3716C1CO1.291 | cgpGmo-S1373 | V | 2 | 0.92 |
| 386 | 371C1CO1.180 | cgpGmo-S1374 |  | 2 | 0.86 |
| 387 | 3752C2CO1.448 | cgpGmo-S1376 |  | 2 | 0.98 |
| 388 | 3767C1CO1.577 | cgpGmo-S1377 | V | 2 | 0.9 |
| 389 | 3778C1CO1.166 | cgpGmo-S1378 | V | 2 | 0.96 |
| 390 | 3819C1CO1.92 | cgpGmo-S1379 | V | 2 | 0.91 |
| 391 | 1048C1CO1.744 | cgpGmo-S138 | V | 1 | 0.828 |
| 392 | 3820C1CO1.229 | cgpGmo-S1380 |  | 2 | 0.92 |
| 393 | 3850C1CO1.120 | cgpGmo-S1381 |  | 2 | 0.84 |
| 394 | 3864C1CO1.1100 | cgpGmo-S1382 | V | 2 | 0.99 |
| 395 | 3872C1CO1.504 | cgpGmo-S1384 | V | 2 | 0.91 |
| 396 | 3890C1CO1.337 | cgpGmo-S1385a | V | 2 | 0.99 |
| 397 | 3890C1CO1.552 | cgpGmo-S1385b | V | 2 | 0.95 |
| 398 | 389C9CO1.314 | cgpGmo-S1387a |  | 1 | 0.876 |
| 399 | 389C9CO1.467 | cgpGmo-S1387b |  | 2 | 0.96 |
| 400 | 3933C1CO1.224 | cgpGmo-S1389 |  | 2 | 0.92 |
| 401 | 10521C1CO1.80 | cgpGmo-S139 |  | 1 | 0.774 |
| 402 | 3990C1CO1.240 | cgpGmo-S1390a | V | 2 | 0.97 |
| 403 | 3990C1CO1.411 | cgpGmo-S1390b |  | 2 | 0.99 |
| 404 | 399C4CO1.141 | cgpGmo-S1391 | V | 2 | 0.74 |
| 405 | 399C5CO1.668 | cgpGmo-S1392 |  | 2 | 0.48 |
| 406 | 4037C1CO1.293 | cgpGmo-S1393a | V | 2 | 0.98 |
| 407 | 4037C1CO1.554 | cgpGmo-S1393b | V | 2 | 0.97 |
| 408 | 4048C1CO1.289 | cgpGmo-S1394a | V | 2 | 0.78 |
| 409 | 4048C1CO1.570 | cgpGmo-S1394b | V | 2 | 0.94 |
| 410 | 4076C1CO1.382 | cgpGmo-S1396 |  | 2 | 0.96 |
| 411 | 4096C2CO1.177 | cgpGmo-S1397 | V | 2 | 0.97 |
| 412 | 4113C2CO1.349 | cgpGmo-S1399a | V | 2 | 0.97 |
| 413 | 4113C2CO1.423 | cgpGmo-S1399b | V | 2 | 0.93 |
| 414 | 10465C1CO1.148 | cgpGmo-S13a |  | 1 | 0.875 |
| 415 | 10465C1CO1.547 | cgpGmo-S13b | V | 2 | 0.9 |
| 416 | 452C2CO1.147 | cgpGmo-S14 |  | 1 | 0.437 |
| 417 | 10557C1CO1.376 | cgpGmo-S140 | V | 1 | 0.811 |
| 418 | 4153C2CO1.564 | cgpGmo-S1401 | V | 2 | 0.9 |
| 419 | 4287C1CO1.501 | cgpGmo-S1404 |  | 2 | 0.7 |
| 420 | 4321C1CO1.398 | cgpGmo-S1406 | V | 2 | 0.95 |
| 421 | 4325C1CO1.157 | cgpGmo-S1407 | V | 2 | 0.94 |
| 422 | 432C1CO1.327 | cgpGmo-S1408 | V | 2 | 0.94 |
| 423 | 4354C1CO1.459 | cgpGmo-S1410 | V | 2 | 0.88 |
| 424 | 4377C1CO1.292 | cgpGmo-S1412 | V | 2 | 0.87 |
| 425 | 4387C1CO1.490 | cgpGmo-S1413 |  | 2 | 0.93 |
| 426 | 4457C1CO1.289 | cgpGmo-S1417 | V | 2 | 0.68 |
| 427 | 4471C1CO1.301 | cgpGmo-S1418 | V | 2 | 0.97 |
| 428 | 10580C1CO1.134 | cgpGmo-S142 | V | 1 | 0.639 |
| 429 | 4510C1CO1.286 | cgpGmo-S1421 |  | 2 | 0.9 |
| 430 | 4543C2CO1.545 | cgpGmo-S1423a | V | 2 | 0.97 |
| 431 | 4543C2CO1.672 | cgpGmo-S1423b |  | 1 | 0.785 |
| 432 | 456C1CO1.220 | cgpGmo-S1424a |  | 1 | 0.806 |
| 433 | 456C1CO1.367 | cgpGmo-S1424b | V | 2 | 0.99 |
| 434 | 4594C1CO1.1283 | cgpGmo-S1425 | V | 2 | 0.9 |
| 435 | 4636C2CO1.324 | cgpGmo-S1426 | V | 2 | 0.94 |
| 436 | 4647C1CO1.423 | cgpGmo-S1427 |  | 2 | 0.67 |
| 437 | 4659C1CO1.435 | cgpGmo-S1428 | V | 2 | 0.81 |
| 438 | 1060C1CO1.304 | cgpGmo-S143 | V | 1 | 0.823 |
| 439 | 4697C1CO1.270 | cgpGmo-S1430a | V | 2 | 0.96 |
| 440 | 4697C1CO1.624 | cgpGmo-S1430b | V | 2 | 0.94 |
| 441 | 4699C1CO1.364 | cgpGmo-S1431a | V | 2 | 0.91 |
| 442 | 4699C1CO1.442 | cgpGmo-S1431b |  | 1 | 0.889 |
| 443 | 4699C1CO1.531 | cgpGmo-S1431c |  | 2 | 0.9 |
| 444 | 4712C1CO1.592 | cgpGmo-S1432 | V | 2 | 0.84 |
| 445 | 4748C1CO1.393 | cgpGmo-S1435 | V | 2 | 0.98 |
| 446 | 4802C1CO1.592 | cgpGmo-S1438 | V | 2 | 0.98 |
| 447 | 10641C1CO1.392 | cgpGmo-S144 |  | 1 | 0.665 |
| 448 | 4843C1CO1.114 | cgpGmo-S1441 |  | 2 | 0.91 |
| 449 | 4847C1CO1.268 | cgpGmo-S1442 | V | 2 | 0.96 |
| 450 | 4888C1CO1.932 | cgpGmo-S1445 |  | 2 | 0.96 |
| 451 | 1065C1CO1.551 | cgpGmo-S145 | V | 1 | 0.776 |
| 452 | 4998C1CO1.73 | cgpGmo-S1451 |  | 2 | 0.89 |
| 453 | 503C1CO1.465 | cgpGmo-S1452 |  | 2 | 0.83 |
| 454 | 5089C1CO1.163 | cgpGmo-S1454 | V | 2 | 0.81 |
| 455 | 516C1CO1.428 | cgpGmo-S1455 |  | 2 | 0.92 |
| 456 | 518C1CO1.546 | cgpGmo-S1456 |  | 2 | 0.73 |
| 457 | 5280C1CO1.264 | cgpGmo-S1457 |  | 2 | 0.84 |
| 458 | 5296C1CO1.152 | cgpGmo-S1459a | V | 2 | 0.93 |
| 459 | 5296C1CO1.280 | cgpGmo-S1459b |  | 2 | 0.92 |
| 460 | 106C1CO1.209 | cgpGmo-S146 |  | 1 | 0.898 |
| 461 | 5322C1CO1.227 | cgpGmo-S1461a | V | 2 | 0.93 |
| 462 | 5322C1CO1.297 | cgpGmo-S1461b | V | 2 | 0.92 |
| 463 | 5346C2CO1.215 | cgpGmo-S1463a | V | 1 | 0.722 |
| 464 | 5346C2CO1.499 | cgpGmo-S1463b | V | 2 | 0.93 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 465 | 5373C1CO1.823 | cgpGmo-S1465 | V | 2 | 0.95 |
| 466 | 5375C1CO2.253 | cgpGmo-S1466a | V | 2 | 0.96 |
| 467 | 5375C1CO2.398 | cgpGmo-S1466b | V | 2 | 0.94 |
| 468 | 5375C2CO1.93 | cgpGmo-S1467 | V | 2 | 0.85 |
| 469 | 5421C1CO1.240 | cgpGmo-S1469 | V | 2 | 0.93 |
| 470 | 1073C1CO1.202 | cgpGmo-S147 | V | 1 | 0.851 |
| 471 | 5467C1CO1.160 | cgpGmo-S1470 |   | 2 | 0.78 |
| 472 | 5504C1CO1.387 | cgpGmo-S1471 | V | 2 | 0.93 |
| 473 | 5517C1CO1.337 | cgpGmo-S1473 | V | 2 | 0.69 |
| 474 | 5600C1CO1.268 | cgpGmo-S1474 | V | 2 | 0.93 |
| 475 | 5617C1CO1.103 | cgpGmo-S1475 | V | 2 | 0.97 |
| 476 | 5625C1CO1.558 | cgpGmo-S1476a |   | 2 | 0.99 |
| 477 | 5625C1CO1.630 | cgpGmo-S1476b |   | 2 | 0.98 |
| 478 | 1074C2CO1.571 | cgpGmo-S148 |   | 1 | 0.483 |
| 479 | 568C2CO1.420 | cgpGmo-S1480 |   | 2 | 0.77 |
| 480 | 5737C1CO1.405 | cgpGmo-S1482 | V | 2 | 0.93 |
| 481 | 5743C2CO1.555 | cgpGmo-S1483 | V | 2 | 0.65 |
| 482 | 5747C1CO1.415 | cgpGmo-S1484 | V | 2 | 0.93 |
| 483 | 5827C1CO1.980 | cgpGmo-S1487a |   | 2 | 0.98 |
| 484 | 5827C1CO1.1105 | cgpGmo-S1487b |   | 2 | 0.95 |
| 485 | 5827C1CO1.1331 | cgpGmo-S1487c |   | 2 | 0.96 |
| 486 | 5827C1CO1.1420 | cgpGmo-S1487d |   | 1 | 0.474 |
| 487 | 5854C1CO1.475 | cgpGmo-S1489 | V | 2 | 0.96 |
| 488 | 1077C1CO1.170 | cgpGmo-S149 | V | 1 | 0.7 |
| 489 | 5869C1CO1.1200 | cgpGmo-S1490 |   | 2 | 0.67 |
| 490 | 5905C1CO1.177 | cgpGmo-S1491a |   | 2 | 0.64 |
| 491 | 5905C1CO2.292 | cgpGmo-S1491b | V | 1 | 0.561 |
| 492 | 5905C1CO2.516 | cgpGmo-S1491c | V | 2 | 0.97 |
| 493 | 5913C1CO1.190 | cgpGmo-S1492 |   | 2 | 0.86 |
| 494 | 5927C1CO1.395 | cgpGmo-S1493 |   | 2 | 0.9 |
| 495 | 5940C2CO1.1110 | cgpGmo-S1495 | V | 2 | 0.94 |
| 496 | 5977C2CO1.185 | cgpGmo-S1497 | V | 2 | 0.94 |
| 497 | 10876C1CO1.410 | cgpGmo-S150 | V | 1 | 0.88 |
| 498 | 6017C1CO1.424 | cgpGmo-S1501a |   | 2 | 0.81 |
| 499 | 6017C1CO1.552 | cgpGmo-S1501b |   | 2 | 0.88 |
| 500 | 604C1CO1.333 | cgpGmo-S1503 | V | 2 | 0.94 |
| 501 | 6051C2CO1.253 | cgpGmo-S1504 | V | 2 | 0.92 |
| 502 | 6096C1CO1.150 | cgpGmo-S1505 |   | 2 | 0.76 |
| 503 | 6142C1CO1.242 | cgpGmo-S1506 | V | 2 | 0.96 |
| 504 | 6160C1CO1.86 | cgpGmo-S1507 | V | 2 | 0.75 |
| 505 | 6186C2CO1.571 | cgpGmo-S1509 |   | 2 | 0.63 |
| 506 | 1087C1CO1.259 | cgpGmo-S151 |   | 1 | 0.69 |
| 507 | 6262C1CO1.354 | cgpGmo-S1510 | V | 2 | 0.92 |
| 508 | 6370C1CO1.457 | cgpGmo-S1513 | V | 2 | 0.72 |
| 509 | 6401C1CO1.317 | cgpGmo-S1515 |   | 2 | 0.76 |
| 510 | 6462C2CO1.671 | cgpGmo-S1517 |   | 2 | 0.43 |
| 511 | 6479C1CO1.478 | cgpGmo-S1518a |   | 2 | 0.92 |
| 512 | 6479C1CO1.611 | cgpGmo-S1518b |   | 2 | 0.98 |
| 513 | 6489C1CO1.213 | cgpGmo-S1519 | V | 2 | 0.53 |
| 514 | 1098C1CO1.297 | cgpGmo-S152 | V | 1 | 0.611 |
| 515 | 6495C1CO1.380 | cgpGmo-S1520 | V | 2 | 0.94 |
| 516 | 6499C1CO1.445 | cgpGmo-S1521 |   | 2 | 0.93 |
| 517 | 655C2CO1.489 | cgpGmo-S1522 | V | 2 | 0.87 |
| 518 | 6608C1CO1.243 | cgpGmo-S1523 |   | 2 | 0.92 |
| 519 | 664C3CO1.85 | cgpGmo-S1527 |   | 2 | 0.98 |
| 520 | 6672C1CO1.288 | cgpGmo-S1528a | V | 2 | 0.66 |
| 521 | 6672C1CO1.562 | cgpGmo-S1528b |   | 2 | 0.81 |
| 522 | 6673C1CO1.387 | cgpGmo-S1529 |   | 2 | 0.92 |
| 523 | 6688C1CO1.485 | cgpGmo-S1530 | V | 2 | 0.95 |
| 524 | 6720C1CO1.684 | cgpGmo-S1532 | V | 2 | 0.96 |
| 525 | 6818C2CO1.136 | cgpGmo-S1538a | V | 2 | 0.65 |
| 526 | 6818C2CO1.369 | cgpGmo-S1538b | V | 2 | 0.95 |
| 527 | 10990C1CO1.218 | cgpGmo-S153a | V | 2 | 0.86 |
| 528 | 10990C1CO1.536 | cgpGmo-S153b |   | 1 | 0.785 |
| 529 | 10C1CO1.172 | cgpGmo-S154 | V | 1 | 0.754 |
| 530 | 6821C1CO1.174 | cgpGmo-S1540 |   | 2 | 0.99 |
| 531 | 6849C3CO1.262 | cgpGmo-S1541a | V | 2 | 0.99 |
| 532 | 6849C3CO1.403 | cgpGmo-S1541b | V | 2 | 0.95 |
| 533 | 6864C2CO1.532 | cgpGmo-S1542 |   | 2 | 0.95 |
| 534 | 6903C1CO1.213 | cgpGmo-S1543 | V | 2 | 0.94 |
| 535 | 6925C1CO1.616 | cgpGmo-S1545 |   | 2 | 0.82 |
| 536 | 7086C1CO1.118 | cgpGmo-S1547 |   | 2 | 0.83 |
| 537 | 7091C1CO1.664 | cgpGmo-S1548 | V | 2 | 0.94 |
| 538 | 712C1CO1.182 | cgpGmo-S1549 | V | 2 | 0.92 |
| 539 | 11004C1CO1.105 | cgpGmo-S155 | V | 1 | 0.796 |
| 540 | 7183C1CO1.151 | cgpGmo-S1550 |   | 2 | 0.97 |
| 541 | 7219C1CO1.301 | cgpGmo-S1552a | V | 2 | 0.88 |
| 542 | 7219C1CO1.427 | cgpGmo-S1552b | V | 1 | 0.655 |
| 543 | 724C1CO1.72 | cgpGmo-S1553a | V | 2 | 0.98 |
| 544 | 724C1CO1.555 | cgpGmo-S1553b | V | 2 | 0.85 |
| 545 | 7265C2CO1.448 | cgpGmo-S1555 |   | 2 | 0.61 |
| 546 | 7288C1CO1.182 | cgpGmo-S1556 | V | 2 | 0.66 |
| 547 | 729C1CO1.665 | cgpGmo-S1557 |   | 2 | 0.82 |
| 548 | 730C1CO1.404 | cgpGmo-S1558 | V | 2 | 0.87 |
| 549 | 7378C1CO1.1238 | cgpGmo-S1559 |   | 2 | 0.87 |
| 550 | 11012C1CO1.180 | cgpGmo-S156 | V | 1 | 0.864 |
| 551 | 7440C1CO1.213 | cgpGmo-S1562 |   | 2 | 0.69 |
| 552 | 272C1CO1.398 | cgpGmo-S1563 | V | 2 | 0.98 |
| 553 | 7441C1CO1.215 | cgpGmo-S1563a |   | 2 | 0.98 |
| 554 | 7441C1CO1.352 | cgpGmo-S1563b |   | 2 | 0.91 |
| 555 | 7441C1CO1.485 | cgpGmo-S1563c | V | 1 | 0.63 |
| 556 | 7444C1CO1.472 | cgpGmo-S1564 | V | 2 | 0.82 |
| 557 | 7451C1CO1.180 | cgpGmo-S1565 |   | 2 | 0.99 |
| 558 | 7470C1CO1.89 | cgpGmo-S1568 | V | 2 | 0.92 |
| 559 | 7505C1CO1.318 | cgpGmo-S1569 |   | 2 | 0.93 |
| 560 | 11032C1CO1.105 | cgpGmo-S157 | V | 1 | 0.718 |
| 561 | 7560C1CO1.245 | cgpGmo-S1571 | V | 2 | 0.87 |
| 562 | 7562C1CO1.138 | cgpGmo-S1572 | V | 2 | 0.93 |
| 563 | 757C1CO1.525 | cgpGmo-S1573 | V | 2 | 0.96 |
| 564 | 7607C1CO1.301 | cgpGmo-S1575 |   | 2 | 0.81 |
| 565 | 7617C1CO1.417 | cgpGmo-S1576 |   | 2 | 0.95 |
| 566 | 7620C1CO1.346 | cgpGmo-S1577 | V | 2 | 0.86 |
| 567 | 7679C1CO1.155 | cgpGmo-S1578 |   | 2 | 0.96 |
| 568 | 7695C1CO1.414 | cgpGmo-S1579 | V | 2 | 0.8 |
| 569 | 7806C1CO1.266 | cgpGmo-S1584 |   | 2 | 0.9 |
| 570 | 7810C1CO1.187 | cgpGmo-S1585a |   | 2 | 0.93 |
| 571 | 7810C1CO1.575 | cgpGmo-S1585b |   | 1 | 0.866 |
| 572 | 7861C1CO1.689 | cgpGmo-S1587 | V | 2 | 0.96 |
| 573 | 787C1CO1.313 | cgpGmo-S1588a | V | 2 | 0.96 |
| 574 | 787C1CO1.484 | cgpGmo-S1588b |   | 2 | 0.9 |
| 575 | 1103C1CO1.328 | cgpGmo-S158a | V | 1 | 0.848 |
| 576 | 1103C1CO1.495 | cgpGmo-S158b |   | 2 | 0.98 |
| 577 | 1116C1CO1.602 | cgpGmo-S159 | V | 1 | 0.899 |
| 578 | 8125C1CO1.311 | cgpGmo-S1594 |   | 2 | 0.9 |
| 579 | 8145C1CO1.316 | cgpGmo-S1596a |   | 2 | 0.87 |
| 580 | 8145C1CO1.536 | cgpGmo-S1596b | V | 2 | 0.98 |
| 581 | 8158C1CO1.520 | cgpGmo-S1597 |   | 2 | 0.82 |
| 582 | 8195C2CO1.467 | cgpGmo-S1598a | V | 1 | 0.476 |
| 583 | 8195C2CO1.572 | cgpGmo-S1598b | V | 2 | 0.82 |
| 584 | 827C1CO1.119 | cgpGmo-S1599 |   | 2 | 0.71 |
| 585 | 111C1CO1.417 | cgpGmo-S160 | V | 1 | 0.86 |
| 586 | 8283C2CO1.598 | cgpGmo-S1600 |   | 2 | 0.98 |
| 587 | 8368C1CO1.536 | cgpGmo-S1603 |   | 2 | 0.96 |
| 588 | 8371C1CO1.166 | cgpGmo-S1604a |   | 1 | 0.528 |
| 589 | 8371C1CO1.384 | cgpGmo-S1604b | V | 2 | 0.88 |
| 590 | 8371C1CO1.500 | cgpGmo-S1604c |   | 2 | 0.93 |
| 591 | 8385C1CO1.625 | cgpGmo-S1607 |   | 2 | 0.68 |
| 592 | 846C1CO1.541 | cgpGmo-S1608 |   | 2 | 0.88 |
| 593 | 8513C1CO1.348 | cgpGmo-S1609a | V | 2 | 0.98 |
| 594 | 8513C1CO1.524 | cgpGmo-S1609b | V | 2 | 0.93 |
| 595 | 854C1CO1.465 | cgpGmo-S1610a |   | 1 | 0.649 |
| 596 | 854C1CO1.634 | cgpGmo-S1610b |   | 2 | 0.87 |
| 597 | 8670C1CO1.300 | cgpGmo-S1612 |   | 2 | 0.99 |
| 598 | 880C1CO1.419 | cgpGmo-S1614 |   | 2 | 0.71 |
| 599 | 8828C1CO1.225 | cgpGmo-S1616 |   | 2 | 0.72 |
| 600 | 891C1CO1.639 | cgpGmo-S1617 | V | 2 | 0.95 |
| 601 | 1120C1CO1.377 | cgpGmo-S161a |   | 1 | 0.876 |
| 602 | 1120C1CO1.604 | cgpGmo-S161b |   | 2 | 0.88 |
| 603 | 1128C1CO1.668 | cgpGmo-S162 | V | 1 | 0.867 |
| 604 | 9139C1CO1.437 | cgpGmo-S1620 |   | 2 | 0.99 |
| 605 | 9149C1CO1.200 | cgpGmo-S1621 | V | 2 | 0.98 |
| 606 | 914C1CO1.610 | cgpGmo-S1622 | V | 2 | 0.99 |
| 607 | 9151C1CO1.430 | cgpGmo-S1623 |   | 2 | 0.68 |
| 608 | 924C13CO1.395 | cgpGmo-S1625a |   | 2 | 0.7 |
| 609 | 924C13CO1.559 | cgpGmo-S1625b |   | 2 | 0.91 |
| 610 | 924C13CO1.695 | cgpGmo-S1625c |   | 1 | 0.589 |
| 611 | 939C1CO1.92 | cgpGmo-S1628 |   | 2 | 0.93 |
| 612 | 9401C1CO1.538 | cgpGmo-S1629 | V | 2 | 0.93 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 613 | 1129C1CO1.235 | cgpGmo-S163 | V | 1 | 0.445 |
| 614 | 969C1CO1.243 | cgpGmo-S1634 | V | 2 | 0.94 |
| 615 | 9826C1CO1.566 | cgpGmo-S1637 |   | 2 | 0.66 |
| 616 | 9837C1CO1.266 | cgpGmo-S1638 | V | 2 | 0.95 |
| 617 | 983C1CO1.436 | cgpGmo-S1639 | V | 2 | 0.67 |
| 618 | 1136C1CO1.319 | cgpGmo-S164 |   | 1 | 0.707 |
| 619 | 999C3CO1.354 | cgpGmo-S1641 |   | 2 | 0.55 |
| 620 | 999C5CO1.201 | cgpGmo-S1642 |   | 2 | 0.89 |
| 621 | 0C1CO1.218 | cgpGmo-S1643 | V | 2 | 0.92 |
| 622 | 10005C1CO1.458 | cgpGmo-S1644 | V | 2 | 0.95 |
| 623 | 1005C1CO1.1075 | cgpGmo-S1645 | V | 2 | 0.92 |
| 624 | 10109C2CO1.620 | cgpGmo-S1646 |   | 2 | 0.99 |
| 625 | 1010C2CO1.377 | cgpGmo-S1647 | V | 2 | 0.93 |
| 626 | 10169C1CO1.281 | cgpGmo-S1648 |   | 2 | 0.92 |
| 627 | 1019C1CO1.263 | cgpGmo-S1649 | V | 2 | 0.8 |
| 628 | 11469C1CO1.99 | cgpGmo-S165 |   | 1 | 0.798 |
| 629 | 10218C1CO1.510 | cgpGmo-S1650 | V | 2 | 0.97 |
| 630 | 10265C1CO1.512 | cgpGmo-S1651 | V | 2 | 0.93 |
| 631 | 10363C1CO1.597 | cgpGmo-S1652 | V | 2 | 0.97 |
| 632 | 10377C1CO1.101 | cgpGmo-S1653 | V | 2 | 0.95 |
| 633 | 1044C1CO1.603 | cgpGmo-S1654 | V | 2 | 0.86 |
| 634 | 10481C1CO1.582 | cgpGmo-S1655 | V | 2 | 0.59 |
| 635 | 10487C1CO1.276 | cgpGmo-S1656 | V | 2 | 0.95 |
| 636 | 10509C1CO1.119 | cgpGmo-S1657 | V | 2 | 0.95 |
| 637 | 1053C1CO1.334 | cgpGmo-S1658 | V | 2 | 0.93 |
| 638 | 10568C1CO1.478 | cgpGmo-S1659 | V | 2 | 0.97 |
| 639 | 11488C1CO1.362 | cgpGmo-S166 | V | 1 | 0.723 |
| 640 | 10590C1CO1.513 | cgpGmo-S1660 | V | 2 | 0.94 |
| 641 | 105C1CO1.677 | cgpGmo-S1661 |   | 2 | 0.99 |
| 642 | 10609C1CO1.578 | cgpGmo-S1662 | V | 2 | 0.97 |
| 643 | 1072C1CO1.243 | cgpGmo-S1663 | V | 2 | 0.75 |
| 644 | 1083C1CO1.649 | cgpGmo-S1664 | V | 2 | 0.54 |
| 645 | 10869C1CO1.488 | cgpGmo-S1665 | V | 2 | 0.82 |
| 646 | 11034C1CO1.83 | cgpGmo-S1666 | V | 2 | 0.96 |
| 647 | 1113C1CO1.293 | cgpGmo-S1667 | V | 2 | 0.94 |
| 648 | 1117C1CO1.167 | cgpGmo-S1668 | V | 2 | 0.92 |
| 649 | 11217C1CO1.193 | cgpGmo-S1669 |   | 2 | 0.98 |
| 650 | 1148C1CO1.600 | cgpGmo-S167 | V | 1 | 0.79 |
| 651 | 11305C1CO1.338 | cgpGmo-S1670 | V | 2 | 0.94 |
| 652 | 11382C1CO1.599 | cgpGmo-S1671 |   | 2 | 0.96 |
| 653 | 1152C1CO1.129 | cgpGmo-S1672 | V | 2 | 0.99 |
| 654 | 11916C1CO1.209 | cgpGmo-S1673 | V | 2 | 0.92 |
| 655 | 1201C1CO1.742 | cgpGmo-S1674 | V | 2 | 0.92 |
| 656 | 1211C1CO1.141 | cgpGmo-S1675 | V | 2 | 0.95 |
| 657 | 1247C3CO1.876 | cgpGmo-S1676 |   | 2 | 0.97 |
| 658 | 125C1CO1.584 | cgpGmo-S1677 | V | 2 | 0.92 |
| 659 | 1274C1CO1.245 | cgpGmo-S1678 | V | 2 | 0.97 |
| 660 | 1308C1CO1.110 | cgpGmo-S1679 | V | 2 | 0.65 |
| 661 | 11503C1CO1.495 | cgpGmo-S168 |   | 1 | 0.892 |
| 662 | 1316C1CO1.1402 | cgpGmo-S1680 |   | 2 | 0.93 |
| 663 | 1339C1CO1.304 | cgpGmo-S1681 | V | 2 | 0.98 |
| 664 | 1346C1CO1.209 | cgpGmo-S1682 |   | 2 | 0.94 |
| 665 | 1350C5CO1.168 | cgpGmo-S1683 | V | 2 | 0.97 |
| 666 | 1360C1CO1.269 | cgpGmo-S1684 |   | 2 | 0.98 |
| 667 | 1391C2CO1.215 | cgpGmo-S1685 |   | 2 | 0.71 |
| 668 | 1404C1CO1.66 | cgpGmo-S1686 |   | 2 | 0.97 |
| 669 | 1409C1CO1.1090 | cgpGmo-S1687 |   | 2 | 0.92 |
| 670 | 1410C1CO1.168 | cgpGmo-S1688 |   | 2 | 0.98 |
| 671 | 1414C1CO1.566 | cgpGmo-S1689 | V | 2 | 0.94 |
| 672 | 1415C1CO1.677 | cgpGmo-S1690 |   | 2 | 0.87 |
| 673 | 1426C1CO1.246 | cgpGmo-S1691 | V | 2 | 0.92 |
| 674 | 1434C1CO1.283 | cgpGmo-S1692 |   | 2 | 0.98 |
| 675 | 1453C1CO1.298 | cgpGmo-S1693 | V | 2 | 0.7 |
| 676 | 145C1CO1.261 | cgpGmo-S1694 |   | 2 | 0.92 |
| 677 | 1467C1CO1.440 | cgpGmo-S1695 |   | 2 | 0.99 |
| 678 | 1479C1CO1.257 | cgpGmo-S1696 |   | 2 | 0.94 |
| 679 | 1495C2CO1.341 | cgpGmo-S1697 | V | 2 | 0.95 |
| 680 | 1507C1CO1.82 | cgpGmo-S1698 | V | 2 | 1 |
| 681 | 1512C1CO1.647 | cgpGmo-S1699 |   | 2 | 0.9 |
| 682 | 8106C1CO1.230 | cgpGmo-S16a | V | 2 | 0.93 |
| 683 | 8106C1CO1.666 | cgpGmo-S16b |   | 1 | 0.85 |
| 684 | 1155C1CO1.267 | cgpGmo-S170 | V | 1 | 0.805 |
| 685 | 1524C1CO1.369 | cgpGmo-S1700 | V | 2 | 0.92 |
| 686 | 1536C2CO1.241 | cgpGmo-S1701 | V | 2 | 0.97 |
| 687 | 1540C1CO1.292 | cgpGmo-S1702 | V | 2 | 0.97 |
| 688 | 1591C1CO1.509 | cgpGmo-S1703 | V | 2 | 0.93 |
| 689 | 1597C1CO1.313 | cgpGmo-S1704 | V | 2 | 0.88 |
| 690 | 1612C1CO1.537 | cgpGmo-S1705 | V | 2 | 0.59 |
| 691 | 1625C1CO1.549 | cgpGmo-S1706 | V | 2 | 0.96 |
| 692 | 1630C3CO1.531 | cgpGmo-S1707 | V | 2 | 0.94 |
| 693 | 1637C1CO2.549 | cgpGmo-S1708 | V | 2 | 0.94 |
| 694 | 1652C1CO1.629 | cgpGmo-S1709 |   | 2 | 0.96 |
| 695 | 1161C1CO1.368 | cgpGmo-S171 | V | 1 | 0.841 |
| 696 | 1671C1CO1.340 | cgpGmo-S1710 | V | 2 | 0.96 |
| 697 | 1678C1CO1.81 | cgpGmo-S1711 |   | 2 | 0.97 |
| 698 | 168C1CO1.196 | cgpGmo-S1712 | V | 2 | 0.87 |
| 699 | 170C1CO1.698 | cgpGmo-S1713 | V | 2 | 0.98 |
| 700 | 1733C1CO1.202 | cgpGmo-S1714 | V | 2 | 0.82 |
| 701 | 1739C1CO1.533 | cgpGmo-S1715 | V | 2 | 0.93 |
| 702 | 1754C2CO1.245 | cgpGmo-S1716 | V | 2 | 0.94 |
| 703 | 1771C1CO1.522 | cgpGmo-S1717 |   | 2 | 0.98 |
| 704 | 1775C1CO1.606 | cgpGmo-S1718 | V | 2 | 0.93 |
| 705 | 1799C2CO1.554 | cgpGmo-S1719 |   | 2 | 0.98 |
| 706 | 1161C2CO1.166 | cgpGmo-S172 | V | 1 | 0.511 |
| 707 | 179C1CO1.565 | cgpGmo-S1720 | V | 2 | 0.92 |
| 708 | 17C2CO1.357 | cgpGmo-S1721 | V | 2 | 0.94 |
| 709 | 181C1CO1.65 | cgpGmo-S1722 |   | 2 | 0.99 |
| 710 | 184C1CO1.525 | cgpGmo-S1723 |   | 2 | 0.97 |
| 711 | 1867C2CO1.217 | cgpGmo-S1724 | V | 2 | 0.91 |
| 712 | 1876C1CO1.204 | cgpGmo-S1725 | V | 2 | 0.93 |
| 713 | 187C1CO1.589 | cgpGmo-S1726 |   | 2 | 0.99 |
| 714 | 1926C1CO1.284 | cgpGmo-S1727 | V | 2 | 1 |
| 715 | 1944C2CO1.941 | cgpGmo-S1728 | V | 2 | 0.85 |
| 716 | 1952C1CO1.559 | cgpGmo-S1729 |   | 2 | 0.94 |
| 717 | 1167C1CO1.107 | cgpGmo-S173 | V | 1 | 0.902 |
| 718 | 1959C2CO1.349 | cgpGmo-S1730 | V | 2 | 0.98 |
| 719 | 1965C1CO1.481 | cgpGmo-S1731 | V | 2 | 0.9 |
| 720 | 1966C1CO1.301 | cgpGmo-S1732 |   | 2 | 0.98 |
| 721 | 2011C1CO1.141 | cgpGmo-S1733 | V | 2 | 0.96 |
| 722 | 2022C1CO1.75 | cgpGmo-S1734 |   | 2 | 0.97 |
| 723 | 2025C1CO1.702 | cgpGmo-S1735 |   | 2 | 0.99 |
| 724 | 2052C1CO1.474 | cgpGmo-S1736 | V | 2 | 0.93 |
| 725 | 2075C1CO1.706 | cgpGmo-S1737 | V | 2 | 0.93 |
| 726 | 2089C1CO1.534 | cgpGmo-S1738 | V | 2 | 0.93 |
| 727 | 208C1CO1.333 | cgpGmo-S1739 | V | 2 | 0.94 |
| 728 | 116C1CO1.664 | cgpGmo-S174 | V | 1 | 0.747 |
| 729 | 2095C1CO1.513 | cgpGmo-S1740 |   | 2 | 0.98 |
| 730 | 2118C1CO1.434 | cgpGmo-S1741 | V | 2 | 0.98 |
| 731 | 2131C1CO1.96 | cgpGmo-S1742 | V | 2 | 0.82 |
| 732 | 2134C2CO1.476 | cgpGmo-S1743 | V | 2 | 0.92 |
| 733 | 2150C1CO1.441 | cgpGmo-S1744 | V | 2 | 0.98 |
| 734 | 2158C1CO1.167 | cgpGmo-S1745 | V | 2 | 0.95 |
| 735 | 2165C1CO1.266 | cgpGmo-S1746 |   | 2 | 0.96 |
| 736 | 2166C1CO1.198 | cgpGmo-S1747 | V | 2 | 0.94 |
| 737 | 2168C1CO1.530 | cgpGmo-S1748 | V | 2 | 0.93 |
| 738 | 216C1CO1.473 | cgpGmo-S1749 | V | 2 | 0.94 |
| 739 | 11702C1CO1.644 | cgpGmo-S175 | V | 1 | 0.66 |
| 740 | 2188C2CO1.590 | cgpGmo-S1750 |   | 2 | 0.94 |
| 741 | 2193C1CO1.209 | cgpGmo-S1751 | V | 2 | 0.97 |
| 742 | 2197C1CO1.227 | cgpGmo-S1752 | V | 2 | 0.96 |
| 743 | 2201C2CO1.551 | cgpGmo-S1753 |   | 2 | 0.99 |
| 744 | 2202C1CO1.119 | cgpGmo-S1754 | V | 2 | 0.93 |
| 745 | 2205C1CO1.258 | cgpGmo-S1755 | V | 2 | 0.99 |
| 746 | 2231C1CO1.172 | cgpGmo-S1756 |   | 2 | 0.96 |
| 747 | 2237C1CO1.125 | cgpGmo-S1757 | V | 2 | 0.76 |
| 748 | 2254C17CO1.279 | cgpGmo-S1758 |   | 2 | 0.99 |
| 749 | 2254C18CO1.313 | cgpGmo-S1759 |   | 2 | 0.92 |
| 750 | 1172C1CO1.662 | cgpGmo-S176 |   | 1 | 0.819 |
| 751 | 2263C1CO1.402 | cgpGmo-S1760 | V | 2 | 0.97 |
| 752 | 2269C1CO1.558 | cgpGmo-S1761 | V | 2 | 0.96 |
| 753 | 2277C1CO1.176 | cgpGmo-S1762 | V | 2 | 0.96 |
| 754 | 2295C1CO1.556 | cgpGmo-S1763 | V | 2 | 0.92 |
| 755 | 2306C2CO1.268 | cgpGmo-S1764 | V | 2 | 0.95 |
| 756 | 2318C1CO1.1248 | cgpGmo-S1765 |   | 2 | 0.75 |
| 757 | 232C2CO1.253 | cgpGmo-S1766 |   | 2 | 0.9 |
| 758 | 2361C1CO1.632 | cgpGmo-S1767 | V | 2 | 0.95 |
| 759 | 2387C1CO1.345 | cgpGmo-S1768 | V | 2 | 0.94 |
| 760 | 2399C1CO1.352 | cgpGmo-S1769 | V | 2 | 0.93 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 761 | 2401C2CO1.418 | cgpGmo-S1770 | V | 2 | 0.59 |
| 762 | 2410C1CO1.282 | cgpGmo-S1771 | V | 2 | 0.98 |
| 763 | 2422C1CO1.421 | cgpGmo-S1772 |   | 2 | 0.93 |
| 764 | 2426C1CO1.333 | cgpGmo-S1773 | V | 2 | 0.95 |
| 765 | 2451C1CO1.369 | cgpGmo-S1774 | V | 2 | 0.98 |
| 766 | 2491C1CO1.326 | cgpGmo-S1775 | V | 2 | 0.6 |
| 767 | 2504C1CO1.331 | cgpGmo-S1776 |   | 2 | 0.99 |
| 768 | 2518C2CO1.326 | cgpGmo-S1777 | V | 2 | 0.92 |
| 769 | 2530C2CO1.233 | cgpGmo-S1778 | V | 2 | 0.62 |
| 770 | 2531C3CO1.1174 | cgpGmo-S1779 | V | 2 | 0.92 |
| 771 | 1173C2CO1.290 | cgpGmo-S177a | V | 2 | 0.92 |
| 772 | 1173C2CO1.633 | cgpGmo-S177b |   | 1 | 0.882 |
| 773 | 1178C1CO1.90 | cgpGmo-S178 | V | 1 | 0.848 |
| 774 | 253C1CO1.585 | cgpGmo-S1780 | V | 2 | 0.97 |
| 775 | 2549C1CO1.338 | cgpGmo-S1781 | V | 2 | 0.97 |
| 776 | 2554C1CO1.481 | cgpGmo-S1782 | V | 2 | 0.93 |
| 777 | 2589C1CO1.497 | cgpGmo-S1783 | V | 2 | 0.95 |
| 778 | 2641C1CO1.115 | cgpGmo-S1784 | V | 2 | 0.95 |
| 779 | 2649C1CO1.248 | cgpGmo-S1785 | V | 2 | 0.93 |
| 780 | 2672C1CO1.370 | cgpGmo-S1786 |   | 2 | 0.96 |
| 781 | 2695C1CO1.336 | cgpGmo-S1787 | V | 2 | 0.94 |
| 782 | 2699C2CO1.717 | cgpGmo-S1788 |   | 2 | 0.99 |
| 783 | 2715C1CO1.505 | cgpGmo-S1789 | V | 2 | 0.9 |
| 784 | 2719C1CO1.185 | cgpGmo-S1790 |   | 2 | 0.93 |
| 785 | 2739C1CO1.505 | cgpGmo-S1792 | V | 2 | 0.81 |
| 786 | 2741C1CO1.707 | cgpGmo-S1793 |   | 2 | 0.97 |
| 787 | 2757C1CO1.356 | cgpGmo-S1794 | V | 2 | 0.98 |
| 788 | 2779C1CO1.229 | cgpGmo-S1795 | V | 2 | 0.93 |
| 789 | 277C1CO1.325 | cgpGmo-S1796 |   | 2 | 0.87 |
| 790 | 2788C1CO1.799 | cgpGmo-S1797 | V | 2 | 0.98 |
| 791 | 2792C1CO1.662 | cgpGmo-S1798 | V | 2 | 0.93 |
| 792 | 2796C1CO1.101 | cgpGmo-S1799 | V | 2 | 0.97 |
| 793 | 11900C1CO1.175 | cgpGmo-S179a |   | 2 | 0.96 |
| 794 | 11900C1CO1.303 | cgpGmo-S179b |   | 1 | 0.884 |
| 795 | 372C1CO1.601 | cgpGmo-S17a |   | 2 | 0.71 |
| 796 | 372C1CO1.714 | cgpGmo-S17b |   | 1 | 0.569 |
| 797 | 1916C1CO1.417 | cgpGmo-S18 | V | 1 | 0.74 |
| 798 | 279C1CO1.700 | cgpGmo-S1800 |   | 2 | 0.98 |
| 799 | 2816C1CO1.362 | cgpGmo-S1801 | V | 2 | 0.57 |
| 800 | 2839C1CO1.376 | cgpGmo-S1802 | V | 2 | 0.95 |
| 801 | 284C1CO1.227 | cgpGmo-S1803 | V | 2 | 0.92 |
| 802 | 2859C1CO1.432 | cgpGmo-S1804 | V | 2 | 0.96 |
| 803 | 2884C1CO1.704 | cgpGmo-S1805 | V | 2 | 0.95 |
| 804 | 2899C1CO1.656 | cgpGmo-S1806 | V | 2 | 0.96 |
| 805 | 2914C1CO1.463 | cgpGmo-S1807 | V | 2 | 0.95 |
| 806 | 2916C1CO1.327 | cgpGmo-S1808 | V | 2 | 0.75 |
| 807 | 2917C2CO1.452 | cgpGmo-S1809 | V | 2 | 0.99 |
| 808 | 1215C1CO1.327 | cgpGmo-S180a | V | 2 | 0.91 |
| 809 | 1215C1CO1.596 | cgpGmo-S180b | V | 1 | 0.71 |
| 810 | 1216C1CO1.411 | cgpGmo-S181 |   | 1 | 0.817 |
| 811 | 2936C1CO1.325 | cgpGmo-S1810 | V | 2 | 0.97 |
| 812 | 2948C1CO1.662 | cgpGmo-S1811 |   | 2 | 0.97 |
| 813 | 2954C1CO1.222 | cgpGmo-S1812 |   | 2 | 0.92 |
| 814 | 2957C1CO1.841 | cgpGmo-S1813 | V | 2 | 0.89 |
| 815 | 2965C2CO1.622 | cgpGmo-S1814 | V | 2 | 0.94 |
| 816 | 296C1CO1.398 | cgpGmo-S1815 |   | 2 | 0.94 |
| 817 | 3000C1CO1.525 | cgpGmo-S1816 |   | 2 | 0.93 |
| 818 | 3004C1CO1.111 | cgpGmo-S1817 | V | 2 | 0.98 |
| 819 | 3008C1CO1.223 | cgpGmo-S1818 | V | 2 | 0.96 |
| 820 | 3059C1CO1.1264 | cgpGmo-S1819 |   | 2 | 0.96 |
| 821 | 1223C1CO1.312 | cgpGmo-S182 | V | 1 | 0.541 |
| 822 | 3091C1CO1.392 | cgpGmo-S1820 | V | 2 | 0.92 |
| 823 | 3100C1CO1.92 | cgpGmo-S1821 | V | 2 | 0.98 |
| 824 | 310C1CO1.149 | cgpGmo-S1822 |   | 2 | 0.92 |
| 825 | 3114C1CO1.287 | cgpGmo-S1823 | V | 2 | 0.98 |
| 826 | 3117C1CO1.252 | cgpGmo-S1824 | V | 2 | 0.99 |
| 827 | 3140C1CO1.133 | cgpGmo-S1825 | V | 2 | 0.97 |
| 828 | 3162C1CO1.368 | cgpGmo-S1826 | V | 2 | 0.98 |
| 829 | 3166C2CO1.459 | cgpGmo-S1827 |   | 2 | 0.93 |
| 830 | 3177C1CO1.488 | cgpGmo-S1828 |   | 2 | 0.96 |
| 831 | 318C1CO1.160 | cgpGmo-S1829 |   | 2 | 0.97 |
| 832 | 1224C1CO1.341 | cgpGmo-S183 | V | 1 | 0.839 |
| 833 | 31C1CO1.398 | cgpGmo-S1830 | V | 2 | 0.95 |
| 834 | 3221C1CO1.559 | cgpGmo-S1831 |   | 2 | 0.99 |
| 835 | 322C2CO1.674 | cgpGmo-S1832 | V | 2 | 0.96 |
| 836 | 3237C1CO1.471 | cgpGmo-S1833 | V | 2 | 0.98 |
| 837 | 3247C1CO1.95 | cgpGmo-S1834 | V | 2 | 0.98 |
| 838 | 3254C2CO1.516 | cgpGmo-S1835 | V | 2 | 0.96 |
| 839 | 3281C1CO1.427 | cgpGmo-S1836 | V | 2 | 0.96 |
| 840 | 3283C1CO1.243 | cgpGmo-S1837 | V | 2 | 0.99 |
| 841 | 3298C1CO1.396 | cgpGmo-S1838 |   | 2 | 0.97 |
| 842 | 3300C2CO1.459 | cgpGmo-S1839 | V | 2 | 0.99 |
| 843 | 1225C2CO1.618 | cgpGmo-S184 | V | 1 | 0.891 |
| 844 | 3302C1CO1.524 | cgpGmo-S1840 | V | 2 | 0.81 |
| 845 | 3321C2CO1.408 | cgpGmo-S1841 | V | 2 | 0.96 |
| 846 | 332C1CO1.302 | cgpGmo-S1842 | V | 2 | 0.99 |
| 847 | 3332C1CO1.415 | cgpGmo-S1843 | V | 2 | 0.92 |
| 848 | 3337C4CO1.558 | cgpGmo-S1844 | V | 2 | 0.98 |
| 849 | 3350C1CO1.531 | cgpGmo-S1845 | V | 2 | 0.96 |
| 850 | 3364C1CO1.455 | cgpGmo-S1846 |   | 2 | 0.94 |
| 851 | 336C1CO1.89 | cgpGmo-S1847 | V | 2 | 0.98 |
| 852 | 3375C1CO1.221 | cgpGmo-S1848 |   | 2 | 0.97 |
| 853 | 3381C2CO1.205 | cgpGmo-S1849 |   | 2 | 0.98 |
| 854 | 1229C1CO1.545 | cgpGmo-S185 | V | 1 | 0.841 |
| 855 | 3392C1CO1.288 | cgpGmo-S1850 | V | 2 | 0.98 |
| 856 | 3406C1CO1.454 | cgpGmo-S1851 |   | 2 | 0.98 |
| 857 | 3415C1CO1.401 | cgpGmo-S1852 | V | 2 | 0.88 |
| 858 | 3436C1CO1.182 | cgpGmo-S1853 | V | 2 | 0.95 |
| 859 | 3449C1CO1.691 | cgpGmo-S1854 |   | 2 | 0.97 |
| 860 | 3455C1CO1.171 | cgpGmo-S1855 |   | 2 | 0.99 |
| 861 | 3461C1CO1.307 | cgpGmo-S1856 | V | 2 | 0.94 |
| 862 | 3468C1CO1.447 | cgpGmo-S1857 | V | 2 | 0.95 |
| 863 | 346C1CO1.463 | cgpGmo-S1858 |   | 2 | 0.98 |
| 864 | 3474C1CO1.384 | cgpGmo-S1859 | V | 2 | 0.87 |
| 865 | 1231C2CO1.552 | cgpGmo-S186 |   | 1 | 0.871 |
| 866 | 347C1CO1.552 | cgpGmo-S1860 |   | 2 | 0.96 |
| 867 | 3488C1CO1.138 | cgpGmo-S1861 |   | 2 | 0.95 |
| 868 | 3496C2CO1.222 | cgpGmo-S1862 | V | 2 | 0.91 |
| 869 | 3507C1CO1.479 | cgpGmo-S1863 |   | 2 | 0.92 |
| 870 | 3511C1CO1.570 | cgpGmo-S1864 | V | 2 | 0.98 |
| 871 | 3533C1CO1.216 | cgpGmo-S1865 |   | 2 | 0.95 |
| 872 | 3554C1CO1.108 | cgpGmo-S1866 |   | 2 | 0.59 |
| 873 | 3585C2CO1.295 | cgpGmo-S1867 | V | 2 | 0.98 |
| 874 | 3590C1CO1.517 | cgpGmo-S1868 | V | 2 | 0.94 |
| 875 | 3596C1CO1.655 | cgpGmo-S1869 | V | 2 | 0.96 |
| 876 | 1236C2CO1.382 | cgpGmo-S187 |   | 1 | 0.613 |
| 877 | 3607C1CO1.386 | cgpGmo-S1870 |   | 2 | 0.75 |
| 878 | 3617C1CO1.152 | cgpGmo-S1871 |   | 2 | 0.92 |
| 879 | 362C1CO1.369 | cgpGmo-S1872 | V | 2 | 0.92 |
| 880 | 3636C1CO1.302 | cgpGmo-S1873 |   | 2 | 0.97 |
| 881 | 3647C1CO1.572 | cgpGmo-S1874 | V | 2 | 0.72 |
| 882 | 3649C1CO1.129 | cgpGmo-S1875 |   | 2 | 1 |
| 883 | 3676C1CO1.262 | cgpGmo-S1876 |   | 2 | 0.94 |
| 884 | 3679C1CO1.474 | cgpGmo-S1877 |   | 2 | 1 |
| 885 | 36C9CO1.1008 | cgpGmo-S1878 |   | 2 | 0.93 |
| 886 | 3706C1CO1.417 | cgpGmo-S1879 | V | 2 | 0.92 |
| 887 | 1237C1CO1.1032 | cgpGmo-S188 |   | 1 | 0.6 |
| 888 | 3712C3CO1.570 | cgpGmo-S1880 |   | 2 | 0.92 |
| 889 | 3718C1CO1.677 | cgpGmo-S1881 |   | 2 | 0.92 |
| 890 | 371C3CO1.234 | cgpGmo-S1882 |   | 2 | 0.95 |
| 891 | 3727C1CO1.552 | cgpGmo-S1883 | V | 2 | 0.69 |
| 892 | 3729C1CO1.531 | cgpGmo-S1884 |   | 2 | 0.92 |
| 893 | 3737C1CO1.561 | cgpGmo-S1885 |   | 2 | 0.97 |
| 894 | 3742C1CO1.649 | cgpGmo-S1886 |   | 2 | 0.94 |
| 895 | 3761C2CO1.570 | cgpGmo-S1887 | V | 2 | 0.95 |
| 896 | 3806C1CO1.849 | cgpGmo-S1888 |   | 2 | 0.92 |
| 897 | 3851C1CO1.498 | cgpGmo-S1889 |   | 2 | 0.99 |
| 898 | 1238C2CO1.220 | cgpGmo-S189 | V | 1 | 0.498 |
| 899 | 3867C1CO1.881 | cgpGmo-S1890 |   | 2 | 1 |
| 900 | 3870C1CO1.538 | cgpGmo-S1891 |   | 2 | 0.99 |
| 901 | 3881C1CO1.74 | cgpGmo-S1892 |   | 2 | 0.94 |
| 902 | 3883C1CO1.678 | cgpGmo-S1893 |   | 2 | 0.98 |
| 903 | 3894C1CO1.506 | cgpGmo-S1894 |   | 2 | 0.97 |
| 904 | 3901C1CO1.899 | cgpGmo-S1895 |   | 2 | 1 |
| 905 | 3905C1CO1.885 | cgpGmo-S1896 | V | 2 | 0.97 |
| 906 | 3918C3CO1.370 | cgpGmo-S1897 |   | 2 | 0.96 |
| 907 | 3937C1CO1.511 | cgpGmo-S1898 |   | 2 | 0.93 |
| 908 | 394C2CO1.548 | cgpGmo-S1899 | V | 2 | 0.99 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 909 | 4988C1CO1.610 | cgpGmo-S19 | V | 1 | 0.642 |
| 910 | 1259C1CO1.160 | cgpGmo-S190 | V | 1 | 0.91 |
| 911 | 3978C1CO1.163 | cgpGmo-S1900 | V | 2 | 0.92 |
| 912 | 3980C1CO1.638 | cgpGmo-S1901 |   | 2 | 0.95 |
| 913 | 3983C1CO1.275 | cgpGmo-S1902 | V | 2 | 0.97 |
| 914 | 3987C1CO1.739 | cgpGmo-S1903 | V | 2 | 0.98 |
| 915 | 4008C1CO1.545 | cgpGmo-S1904 | V | 2 | 0.95 |
| 916 | 4016C1CO1.62 | cgpGmo-S1905 | V | 2 | 0.98 |
| 917 | 4041C1CO1.449 | cgpGmo-S1906 | V | 2 | 0.93 |
| 918 | 4044C1CO1.406 | cgpGmo-S1907 | V | 2 | 0.67 |
| 919 | 4049C1CO1.243 | cgpGmo-S1908 | V | 2 | 1 |
| 920 | 4056C1CO1.674 | cgpGmo-S1909 | V | 2 | 0.96 |
| 921 | 1261C1CO1.474 | cgpGmo-S191 | V | 1 | 0.877 |
| 922 | 4068C1CO1.600 | cgpGmo-S1910 | V | 2 | 0.98 |
| 923 | 4075C1CO1.170 | cgpGmo-S1911 |   | 2 | 0.95 |
| 924 | 4082C1CO1.702 | cgpGmo-S1912 |   | 2 | 0.97 |
| 925 | 4114C1CO1.129 | cgpGmo-S1913 | V | 2 | 0.97 |
| 926 | 4115C1CO1.515 | cgpGmo-S1914 | V | 2 | 0.95 |
| 927 | 4119C1CO1.637 | cgpGmo-S1915 |   | 2 | 0.95 |
| 928 | 4138C1CO1.447 | cgpGmo-S1916 | V | 2 | 0.94 |
| 929 | 4139C1CO1.443 | cgpGmo-S1917 | V | 2 | 0.94 |
| 930 | 4141C1CO1.376 | cgpGmo-S1918 |   | 2 | 0.96 |
| 931 | 414C1CO1.432 | cgpGmo-S1919 | V | 2 | 0.99 |
| 932 | 4156C1CO1.400 | cgpGmo-S1920 | V | 2 | 0.96 |
| 933 | 415C2CO1.634 | cgpGmo-S1921 |   | 2 | 0.96 |
| 934 | 4176C1CO1.533 | cgpGmo-S1922 | V | 2 | 0.97 |
| 935 | 4185C1CO1.502 | cgpGmo-S1923 |   | 2 | 0.97 |
| 936 | 4192C1CO1.248 | cgpGmo-S1924 | V | 2 | 0.93 |
| 937 | 4203C1CO1.217 | cgpGmo-S1925 | V | 2 | 0.63 |
| 938 | 420C1CO1.249 | cgpGmo-S1926 | V | 2 | 0.82 |
| 939 | 4211C1CO1.447 | cgpGmo-S1927 | V | 2 | 0.99 |
| 940 | 4239C1CO1.62 | cgpGmo-S1928 | V | 2 | 0.92 |
| 941 | 4242C1CO1.285 | cgpGmo-S1929 | V | 2 | 0.92 |
| 942 | 1266C1CO1.382 | cgpGmo-S192a |   | 1 | 0.734 |
| 943 | 1266C1CO1.559 | cgpGmo-S192b | V | 2 | 0.77 |
| 944 | 126C1CO1.199 | cgpGmo-S193 | V | 1 | 0.873 |
| 945 | 4245C1CO1.390 | cgpGmo-S1930 |   | 2 | 0.96 |
| 946 | 426C1CO1.361 | cgpGmo-S1931 | V | 2 | 0.97 |
| 947 | 4272C1CO1.610 | cgpGmo-S1932 | V | 2 | 0.93 |
| 948 | 4279C1CO1.485 | cgpGmo-S1933 |   | 2 | 1 |
| 949 | 428C2CO1.100 | cgpGmo-S1934 |   | 2 | 0.99 |
| 950 | 429C1CO1.366 | cgpGmo-S1935 | V | 2 | 0.92 |
| 951 | 4315C1CO1.451 | cgpGmo-S1936 | V | 2 | 0.93 |
| 952 | 4358C1CO1.138 | cgpGmo-S1937 | V | 2 | 0.99 |
| 953 | 4360C1CO1.240 | cgpGmo-S1938 | V | 2 | 0.93 |
| 954 | 4380C1CO1.92 | cgpGmo-S1939 |   | 2 | 0.83 |
| 955 | 4381C1CO1.462 | cgpGmo-S1940 |   | 2 | 0.73 |
| 956 | 4382C1CO1.533 | cgpGmo-S1941 | V | 2 | 0.94 |
| 957 | 4390C2CO1.279 | cgpGmo-S1942 | V | 2 | 0.94 |
| 958 | 4416C1CO1.539 | cgpGmo-S1943 | V | 2 | 0.93 |
| 959 | 4417C1CO1.672 | cgpGmo-S1944 | V | 2 | 0.82 |
| 960 | 4427C1CO1.243 | cgpGmo-S1945 | V | 2 | 0.77 |
| 961 | 443C1CO1.429 | cgpGmo-S1946 |   | 2 | 0.96 |
| 962 | 4476C1CO1.672 | cgpGmo-S1947 | V | 2 | 0.92 |
| 963 | 4503C1CO1.307 | cgpGmo-S1948 | V | 2 | 0.88 |
| 964 | 4506C1CO1.249 | cgpGmo-S1949 | V | 2 | 0.98 |
| 965 | 1272C1CO1.263 | cgpGmo-S194a |   | 1 | 0.754 |
| 966 | 1272C1CO1.421 | cgpGmo-S194b |   | 2 | 0.98 |
| 967 | 1273C1CO1.203 | cgpGmo-S195 | V | 1 | 0.82 |
| 968 | 4508C1CO1.421 | cgpGmo-S1950 |   | 2 | 0.95 |
| 969 | 4513C1CO1.397 | cgpGmo-S1951 | V | 2 | 0.94 |
| 970 | 4517C1CO1.551 | cgpGmo-S1952 | V | 2 | 0.93 |
| 971 | 4518C1CO1.201 | cgpGmo-S1953 |   | 2 | 0.82 |
| 972 | 4524C1CO1.341 | cgpGmo-S1954 | V | 2 | 0.99 |
| 973 | 4525C1CO1.195 | cgpGmo-S1955 | V | 2 | 0.92 |
| 974 | 4529C2CO1.276 | cgpGmo-S1956 |   | 2 | 0.92 |
| 975 | 453C1CO1.285 | cgpGmo-S1957 | V | 2 | 0.94 |
| 976 | 4542C1CO1.233 | cgpGmo-S1958 |   | 2 | 0.94 |
| 977 | 4546C1CO1.322 | cgpGmo-S1959 | V | 2 | 0.95 |
| 978 | 1287C1CO1.483 | cgpGmo-S196 | V | 1 | 0.894 |
| 979 | 457C1CO1.164 | cgpGmo-S1960 |   | 2 | 0.87 |
| 980 | 4598C1CO1.135 | cgpGmo-S1961 | V | 2 | 0.96 |
| 981 | 4649C1CO1.962 | cgpGmo-S1962 | V | 2 | 0.97 |
| 982 | 4663C1CO1.477 | cgpGmo-S1963 |   | 2 | 0.99 |
| 983 | 4681C1CO1.1426 | cgpGmo-S1964 |   | 2 | 0.99 |
| 984 | 471C1CO1.410 | cgpGmo-S1965 | V | 2 | 0.95 |
| 985 | 4777C1CO1.396 | cgpGmo-S1966 | V | 2 | 0.93 |
| 986 | 477C1CO1.378 | cgpGmo-S1967 |   | 2 | 0.95 |
| 987 | 4786C1CO1.378 | cgpGmo-S1968 | V | 2 | 0.99 |
| 988 | 4800C1CO1.627 | cgpGmo-S1969 | V | 2 | 0.96 |
| 989 | 482C1CO1.348 | cgpGmo-S1970 | V | 2 | 0.95 |
| 990 | 4831C1CO1.304 | cgpGmo-S1971 |   | 2 | 0.99 |
| 991 | 4839C1CO1.476 | cgpGmo-S1972 | V | 2 | 0.97 |
| 992 | 4842C1CO1.414 | cgpGmo-S1973 |   | 2 | 0.95 |
| 993 | 4853C1CO1.120 | cgpGmo-S1974 | V | 2 | 0.99 |
| 994 | 4860C1CO1.414 | cgpGmo-S1975 |   | 2 | 0.99 |
| 995 | 4862C1CO1.250 | cgpGmo-S1976 |   | 2 | 0.98 |
| 996 | 4863C1CO1.276 | cgpGmo-S1977 | V | 2 | 0.96 |
| 997 | 4879C1CO1.438 | cgpGmo-S1978 | V | 2 | 0.94 |
| 998 | 4887C1CO1.509 | cgpGmo-S1979 | V | 2 | 0.97 |
| 999 | 1288C1CO1.252 | cgpGmo-S197a | V | 2 | 0.67 |
| 1000 | 1288C1CO1.322 | cgpGmo-S197b | V | 1 | 0.67 |
| 1001 | 1295C2CO1.333 | cgpGmo-S198 | V | 1 | 0.704 |
| 1002 | 4890C1CO1.276 | cgpGmo-S1980 |   | 2 | 0.92 |
| 1003 | 4896C1CO1.513 | cgpGmo-S1981 | V | 2 | 0.96 |
| 1004 | 4901C1CO1.320 | cgpGmo-S1982 | V | 2 | 0.98 |
| 1005 | 490C2CO2.634 | cgpGmo-S1983 |   | 2 | 0.96 |
| 1006 | 4927C1CO1.643 | cgpGmo-S1984 | V | 2 | 0.88 |
| 1007 | 4933C1CO1.252 | cgpGmo-S1985 | V | 2 | 0.92 |
| 1008 | 4957C1CO1.395 | cgpGmo-S1986 |   | 2 | 0.99 |
| 1009 | 4971C1CO1.339 | cgpGmo-S1987 |   | 2 | 0.93 |
| 1010 | 5012C1CO1.576 | cgpGmo-S1988 | V | 2 | 0.92 |
| 1011 | 5023C1CO1.317 | cgpGmo-S1989 | V | 2 | 0.53 |
| 1012 | 129C1CO1.231 | cgpGmo-S199 | V | 1 | 0.455 |
| 1013 | 502C1CO1.201 | cgpGmo-S1990 | V | 2 | 0.95 |
| 1014 | 5069C1CO1.199 | cgpGmo-S1991 | V | 2 | 0.95 |
| 1015 | 509C1CO1.113 | cgpGmo-S1992 | V | 2 | 0.96 |
| 1016 | 5104C1CO1.561 | cgpGmo-S1993 | V | 2 | 0.93 |
| 1017 | 510C4CO1.196 | cgpGmo-S1994 | V | 2 | 0.92 |
| 1018 | 5111C1CO1.515 | cgpGmo-S1995 | V | 2 | 0.96 |
| 1019 | 5125C1CO1.509 | cgpGmo-S1996 |   | 2 | 0.98 |
| 1020 | 5133C1CO1.220 | cgpGmo-S1997 | V | 2 | 0.94 |
| 1021 | 5140C1CO1.323 | cgpGmo-S1998 | V | 2 | 0.96 |
| 1022 | 515C1CO1.168 | cgpGmo-S1999 | V | 2 | 0.93 |
| 1023 | 1691C1CO1.196 | cgpGmo-S2 | V | 1 | 0.76 |
| 1024 | 5992C2CO1.479 | cgpGmo-S20 | V | 1 | 0.577 |
| 1025 | 5187C1CO1.229 | cgpGmo-S2000 |   | 2 | 0.85 |
| 1026 | 5193C1CO1.860 | cgpGmo-S2001 | V | 2 | 0.95 |
| 1027 | 5203C1CO1.431 | cgpGmo-S2002 |   | 2 | 0.93 |
| 1028 | 5209C1CO1.196 | cgpGmo-S2003 |   | 2 | 0.95 |
| 1029 | 5227C1CO1.556 | cgpGmo-S2004 |   | 2 | 0.94 |
| 1030 | 5247C1CO1.124 | cgpGmo-S2005 | V | 2 | 0.96 |
| 1031 | 5251C1CO1.339 | cgpGmo-S2006 |   | 2 | 0.97 |
| 1032 | 5269C1CO1.250 | cgpGmo-S2007 |   | 2 | 0.69 |
| 1033 | 5275C1CO1.461 | cgpGmo-S2008 | V | 2 | 0.96 |
| 1034 | 5281C1CO1.614 | cgpGmo-S2009 |   | 2 | 1 |
| 1035 | 1306C2CO1.180 | cgpGmo-S200a |   | 1 | 0.81 |
| 1036 | 1306C2CO1.379 | cgpGmo-S200b |   | 2 | 0.91 |
| 1037 | 1309C2CO1.282 | cgpGmo-S201 | V | 1 | 0.595 |
| 1038 | 5309C1CO1.854 | cgpGmo-S2010 |   | 2 | 0.99 |
| 1039 | 5325C2CO1.319 | cgpGmo-S2011 | V | 2 | 0.54 |
| 1040 | 5337C1CO1.622 | cgpGmo-S2012 |   | 2 | 0.95 |
| 1041 | 5348C1CO1.397 | cgpGmo-S2013 | V | 2 | 0.82 |
| 1042 | 5354C1CO1.536 | cgpGmo-S2014 |   | 2 | 0.97 |
| 1043 | 5364C1CO1.252 | cgpGmo-S2015 |   | 2 | 0.97 |
| 1044 | 5372C1CO1.323 | cgpGmo-S2016 |   | 2 | 0.98 |
| 1045 | 5427C1CO1.364 | cgpGmo-S2017 |   | 2 | 0.91 |
| 1046 | 5444C1CO1.522 | cgpGmo-S2018 | V | 2 | 0.97 |
| 1047 | 5451C2CO1.120 | cgpGmo-S2019 | V | 2 | 0.97 |
| 1048 | 1310C2CO1.430 | cgpGmo-S202 |   | 1 | 0.912 |
| 1049 | 5471C1CO1.330 | cgpGmo-S2020 |   | 2 | 0.74 |
| 1050 | 5498C1CO1.225 | cgpGmo-S2021 | V | 2 | 0.95 |
| 1051 | 5531C1CO1.199 | cgpGmo-S2022 |   | 2 | 0.69 |
| 1052 | 5538C1CO1.603 | cgpGmo-S2023 |   | 2 | 0.97 |
| 1053 | 553C2CO1.735 | cgpGmo-S2024 |   | 2 | 0.97 |
| 1054 | 5566C1CO1.300 | cgpGmo-S2025 | V | 2 | 0.95 |
| 1055 | 557C1CO1.537 | cgpGmo-S2026 |   | 2 | 0.98 |
| 1056 | 558C1CO1.485 | cgpGmo-S2027 | V | 2 | 0.94 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1057 | 5618C1CO1.373 | cgpGmo-S2028 | V | 2 | 0.94 |
| 1058 | 5643C1CO1.151 | cgpGmo-S2029 | V | 2 | 0.99 |
| 1059 | 1317C1CO1.397 | cgpGmo-S203 | V | 1 | 0.626 |
| 1060 | 5646C1CO1.323 | cgpGmo-S2030 |   | 2 | 0.94 |
| 1061 | 5655C1CO1.488 | cgpGmo-S2031 | V | 2 | 0.97 |
| 1062 | 5693C1CO1.230 | cgpGmo-S2032 | V | 2 | 0.98 |
| 1063 | 5722C1CO1.385 | cgpGmo-S2033 |   | 2 | 0.95 |
| 1064 | 5728C1CO1.359 | cgpGmo-S2034 | V | 2 | 0.92 |
| 1065 | 5735C1CO1.103 | cgpGmo-S2035 | V | 2 | 0.96 |
| 1066 | 5751C2CO1.588 | cgpGmo-S2036 |   | 2 | 0.99 |
| 1067 | 576C1CO1.897 | cgpGmo-S2037 | V | 2 | 0.96 |
| 1068 | 5770C1CO1.326 | cgpGmo-S2038 |   | 2 | 0.9 |
| 1069 | 5773C1CO1.627 | cgpGmo-S2039 |   | 2 | 0.82 |
| 1070 | 1324C1CO1.469 | cgpGmo-S204 | V | 1 | 0.722 |
| 1071 | 5781C1CO1.623 | cgpGmo-S2040 |   | 2 | 0.75 |
| 1072 | 5785C1CO1.591 | cgpGmo-S2041 | V | 2 | 0.89 |
| 1073 | 578C7CO1.96 | cgpGmo-S2042 | V | 2 | 0.93 |
| 1074 | 5799C1CO1.78 | cgpGmo-S2043 |   | 2 | 0.93 |
| 1075 | 581C1CO1.143 | cgpGmo-S2044 | V | 2 | 0.92 |
| 1076 | 5873C1CO1.341 | cgpGmo-S2045 |   | 2 | 0.97 |
| 1077 | 5875C1CO1.173 | cgpGmo-S2046 | V | 2 | 0.76 |
| 1078 | 5886C1CO1.527 | cgpGmo-S2047 |   | 2 | 0.97 |
| 1079 | 5892C1CO1.292 | cgpGmo-S2048 | V | 2 | 0.76 |
| 1080 | 5895C1CO1.188 | cgpGmo-S2049 | V | 2 | 0.99 |
| 1081 | 1325C1CO1.381 | cgpGmo-S205 | V | 1 | 0.764 |
| 1082 | 5896C1CO1.552 | cgpGmo-S2050 | V | 2 | 0.99 |
| 1083 | 5920C1CO1.432 | cgpGmo-S2051 |   | 2 | 0.92 |
| 1084 | 5933C1CO1.286 | cgpGmo-S2052 |   | 2 | 0.89 |
| 1085 | 5934C1CO1.667 | cgpGmo-S2053 | V | 2 | 0.75 |
| 1086 | 5941C2CO1.1141 | cgpGmo-S2054 | V | 2 | 0.98 |
| 1087 | 5964C1CO1.273 | cgpGmo-S2055 | V | 2 | 0.9 |
| 1088 | 597C1CO1.667 | cgpGmo-S2056 | V | 2 | 0.95 |
| 1089 | 5987C1CO1.226 | cgpGmo-S2057 |   | 2 | 0.98 |
| 1090 | 6007C1CO1.377 | cgpGmo-S2058 | V | 2 | 0.96 |
| 1091 | 6014C1CO1.360 | cgpGmo-S2059 | V | 2 | 0.95 |
| 1092 | 1328C1CO1.195 | cgpGmo-S206 | V | 1 | 0.861 |
| 1093 | 6040C1CO1.208 | cgpGmo-S2060 |   | 2 | 0.94 |
| 1094 | 6042C1CO1.676 | cgpGmo-S2061 |   | 2 | 0.71 |
| 1095 | 6093C1CO1.385 | cgpGmo-S2062 |   | 2 | 0.94 |
| 1096 | 6113C1CO1.385 | cgpGmo-S2063 | V | 2 | 0.92 |
| 1097 | 6188C2CO1.248 | cgpGmo-S2064 |   | 2 | 0.98 |
| 1098 | 618C1CO1.108 | cgpGmo-S2065 | V | 2 | 0.93 |
| 1099 | 6204C1CO1.260 | cgpGmo-S2066 | V | 2 | 0.98 |
| 1100 | 6215C2CO1.408 | cgpGmo-S2067 | V | 2 | 0.93 |
| 1101 | 6222C1CO1.639 | cgpGmo-S2068 | V | 2 | 0.93 |
| 1102 | 6224C1CO1.445 | cgpGmo-S2069 | V | 2 | 0.96 |
| 1103 | 132C1CO1.1121 | cgpGmo-S207 | V | 1 | 0.755 |
| 1104 | 6267C1CO1.461 | cgpGmo-S2070 | V | 2 | 0.97 |
| 1105 | 6275C1CO1.576 | cgpGmo-S2071 | V | 2 | 0.95 |
| 1106 | 6281C1CO1.393 | cgpGmo-S2072 | V | 2 | 0.92 |
| 1107 | 6289C1CO1.349 | cgpGmo-S2073 | V | 2 | 0.97 |
| 1108 | 6314C1CO1.109 | cgpGmo-S2074 | V | 2 | 0.96 |
| 1109 | 6315C1CO1.486 | cgpGmo-S2075 | V | 2 | 0.96 |
| 1110 | 631C1CO1.294 | cgpGmo-S2076 |   | 2 | 0.93 |
| 1111 | 6330C1CO1.317 | cgpGmo-S2077 | V | 2 | 0.94 |
| 1112 | 6332C1CO1.180 | cgpGmo-S2078 | V | 2 | 0.99 |
| 1113 | 6344C2CO1.292 | cgpGmo-S2079 | V | 2 | 0.94 |
| 1114 | 6357C1CO1.620 | cgpGmo-S2080 | V | 2 | 0.97 |
| 1115 | 635C3CO1.135 | cgpGmo-S2081 |   | 2 | 0.75 |
| 1116 | 6375C2CO1.601 | cgpGmo-S2082 |   | 2 | 0.75 |
| 1117 | 643C1CO1.353 | cgpGmo-S2083 | V | 2 | 0.95 |
| 1118 | 6446C1CO1.446 | cgpGmo-S2084 |   | 2 | 0.97 |
| 1119 | 6467C1CO1.105 | cgpGmo-S2085 | V | 2 | 0.93 |
| 1120 | 64C1CO1.515 | cgpGmo-S2086 |   | 2 | 0.94 |
| 1121 | 652C8CO1.491 | cgpGmo-S2087 | V | 2 | 0.92 |
| 1122 | 6544C1CO1.127 | cgpGmo-S2088 | V | 2 | 0.98 |
| 1123 | 6545C1CO2.558 | cgpGmo-S2089 | V | 2 | 0.97 |
| 1124 | 1345C1CO1.663 | cgpGmo-S209 | V | 1 | 0.639 |
| 1125 | 6547C2CO1.298 | cgpGmo-S2090 | V | 2 | 0.97 |
| 1126 | 6558C1CO1.582 | cgpGmo-S2091 | V | 2 | 0.93 |
| 1127 | 6598C2CO1.475 | cgpGmo-S2092 |   | 2 | 0.97 |
| 1128 | 6599C1CO1.463 | cgpGmo-S2093 | V | 2 | 0.98 |
| 1129 | 6600C1CO1.1338 | cgpGmo-S2094 | V | 2 | 0.92 |
| 1130 | 6658C1CO1.252 | cgpGmo-S2095 | V | 2 | 0.76 |
| 1131 | 665C3CO1.351 | cgpGmo-S2096 |   | 2 | 0.83 |
| 1132 | 6675C1CO1.512 | cgpGmo-S2097 | V | 2 | 0.95 |
| 1133 | 6704C1CO1.367 | cgpGmo-S2098 | V | 2 | 0.97 |
| 1134 | 6746C2CO1.793 | cgpGmo-S2099 | V | 2 | 0.93 |
| 1135 | 6523C1CO1.223 | cgpGmo-S21 |   | 1 | 0.641 |
| 1136 | 1347C2CO1.580 | cgpGmo-S210 | V | 1 | 0.831 |
| 1137 | 6754C1CO1.440 | cgpGmo-S2100 | V | 2 | 1 |
| 1138 | 6795C1CO1.507 | cgpGmo-S2101 | V | 2 | 0.93 |
| 1139 | 679C1CO1.356 | cgpGmo-S2102 | V | 2 | 0.84 |
| 1140 | 6808C1CO1.468 | cgpGmo-S2103 |   | 2 | 0.99 |
| 1141 | 6810C2CO1.586 | cgpGmo-S2104 | V | 2 | 0.97 |
| 1142 | 6811C1CO1.170 | cgpGmo-S2105 | V | 2 | 0.94 |
| 1143 | 6812C1CO1.509 | cgpGmo-S2106 | V | 2 | 1 |
| 1144 | 6828C1CO1.1167 | cgpGmo-S2107 |   | 2 | 0.95 |
| 1145 | 6857C1CO1.79 | cgpGmo-S2108 | V | 2 | 0.97 |
| 1146 | 687C2CO1.560 | cgpGmo-S2109 |   | 2 | 0.97 |
| 1147 | 135C1CO1.519 | cgpGmo-S211 | V | 1 | 0.652 |
| 1148 | 691C1CO1.671 | cgpGmo-S2110 |   | 2 | 0.96 |
| 1149 | 6926C1CO1.485 | cgpGmo-S2111 | V | 2 | 0.99 |
| 1150 | 694C1CO1.395 | cgpGmo-S2112 | V | 2 | 0.99 |
| 1151 | 6950C1CO1.291 | cgpGmo-S2113 |   | 2 | 0.95 |
| 1152 | 7049C1CO1.146 | cgpGmo-S2114 |   | 2 | 0.95 |
| 1153 | 7051C1CO1.285 | cgpGmo-S2115 | V | 2 | 0.97 |
| 1154 | 7055C1CO1.503 | cgpGmo-S2116 |   | 2 | 0.97 |
| 1155 | 705C1CO1.407 | cgpGmo-S2117 |   | 2 | 0.98 |
| 1156 | 70C1CO1.445 | cgpGmo-S2118 | V | 2 | 0.59 |
| 1157 | 7104C1CO1.130 | cgpGmo-S2119 | V | 2 | 0.98 |
| 1158 | 1377C1CO1.291 | cgpGmo-S212 | V | 1 | 0.807 |
| 1159 | 7129C1CO1.239 | cgpGmo-S2120 |   | 2 | 0.85 |
| 1160 | 714C1CO1.458 | cgpGmo-S2121 |   | 2 | 0.9 |
| 1161 | 7168C1CO1.214 | cgpGmo-S2122 |   | 2 | 0.93 |
| 1162 | 7178C1CO1.556 | cgpGmo-S2123 | V | 2 | 0.99 |
| 1163 | 7182C1CO1.531 | cgpGmo-S2124 |   | 2 | 0.94 |
| 1164 | 7188C1CO1.509 | cgpGmo-S2125 |   | 2 | 0.95 |
| 1165 | 71C1CO1.1376 | cgpGmo-S2126 | V | 2 | 0.97 |
| 1166 | 7224C1CO1.451 | cgpGmo-S2127 |   | 2 | 0.95 |
| 1167 | 7233C1CO1.882 | cgpGmo-S2128 |   | 2 | 0.98 |
| 1168 | 7331C1CO1.733 | cgpGmo-S2129 |   | 2 | 0.92 |
| 1169 | 1378C1CO1.487 | cgpGmo-S213 | V | 1 | 0.86 |
| 1170 | 7333C1CO1.612 | cgpGmo-S2130 | V | 2 | 0.92 |
| 1171 | 7338C1CO1.690 | cgpGmo-S2131 | V | 2 | 0.94 |
| 1172 | 7341C1CO1.253 | cgpGmo-S2132 | V | 2 | 0.93 |
| 1173 | 7410C1CO1.215 | cgpGmo-S2133 |   | 2 | 0.96 |
| 1174 | 7414C1CO1.170 | cgpGmo-S2134 | V | 2 | 0.94 |
| 1175 | 7416C2CO1.108 | cgpGmo-S2135 |   | 2 | 0.98 |
| 1176 | 7421C1CO1.345 | cgpGmo-S2136 |   | 2 | 0.98 |
| 1177 | 7443C1CO1.127 | cgpGmo-S2137 | V | 2 | 0.92 |
| 1178 | 7465C1CO1.496 | cgpGmo-S2138 | V | 2 | 0.93 |
| 1179 | 7467C1CO1.388 | cgpGmo-S2139 | V | 2 | 0.95 |
| 1180 | 1384C2CO2.257 | cgpGmo-S214 |   | 1 | 0.914 |
| 1181 | 7468C1CO1.284 | cgpGmo-S2140 | V | 2 | 0.89 |
| 1182 | 7484C1CO1.527 | cgpGmo-S2141 |   | 2 | 0.92 |
| 1183 | 7488C1CO1.331 | cgpGmo-S2142 | V | 2 | 0.65 |
| 1184 | 7507C1CO1.601 | cgpGmo-S2143 |   | 2 | 0.98 |
| 1185 | 7522C1CO1.150 | cgpGmo-S2144 | V | 2 | 0.93 |
| 1186 | 7565C1CO1.470 | cgpGmo-S2145 | V | 2 | 0.41 |
| 1187 | 7590C1CO1.381 | cgpGmo-S2146 | V | 2 | 0.94 |
| 1188 | 7671C1CO1.220 | cgpGmo-S2147 |   | 2 | 0.92 |
| 1189 | 7704C1CO1.327 | cgpGmo-S2148 | V | 2 | 0.65 |
| 1190 | 7733C1CO1.585 | cgpGmo-S2149 |   | 2 | 0.98 |
| 1191 | 1406C1CO1.183 | cgpGmo-S215 | V | 1 | 0.897 |
| 1192 | 7738C1CO1.109 | cgpGmo-S2150 |   | 2 | 0.98 |
| 1193 | 773C1CO1.467 | cgpGmo-S2151 |   | 2 | 0.92 |
| 1194 | 7796C1CO1.133 | cgpGmo-S2152 |   | 2 | 0.95 |
| 1195 | 7803C1CO1.283 | cgpGmo-S2153 | V | 2 | 0.99 |
| 1196 | 7819C1CO1.388 | cgpGmo-S2154 | V | 2 | 0.97 |
| 1197 | 7828C1CO1.123 | cgpGmo-S2155 | V | 2 | 0.99 |
| 1198 | 7828C2CO1.226 | cgpGmo-S2156 |   | 2 | 0.94 |
| 1199 | 7841C1CO1.404 | cgpGmo-S2157 | V | 2 | 0.93 |
| 1200 | 7875C2CO1.405 | cgpGmo-S2158 | V | 2 | 0.92 |
| 1201 | 789C1CO1.334 | cgpGmo-S2159 |   | 2 | 0.85 |
| 1202 | 1417C2CO1.292 | cgpGmo-S216 | V | 1 | 0.765 |
| 1203 | 7916C1CO1.445 | cgpGmo-S2160 | V | 2 | 0.98 |
| 1204 | 797C2CO1.586 | cgpGmo-S2161 | V | 2 | 0.93 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1205 | 798C1CO2.515 | cgpGmo-S2162 | V | 2 | 0.95 |
| 1206 | 7996C1CO1.453 | cgpGmo-S2163 |   | 2 | 0.97 |
| 1207 | 8020C1CO1.453 | cgpGmo-S2164 | V | 2 | 0.97 |
| 1208 | 8049C1CO1.91 | cgpGmo-S2165 | V | 2 | 0.98 |
| 1209 | 8057C1CO1.606 | cgpGmo-S2166 | V | 2 | 0.96 |
| 1210 | 805C2CO1.110 | cgpGmo-S2167 |   | 2 | 0.95 |
| 1211 | 8086C1CO1.241 | cgpGmo-S2168 |   | 2 | 0.98 |
| 1212 | 8171C1CO1.607 | cgpGmo-S2169 | V | 2 | 0.68 |
| 1213 | 8209C1CO1.528 | cgpGmo-S2170 |   | 2 | 0.99 |
| 1214 | 8273C1CO1.123 | cgpGmo-S2171 | V | 2 | 0.97 |
| 1215 | 8308C1CO1.595 | cgpGmo-S2172 | V | 2 | 0.92 |
| 1216 | 8313C1CO1.586 | cgpGmo-S2173 | V | 2 | 0.83 |
| 1217 | 835C1CO1.283 | cgpGmo-S2174 | V | 2 | 0.98 |
| 1218 | 8414C1CO1.491 | cgpGmo-S2175 | V | 2 | 0.94 |
| 1219 | 8432C1CO1.615 | cgpGmo-S2176 | V | 2 | 0.95 |
| 1220 | 8476C1CO1.67 | cgpGmo-S2177 | V | 2 | 0.95 |
| 1221 | 8563C1CO1.434 | cgpGmo-S2178 | V | 2 | 0.57 |
| 1222 | 8596C1CO1.466 | cgpGmo-S2179 | V | 2 | 0.94 |
| 1223 | 1428C2CO1.182 | cgpGmo-S217a | V | 2 | 0.99 |
| 1224 | 1428C2CO1.386 | cgpGmo-S217b |   | 1 | 0.758 |
| 1225 | 1432C2CO1.416 | cgpGmo-S218 | V | 1 | 0.893 |
| 1226 | 8602C1CO1.579 | cgpGmo-S2180 | V | 2 | 0.96 |
| 1227 | 8631C1CO1.626 | cgpGmo-S2181 |   | 2 | 0.94 |
| 1228 | 865C1CO1.461 | cgpGmo-S2182 | V | 2 | 0.97 |
| 1229 | 8672C1CO1.556 | cgpGmo-S2183 | V | 2 | 0.96 |
| 1230 | 8682C1CO1.523 | cgpGmo-S2184 | V | 2 | 0.93 |
| 1231 | 8701C1CO1.529 | cgpGmo-S2185 | V | 2 | 0.94 |
| 1232 | 8702C1CO1.249 | cgpGmo-S2186 | V | 2 | 0.97 |
| 1233 | 871C1CO1.526 | cgpGmo-S2187 | V | 2 | 0.95 |
| 1234 | 8758C1CO1.314 | cgpGmo-S2188 |   | 2 | 0.83 |
| 1235 | 876C1CO1.776 | cgpGmo-S2189 | V | 2 | 0.94 |
| 1236 | 1444C2CO1.320 | cgpGmo-S219 |   | 1 | 0.897 |
| 1237 | 8873C1CO1.564 | cgpGmo-S2190 |   | 2 | 0.68 |
| 1238 | 892C2CO1.725 | cgpGmo-S2191 | V | 2 | 0.97 |
| 1239 | 8985C1CO1.393 | cgpGmo-S2192 |   | 2 | 0.95 |
| 1240 | 9036C1CO1.107 | cgpGmo-S2193 | V | 2 | 0.96 |
| 1241 | 9062C1CO1.638 | cgpGmo-S2194 |   | 2 | 0.93 |
| 1242 | 9065C1CO1.607 | cgpGmo-S2195 |   | 2 | 0.95 |
| 1243 | 908C1CO1.144 | cgpGmo-S2196 | V | 2 | 0.97 |
| 1244 | 9119C1CO1.819 | cgpGmo-S2197 |   | 2 | 0.93 |
| 1245 | 9128C1CO1.196 | cgpGmo-S2198 | V | 2 | 0.93 |
| 1246 | 9176C1CO1.128 | cgpGmo-S2199 | V | 2 | 0.9 |
| 1247 | 1469C2CO1.175 | cgpGmo-S220 | V | 1 | 0.868 |
| 1248 | 91C1CO1.105 | cgpGmo-S2200 | V | 2 | 1 |
| 1249 | 9212C1CO1.604 | cgpGmo-S2201 | V | 2 | 0.89 |
| 1250 | 9222C1CO1.512 | cgpGmo-S2202 | V | 2 | 0.97 |
| 1251 | 925C1CO1.592 | cgpGmo-S2203 |   | 2 | 0.99 |
| 1252 | 92C3CO1.78 | cgpGmo-S2204 |   | 2 | 0.92 |
| 1253 | 9312C1CO1.390 | cgpGmo-S2205 | V | 2 | 0.94 |
| 1254 | 9359C1CO1.210 | cgpGmo-S2206 |   | 2 | 0.96 |
| 1255 | 9376C1CO1.103 | cgpGmo-S2207 | V | 2 | 0.71 |
| 1256 | 9456C1CO1.448 | cgpGmo-S2208 | V | 2 | 0.58 |
| 1257 | 9481C1CO1.506 | cgpGmo-S2209 |   | 2 | 0.98 |
| 1258 | 9482C1CO1.221 | cgpGmo-S2210 |   | 2 | 0.84 |
| 1259 | 9493C1CO1.74 | cgpGmo-S2211 | V | 2 | 0.93 |
| 1260 | 9550C1CO1.233 | cgpGmo-S2212 | V | 2 | 0.96 |
| 1261 | 955C2CO1.742 | cgpGmo-S2213 |   | 2 | 0.97 |
| 1262 | 9627C1CO1.195 | cgpGmo-S2214 |   | 2 | 0.99 |
| 1263 | 964C2CO1.354 | cgpGmo-S2215 | V | 2 | 0.98 |
| 1264 | 9669C1CO1.339 | cgpGmo-S2216 | V | 2 | 0.94 |
| 1265 | 96C1CO1.251 | cgpGmo-S2217 | V | 2 | 0.66 |
| 1266 | 970C1CO1.355 | cgpGmo-S2218 |   | 2 | 0.92 |
| 1267 | 9737C1CO1.325 | cgpGmo-S2219 | V | 2 | 0.95 |
| 1268 | 1470C1CO1.120 | cgpGmo-S221a | V | 1 | 0.664 |
| 1269 | 1470C1CO1.565 | cgpGmo-S221b |   | 2 | 0.96 |
| 1270 | 1472C1CO1.417 | cgpGmo-S222 |   | 1 | 0.753 |
| 1271 | 9768C1CO1.270 | cgpGmo-S2220 | V | 2 | 0.79 |
| 1272 | 9810C1CO1.661 | cgpGmo-S2221 | V | 2 | 0.99 |
| 1273 | 9902C1CO1.599 | cgpGmo-S2222 |   | 2 | 0.95 |
| 1274 | 9917C1CO1.442 | cgpGmo-S2223 |   | 2 | 0.98 |
| 1275 | 991C1CO1.245 | cgpGmo-S2224 | V | 2 | 0.94 |
| 1276 | 6866C1CO1.522 | cgpGmo-S2225 |   | 1 | 0.551 |
| 1277 | 2016C2CO1.583 | cgpGmo-S2227 |   | 1 | 0.847 |
| 1278 | 374C3CO1.279 | cgpGmo-S2228 |   | 1 | 0.913 |
| 1279 | 4309C1CO1.573 | cgpGmo-S2229 | V | 1 | 0.622 |
| 1280 | 1489C2CO1.404 | cgpGmo-S223 | V | 1 | 0.888 |
| 1281 | 520C1CO1.693 | cgpGmo-S2230 |   | 1 | 0.429 |
| 1282 | 676C1CO1.577 | cgpGmo-S2231 |   | 1 | 0.64 |
| 1283 | 805C1CO1.323 | cgpGmo-S2232 |   | 1 | 0.528 |
| 1284 | 1031C1CO1.106 | cgpGmo-S2234 |   | 1 | 0.724 |
| 1285 | 1332C1CO1.754 | cgpGmo-S2235 | V | 1 | 0.638 |
| 1286 | 1556C1CO1.215 | cgpGmo-S2236 |   | 1 | 0.614 |
| 1287 | 1872C3CO1.115 | cgpGmo-S2238 |   | 1 | 0.542 |
| 1288 | 2112C1CO1.685 | cgpGmo-S2239 | V | 1 | 0.865 |
| 1289 | 1499C1CO1.634 | cgpGmo-S224 | V | 1 | 0.769 |
| 1290 | 2225C1CO1.256 | cgpGmo-S2240 |   | 1 | 0.821 |
| 1291 | 3360C1CO1.575 | cgpGmo-S2242 | V | 1 | 0.806 |
| 1292 | 4143C2CO1.407 | cgpGmo-S2244 |   | 1 | 0.617 |
| 1293 | 5344C1CO1.582 | cgpGmo-S2247 |   | 1 | 0.598 |
| 1294 | 6649C2CO1.422 | cgpGmo-S2249 |   | 1 | 0.89 |
| 1295 | 1137C1CO1.79 | cgpGmo-S2254 | V | 1 | 0.837 |
| 1296 | 115C1CO1.558 | cgpGmo-S2255 | V | 1 | 0.783 |
| 1297 | 1222C1CO1.325 | cgpGmo-S2256 | V | 1 | 0.53 |
| 1298 | 1445C1CO1.228 | cgpGmo-S2257 |   | 1 | 0.902 |
| 1299 | 1554C1CO1.295 | cgpGmo-S2258 |   | 1 | 0.898 |
| 1300 | 1686C1CO1.79 | cgpGmo-S2259 | V | 1 | 0.749 |
| 1301 | 1501C1CO1.105 | cgpGmo-S225a |   | 1 | 0.826 |
| 1302 | 1501C1CO1.189 | cgpGmo-S225b | V | 2 | 0.96 |
| 1303 | 1504C1CO1.358 | cgpGmo-S226 | V | 1 | 0.54 |
| 1304 | 1697C1CO1.128 | cgpGmo-S2260 |   | 1 | 0.895 |
| 1305 | 1747C1CO1.551 | cgpGmo-S2261 |   | 1 | 0.424 |
| 1306 | 1821C1CO1.434 | cgpGmo-S2262 | V | 1 | 0.824 |
| 1307 | 1875C1CO1.211 | cgpGmo-S2263 |   | 1 | 0.561 |
| 1308 | 1913C1CO1.315 | cgpGmo-S2264 | V | 1 | 0.807 |
| 1309 | 2346C1CO1.128 | cgpGmo-S2265 |   | 1 | 0.578 |
| 1310 | 2456C1CO1.115 | cgpGmo-S2266 | V | 1 | 0.887 |
| 1311 | 273C1CO1.366 | cgpGmo-S2267 |   | 1 | 0.812 |
| 1312 | 2838C2CO1.276 | cgpGmo-S2268 |   | 1 | 0.886 |
| 1313 | 2877C1CO1.254 | cgpGmo-S2269 | V | 1 | 0.861 |
| 1314 | 1519C3CO1.144 | cgpGmo-S227 | V | 1 | 0.785 |
| 1315 | 3015C2CO1.529 | cgpGmo-S2270 |   | 1 | 0.834 |
| 1316 | 3098C1CO1.241 | cgpGmo-S2271 |   | 1 | 0.671 |
| 1317 | 3412C1CO1.431 | cgpGmo-S2272 |   | 1 | 0.853 |
| 1318 | 360C1CO1.520 | cgpGmo-S2273 |   | 1 | 0.768 |
| 1319 | 3858C1CO1.259 | cgpGmo-S2274 |   | 1 | 0.841 |
| 1320 | 4030C1CO1.338 | cgpGmo-S2275 |   | 1 | 0.664 |
| 1321 | 4186C1CO1.425 | cgpGmo-S2276 |   | 1 | 0.779 |
| 1322 | 4213C1CO1.163 | cgpGmo-S2277 | V | 1 | 0.823 |
| 1323 | 4486C1CO1.473 | cgpGmo-S2278 |   | 1 | 0.853 |
| 1324 | 5279C1CO1.392 | cgpGmo-S2279 | V | 1 | 0.832 |
| 1325 | 1523C1CO1.166 | cgpGmo-S228 | V | 1 | 0.713 |
| 1326 | 536C1CO1.663 | cgpGmo-S2280 |   | 1 | 0.837 |
| 1327 | 5708C1CO1.378 | cgpGmo-S2281 | V | 1 | 0.719 |
| 1328 | 6269C1CO1.137 | cgpGmo-S2282 |   | 1 | 0.636 |
| 1329 | 6427C1CO1.158 | cgpGmo-S2283 | V | 1 | 0.786 |
| 1330 | 664C2CO1.431 | cgpGmo-S2284 |   | 1 | 0.779 |
| 1331 | 7459C1CO1.298 | cgpGmo-S2285 | V | 1 | 0.658 |
| 1332 | 8512C1CO1.228 | cgpGmo-S2286 | V | 1 | 0.612 |
| 1333 | 926C1CO1.133 | cgpGmo-S2287 | V | 1 | 0.902 |
| 1334 | 967C1CO1.81 | cgpGmo-S2288 | V | 2 | 0.88 |
| 1335 | 1525C1CO1.126 | cgpGmo-S229 | V | 1 | 0.717 |
| 1336 | 11545C1CO1.529 | cgpGmo-S22a |   | 1 | 0.663 |
| 1337 | 11545C1CO1.595 | cgpGmo-S22b | V | 2 | 0.83 |
| 1338 | 1592C1CO1.432 | cgpGmo-S23 | V | 1 | 0.77 |
| 1339 | 152C1CO1.368 | cgpGmo-S230 |   | 1 | 0.543 |
| 1340 | 1533C1CO1.128 | cgpGmo-S231 |   | 1 | 0.831 |
| 1341 | 1534C1CO1.355 | cgpGmo-S232a | V | 1 | 0.455 |
| 1342 | 1534C1CO1.626 | cgpGmo-S232b | V | 2 | 0.89 |
| 1343 | 153C1CO1.459 | cgpGmo-S233 | V | 1 | 0.766 |
| 1344 | 1553C1CO1.428 | cgpGmo-S234 | V | 1 | 0.822 |
| 1345 | 1560C1CO1.117 | cgpGmo-S237a | V | 2 | 0.93 |
| 1346 | 1560C1CO1.217 | cgpGmo-S237b |   | 1 | 0.673 |
| 1347 | 156C2CO1.270 | cgpGmo-S238 |   | 1 | 0.825 |
| 1348 | 1576C2CO1.75 | cgpGmo-S239a | V | 1 | 0.622 |
| 1349 | 1576C2CO1.425 | cgpGmo-S239b | V | 2 | 0.86 |
| 1350 | 1579C1CO1.472 | cgpGmo-S240 | V | 1 | 0.908 |
| 1351 | 1582C1CO1.183 | cgpGmo-S241 | V | 1 | 0.913 |
| 1352 | 1585C1CO1.325 | cgpGmo-S242 | V | 1 | 0.649 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1353 | 1590C1CO1.605 | cgpGmo-S244 | V | 1 | 0.729 |
| 1354 | 1596C2CO1.327 | cgpGmo-S245a | V | 1 | 0.881 |
| 1355 | 1596C2CO1.428 | cgpGmo-S245b | V | 2 | 0.93 |
| 1356 | 1599C11CO1.713 | cgpGmo-S246 | | 1 | 0.895 |
| 1357 | 1599C23CO1.156 | cgpGmo-S247 | V | 1 | 0.68 |
| 1358 | 1605C1CO1.535 | cgpGmo-S248a | V | 2 | 0.95 |
| 1359 | 1605C1CO1.907 | cgpGmo-S248b | | 1 | 0.82 |
| 1360 | 1609C2CO1.678 | cgpGmo-S249 | V | 1 | 0.836 |
| 1361 | 2053C1CO1.439 | cgpGmo-S24a | | 1 | 0.755 |
| 1362 | 2053C1CO1.533 | cgpGmo-S24b | V | 2 | 0.88 |
| 1363 | 21C1CO1.359 | cgpGmo-S25 | V | 1 | 0.478 |
| 1364 | 160C1CO1.474 | cgpGmo-S250 | V | 1 | 0.801 |
| 1365 | 1616C1CO2.570 | cgpGmo-S251 | V | 1 | 0.768 |
| 1366 | 1619C1CO1.174 | cgpGmo-S252 | V | 1 | 0.479 |
| 1367 | 1622C1CO1.390 | cgpGmo-S253 | | 1 | 0.718 |
| 1368 | 1628C1CO1.246 | cgpGmo-S254 | V | 1 | 0.495 |
| 1369 | 1636C1CO1.239 | cgpGmo-S255 | V | 1 | 0.873 |
| 1370 | 164C1CO1.1157 | cgpGmo-S256 | V | 1 | 0.796 |
| 1371 | 1653C3CO1.734 | cgpGmo-S257 | | 1 | 0.908 |
| 1372 | 1656C1CO1.775 | cgpGmo-S258 | V | 1 | 0.912 |
| 1373 | 1665C1CO1.118 | cgpGmo-S259 | V | 1 | 0.552 |
| 1374 | 3935C1CO1.607 | cgpGmo-S26 | V | 1 | 0.668 |
| 1375 | 1673C1CO1.714 | cgpGmo-S260a | V | 2 | 0.96 |
| 1376 | 1673C1CO1.999 | cgpGmo-S260b | V | 1 | 0.856 |
| 1377 | 1673C2CO1.405 | cgpGmo-S261a | | 1 | 0.722 |
| 1378 | 1673C2CO1.615 | cgpGmo-S261b | V | 2 | 0.87 |
| 1379 | 1675C1CO1.371 | cgpGmo-S262a | | 2 | 0.83 |
| 1380 | 1675C1CO1.542 | cgpGmo-S262b | | 1 | 0.656 |
| 1381 | 167C1CO1.210 | cgpGmo-S263 | V | 1 | 0.894 |
| 1382 | 1680C1CO1.113 | cgpGmo-S264 | V | 1 | 0.861 |
| 1383 | 1693C1CO1.284 | cgpGmo-S265 | | 1 | 0.7 |
| 1384 | 1696C1CO1.436 | cgpGmo-S266 | V | 1 | 0.854 |
| 1385 | 1701C1CO1.117 | cgpGmo-S267 | V | 1 | 0.817 |
| 1386 | 1702C2CO1.1095 | cgpGmo-S268 | V | 1 | 0.809 |
| 1387 | 1704C1CO1.949 | cgpGmo-S269 | | 1 | 0.898 |
| 1388 | 1712C1CO1.270 | cgpGmo-S270 | V | 1 | 0.635 |
| 1389 | 1725C1CO1.294 | cgpGmo-S271 | V | 1 | 0.78 |
| 1390 | 1726C1CO1.472 | cgpGmo-S272 | V | 1 | 0.871 |
| 1391 | 1727C1CO1.403 | cgpGmo-S273 | | 1 | 0.908 |
| 1392 | 1738C1CO1.518 | cgpGmo-S274 | | 1 | 0.832 |
| 1393 | 1742C1CO1.369 | cgpGmo-S275 | V | 1 | 0.775 |
| 1394 | 1751C1CO1.270 | cgpGmo-S276a | | 1 | 0.724 |
| 1395 | 1751C1CO1.506 | cgpGmo-S276b | V | 2 | 0.96 |
| 1396 | 1752C1CO1.651 | cgpGmo-S277 | V | 1 | 0.857 |
| 1397 | 1754C1CO1.217 | cgpGmo-S278 | | 1 | 0.76 |
| 1398 | 1766C2CO1.495 | cgpGmo-S279 | | 1 | 0.518 |
| 1399 | 58C14CO1.502 | cgpGmo-S28 | V | 1 | 0.499 |
| 1400 | 177C1CO1.664 | cgpGmo-S280 | | 1 | 0.901 |
| 1401 | 1780C1CO1.581 | cgpGmo-S281 | V | 1 | 0.909 |
| 1402 | 1801C1CO1.133 | cgpGmo-S282 | V | 1 | 0.884 |
| 1403 | 1813C1CO1.243 | cgpGmo-S283 | V | 1 | 0.83 |
| 1404 | 1831C1CO1.182 | cgpGmo-S284 | V | 1 | 0.828 |
| 1405 | 1835C1CO1.230 | cgpGmo-S285 | V | 1 | 0.543 |
| 1406 | 1838C1CO1.657 | cgpGmo-S286 | V | 1 | 0.723 |
| 1407 | 1840C1CO1.843 | cgpGmo-S287a | V | 2 | 0.98 |
| 1408 | 1840C1CO1.1060 | cgpGmo-S287b | V | 1 | 0.831 |
| 1409 | 1844C1CO1.86 | cgpGmo-S288 | | 1 | 0.657 |
| 1410 | 1851C2CO1.600 | cgpGmo-S289 | V | 1 | 0.908 |
| 1411 | 5994C2CO1.923 | cgpGmo-S29 | V | 1 | 0.521 |
| 1412 | 1866C1CO1.549 | cgpGmo-S290 | V | 1 | 0.842 |
| 1413 | 1878C1CO1.634 | cgpGmo-S291 | V | 1 | 0.808 |
| 1414 | 1880C1CO1.585 | cgpGmo-S292a | | 1 | 0.862 |
| 1415 | 1880C1CO1.679 | cgpGmo-S292b | V | 2 | 0.93 |
| 1416 | 188C1CO1.944 | cgpGmo-S293 | | 1 | 0.882 |
| 1417 | 1893C1CO1.504 | cgpGmo-S294 | V | 1 | 0.906 |
| 1418 | 189C1CO1.216 | cgpGmo-S295 | | 1 | 0.778 |
| 1419 | 1905C1CO1.95 | cgpGmo-S296 | V | 1 | 0.74 |
| 1420 | 1908C1CO1.505 | cgpGmo-S297 | V | 1 | 0.902 |
| 1421 | 1911C1CO1.133 | cgpGmo-S298 | V | 1 | 0.879 |
| 1422 | 1931C1CO1.722 | cgpGmo-S299 | | 1 | 0.78 |
| 1423 | 2099C1CO1.1415 | cgpGmo-S30 | V | 1 | 0.803 |
| 1424 | 1934C1CO1.220 | cgpGmo-S300 | V | 1 | 0.804 |
| 1425 | 1937C2CO1.890 | cgpGmo-S301 | V | 1 | 0.852 |
| 1426 | 193C2CO1.193 | cgpGmo-S302 | V | 1 | 0.815 |
| 1427 | 1940C1CO1.154 | cgpGmo-S303 | | 1 | 0.658 |
| 1428 | 194C1CO1.354 | cgpGmo-S304a | V | 2 | 0.89 |
| 1429 | 194C1CO1.498 | cgpGmo-S304b | | 1 | 0.801 |
| 1430 | 194C2CO1.363 | cgpGmo-S305 | V | 1 | 0.83 |
| 1431 | 1950C1CO1.457 | cgpGmo-S306a | V | 2 | 0.96 |
| 1432 | 1950C1CO1.551 | cgpGmo-S306b | V | 1 | 0.777 |
| 1433 | 1958C1CO1.298 | cgpGmo-S307 | | 1 | 0.859 |
| 1434 | 1962C1CO1.254 | cgpGmo-S308 | V | 1 | 0.883 |
| 1435 | 1973C1CO1.726 | cgpGmo-S309 | V | 1 | 0.896 |
| 1436 | 3134C2CO3.400 | cgpGmo-S31 | V | 1 | 0.907 |
| 1437 | 1975C1CO1.244 | cgpGmo-S310 | V | 1 | 0.745 |
| 1438 | 1985C1CO1.89 | cgpGmo-S311a | | 1 | 0.512 |
| 1439 | 1985C1CO1.537 | cgpGmo-S311b | V | 2 | 0.91 |
| 1440 | 1987C1CO1.1249 | cgpGmo-S312 | V | 1 | 0.852 |
| 1441 | 198C1CO1.206 | cgpGmo-S313 | V | 1 | 0.795 |
| 1442 | 2006C1CO1.538 | cgpGmo-S314 | V | 1 | 0.902 |
| 1443 | 2008C2CO1.96 | cgpGmo-S315 | V | 1 | 0.809 |
| 1444 | 2010C1CO1.451 | cgpGmo-S316 | V | 1 | 0.899 |
| 1445 | 2013C1CO1.894 | cgpGmo-S317 | | 1 | 0.569 |
| 1446 | 2018C1CO1.166 | cgpGmo-S318 | V | 1 | 0.621 |
| 1447 | 2020C1CO1.240 | cgpGmo-S319a | | 2 | 0.98 |
| 1448 | 2020C1CO1.363 | cgpGmo-S319b | | 1 | 0.67 |
| 1449 | 3262C1CO1.135 | cgpGmo-S32 | V | 1 | 0.752 |
| 1450 | 2024C2CO1.232 | cgpGmo-S320 | V | 1 | 0.697 |
| 1451 | 2032C2CO1.221 | cgpGmo-S321 | V | 1 | 0.912 |
| 1452 | 2040C2CO1.850 | cgpGmo-S322 | V | 1 | 0.677 |
| 1453 | 2048C1CO1.312 | cgpGmo-S324 | V | 1 | 0.662 |
| 1454 | 2055C1CO1.905 | cgpGmo-S326 | | 1 | 0.868 |
| 1455 | 2064C1CO1.454 | cgpGmo-S327 | V | 1 | 0.493 |
| 1456 | 2071C1CO1.460 | cgpGmo-S328 | V | 1 | 0.701 |
| 1457 | 2071C2CO1.599 | cgpGmo-S329 | V | 1 | 0.701 |
| 1458 | 3349C1CO1.203 | cgpGmo-S33 | | 1 | 0.875 |
| 1459 | 2079C1CO1.429 | cgpGmo-S330 | V | 1 | 0.659 |
| 1460 | 2092C1CO1.471 | cgpGmo-S331a | V | 2 | 0.96 |
| 1461 | 2092C1CO1.567 | cgpGmo-S331b | V | 1 | 0.839 |
| 1462 | 2093C1CO1.254 | cgpGmo-S332a | V | 1 | 0.76 |
| 1463 | 2093C1CO1.477 | cgpGmo-S332b | V | 2 | 0.79 |
| 1464 | 2119C2CO1.362 | cgpGmo-S333 | V | 1 | 0.859 |
| 1465 | 2126C1CO1.342 | cgpGmo-S334 | V | 1 | 0.759 |
| 1466 | 2136C1CO1.228 | cgpGmo-S335 | V | 1 | 0.68 |
| 1467 | 2173C1CO1.234 | cgpGmo-S336 | V | 1 | 0.683 |
| 1468 | 2176C1CO1.539 | cgpGmo-S337 | | 1 | 0.838 |
| 1469 | 2177C1CO1.202 | cgpGmo-S338a | V | 2 | 0.98 |
| 1470 | 2177C1CO1.354 | cgpGmo-S338b | V | 1 | 0.597 |
| 1471 | 2185C1CO1.519 | cgpGmo-S339 | V | 1 | 0.901 |
| 1472 | 2187C3CO1.371 | cgpGmo-S340a | | 1 | 0.597 |
| 1473 | 2187C3CO1.565 | cgpGmo-S340b | | 2 | 0.98 |
| 1474 | 2203C1CO1.184 | cgpGmo-S341 | V | 1 | 0.794 |
| 1475 | 2222C2CO1.288 | cgpGmo-S342 | V | 1 | 0.716 |
| 1476 | 2224C2CO1.330 | cgpGmo-S343 | | 1 | 0.682 |
| 1477 | 2254C3CO1.909 | cgpGmo-S345 | | 1 | 0.782 |
| 1478 | 2254C4CO1.617 | cgpGmo-S346a | | 1 | 0.62 |
| 1479 | 2254C4CO1.685 | cgpGmo-S346b | | 2 | 0.98 |
| 1480 | 2254C9CO1.245 | cgpGmo-S347 | V | 1 | 0.894 |
| 1481 | 2257C1CO1.434 | cgpGmo-S348 | V | 1 | 0.741 |
| 1482 | 225C1CO1.254 | cgpGmo-S349 | | 1 | 0.814 |
| 1483 | 2276C1CO1.375 | cgpGmo-S350 | V | 1 | 0.822 |
| 1484 | 2296C6CO1.459 | cgpGmo-S351 | | 1 | 0.706 |
| 1485 | 2308C2CO1.226 | cgpGmo-S352 | V | 1 | 0.726 |
| 1486 | 2319C1CO1.392 | cgpGmo-S354 | V | 1 | 0.716 |
| 1487 | 2322C1CO1.359 | cgpGmo-S355 | | 1 | 0.525 |
| 1488 | 2327C1CO1.85 | cgpGmo-S356a | | 1 | 0.629 |
| 1489 | 2327C1CO1.186 | cgpGmo-S356b | V | 2 | 0.68 |
| 1490 | 2332C1CO1.139 | cgpGmo-S357 | V | 1 | 0.623 |
| 1491 | 2340C1CO1.521 | cgpGmo-S358 | | 1 | 0.852 |
| 1492 | 2343C1CO1.854 | cgpGmo-S359 | V | 1 | 0.896 |
| 1493 | 386C1CO1.1015 | cgpGmo-S35a | V | 2 | 0.87 |
| 1494 | 386C1CO1.1108 | cgpGmo-S35b | | 1 | 0.759 |
| 1495 | 2344C1CO1.95 | cgpGmo-S360 | | 1 | 0.768 |
| 1496 | 2358C1CO1.560 | cgpGmo-S361 | V | 1 | 0.824 |
| 1497 | 235C1CO1.144 | cgpGmo-S362 | | 1 | 0.629 |
| 1498 | 2369C1CO1.769 | cgpGmo-S363 | V | 1 | 0.727 |
| 1499 | 236C1CO1.125 | cgpGmo-S364 | V | 1 | 0.828 |
| 1500 | 2374C1CO1.173 | cgpGmo-S365a | | 2 | 0.92 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1501 | 2374C1CO1.298 | cgpGmo-S365b | V | 1 | 0.903 |
| 1502 | 237C1CO1.474 | cgpGmo-S366 | V | 1 | 0.829 |
| 1503 | 2386C1CO1.430 | cgpGmo-S367 | V | 1 | 0.702 |
| 1504 | 2390C1CO1.669 | cgpGmo-S368 |   | 1 | 0.799 |
| 1505 | 2393C1CO1.600 | cgpGmo-S369 | V | 1 | 0.907 |
| 1506 | 3914C1CO1.331 | cgpGmo-S36a | V | 2 | 0.89 |
| 1507 | 3914C1CO1.466 | cgpGmo-S36b | V | 1 | 0.849 |
| 1508 | 2397C2CO1.558 | cgpGmo-S370 |   | 1 | 0.906 |
| 1509 | 23C1CO1.446 | cgpGmo-S371 | V | 1 | 0.665 |
| 1510 | 2429C1CO1.500 | cgpGmo-S372a | V | 1 | 0.454 |
| 1511 | 2429C1CO1.691 | cgpGmo-S372b |   | 2 | 0.93 |
| 1512 | 2437C1CO1.472 | cgpGmo-S373 |   | 1 | 0.465 |
| 1513 | 2440C1CO1.211 | cgpGmo-S374 | V | 1 | 0.591 |
| 1514 | 2479C1CO1.447 | cgpGmo-S375 |   | 1 | 0.914 |
| 1515 | 2485C1CO1.141 | cgpGmo-S376 | V | 1 | 0.662 |
| 1516 | 2486C1CO1.952 | cgpGmo-S377 | V | 1 | 0.796 |
| 1517 | 2489C1CO1.536 | cgpGmo-S378a |   | 1 | 0.741 |
| 1518 | 2489C1CO1.613 | cgpGmo-S378b |   | 2 | 0.84 |
| 1519 | 2509C1CO1.191 | cgpGmo-S379 |   | 1 | 0.895 |
| 1520 | 4792C1CO1.95 | cgpGmo-S37a | V | 2 | 0.97 |
| 1521 | 4792C1CO1.189 | cgpGmo-S37b | V | 1 | 0.876 |
| 1522 | 2522C1CO1.130 | cgpGmo-S380 |   | 1 | 0.845 |
| 1523 | 2525C1CO1.257 | cgpGmo-S381 | V | 1 | 0.865 |
| 1524 | 2527C1CO1.337 | cgpGmo-S382 | V | 1 | 0.891 |
| 1525 | 2531C2CO1.679 | cgpGmo-S383 |   | 1 | 0.498 |
| 1526 | 2535C1CO1.457 | cgpGmo-S384 |   | 1 | 0.757 |
| 1527 | 2539C1CO1.123 | cgpGmo-S385a | V | 1 | 0.661 |
| 1528 | 2539C1CO1.218 | cgpGmo-S385b | V | 2 | 0.87 |
| 1529 | 2542C1CO1.220 | cgpGmo-S386 | V | 1 | 0.863 |
| 1530 | 2544C1CO1.1109 | cgpGmo-S387a | V | 2 | 0.82 |
| 1531 | 2544C1CO1.1873 | cgpGmo-S387b |   | 1 | 0.701 |
| 1532 | 2545C1CO1.366 | cgpGmo-S388 | V | 1 | 0.849 |
| 1533 | 2548C1CO1.260 | cgpGmo-S389 | V | 1 | 0.899 |
| 1534 | 5440C1CO1.234 | cgpGmo-S39 | V | 1 | 0.898 |
| 1535 | 257C2CO1.76 | cgpGmo-S390a |   | 2 | 0.96 |
| 1536 | 257C2CO1.478 | cgpGmo-S390b | V | 1 | 0.884 |
| 1537 | 2580C1CO1.109 | cgpGmo-S391 | V | 1 | 0.84 |
| 1538 | 2581C1CO1.764 | cgpGmo-S392 | V | 1 | 0.75 |
| 1539 | 2582C1CO1.717 | cgpGmo-S393 | V | 1 | 0.849 |
| 1540 | 2584C1CO1.520 | cgpGmo-S394 |   | 1 | 0.629 |
| 1541 | 2596C1CO1.273 | cgpGmo-S395 | V | 1 | 0.715 |
| 1542 | 2606C1CO1.133 | cgpGmo-S396 | V | 1 | 0.613 |
| 1543 | 2609C1CO1.386 | cgpGmo-S397 | V | 1 | 0.449 |
| 1544 | 2616C1CO1.882 | cgpGmo-S398 | V | 1 | 0.833 |
| 1545 | 2617C2CO1.465 | cgpGmo-S399 | V | 1 | 0.834 |
| 1546 | 6460C1CO1.340 | cgpGmo-S4 | V | 1 | 0.46 |
| 1547 | 56C2CO1.324 | cgpGmo-S40 | V | 1 | 0.587 |
| 1548 | 2625C1CO1.237 | cgpGmo-S400 | V | 1 | 0.568 |
| 1549 | 2628C1CO1.274 | cgpGmo-S401 | V | 1 | 0.915 |
| 1550 | 2632C1CO1.566 | cgpGmo-S402 |   | 1 | 0.599 |
| 1551 | 2635C1CO1.301 | cgpGmo-S403 | V | 1 | 0.677 |
| 1552 | 2645C1CO1.352 | cgpGmo-S404a | V | 1 | 0.799 |
| 1553 | 2645C1CO1.557 | cgpGmo-S404b | V | 2 | 0.87 |
| 1554 | 2646C1CO1.695 | cgpGmo-S405a |   | 1 | 0.494 |
| 1555 | 2646C1CO1.769 | cgpGmo-S405b | V | 2 | 0.87 |
| 1556 | 2673C1CO1.439 | cgpGmo-S406 | V | 1 | 0.911 |
| 1557 | 2687C1CO1.438 | cgpGmo-S407 | V | 1 | 0.647 |
| 1558 | 2693C1CO1.678 | cgpGmo-S408 | V | 1 | 0.901 |
| 1559 | 2698C1CO1.464 | cgpGmo-S409 | V | 1 | 0.897 |
| 1560 | 5704C1CO2.488 | cgpGmo-S41 | V | 1 | 0.555 |
| 1561 | 2706C1CO1.355 | cgpGmo-S410 | V | 1 | 0.881 |
| 1562 | 270C2CO1.126 | cgpGmo-S411 |   | 1 | 0.876 |
| 1563 | 2718C2CO1.1134 | cgpGmo-S412 | V | 1 | 0.883 |
| 1564 | 2723C1CO1.364 | cgpGmo-S413 | V | 1 | 0.526 |
| 1565 | 2724C1CO1.690 | cgpGmo-S414 |   | 1 | 0.66 |
| 1566 | 2735C1CO1.390 | cgpGmo-S415 | V | 1 | 0.795 |
| 1567 | 2736C2CO1.215 | cgpGmo-S416a | V | 1 | 0.799 |
| 1568 | 2736C2CO1.493 | cgpGmo-S416b | V | 2 | 0.93 |
| 1569 | 2745C1CO1.121 | cgpGmo-S417 | V | 1 | 0.857 |
| 1570 | 2750C2CO1.1006 | cgpGmo-S418 |   | 1 | 0.822 |
| 1571 | 2752C1CO1.338 | cgpGmo-S419 | V | 1 | 0.837 |
| 1572 | 5749C1CO1.404 | cgpGmo-S42 | V | 1 | 0.413 |
| 1573 | 2756C3CO1.530 | cgpGmo-S420 | V | 1 | 0.816 |
| 1574 | 2762C1CO1.366 | cgpGmo-S421 | V | 1 | 0.784 |
| 1575 | 2764C1CO1.784 | cgpGmo-S422 | V | 1 | 0.87 |
| 1576 | 2767C1CO1.502 | cgpGmo-S423 | V | 1 | 0.793 |
| 1577 | 2770C2CO1.347 | cgpGmo-S424 | V | 1 | 0.864 |
| 1578 | 2781C3CO1.955 | cgpGmo-S425 | V | 1 | 0.849 |
| 1579 | 2793C1CO1.551 | cgpGmo-S426 | V | 1 | 0.557 |
| 1580 | 2798C2CO1.402 | cgpGmo-S427 | V | 1 | 0.843 |
| 1581 | 2805C1CO1.1000 | cgpGmo-S428 | V | 1 | 0.768 |
| 1582 | 280C1CO1.580 | cgpGmo-S429 | V | 1 | 0.905 |
| 1583 | 2814C1CO1.108 | cgpGmo-S430a | V | 2 | 0.98 |
| 1584 | 2814C1CO1.309 | cgpGmo-S430b | V | 1 | 0.728 |
| 1585 | 2818C1CO1.284 | cgpGmo-S431 | V | 1 | 0.683 |
| 1586 | 281C3CO1.82 | cgpGmo-S432 |   | 1 | 0.887 |
| 1587 | 2826C1CO1.252 | cgpGmo-S433 | V | 1 | 0.561 |
| 1588 | 2830C1CO1.138 | cgpGmo-S434a | V | 1 | 0.572 |
| 1589 | 2830C1CO1.324 | cgpGmo-S434b | V | 2 | 0.89 |
| 1590 | 2834C2CO1.556 | cgpGmo-S435 | V | 1 | 0.674 |
| 1591 | 2838C1CO1.169 | cgpGmo-S436 | V | 1 | 0.823 |
| 1592 | 2841C1CO1.368 | cgpGmo-S437 | V | 1 | 0.913 |
| 1593 | 2845C2CO1.189 | cgpGmo-S438 | V | 1 | 0.899 |
| 1594 | 2848C2CO1.512 | cgpGmo-S439 | V | 1 | 0.792 |
| 1595 | 6873C1CO1.107 | cgpGmo-S44 | V | 1 | 0.839 |
| 1596 | 2878C2CO1.535 | cgpGmo-S440 |   | 1 | 0.887 |
| 1597 | 2887C1CO1.337 | cgpGmo-S441 | V | 1 | 0.696 |
| 1598 | 2889C1CO1.517 | cgpGmo-S442a | V | 2 | 0.97 |
| 1599 | 2889C1CO1.588 | cgpGmo-S442b | V | 1 | 0.881 |
| 1600 | 288C1CO1.128 | cgpGmo-S443 | V | 1 | 0.562 |
| 1601 | 2895C1CO1.348 | cgpGmo-S444 | V | 1 | 0.503 |
| 1602 | 290C1CO1.627 | cgpGmo-S446 | V | 1 | 0.672 |
| 1603 | 2911C1CO1.553 | cgpGmo-S447 | V | 1 | 0.845 |
| 1604 | 2915C1CO1.620 | cgpGmo-S448 | V | 1 | 0.676 |
| 1605 | 2917C1CO1.596 | cgpGmo-S449a | V | 1 | 0.697 |
| 1606 | 2917C1CO1.307 | cgpGmo-S449b | V | 2 | 0.76 |
| 1607 | 7167C1CO1.101 | cgpGmo-S45 | V | 1 | 0.755 |
| 1608 | 2923C1CO1.1592 | cgpGmo-S450 |   | 1 | 0.913 |
| 1609 | 2925C1CO1.421 | cgpGmo-S451a |   | 1 | 0.804 |
| 1610 | 2925C1CO1.307 | cgpGmo-S451b |   | 2 | 0.91 |
| 1611 | 2929C2CO1.807 | cgpGmo-S452 |   | 1 | 0.69 |
| 1612 | 292C1CO1.151 | cgpGmo-S453 |   | 1 | 0.778 |
| 1613 | 2931C1CO1.307 | cgpGmo-S454 |   | 1 | 0.736 |
| 1614 | 2935C1CO1.592 | cgpGmo-S455 | V | 1 | 0.898 |
| 1615 | 293C1CO1.303 | cgpGmo-S456 |   | 1 | 0.877 |
| 1616 | 2968C1CO1.121 | cgpGmo-S458a | V | 2 | 0.93 |
| 1617 | 2968C1CO1.207 | cgpGmo-S458b |   | 1 | 0.885 |
| 1618 | 2979C1CO1.280 | cgpGmo-S459 | V | 1 | 0.785 |
| 1619 | 298C1CO1.798 | cgpGmo-S460 | V | 1 | 0.842 |
| 1620 | 2991C1CO1.142 | cgpGmo-S461 |   | 1 | 0.772 |
| 1621 | 3001C1CO1.562 | cgpGmo-S462 | V | 1 | 0.782 |
| 1622 | 3002C1CO1.163 | cgpGmo-S463a | V | 1 | 0.545 |
| 1623 | 3002C1CO1.472 | cgpGmo-S463b | V | 2 | 0.85 |
| 1624 | 3003C2CO1.143 | cgpGmo-S464 | V | 1 | 0.849 |
| 1625 | 3006C1CO1.620 | cgpGmo-S465 | V | 1 | 0.872 |
| 1626 | 3022C2CO1.138 | cgpGmo-S466 | V | 1 | 0.707 |
| 1627 | 3038C1CO1.104 | cgpGmo-S467 |   | 1 | 0.785 |
| 1628 | 3039C1CO1.87 | cgpGmo-S468 |   | 1 | 0.826 |
| 1629 | 3043C1CO1.564 | cgpGmo-S469 | V | 1 | 0.887 |
| 1630 | 9323C1CO1.317 | cgpGmo-S46a | V | 1 | 0.765 |
| 1631 | 9323C1CO1.439 | cgpGmo-S46b | V | 2 | 0.89 |
| 1632 | 10327C1CO1.345 | cgpGmo-S47 |   | 1 | 0.851 |
| 1633 | 3049C1CO1.721 | cgpGmo-S470 | V | 1 | 0.814 |
| 1634 | 3057C2CO1.742 | cgpGmo-S471 | V | 1 | 0.852 |
| 1635 | 3061C1CO1.302 | cgpGmo-S472 | V | 1 | 0.569 |
| 1636 | 3072C1CO1.137 | cgpGmo-S473 |   | 1 | 0.903 |
| 1637 | 3077C1CO1.326 | cgpGmo-S474 | V | 1 | 0.533 |
| 1638 | 3097C1CO1.589 | cgpGmo-S475 | V | 1 | 0.872 |
| 1639 | 3112C1CO1.126 | cgpGmo-S476 | V | 1 | 0.754 |
| 1640 | 3123C1CO1.522 | cgpGmo-S477 | V | 1 | 0.865 |
| 1641 | 3129C1CO1.316 | cgpGmo-S478 | V | 1 | 0.837 |
| 1642 | 3150C1CO1.167 | cgpGmo-S479 | V | 1 | 0.883 |
| 1643 | 10714C1CO1.610 | cgpGmo-S48 |   | 1 | 0.759 |
| 1644 | 3155C1CO1.1902 | cgpGmo-S480 | V | 1 | 0.869 |
| 1645 | 3157C1CO1.686 | cgpGmo-S481 | V | 1 | 0.716 |
| 1646 | 3167C1CO1.676 | cgpGmo-S482 |   | 1 | 0.693 |
| 1647 | 3197C2CO1.89 | cgpGmo-S483 |   | 1 | 0.855 |
| 1648 | 3211C1CO1.550 | cgpGmo-S485 |   | 1 | 0.866 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1649 | 321C1CO1.535 | cgpGmo-S486 | V | 1 | 0.659 |
| 1650 | 3220C1CO1.430 | cgpGmo-S487 | V | 1 | 0.823 |
| 1651 | 3230C1CO1.997 | cgpGmo-S488 | V | 1 | 0.855 |
| 1652 | 3233C2CO1.234 | cgpGmo-S489 | V | 1 | 0.857 |
| 1653 | 1126C1CO1.377 | cgpGmo-S49 | V | 1 | 0.859 |
| 1654 | 3238C1CO1.625 | cgpGmo-S490 | V | 1 | 0.791 |
| 1655 | 3244C1CO1.519 | cgpGmo-S491 | V | 1 | 0.756 |
| 1656 | 324C2CO2.536 | cgpGmo-S492 | | 1 | 0.897 |
| 1657 | 325C1CO1.835 | cgpGmo-S493 | V | 1 | 0.72 |
| 1658 | 3270C1CO1.150 | cgpGmo-S495 | V | 1 | 0.428 |
| 1659 | 3271C1CO1.491 | cgpGmo-S496 | V | 1 | 0.895 |
| 1660 | 3287C1CO1.499 | cgpGmo-S497 | V | 1 | 0.783 |
| 1661 | 328C16CO1.715 | cgpGmo-S498 | | 1 | 0.467 |
| 1662 | 3291C1CO1.521 | cgpGmo-S499 | | 1 | 0.91 |
| 1663 | 1189C1CO1.555 | cgpGmo-S50 | | 1 | 0.683 |
| 1664 | 32C1CO1.727 | cgpGmo-S500 | V | 1 | 0.913 |
| 1665 | 3315C1CO1.250 | cgpGmo-S501 | V | 1 | 0.809 |
| 1666 | 331C1CO1.327 | cgpGmo-S502 | V | 1 | 0.848 |
| 1667 | 3326C1CO1.186 | cgpGmo-S503 | V | 1 | 0.601 |
| 1668 | 3330C1CO1.353 | cgpGmo-S504 | V | 1 | 0.868 |
| 1669 | 3337C1CO1.1263 | cgpGmo-S505 | V | 1 | 0.638 |
| 1670 | 3359C1CO1.602 | cgpGmo-S507 | | 1 | 0.893 |
| 1671 | 3373C1CO1.440 | cgpGmo-S508 | V | 1 | 0.737 |
| 1672 | 3376C1CO1.606 | cgpGmo-S509 | V | 1 | 0.691 |
| 1673 | 1322C1CO1.760 | cgpGmo-S51 | | 1 | 0.793 |
| 1674 | 3377C1CO1.412 | cgpGmo-S510 | V | 1 | 0.593 |
| 1675 | 337C1CO1.374 | cgpGmo-S511a | | 1 | 0.908 |
| 1676 | 337C1CO1.592 | cgpGmo-S511b | V | 2 | 0.98 |
| 1677 | 3383C1CO1.457 | cgpGmo-S512 | V | 1 | 0.8 |
| 1678 | 3384C1CO1.157 | cgpGmo-S513 | V | 1 | 0.758 |
| 1679 | 3388C1CO1.350 | cgpGmo-S514 | V | 1 | 0.907 |
| 1680 | 3399C1CO1.407 | cgpGmo-S515 | V | 1 | 0.549 |
| 1681 | 33C2CO1.816 | cgpGmo-S516 | V | 1 | 0.663 |
| 1682 | 3402C1CO1.108 | cgpGmo-S517a | | 1 | 0.687 |
| 1683 | 3402C1CO1.591 | cgpGmo-S517b | V | 2 | 0.95 |
| 1684 | 3410C1CO1.325 | cgpGmo-S518 | V | 1 | 0.669 |
| 1685 | 341C1CO1.343 | cgpGmo-S519 | | 1 | 0.765 |
| 1686 | 1388C1CO1.162 | cgpGmo-S52 | V | 1 | 0.665 |
| 1687 | 3421C1CO1.642 | cgpGmo-S520 | V | 1 | 0.74 |
| 1688 | 3426C1CO1.249 | cgpGmo-S521a | | 2 | 0.81 |
| 1689 | 3426C1CO1.420 | cgpGmo-S521b | V | 1 | 0.708 |
| 1690 | 342C1CO1.186 | cgpGmo-S522 | | 1 | 0.78 |
| 1691 | 3445C1CO1.593 | cgpGmo-S523 | V | 1 | 0.906 |
| 1692 | 3452C4CO1.423 | cgpGmo-S524 | | 1 | 0.745 |
| 1693 | 3462C1CO1.300 | cgpGmo-S525 | V | 1 | 0.911 |
| 1694 | 3467C2CO1.503 | cgpGmo-S526 | V | 1 | 0.829 |
| 1695 | 3469C1CO1.87 | cgpGmo-S527 | | 1 | 0.864 |
| 1696 | 3472C2CO1.436 | cgpGmo-S528 | V | 1 | 0.759 |
| 1697 | 3478C1CO1.165 | cgpGmo-S529 | V | 1 | 0.638 |
| 1698 | 1667C1CO1.662 | cgpGmo-S53 | | 1 | 0.831 |
| 1699 | 3479C1CO1.279 | cgpGmo-S530a | V | 2 | 0.9 |
| 1700 | 3479C1CO1.494 | cgpGmo-S530b | | 1 | 0.65 |
| 1701 | 3500C1CO1.593 | cgpGmo-S531 | | 1 | 0.911 |
| 1702 | 3505C2CO1.243 | cgpGmo-S532 | V | 1 | 0.797 |
| 1703 | 3508C1CO1.259 | cgpGmo-S533a | | 2 | 0.95 |
| 1704 | 3508C1CO1.400 | cgpGmo-S533b | V | 1 | 0.81 |
| 1705 | 3513C8CO1.666 | cgpGmo-S534 | | 1 | 0.55 |
| 1706 | 3522C1CO1.148 | cgpGmo-S535a | V | 2 | 0.99 |
| 1707 | 3522C1CO1.330 | cgpGmo-S535b | V | 1 | 0.658 |
| 1708 | 3530C1CO1.317 | cgpGmo-S536 | V | 1 | 0.861 |
| 1709 | 3552C1CO1.717 | cgpGmo-S537 | V | 1 | 0.763 |
| 1710 | 3556C5CO1.281 | cgpGmo-S539 | V | 1 | 0.473 |
| 1711 | 1759C1CO1.591 | cgpGmo-S54 | | 1 | 0.677 |
| 1712 | 3563C1CO1.611 | cgpGmo-S540 | | 1 | 0.821 |
| 1713 | 3569C1CO1.254 | cgpGmo-S541a | V | 2 | 0.96 |
| 1714 | 3569C1CO1.391 | cgpGmo-S541b | V | 1 | 0.904 |
| 1715 | 3579C1CO1.114 | cgpGmo-S542 | V | 1 | 0.888 |
| 1716 | 357C1CO1.533 | cgpGmo-S543 | V | 1 | 0.554 |
| 1717 | 3594C1CO1.850 | cgpGmo-S544 | V | 1 | 0.761 |
| 1718 | 3599C1CO2.748 | cgpGmo-S545 | | 1 | 0.912 |
| 1719 | 359C1CO1.275 | cgpGmo-S546 | V | 1 | 0.643 |
| 1720 | 3610C1CO1.450 | cgpGmo-S547 | V | 1 | 0.668 |
| 1721 | 3648C1CO1.134 | cgpGmo-S548 | V | 1 | 0.889 |
| 1722 | 3653C1CO1.565 | cgpGmo-S549 | V | 1 | 0.863 |
| 1723 | 1795C1CO1.524 | cgpGmo-S55 | V | 1 | 0.795 |
| 1724 | 3657C1CO1.1328 | cgpGmo-S550 | V | 1 | 0.879 |
| 1725 | 365C2CO1.268 | cgpGmo-S551 | V | 1 | 0.46 |
| 1726 | 3675C1CO1.715 | cgpGmo-S552 | V | 1 | 0.652 |
| 1727 | 3678C1CO1.588 | cgpGmo-S553 | V | 1 | 0.88 |
| 1728 | 3692C1CO1.194 | cgpGmo-S554 | | 1 | 0.843 |
| 1729 | 36C19CO1.189 | cgpGmo-S555a | | 2 | 0.93 |
| 1730 | 36C19CO1.264 | cgpGmo-S555b | | 1 | 0.821 |
| 1731 | 3700C1CO1.185 | cgpGmo-S556 | V | 1 | 0.898 |
| 1732 | 3713C1CO1.312 | cgpGmo-S557 | V | 1 | 0.575 |
| 1733 | 372C3CO1.448 | cgpGmo-S558 | | 1 | 0.786 |
| 1734 | 3732C1CO1.72 | cgpGmo-S559 | V | 1 | 0.851 |
| 1735 | 1924C1CO1.537 | cgpGmo-S56 | | 1 | 0.724 |
| 1736 | 373C1CO1.221 | cgpGmo-S560 | V | 1 | 0.891 |
| 1737 | 3745C1CO1.383 | cgpGmo-S561 | V | 1 | 0.888 |
| 1738 | 3752C1CO1.308 | cgpGmo-S562 | V | 1 | 0.84 |
| 1739 | 3753C2CO1.291 | cgpGmo-S563 | V | 1 | 0.817 |
| 1740 | 3753C3CO1.413 | cgpGmo-S564 | V | 1 | 0.811 |
| 1741 | 3760C2CO1.483 | cgpGmo-S565 | V | 1 | 0.425 |
| 1742 | 3760C3CO1.508 | cgpGmo-S566 | V | 1 | 0.595 |
| 1743 | 3768C2CO1.142 | cgpGmo-S567 | | 1 | 0.524 |
| 1744 | 3780C1CO1.291 | cgpGmo-S568 | | 1 | 0.869 |
| 1745 | 3799C1CO1.161 | cgpGmo-S569 | | 1 | 0.811 |
| 1746 | 2153C2CO1.693 | cgpGmo-S57 | V | 1 | 0.767 |
| 1747 | 37C1CO1.182 | cgpGmo-S570 | | 1 | 0.845 |
| 1748 | 3804C1CO1.1043 | cgpGmo-S571 | | 1 | 0.597 |
| 1749 | 3826C1CO1.474 | cgpGmo-S572 | V | 1 | 0.779 |
| 1750 | 3833C1CO1.461 | cgpGmo-S573 | V | 1 | 0.822 |
| 1751 | 3839C1CO1.555 | cgpGmo-S574 | | 1 | 0.814 |
| 1752 | 3841C1CO1.335 | cgpGmo-S575 | V | 1 | 0.903 |
| 1753 | 3846C1CO1.881 | cgpGmo-S576 | V | 1 | 0.873 |
| 1754 | 3863C1CO1.284 | cgpGmo-S577 | V | 1 | 0.868 |
| 1755 | 3865C1CO1.138 | cgpGmo-S578 | V | 1 | 0.755 |
| 1756 | 3868C1CO1.680 | cgpGmo-S579 | V | 1 | 0.686 |
| 1757 | 3871C1CO1.249 | cgpGmo-S580 | V | 1 | 0.619 |
| 1758 | 3877C2CO1.148 | cgpGmo-S581 | V | 1 | 0.748 |
| 1759 | 388C1CO1.385 | cgpGmo-S582 | V | 1 | 0.897 |
| 1760 | 3892C1CO1.494 | cgpGmo-S583 | V | 1 | 0.807 |
| 1761 | 3899C1CO1.483 | cgpGmo-S584 | V | 1 | 0.898 |
| 1762 | 389C34CO1.88 | cgpGmo-S585a | | 2 | 0.92 |
| 1763 | 389C34CO1.187 | cgpGmo-S585b | | 1 | 0.752 |
| 1764 | 390C1CO1.202 | cgpGmo-S586 | V | 1 | 0.665 |
| 1765 | 3910C1CO1.582 | cgpGmo-S587 | V | 1 | 0.616 |
| 1766 | 3912C1CO1.393 | cgpGmo-S588 | V | 1 | 0.902 |
| 1767 | 391C1CO1.121 | cgpGmo-S589 | | 1 | 0.762 |
| 1768 | 2156C1CO1.318 | cgpGmo-S58a | | 1 | 0.841 |
| 1769 | 2156C1CO1.542 | cgpGmo-S58b | V | 2 | 0.85 |
| 1770 | 393C1CO1.208 | cgpGmo-S590 | V | 1 | 0.523 |
| 1771 | 394C3CO1.540 | cgpGmo-S591 | V | 1 | 0.878 |
| 1772 | 395C1CO1.698 | cgpGmo-S592 | V | 1 | 0.848 |
| 1773 | 3965C2CO1.185 | cgpGmo-S593 | V | 1 | 0.873 |
| 1774 | 3973C1CO1.555 | cgpGmo-S594 | V | 1 | 0.887 |
| 1775 | 3981C1CO1.219 | cgpGmo-S595 | V | 1 | 0.913 |
| 1776 | 3984C1CO1.563 | cgpGmo-S596 | V | 1 | 0.896 |
| 1777 | 3989C1CO1.629 | cgpGmo-S597 | V | 1 | 0.855 |
| 1778 | 3994C1CO1.333 | cgpGmo-S598 | | 1 | 0.91 |
| 1779 | 399C2CO1.514 | cgpGmo-S599 | V | 1 | 0.74 |
| 1780 | 2220C1CO1.459 | cgpGmo-S59a | V | 2 | 0.93 |
| 1781 | 2220C1CO1.542 | cgpGmo-S59b | | 1 | 0.603 |
| 1782 | 6924C1CO1.475 | cgpGmo-S5a | | 2 | 0.96 |
| 1783 | 6924C1CO1.891 | cgpGmo-S5b | | 1 | 0.842 |
| 1784 | 8518C1CO1.523 | cgpGmo-S6 | V | 1 | 0.857 |
| 1785 | 2281C1CO1.125 | cgpGmo-S60 | V | 1 | 0.7 |
| 1786 | 4014C1CO1.594 | cgpGmo-S600 | V | 1 | 0.791 |
| 1787 | 4028C1CO1.713 | cgpGmo-S601 | V | 1 | 0.493 |
| 1788 | 4032C1CO1.611 | cgpGmo-S602 | V | 1 | 0.84 |
| 1789 | 4042C1CO1.577 | cgpGmo-S603 | V | 1 | 0.843 |
| 1790 | 4045C1CO1.331 | cgpGmo-S604 | V | 1 | 0.847 |
| 1791 | 4063C1CO1.378 | cgpGmo-S605 | V | 1 | 0.868 |
| 1792 | 4064C1CO1.123 | cgpGmo-S606a | V | 2 | 0.91 |
| 1793 | 4064C1CO1.422 | cgpGmo-S606b | | 1 | 0.751 |
| 1794 | 4077C1CO1.438 | cgpGmo-S607 | V | 1 | 0.91 |
| 1795 | 4078C1CO1.540 | cgpGmo-S608 | V | 1 | 0.707 |
| 1796 | 4079C1CO1.533 | cgpGmo-S609 | V | 1 | 0.89 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1797 | 2317C1CO1.570 | cgpGmo-S61 | V | 1 | 0.677 |
| 1798 | 408C1CO1.173 | cgpGmo-S610 | | 1 | 0.761 |
| 1799 | 4090C2CO1.179 | cgpGmo-S611 | V | 1 | 0.854 |
| 1800 | 40C1CO1.223 | cgpGmo-S612 | | 1 | 0.914 |
| 1801 | 4109C1CO1.399 | cgpGmo-S613a | | 1 | 0.493 |
| 1802 | 4109C1CO1.558 | cgpGmo-S613b | V | 2 | 0.9 |
| 1803 | 412C2CO1.446 | cgpGmo-S614a | V | 1 | 0.669 |
| 1804 | 412C2CO1.581 | cgpGmo-S614b | V | 2 | 0.8 |
| 1805 | 415C1CO1.306 | cgpGmo-S615 | V | 1 | 0.888 |
| 1806 | 4202C1CO1.408 | cgpGmo-S616 | V | 1 | 0.805 |
| 1807 | 4206C1CO1.337 | cgpGmo-S617 | V | 1 | 0.588 |
| 1808 | 4217C1CO1.355 | cgpGmo-S618 | V | 1 | 0.58 |
| 1809 | 4218C1CO1.1046 | cgpGmo-S619 | | 1 | 0.851 |
| 1810 | 2449C1CO1.207 | cgpGmo-S62 | V | 1 | 0.672 |
| 1811 | 422C1CO1.425 | cgpGmo-S620 | | 1 | 0.666 |
| 1812 | 4232C1CO1.517 | cgpGmo-S621 | V | 1 | 0.906 |
| 1813 | 4244C1CO1.497 | cgpGmo-S622 | | 1 | 0.864 |
| 1814 | 4268C1CO1.189 | cgpGmo-S623 | V | 1 | 0.782 |
| 1815 | 4276C1CO1.120 | cgpGmo-S624 | V | 1 | 0.712 |
| 1816 | 4277C1CO1.111 | cgpGmo-S625a | | 1 | 0.812 |
| 1817 | 4277C1CO1.629 | cgpGmo-S625b | | 2 | 0.99 |
| 1818 | 4282C1CO1.389 | cgpGmo-S626a | V | 2 | 0.95 |
| 1819 | 4282C1CO1.613 | cgpGmo-S626b | V | 1 | 0.883 |
| 1820 | 4288C1CO1.320 | cgpGmo-S627 | V | 1 | 0.616 |
| 1821 | 4289C2CO1.374 | cgpGmo-S628 | V | 1 | 0.767 |
| 1822 | 4292C1CO1.580 | cgpGmo-S629 | V | 1 | 0.781 |
| 1823 | 246C1CO1.437 | cgpGmo-S63 | V | 1 | 0.453 |
| 1824 | 4296C1CO1.192 | cgpGmo-S630 | V | 1 | 0.834 |
| 1825 | 4304C1CO1.155 | cgpGmo-S631 | V | 1 | 0.756 |
| 1826 | 4307C2CO1.977 | cgpGmo-S632a | V | 2 | 0.89 |
| 1827 | 4307C2CO1.1077 | cgpGmo-S632b | V | 1 | 0.616 |
| 1828 | 430C1CO1.803 | cgpGmo-S633 | V | 1 | 0.871 |
| 1829 | 4313C1CO1.551 | cgpGmo-S634 | V | 1 | 0.575 |
| 1830 | 4322C1CO1.502 | cgpGmo-S635 | V | 1 | 0.784 |
| 1831 | 4332C1CO1.346 | cgpGmo-S636 | V | 1 | 0.901 |
| 1832 | 4335C1CO1.445 | cgpGmo-S637 | V | 1 | 0.762 |
| 1833 | 4345C1CO1.539 | cgpGmo-S638a | V | 2 | 0.98 |
| 1834 | 4345C1CO1.634 | cgpGmo-S638b | V | 1 | 0.725 |
| 1835 | 4359C1CO1.400 | cgpGmo-S639 | V | 1 | 0.764 |
| 1836 | 4367C1CO1.509 | cgpGmo-S640a | | 1 | 0.809 |
| 1837 | 4367C1CO1.896 | cgpGmo-S640b | V | 2 | 0.98 |
| 1838 | 4372C1CO1.554 | cgpGmo-S641 | | 1 | 0.915 |
| 1839 | 437C1CO1.241 | cgpGmo-S642 | V | 1 | 0.62 |
| 1840 | 4393C1CO1.574 | cgpGmo-S643a | V | 1 | 0.53 |
| 1841 | 4393C1CO1.662 | cgpGmo-S643b | V | 2 | 0.91 |
| 1842 | 4404C1CO1.224 | cgpGmo-S644 | V | 1 | 0.861 |
| 1843 | 4412C2CO1.371 | cgpGmo-S645 | | 1 | 0.662 |
| 1844 | 4415C1CO2.571 | cgpGmo-S646 | V | 1 | 0.887 |
| 1845 | 4421C1CO1.124 | cgpGmo-S647 | | 1 | 0.566 |
| 1846 | 442C1CO1.532 | cgpGmo-S648 | | 1 | 0.661 |
| 1847 | 4440C1CO1.817 | cgpGmo-S649a | V | 1 | 0.667 |
| 1848 | 4440C1CO1.1126 | cgpGmo-S649b | V | 2 | 0.7 |
| 1849 | 2690C2CO1.466 | cgpGmo-S65 | | 1 | 0.889 |
| 1850 | 4449C1CO1.162 | cgpGmo-S650a | | 2 | 0.91 |
| 1851 | 4449C1CO1.293 | cgpGmo-S650b | V | 1 | 0.879 |
| 1852 | 4458C1CO1.386 | cgpGmo-S651 | | 1 | 0.811 |
| 1853 | 445C1CO1.820 | cgpGmo-S652 | V | 1 | 0.46 |
| 1854 | 4469C1CO1.201 | cgpGmo-S653 | V | 1 | 0.875 |
| 1855 | 446C1CO1.409 | cgpGmo-S654 | | 1 | 0.499 |
| 1856 | 4484C1CO1.459 | cgpGmo-S655a | | 2 | 0.91 |
| 1857 | 4484C1CO1.568 | cgpGmo-S655b | | 1 | 0.908 |
| 1858 | 448C1CO1.858 | cgpGmo-S656 | | 1 | 0.893 |
| 1859 | 4497C1CO1.350 | cgpGmo-S657a | V | 2 | 0.93 |
| 1860 | 4497C1CO1.521 | cgpGmo-S657b | V | 1 | 0.851 |
| 1861 | 4508C2CO1.152 | cgpGmo-S658 | V | 1 | 0.823 |
| 1862 | 4511C1CO1.665 | cgpGmo-S659 | | 1 | 0.804 |
| 1863 | 2690C3CO1.239 | cgpGmo-S66 | | 1 | 0.907 |
| 1864 | 4512C2CO1.327 | cgpGmo-S660 | | 1 | 0.58 |
| 1865 | 4514C1CO1.79 | cgpGmo-S661a | V | 1 | 0.878 |
| 1866 | 4514C1CO1.690 | cgpGmo-S661b | V | 2 | 0.98 |
| 1867 | 4547C2CO1.299 | cgpGmo-S662 | | 1 | 0.781 |
| 1868 | 4558C2CO1.386 | cgpGmo-S663 | V | 1 | 0.709 |
| 1869 | 4569C2CO1.241 | cgpGmo-S664 | V | 1 | 0.749 |
| 1870 | 4571C1CO1.453 | cgpGmo-S665 | V | 1 | 0.789 |
| 1871 | 4576C1CO1.585 | cgpGmo-S666 | V | 1 | 0.794 |
| 1872 | 4591C1CO1.622 | cgpGmo-S667 | V | 1 | 0.883 |
| 1873 | 4592C1CO1.326 | cgpGmo-S668 | V | 1 | 0.898 |
| 1874 | 4603C1CO1.532 | cgpGmo-S669 | V | 1 | 0.425 |
| 1875 | 2722C3CO1.535 | cgpGmo-S67 | | 1 | 0.632 |
| 1876 | 4618C1CO1.148 | cgpGmo-S670 | V | 1 | 0.517 |
| 1877 | 4660C1CO1.434 | cgpGmo-S671 | | 1 | 0.847 |
| 1878 | 4664C2CO1.271 | cgpGmo-S672 | V | 1 | 0.635 |
| 1879 | 466C1CO1.619 | cgpGmo-S673 | V | 1 | 0.848 |
| 1880 | 466C2CO1.340 | cgpGmo-S674 | V | 1 | 0.882 |
| 1881 | 4679C1CO1.249 | cgpGmo-S675a | V | 1 | 0.908 |
| 1882 | 4679C1CO1.677 | cgpGmo-S675b | V | 2 | 0.94 |
| 1883 | 4688C1CO1.934 | cgpGmo-S676 | V | 1 | 0.562 |
| 1884 | 4688C2CO1.109 | cgpGmo-S677 | V | 1 | 0.768 |
| 1885 | 4711C2CO1.437 | cgpGmo-S679 | V | 1 | 0.759 |
| 1886 | 2906C1CO1.115 | cgpGmo-S68 | V | 1 | 0.63 |
| 1887 | 4729C1CO1.514 | cgpGmo-S680 | | 1 | 0.882 |
| 1888 | 472C1CO1.283 | cgpGmo-S681a | V | 2 | 0.96 |
| 1889 | 472C1CO1.667 | cgpGmo-S681b | V | 1 | 0.593 |
| 1890 | 4744C1CO1.242 | cgpGmo-S682 | V | 1 | 0.707 |
| 1891 | 4747C1CO1.505 | cgpGmo-S683a | V | 2 | 0.89 |
| 1892 | 4747C1CO1.627 | cgpGmo-S683b | | 1 | 0.855 |
| 1893 | 4749C1CO1.390 | cgpGmo-S684 | V | 1 | 0.856 |
| 1894 | 4755C1CO1.422 | cgpGmo-S685 | | 1 | 0.778 |
| 1895 | 4764C1CO1.123 | cgpGmo-S686a | V | 2 | 0.81 |
| 1896 | 4764C1CO1.451 | cgpGmo-S686b | V | 1 | 0.762 |
| 1897 | 4767C1CO1.360 | cgpGmo-S687 | V | 1 | 0.861 |
| 1898 | 4773C1CO1.458 | cgpGmo-S688 | V | 1 | 0.911 |
| 1899 | 4797C1CO1.419 | cgpGmo-S689 | V | 1 | 0.864 |
| 1900 | 3030C1CO1.290 | cgpGmo-S69 | | 1 | 0.887 |
| 1901 | 4809C1CO1.272 | cgpGmo-S690a | | 2 | 0.99 |
| 1902 | 4809C1CO1.334 | cgpGmo-S690b | | 1 | 0.599 |
| 1903 | 4810C1CO1.310 | cgpGmo-S691 | V | 1 | 0.837 |
| 1904 | 4817C1CO1.234 | cgpGmo-S692a | V | 1 | 0.793 |
| 1905 | 4817C1CO1.391 | cgpGmo-S692b | V | 2 | 0.91 |
| 1906 | 4818C1CO1.453 | cgpGmo-S693 | V | 1 | 0.827 |
| 1907 | 4823C1CO1.458 | cgpGmo-S694 | V | 1 | 0.716 |
| 1908 | 4824C1CO1.286 | cgpGmo-S695 | V | 1 | 0.873 |
| 1909 | 4831C2CO1.175 | cgpGmo-S696 | V | 1 | 0.642 |
| 1910 | 4852C1CO1.132 | cgpGmo-S697 | V | 1 | 0.655 |
| 1911 | 4858C1CO1.162 | cgpGmo-S698 | V | 1 | 0.899 |
| 1912 | 4866C1CO1.75 | cgpGmo-S699a | V | 2 | 0.73 |
| 1913 | 4866C1CO1.262 | cgpGmo-S699b | V | 1 | 0.593 |
| 1914 | 3132C1CO1.191 | cgpGmo-S70 | V | 1 | 0.817 |
| 1915 | 4894C1CO1.903 | cgpGmo-S700 | | 1 | 0.776 |
| 1916 | 4911C1CO1.607 | cgpGmo-S701 | V | 1 | 0.638 |
| 1917 | 4915C1CO1.272 | cgpGmo-S702a | | 2 | 0.94 |
| 1918 | 4915C1CO1.379 | cgpGmo-S702b | V | 1 | 0.458 |
| 1919 | 4925C1CO1.270 | cgpGmo-S703 | | 1 | 0.754 |
| 1920 | 4931C1CO1.625 | cgpGmo-S704 | V | 1 | 0.867 |
| 1921 | 4932C1CO1.142 | cgpGmo-S705 | | 1 | 0.856 |
| 1922 | 4936C1CO1.161 | cgpGmo-S706 | V | 1 | 0.774 |
| 1923 | 4940C1CO1.238 | cgpGmo-S707 | V | 1 | 0.589 |
| 1924 | 4946C1CO1.907 | cgpGmo-S708a | | 1 | 0.755 |
| 1925 | 4946C1CO1.988 | cgpGmo-S708b | | 2 | 0.93 |
| 1926 | 4949C1CO1.513 | cgpGmo-S709 | | 1 | 0.77 |
| 1927 | 3170C2CO1.136 | cgpGmo-S71 | V | 1 | 0.746 |
| 1928 | 4961C2CO1.220 | cgpGmo-S710 | | 1 | 0.541 |
| 1929 | 4963C1CO1.90 | cgpGmo-S711a | | 1 | 0.757 |
| 1930 | 4963C1CO1.217 | cgpGmo-S711b | V | 2 | 0.92 |
| 1931 | 496C1CO1.638 | cgpGmo-S712 | V | 1 | 0.587 |
| 1932 | 4975C1CO1.328 | cgpGmo-S713 | | 1 | 0.532 |
| 1933 | 497C1CO1.563 | cgpGmo-S714a | V | 2 | 0.77 |
| 1934 | 497C1CO1.984 | cgpGmo-S714b | | 1 | 0.72 |
| 1935 | 5002C1CO1.225 | cgpGmo-S715 | V | 1 | 0.888 |
| 1936 | 5007C1CO2.776 | cgpGmo-S716 | V | 1 | 0.89 |
| 1937 | 5040C1CO1.700 | cgpGmo-S717 | V | 1 | 0.865 |
| 1938 | 5042C1CO1.183 | cgpGmo-S718a | V | 1 | 0.828 |
| 1939 | 5042C1CO1.449 | cgpGmo-S718b | V | 2 | 0.9 |
| 1940 | 5047C2CO1.566 | cgpGmo-S719 | V | 1 | 0.721 |
| 1941 | 3204C1CO1.65 | cgpGmo-S72 | | 1 | 0.491 |
| 1942 | 5062C1CO1.277 | cgpGmo-S720 | V | 1 | 0.566 |
| 1943 | 5086C1CO1.604 | cgpGmo-S721 | | 1 | 0.889 |
| 1944 | 5114C1CO1.160 | cgpGmo-S722 | V | 1 | 0.525 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 1945 | 512C1CO1.115 | cgpGmo-S723 | V | 1 | 0.693 |
| 1946 | 513C1CO1.511 | cgpGmo-S724 |   | 1 | 0.784 |
| 1947 | 5155C1CO1.111 | cgpGmo-S725 | V | 1 | 0.883 |
| 1948 | 5162C2CO1.544 | cgpGmo-S726 | V | 1 | 0.891 |
| 1949 | 5166C1CO1.290 | cgpGmo-S727 | V | 1 | 0.786 |
| 1950 | 5172C1CO1.598 | cgpGmo-S728 | V | 1 | 0.869 |
| 1951 | 5192C1CO1.138 | cgpGmo-S729 | V | 1 | 0.882 |
| 1952 | 5222C1CO1.351 | cgpGmo-S730 | V | 1 | 0.718 |
| 1953 | 5231C1CO1.189 | cgpGmo-S731 |   | 1 | 0.904 |
| 1954 | 5235C1CO1.747 | cgpGmo-S732 |   | 1 | 0.512 |
| 1955 | 5236C1CO1.575 | cgpGmo-S733 |   | 1 | 0.751 |
| 1956 | 523C1CO1.142 | cgpGmo-S734 | V | 1 | 0.863 |
| 1957 | 5254C1CO1.287 | cgpGmo-S735 | V | 1 | 0.779 |
| 1958 | 5258C1CO1.446 | cgpGmo-S736 |   | 1 | 0.843 |
| 1959 | 5259C1CO1.525 | cgpGmo-S737 | V | 1 | 0.901 |
| 1960 | 527C1CO1.385 | cgpGmo-S739 | V | 1 | 0.496 |
| 1961 | 5284C1CO1.650 | cgpGmo-S740 | V | 1 | 0.824 |
| 1962 | 5286C1CO1.217 | cgpGmo-S741 | V | 1 | 0.903 |
| 1963 | 5289C1CO1.323 | cgpGmo-S742a | V | 1 | 0.572 |
| 1964 | 5289C1CO1.468 | cgpGmo-S742b | V | 2 | 0.83 |
| 1965 | 52C1CO1.728 | cgpGmo-S743 |   | 1 | 0.742 |
| 1966 | 5307C1CO1.406 | cgpGmo-S745 |   | 1 | 0.833 |
| 1967 | 530C1CO1.205 | cgpGmo-S746 | V | 1 | 0.885 |
| 1968 | 5315C1CO1.92 | cgpGmo-S747 | V | 1 | 0.882 |
| 1969 | 5329C1CO1.112 | cgpGmo-S748 | V | 1 | 0.792 |
| 1970 | 5332C1CO1.211 | cgpGmo-S749a | V | 1 | 0.893 |
| 1971 | 5332C1CO1.293 | cgpGmo-S749b | V | 2 | 0.94 |
| 1972 | 3467C1CO1.122 | cgpGmo-S75 | V | 1 | 0.697 |
| 1973 | 5340C1CO1.400 | cgpGmo-S750 |   | 1 | 0.693 |
| 1974 | 5363C1CO1.533 | cgpGmo-S751 | V | 1 | 0.791 |
| 1975 | 5370C1CO1.251 | cgpGmo-S752a | V | 1 | 0.523 |
| 1976 | 5370C1CO1.568 | cgpGmo-S752b | V | 2 | 0.97 |
| 1977 | 537C2CO1.785 | cgpGmo-S753 | V | 1 | 0.716 |
| 1978 | 5393C1CO1.183 | cgpGmo-S754 | V | 1 | 0.403 |
| 1979 | 5400C1CO1.436 | cgpGmo-S755 | V | 1 | 0.795 |
| 1980 | 5413C1CO1.147 | cgpGmo-S756a | V | 1 | 0.498 |
| 1981 | 5413C1CO1.375 | cgpGmo-S756b |   | 2 | 0.75 |
| 1982 | 5431C1CO1.324 | cgpGmo-S757 | V | 1 | 0.719 |
| 1983 | 5472C1CO1.337 | cgpGmo-S758 | V | 1 | 0.524 |
| 1984 | 5485C1CO1.422 | cgpGmo-S759 | V | 1 | 0.668 |
| 1985 | 3528C1CO1.616 | cgpGmo-S76 |   | 1 | 0.878 |
| 1986 | 549C1CO1.508 | cgpGmo-S760 | V | 1 | 0.906 |
| 1987 | 5512C1CO1.292 | cgpGmo-S761a |   | 1 | 0.801 |
| 1988 | 5512C1CO1.720 | cgpGmo-S761b | V | 2 | 0.88 |
| 1989 | 5519C1CO1.403 | cgpGmo-S762 | V | 1 | 0.658 |
| 1990 | 5520C1CO1.147 | cgpGmo-S763 | V | 1 | 0.708 |
| 1991 | 5527C1CO1.218 | cgpGmo-S764 | V | 1 | 0.912 |
| 1992 | 5530C1CO1.395 | cgpGmo-S765 | V | 1 | 0.723 |
| 1993 | 5533C1CO1.524 | cgpGmo-S766 |   | 1 | 0.587 |
| 1994 | 5542C1CO1.76 | cgpGmo-S767 | V | 1 | 0.915 |
| 1995 | 5575C1CO1.211 | cgpGmo-S768 | V | 1 | 0.898 |
| 1996 | 5579C1CO1.463 | cgpGmo-S769 | V | 1 | 0.905 |
| 1997 | 3597C1CO1.329 | cgpGmo-S77 | V | 1 | 0.767 |
| 1998 | 5580C1CO1.70 | cgpGmo-S770 | V | 1 | 0.889 |
| 1999 | 5587C1CO1.102 | cgpGmo-S771 | V | 1 | 0.779 |
| 2000 | 5594C1CO1.137 | cgpGmo-S772 | V | 1 | 0.59 |
| 2001 | 5595C1CO1.346 | cgpGmo-S773 | V | 1 | 0.755 |
| 2002 | 559C1CO1.603 | cgpGmo-S774 | V | 1 | 0.785 |
| 2003 | 5610C1CO1.349 | cgpGmo-S775 | V | 1 | 0.893 |
| 2004 | 5632C2CO1.375 | cgpGmo-S776a | V | 1 | 0.904 |
| 2005 | 5632C2CO1.446 | cgpGmo-S776b | V | 2 | 0.95 |
| 2006 | 5638C1CO2.466 | cgpGmo-S777 | V | 1 | 0.896 |
| 2007 | 5639C1CO1.289 | cgpGmo-S778 | V | 1 | 0.684 |
| 2008 | 5645C1CO1.1566 | cgpGmo-S779 | V | 1 | 0.86 |
| 2009 | 363C1CO1.830 | cgpGmo-S78 | V | 1 | 0.69 |
| 2010 | 5663C1CO1.173 | cgpGmo-S780 | V | 1 | 0.564 |
| 2011 | 5682C1CO1.271 | cgpGmo-S782 | V | 1 | 0.793 |
| 2012 | 5685C1CO1.95 | cgpGmo-S783a |   | 2 | 0.84 |
| 2013 | 5685C1CO1.273 | cgpGmo-S783b |   | 1 | 0.804 |
| 2014 | 5690C1CO1.709 | cgpGmo-S784 | V | 1 | 0.876 |
| 2015 | 5703C1CO1.668 | cgpGmo-S785a | V | 2 | 0.98 |
| 2016 | 5703C1CO1.864 | cgpGmo-S785b | V | 1 | 0.798 |
| 2017 | 5706C1CO1.309 | cgpGmo-S786 | V | 1 | 0.569 |
| 2018 | 570C1CO1.358 | cgpGmo-S787 | V | 1 | 0.871 |
| 2019 | 5713C1CO1.520 | cgpGmo-S788 | V | 1 | 0.855 |
| 2020 | 5724C1CO1.599 | cgpGmo-S789 |   | 1 | 0.767 |
| 2021 | 3748C1CO1.231 | cgpGmo-S79 | V | 1 | 0.712 |
| 2022 | 5736C1CO1.201 | cgpGmo-S790 |   | 1 | 0.532 |
| 2023 | 5748C2CO1.320 | cgpGmo-S791 | V | 1 | 0.786 |
| 2024 | 5771C1CO1.345 | cgpGmo-S792 | V | 1 | 0.683 |
| 2025 | 5783C1CO1.176 | cgpGmo-S793a | V | 1 | 0.731 |
| 2026 | 5783C1CO1.509 | cgpGmo-S793b |   | 2 | 0.98 |
| 2027 | 5784C1CO1.434 | cgpGmo-S794 | V | 1 | 0.889 |
| 2028 | 5794C1CO1.277 | cgpGmo-S795a |   | 2 | 0.98 |
| 2029 | 5794C1CO1.598 | cgpGmo-S795b |   | 1 | 0.822 |
| 2030 | 57C1CO1.170 | cgpGmo-S796 | V | 1 | 0.627 |
| 2031 | 5834C3CO1.565 | cgpGmo-S798 |   | 1 | 0.893 |
| 2032 | 583C1CO1.516 | cgpGmo-S799 | V | 1 | 0.77 |
| 2033 | 3852C1CO1.633 | cgpGmo-S80 |   | 1 | 0.738 |
| 2034 | 5842C1CO1.443 | cgpGmo-S800 |   | 1 | 0.666 |
| 2035 | 5856C1CO1.212 | cgpGmo-S801 |   | 1 | 0.898 |
| 2036 | 5879C1CO1.467 | cgpGmo-S802 |   | 1 | 0.738 |
| 2037 | 5880C1CO1.235 | cgpGmo-S803 | V | 1 | 0.886 |
| 2038 | 5887C1CO1.477 | cgpGmo-S804 |   | 1 | 0.849 |
| 2039 | 58C15CO1.228 | cgpGmo-S805 | V | 1 | 0.819 |
| 2040 | 5909C1CO1.1049 | cgpGmo-S807 |   | 1 | 0.843 |
| 2041 | 5923C1CO1.673 | cgpGmo-S808 | V | 1 | 0.898 |
| 2042 | 5924C1CO1.188 | cgpGmo-S809 |   | 1 | 0.823 |
| 2043 | 3888C1CO1.712 | cgpGmo-S81 | V | 1 | 0.883 |
| 2044 | 592C1CO1.539 | cgpGmo-S810 | V | 1 | 0.816 |
| 2045 | 5938C2CO1.140 | cgpGmo-S811a | V | 2 | 0.97 |
| 2046 | 5938C2CO1.657 | cgpGmo-S811b |   | 1 | 0.901 |
| 2047 | 593C1CO1.282 | cgpGmo-S812 |   | 1 | 0.862 |
| 2048 | 5943C1CO1.466 | cgpGmo-S813 | V | 1 | 0.691 |
| 2049 | 5974C1CO1.393 | cgpGmo-S814a | V | 1 | 0.902 |
| 2050 | 5974C1CO1.537 | cgpGmo-S814b | V | 2 | 0.94 |
| 2051 | 5975C1CO1.154 | cgpGmo-S815 |   | 1 | 0.668 |
| 2052 | 5978C1CO1.943 | cgpGmo-S816a | V | 2 | 0.89 |
| 2053 | 5978C1CO1.572 | cgpGmo-S816b |   | 1 | 0.869 |
| 2054 | 5981C1CO1.613 | cgpGmo-S817 | V | 1 | 0.766 |
| 2055 | 598C1CO1.305 | cgpGmo-S818a | V | 2 | 0.74 |
| 2056 | 598C1CO1.404 | cgpGmo-S818b |   | 1 | 0.698 |
| 2057 | 5995C1CO1.138 | cgpGmo-S819a |   | 1 | 0.899 |
| 2058 | 5995C1CO1.667 | cgpGmo-S819b | V | 2 | 0.9 |
| 2059 | 4043C1CO1.488 | cgpGmo-S82 | V | 1 | 0.903 |
| 2060 | 59C2CO1.325 | cgpGmo-S820 |   | 1 | 0.672 |
| 2061 | 6003C1CO1.427 | cgpGmo-S821 |   | 1 | 0.891 |
| 2062 | 6029C1CO1.93 | cgpGmo-S822a | V | 1 | 0.779 |
| 2063 | 6029C1CO1.183 | cgpGmo-S822b |   | 2 | 0.84 |
| 2064 | 6031C1CO1.666 | cgpGmo-S823 |   | 1 | 0.846 |
| 2065 | 6050C1CO1.216 | cgpGmo-S824 |   | 1 | 0.867 |
| 2066 | 606C1CO1.75 | cgpGmo-S825 |   | 1 | 0.858 |
| 2067 | 6072C1CO1.98 | cgpGmo-S826 |   | 1 | 0.548 |
| 2068 | 6077C1CO1.378 | cgpGmo-S827 |   | 1 | 0.879 |
| 2069 | 607C3CO1.460 | cgpGmo-S828 | V | 1 | 0.846 |
| 2070 | 6090C1CO1.564 | cgpGmo-S829 |   | 1 | 0.806 |
| 2071 | 4231C1CO1.400 | cgpGmo-S83 | V | 1 | 0.909 |
| 2072 | 6118C2CO1.394 | cgpGmo-S830 |   | 1 | 0.744 |
| 2073 | 6125C1CO1.618 | cgpGmo-S831 |   | 1 | 0.788 |
| 2074 | 6127C1CO1.211 | cgpGmo-S832 | V | 1 | 0.895 |
| 2075 | 6148C1CO1.396 | cgpGmo-S833 | V | 1 | 0.558 |
| 2076 | 6148C2CO1.623 | cgpGmo-S834 |   | 1 | 0.64 |
| 2077 | 6156C1CO1.442 | cgpGmo-S835 | V | 1 | 0.708 |
| 2078 | 616C1CO1.1028 | cgpGmo-S836 |   | 1 | 0.596 |
| 2079 | 6177C1CO1.317 | cgpGmo-S837 | V | 1 | 0.628 |
| 2080 | 6180C1CO1.115 | cgpGmo-S838a | V | 1 | 0.545 |
| 2081 | 6180C1CO1.266 | cgpGmo-S838b |   | 2 | 0.78 |
| 2082 | 619C1CO1.715 | cgpGmo-S839 | V | 1 | 0.912 |
| 2083 | 4399C1CO1.1210 | cgpGmo-S84 | V | 1 | 0.699 |
| 2084 | 6214C1CO1.429 | cgpGmo-S840 | V | 1 | 0.513 |
| 2085 | 6221C1CO1.330 | cgpGmo-S841 | V | 1 | 0.91 |
| 2086 | 622C2CO1.675 | cgpGmo-S842 | V | 1 | 0.805 |
| 2087 | 6240C1CO1.341 | cgpGmo-S843 |   | 1 | 0.844 |
| 2088 | 6264C1CO1.262 | cgpGmo-S844 | V | 1 | 0.889 |
| 2089 | 6311C1CO1.131 | cgpGmo-S845a |   | 1 | 0.853 |
| 2090 | 6311C1CO1.197 | cgpGmo-S845b |   | 2 | 0.91 |
| 2091 | 6316C1CO1.149 | cgpGmo-S846a |   | 2 | 0.82 |
| 2092 | 6316C1CO1.362 | cgpGmo-S846b |   | 1 | 0.716 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2093 | 6335C1CO1.469 | cgpGmo-S847 |   | 1 | 0.694 |
| 2094 | 6337C1CO1.305 | cgpGmo-S848 | V | 1 | 0.894 |
| 2095 | 6339C1CO1.418 | cgpGmo-S849 | V | 1 | 0.911 |
| 2096 | 4420C1CO1.165 | cgpGmo-S85 | V | 1 | 0.599 |
| 2097 | 6344C1CO1.431 | cgpGmo-S850 | V | 1 | 0.762 |
| 2098 | 6351C1CO1.494 | cgpGmo-S851 |   | 1 | 0.767 |
| 2099 | 6380C1CO1.242 | cgpGmo-S852 | V | 1 | 0.903 |
| 2100 | 638C1CO1.415 | cgpGmo-S853 | V | 1 | 0.865 |
| 2101 | 6390C1CO1.311 | cgpGmo-S854a |   | 1 | 0.744 |
| 2102 | 6390C1CO1.543 | cgpGmo-S854b | V | 2 | 0.87 |
| 2103 | 6399C1CO1.526 | cgpGmo-S855 | V | 1 | 0.847 |
| 2104 | 6424C1CO1.123 | cgpGmo-S856a |   | 2 | 0.98 |
| 2105 | 6424C1CO1.423 | cgpGmo-S856b |   | 1 | 0.76 |
| 2106 | 642C1CO1.329 | cgpGmo-S857 | V | 1 | 0.726 |
| 2107 | 6431C1CO1.962 | cgpGmo-S858 | V | 1 | 0.703 |
| 2108 | 6434C1CO1.441 | cgpGmo-S859 |   | 1 | 0.595 |
| 2109 | 6435C1CO1.535 | cgpGmo-S860 |   | 1 | 0.87 |
| 2110 | 6438C1CO1.481 | cgpGmo-S861 | V | 1 | 0.894 |
| 2111 | 6474C1CO1.506 | cgpGmo-S862 | V | 1 | 0.89 |
| 2112 | 650C1CO1.476 | cgpGmo-S863 | V | 1 | 0.881 |
| 2113 | 6510C1CO1.276 | cgpGmo-S864 | V | 1 | 0.737 |
| 2114 | 6511C1CO1.374 | cgpGmo-S865 | V | 1 | 0.757 |
| 2115 | 6515C1CO1.247 | cgpGmo-S866 | V | 1 | 0.585 |
| 2116 | 6527C1CO1.346 | cgpGmo-S867 | V | 1 | 0.677 |
| 2117 | 6563C1CO1.347 | cgpGmo-S868 | V | 1 | 0.798 |
| 2118 | 6585C1CO1.422 | cgpGmo-S869 | V | 1 | 0.87 |
| 2119 | 4725C1CO1.293 | cgpGmo-S87 | V | 1 | 0.785 |
| 2120 | 6596C1CO1.587 | cgpGmo-S870 | V | 1 | 0.686 |
| 2121 | 6610C2CO1.273 | cgpGmo-S871a |   | 1 | 0.865 |
| 2122 | 6610C2CO1.607 | cgpGmo-S871b |   | 2 | 0.9 |
| 2123 | 661C1CO1.665 | cgpGmo-S872a | V | 2 | 0.88 |
| 2124 | 661C1CO1.881 | cgpGmo-S872b | V | 1 | 0.827 |
| 2125 | 6629C1CO1.555 | cgpGmo-S873 | V | 1 | 0.805 |
| 2126 | 6636C1CO1.559 | cgpGmo-S874 | V | 1 | 0.53 |
| 2127 | 6645C1CO1.118 | cgpGmo-S875a |   | 2 | 0.91 |
| 2128 | 6645C1CO1.365 | cgpGmo-S875b | V | 1 | 0.753 |
| 2129 | 6645C2CO1.361 | cgpGmo-S876 | V | 1 | 0.817 |
| 2130 | 6650C1CO1.120 | cgpGmo-S877 | V | 1 | 0.896 |
| 2131 | 666C1CO1.341 | cgpGmo-S878 | V | 1 | 0.628 |
| 2132 | 6701C1CO1.248 | cgpGmo-S879 | V | 1 | 0.847 |
| 2133 | 6713C1CO1.85 | cgpGmo-S880a |   | 2 | 0.97 |
| 2134 | 6713C1CO1.169 | cgpGmo-S880b |   | 1 | 0.644 |
| 2135 | 6722C1CO1.248 | cgpGmo-S881 | V | 1 | 0.715 |
| 2136 | 6728C1CO1.428 | cgpGmo-S882a | V | 2 | 0.91 |
| 2137 | 6728C1CO1.578 | cgpGmo-S882b |   | 1 | 0.872 |
| 2138 | 672C2CO1.309 | cgpGmo-S883 | V | 1 | 0.707 |
| 2139 | 672C3CO1.292 | cgpGmo-S884 |   | 1 | 0.893 |
| 2140 | 672C4CO1.165 | cgpGmo-S885a |   | 2 | 0.89 |
| 2141 | 672C4CO1.456 | cgpGmo-S885b |   | 1 | 0.834 |
| 2142 | 6740C1CO1.430 | cgpGmo-S886 |   | 1 | 0.898 |
| 2143 | 6763C1CO1.191 | cgpGmo-S887 |   | 1 | 0.914 |
| 2144 | 6767C1CO1.246 | cgpGmo-S888 | V | 1 | 0.91 |
| 2145 | 6771C2CO1.513 | cgpGmo-S889a |   | 1 | 0.719 |
| 2146 | 6771C2CO1.598 | cgpGmo-S889b | V | 2 | 0.93 |
| 2147 | 4884C1CO1.252 | cgpGmo-S88a | V | 2 | 0.85 |
| 2148 | 4884C1CO1.316 | cgpGmo-S88b | V | 1 | 0.516 |
| 2149 | 677C1CO1.218 | cgpGmo-S890a |   | 1 | 0.631 |
| 2150 | 677C1CO1.540 | cgpGmo-S890b | V | 2 | 0.97 |
| 2151 | 6782C1CO1.172 | cgpGmo-S891 | V | 1 | 0.902 |
| 2152 | 6790C1CO1.106 | cgpGmo-S892a | V | 2 | 0.84 |
| 2153 | 6790C1CO1.272 | cgpGmo-S892b |   | 1 | 0.735 |
| 2154 | 682C1CO1.674 | cgpGmo-S893 | V | 1 | 0.887 |
| 2155 | 6830C1CO1.386 | cgpGmo-S894 | V | 1 | 0.86 |
| 2156 | 6838C1CO1.388 | cgpGmo-S895 | V | 1 | 0.857 |
| 2157 | 6840C1CO1.208 | cgpGmo-S896 | V | 1 | 0.859 |
| 2158 | 6842C1CO1.672 | cgpGmo-S897 | V | 1 | 0.788 |
| 2159 | 6859C1CO1.317 | cgpGmo-S898 |   | 1 | 0.565 |
| 2160 | 686C1CO1.408 | cgpGmo-S899 | V | 1 | 0.816 |
| 2161 | 488C2CO1.316 | cgpGmo-S89a | V | 2 | 0.94 |
| 2162 | 488C2CO1.560 | cgpGmo-S89b |   | 1 | 0.406 |
| 2163 | 690C1CO1.380 | cgpGmo-S900 | V | 1 | 0.89 |
| 2164 | 6911C1CO1.129 | cgpGmo-S901 | V | 1 | 0.782 |
| 2165 | 692C1CO1.249 | cgpGmo-S902 |   | 1 | 0.422 |
| 2166 | 6931C1CO1.136 | cgpGmo-S903a | V | 2 | 0.91 |
| 2167 | 6931C1CO1.545 | cgpGmo-S903b |   | 1 | 0.787 |
| 2168 | 6932C1CO1.138 | cgpGmo-S904 | V | 1 | 0.757 |
| 2169 | 6942C1CO1.597 | cgpGmo-S905 | V | 1 | 0.862 |
| 2170 | 6943C2CO1.435 | cgpGmo-S906 | V | 1 | 0.88 |
| 2171 | 6953C1CO1.493 | cgpGmo-S907 | V | 1 | 0.433 |
| 2172 | 6965C1CO1.344 | cgpGmo-S908 |   | 1 | 0.9 |
| 2173 | 6968C1CO1.191 | cgpGmo-S909 | V | 1 | 0.746 |
| 2174 | 511C2CO1.408 | cgpGmo-S91 | V | 1 | 0.87 |
| 2175 | 6969C1CO1.478 | cgpGmo-S910 |   | 1 | 0.796 |
| 2176 | 6980C2CO1.297 | cgpGmo-S911 | V | 1 | 0.881 |
| 2177 | 6984C1CO1.497 | cgpGmo-S912 |   | 1 | 0.533 |
| 2178 | 69C1CO1.312 | cgpGmo-S913 |   | 1 | 0.77 |
| 2179 | 7006C1CO1.376 | cgpGmo-S914 | V | 1 | 0.904 |
| 2180 | 7014C2CO1.270 | cgpGmo-S915 | V | 1 | 0.541 |
| 2181 | 7017C1CO1.142 | cgpGmo-S916 | V | 1 | 0.756 |
| 2182 | 7024C1CO1.395 | cgpGmo-S917 | V | 1 | 0.806 |
| 2183 | 7032C1CO1.377 | cgpGmo-S918 | V | 1 | 0.905 |
| 2184 | 7044C1CO1.373 | cgpGmo-S919 |   | 1 | 0.868 |
| 2185 | 5194C2CO1.996 | cgpGmo-S92 | V | 1 | 0.892 |
| 2186 | 7048C1CO1.288 | cgpGmo-S920 | V | 1 | 0.624 |
| 2187 | 7053C1CO1.238 | cgpGmo-S921 | V | 1 | 0.719 |
| 2188 | 7065C1CO1.137 | cgpGmo-S922 | V | 1 | 0.792 |
| 2189 | 7081C1CO1.561 | cgpGmo-S923 | V | 1 | 0.899 |
| 2190 | 7118C1CO1.254 | cgpGmo-S925 | V | 1 | 0.844 |
| 2191 | 7158C1CO1.350 | cgpGmo-S927 | V | 1 | 0.905 |
| 2192 | 7184C1CO1.148 | cgpGmo-S928 |   | 1 | 0.695 |
| 2193 | 718C1CO1.225 | cgpGmo-S929 | V | 1 | 0.755 |
| 2194 | 5226C1CO1.830 | cgpGmo-S93 | V | 1 | 0.768 |
| 2195 | 7201C1CO1.450 | cgpGmo-S930 | V | 1 | 0.725 |
| 2196 | 7206C1CO1.263 | cgpGmo-S931 |   | 1 | 0.801 |
| 2197 | 7212C1CO1.96 | cgpGmo-S932a |   | 2 | 0.95 |
| 2198 | 7212C1CO1.389 | cgpGmo-S932b | V | 1 | 0.884 |
| 2199 | 7222C1CO1.431 | cgpGmo-S933 |   | 1 | 0.799 |
| 2200 | 7237C1CO1.458 | cgpGmo-S934 |   | 1 | 0.879 |
| 2201 | 7244C1CO1.431 | cgpGmo-S935 |   | 1 | 0.89 |
| 2202 | 7258C1CO1.334 | cgpGmo-S936 | V | 1 | 0.849 |
| 2203 | 7261C1CO1.148 | cgpGmo-S937 | V | 1 | 0.558 |
| 2204 | 72C1CO1.1666 | cgpGmo-S938 | V | 1 | 0.723 |
| 2205 | 7302C1CO1.277 | cgpGmo-S939 | V | 1 | 0.688 |
| 2206 | 528C1CO1.1038 | cgpGmo-S94 | V | 1 | 0.647 |
| 2207 | 732C3CO1.401 | cgpGmo-S940 | V | 1 | 0.525 |
| 2208 | 7335C1CO1.265 | cgpGmo-S941 |   | 1 | 0.819 |
| 2209 | 734C1CO1.456 | cgpGmo-S942 | V | 1 | 0.791 |
| 2210 | 7352C1CO1.470 | cgpGmo-S943 | V | 1 | 0.896 |
| 2211 | 7365C1CO1.306 | cgpGmo-S944 | V | 1 | 0.913 |
| 2212 | 7392C1CO1.392 | cgpGmo-S945a | V | 2 | 0.99 |
| 2213 | 7392C1CO1.468 | cgpGmo-S945b |   | 1 | 0.762 |
| 2214 | 73C1CO1.706 | cgpGmo-S946 | V | 1 | 0.885 |
| 2215 | 7404C1CO1.161 | cgpGmo-S947 | V | 1 | 0.785 |
| 2216 | 742C1CO1.298 | cgpGmo-S948 | V | 1 | 0.913 |
| 2217 | 7435C2CO1.564 | cgpGmo-S949a | V | 1 | 0.896 |
| 2218 | 7435C2CO1.473 | cgpGmo-S949b |   | 2 | 0.95 |
| 2219 | 5347C1CO1.304 | cgpGmo-S95 |   | 1 | 0.627 |
| 2220 | 7456C1CO1.258 | cgpGmo-S951a |   | 2 | 0.91 |
| 2221 | 7456C1CO1.351 | cgpGmo-S951b | V | 1 | 0.834 |
| 2222 | 745C1CO1.258 | cgpGmo-S952a |   | 1 | 0.823 |
| 2223 | 745C1CO1.386 | cgpGmo-S952b |   | 2 | 0.93 |
| 2224 | 7487C1CO1.186 | cgpGmo-S953 | V | 1 | 0.672 |
| 2225 | 748C2CO1.399 | cgpGmo-S954 | V | 1 | 0.839 |
| 2226 | 7490C1CO1.190 | cgpGmo-S955 | V | 1 | 0.772 |
| 2227 | 7493C1CO1.126 | cgpGmo-S956 |   | 1 | 0.793 |
| 2228 | 7511C1CO1.131 | cgpGmo-S957a |   | 1 | 0.789 |
| 2229 | 7511C1CO1.400 | cgpGmo-S957b |   | 2 | 0.85 |
| 2230 | 7537C1CO1.337 | cgpGmo-S958 | V | 1 | 0.733 |
| 2231 | 7557C1CO1.413 | cgpGmo-S959 |   | 1 | 0.506 |
| 2232 | 5385C1CO1.475 | cgpGmo-S96 |   | 1 | 0.913 |
| 2233 | 7566C1CO1.225 | cgpGmo-S960 | V | 1 | 0.868 |
| 2234 | 7605C1CO1.305 | cgpGmo-S962a |   | 2 | 0.73 |
| 2235 | 7605C1CO1.433 | cgpGmo-S962b | V | 1 | 0.62 |
| 2236 | 761C1CO1.76 | cgpGmo-S963 |   | 1 | 0.85 |
| 2237 | 764C1CO1.349 | cgpGmo-S964 |   | 1 | 0.887 |
| 2238 | 7681C1CO1.185 | cgpGmo-S965 | V | 1 | 0.862 |
| 2239 | 7698C1CO1.381 | cgpGmo-S966 | V | 1 | 0.711 |
| 2240 | 7701C1CO1.175 | cgpGmo-S967a | V | 1 | 0.819 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2241 | 7701C1CO1.256 | cgpGmo-S967b | V | 2 | 0.94 |
| 2242 | 7721C1CO1.390 | cgpGmo-S968 | V | 1 | 0.877 |
| 2243 | 7730C1CO1.572 | cgpGmo-S969 |  | 1 | 0.626 |
| 2244 | 5548C1CO1.254 | cgpGmo-S97 | V | 1 | 0.819 |
| 2245 | 7739C1CO1.384 | cgpGmo-S970 |  | 1 | 0.846 |
| 2246 | 774C1CO1.610 | cgpGmo-S971 |  | 1 | 0.866 |
| 2247 | 7759C1CO1.512 | cgpGmo-S972 | V | 1 | 0.727 |
| 2248 | 775C2CO1.648 | cgpGmo-S973 | V | 1 | 0.686 |
| 2249 | 7768C1CO1.226 | cgpGmo-S974 |  | 1 | 0.876 |
| 2250 | 7769C1CO1.360 | cgpGmo-S975a | V | 2 | 0.94 |
| 2251 | 7769C1CO1.451 | cgpGmo-S975b | V | 1 | 0.909 |
| 2252 | 7785C1CO1.93 | cgpGmo-S976a | V | 1 | 0.582 |
| 2253 | 7785C1CO1.273 | cgpGmo-S976b | V | 2 | 0.82 |
| 2254 | 778C1CO1.411 | cgpGmo-S977 | V | 1 | 0.82 |
| 2255 | 7791C1CO1.314 | cgpGmo-S978 | V | 1 | 0.87 |
| 2256 | 779C1CO1.424 | cgpGmo-S979 |  | 1 | 0.88 |
| 2257 | 5978C3CO1.423 | cgpGmo-S98 | V | 1 | 0.837 |
| 2258 | 77C2CO1.470 | cgpGmo-S980 |  | 1 | 0.836 |
| 2259 | 781C1CO1.305 | cgpGmo-S982a | V | 1 | 0.889 |
| 2260 | 781C1CO1.413 | cgpGmo-S982b | V | 2 | 0.93 |
| 2261 | 7848C1CO1.416 | cgpGmo-S983 |  | 1 | 0.698 |
| 2262 | 7852C1CO1.926 | cgpGmo-S984 | V | 1 | 0.889 |
| 2263 | 7889C1CO1.405 | cgpGmo-S985 | V | 1 | 0.912 |
| 2264 | 7951C1CO1.370 | cgpGmo-S986 | V | 1 | 0.882 |
| 2265 | 7971C1CO1.254 | cgpGmo-S987a |  | 1 | 0.474 |
| 2266 | 7971C1CO1.490 | cgpGmo-S987b |  | 2 | 0.98 |
| 2267 | 7994C1CO1.144 | cgpGmo-S988 | V | 1 | 0.613 |
| 2268 | 799C3CO1.334 | cgpGmo-S989 | V | 1 | 0.822 |
| 2269 | 601C1CO1.289 | cgpGmo-S99 | V | 1 | 0.671 |
| 2270 | 8002C1CO1.427 | cgpGmo-S990 | V | 1 | 0.547 |
| 2271 | 8012C1CO1.267 | cgpGmo-S991a | V | 2 | 0.97 |
| 2272 | 8012C1CO1.350 | cgpGmo-S991b | V | 1 | 0.794 |
| 2273 | 8014C1CO1.990 | cgpGmo-S992 | V | 1 | 0.897 |
| 2274 | 8032C1CO1.827 | cgpGmo-S993 |  | 1 | 0.51 |
| 2275 | 8059C1CO1.346 | cgpGmo-S994 | V | 1 | 0.767 |
| 2276 | 8071C1CO1.187 | cgpGmo-S995a | V | 1 | 0.886 |
| 2277 | 8071C1CO1.414 | cgpGmo-S995b | V | 2 | 0.96 |
| 2278 | 8077C1CO1.314 | cgpGmo-S996 | V | 1 | 0.852 |
| 2279 | 8083C1CO1.458 | cgpGmo-S997a | V | 1 | 0.841 |
| 2280 | 8083C1CO1.621 | cgpGmo-S997b | V | 2 | 1 |
| 2281 | 8101C1CO1.399 | cgpGmo-S998 | V | 1 | 0.622 |
| 2282 | 8123C1CO1.274 | cgpGmo-S999 | V | 1 | 0.864 |
| 2283 | 10331C1CO1.490 | cgpGmo-S9a | V | 1 | 0.503 |
| 2284 | 10331C1CO1.365 | cgpGmo-S9b | V | 2 | 0.85 |
| 2285 | 891C1CO1.198 | N/A |  | 1 | 0.4 |
| 2286 | 2749C1CO1.194 | N/A |  | 1 | 0.406 |
| 2287 | 2905C1CO1.585 | N/A |  | 1 | 0.407 |
| 2288 | 6733C1CO1.91 | N/A |  | 1 | 0.408 |
| 2289 | 3341C1CO1.955 | N/A |  | 1 | 0.414 |
| 2290 | 2201C1CO1.559 | N/A |  | 1 | 0.423 |
| 2291 | 3099C1CO1.280 | N/A |  | 1 | 0.423 |
| 2292 | 1468C2CO1.476 | N/A |  | 1 | 0.429 |
| 2293 | 3618C2CO1.388 | N/A |  | 1 | 0.434 |
| 2294 | 2286C1CO1.197 | N/A |  | 1 | 0.435 |
| 2295 | 323C2CO1.532 | N/A |  | 1 | 0.436 |
| 2296 | 2722C2CO1.722 | N/A |  | 1 | 0.44 |
| 2297 | 1910C1CO1.173 | N/A |  | 1 | 0.443 |
| 2298 | 8246C1CO1.96 | N/A |  | 1 | 0.443 |
| 2299 | 157C3CO1.255 | N/A |  | 1 | 0.446 |
| 2300 | 59C1CO1.642 | N/A |  | 1 | 0.452 |
| 2301 | 8405C1CO1.591 | N/A |  | 1 | 0.457 |
| 2302 | 3767C1CO1.244 | N/A |  | 1 | 0.46 |
| 2303 | 4253C1CO1.596 | N/A |  | 1 | 0.464 |
| 2304 | 2591C3CO1.551 | N/A |  | 1 | 0.465 |
| 2305 | 1093C1CO1.405 | N/A |  | 1 | 0.471 |
| 2306 | 2756C4CO1.292 | N/A |  | 1 | 0.472 |
| 2307 | 8828C1CO1.580 | N/A |  | 1 | 0.475 |
| 2308 | 2083C1CO1.189 | N/A |  | 1 | 0.478 |
| 2309 | 1860C1CO1.251 | N/A |  | 1 | 0.488 |
| 2310 | 1998C1CO1.263 | N/A |  | 1 | 0.488 |
| 2311 | 3037C1CO1.231 | N/A |  | 1 | 0.492 |
| 2312 | 4712C1CO1.164 | N/A |  | 1 | 0.492 |
| 2313 | 1890C1CO1.155 | N/A |  | 1 | 0.494 |
| 2314 | 4819C1CO1.445 | N/A |  | 1 | 0.498 |
| 2315 | 9233C1CO1.494 | N/A |  | 1 | 0.5 |
| 2316 | 4669C1CO1.398 | N/A |  | 1 | 0.501 |
| 2317 | 10501C1CO1.168 | N/A |  | 1 | 0.502 |
| 2318 | 101C1CO1.568 | N/A |  | 1 | 0.503 |
| 2319 | 1675C3CO1.90 | N/A |  | 1 | 0.506 |
| 2320 | 3623C1CO1.407 | N/A |  | 1 | 0.509 |
| 2321 | 2993C1CO1.744 | N/A |  | 1 | 0.51 |
| 2322 | 8368C1CO1.378 | N/A |  | 1 | 0.511 |
| 2323 | 5631C1CO1.406 | N/A |  | 1 | 0.512 |
| 2324 | 5059C1CO1.184 | N/A |  | 1 | 0.519 |
| 2325 | 999C5CO1.285 | N/A |  | 1 | 0.519 |
| 2326 | 7229C1CO1.222 | N/A |  | 1 | 0.52 |
| 2327 | 2780C1CO1.165 | N/A |  | 1 | 0.524 |
| 2328 | 983C1CO1.615 | N/A |  | 1 | 0.528 |
| 2329 | 424C1CO1.648 | N/A |  | 1 | 0.529 |
| 2330 | 503C1CO1.310 | N/A |  | 1 | 0.529 |
| 2331 | 1919C1CO1.579 | N/A |  | 1 | 0.533 |
| 2332 | 3927C2CO1.745 | N/A |  | 1 | 0.533 |
| 2333 | 561C1CO1.241 | N/A |  | 1 | 0.535 |
| 2334 | 3429C2CO1.715 | N/A |  | 1 | 0.537 |
| 2335 | 4923C1CO1.395 | N/A |  | 1 | 0.538 |
| 2336 | 763C1CO1.617 | N/A |  | 1 | 0.539 |
| 2337 | 335C1CO1.530 | N/A |  | 1 | 0.54 |
| 2338 | 2420C1CO1.549 | N/A |  | 1 | 0.541 |
| 2339 | 5024C1CO1.725 | N/A |  | 1 | 0.541 |
| 2340 | 8767C1CO1.165 | N/A |  | 1 | 0.543 |
| 2341 | 1776C2CO1.290 | N/A |  | 1 | 0.545 |
| 2342 | 8478C1CO1.199 | N/A |  | 1 | 0.545 |
| 2343 | 5913C1CO1.405 | N/A |  | 1 | 0.548 |
| 2344 | 261C2CO1.80 | N/A |  | 1 | 0.551 |
| 2345 | 4225C2CO1.506 | N/A |  | 1 | 0.553 |
| 2346 | 5032C1CO1.292 | N/A |  | 1 | 0.553 |
| 2347 | 10391C1CO1.67 | N/A |  | 1 | 0.556 |
| 2348 | 3556C1CO1.112 | N/A |  | 1 | 0.557 |
| 2349 | 1371C1CO1.173 | N/A |  | 1 | 0.559 |
| 2350 | 2581C2CO1.850 | N/A |  | 1 | 0.559 |
| 2351 | 2468C1CO1.333 | N/A |  | 1 | 0.56 |
| 2352 | 6354C1CO2.207 | N/A |  | 1 | 0.561 |
| 2353 | 1809C1CO1.503 | N/A |  | 1 | 0.565 |
| 2354 | 1230C1CO1.477 | N/A |  | 1 | 0.569 |
| 2355 | 172C1CO1.143 | N/A |  | 1 | 0.57 |
| 2356 | 6672C1CO1.381 | N/A |  | 1 | 0.57 |
| 2357 | 304C1CO1.204 | N/A |  | 1 | 0.573 |
| 2358 | 3088C1CO1.988 | N/A |  | 1 | 0.575 |
| 2359 | 3252C1CO1.214 | N/A |  | 1 | 0.575 |
| 2360 | 4594C1CO1.512 | N/A |  | 1 | 0.575 |
| 2361 | 45C2CO1.81 | N/A |  | 1 | 0.575 |
| 2362 | 6720C1CO1.753 | N/A |  | 1 | 0.575 |
| 2363 | 11264C1CO1.99 | N/A |  | 1 | 0.581 |
| 2364 | 289C1CO1.129 | N/A |  | 1 | 0.582 |
| 2365 | 4354C1CO1.537 | N/A |  | 1 | 0.583 |
| 2366 | 7486C1CO1.502 | N/A |  | 1 | 0.584 |
| 2367 | 3323C1CO1.226 | N/A |  | 1 | 0.586 |
| 2368 | 10303C1CO1.226 | N/A |  | 1 | 0.587 |
| 2369 | 2898C1CO1.133 | N/A |  | 1 | 0.587 |
| 2370 | 6603C1CO1.139 | N/A |  | 1 | 0.587 |
| 2371 | 7679C1CO1.537 | N/A |  | 1 | 0.587 |
| 2372 | 2002C1CO1.492 | N/A |  | 1 | 0.588 |
| 2373 | 2107C2CO1.474 | N/A |  | 1 | 0.588 |
| 2374 | 4140C2CO1.622 | N/A |  | 1 | 0.592 |
| 2375 | 3629C2CO1.126 | N/A |  | 1 | 0.593 |
| 2376 | 4457C1CO1.413 | N/A |  | 1 | 0.596 |
| 2377 | 4969C2CO1.298 | N/A |  | 1 | 0.597 |
| 2378 | 1140C1CO1.1195 | N/A |  | 1 | 0.599 |
| 2379 | 9266C1CO1.369 | N/A |  | 1 | 0.599 |
| 2380 | 4715C1CO1.311 | N/A |  | 1 | 0.6 |
| 2381 | 2045C2CO1.270 | N/A |  | 1 | 0.601 |
| 2382 | 3741C2CO1.649 | N/A |  | 1 | 0.605 |
| 2383 | 1421C1CO1.301 | N/A |  | 1 | 0.607 |
| 2384 | 4812C1CO1.233 | N/A |  | 1 | 0.608 |
| 2385 | 7720C1CO1.639 | N/A |  | 1 | 0.61 |
| 2386 | 10744C1CO1.510 | N/A |  | 1 | 0.611 |
| 2387 | 1864C1CO1.593 | N/A |  | 1 | 0.611 |
| 2388 | 2270C1CO1.118 | N/A |  | 1 | 0.611 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2389 | 2749C2CO1.261 | N/A | | 1 | 0.611 |
| 2390 | 7532C1CO1.204 | N/A | | 1 | 0.611 |
| 2391 | 2357C2CO1.634 | N/A | | 1 | 0.613 |
| 2392 | 281C2CO1.405 | N/A | | 1 | 0.614 |
| 2393 | 1486C2CO1.138 | N/A | | 1 | 0.615 |
| 2394 | 3600C1CO1.156 | N/A | | 1 | 0.616 |
| 2395 | 7691C1CO1.612 | N/A | | 1 | 0.616 |
| 2396 | 4847C1CO1.435 | N/A | | 1 | 0.617 |
| 2397 | 269C2CO1.632 | N/A | | 1 | 0.619 |
| 2398 | 2952C2CO1.670 | N/A | | 1 | 0.621 |
| 2399 | 3295C1CO1.136 | N/A | | 1 | 0.621 |
| 2400 | 809C1CO1.380 | N/A | | 1 | 0.621 |
| 2401 | 3498C1CO1.460 | N/A | | 1 | 0.624 |
| 2402 | 4659C1CO1.346 | N/A | | 1 | 0.624 |
| 2403 | 1269C1CO1.765 | N/A | | 1 | 0.626 |
| 2404 | 692C2CO1.520 | N/A | | 1 | 0.626 |
| 2405 | 8632C1CO1.258 | N/A | | 1 | 0.626 |
| 2406 | 7552C1CO1.181 | N/A | | 1 | 0.628 |
| 2407 | 5921C1CO1.410 | N/A | | 1 | 0.629 |
| 2408 | 7695C1CO1.534 | N/A | | 1 | 0.629 |
| 2409 | 2162C2CO1.369 | N/A | | 1 | 0.631 |
| 2410 | 5432C1CO1.508 | N/A | | 1 | 0.631 |
| 2411 | 2215C1CO1.197 | N/A | | 1 | 0.632 |
| 2412 | 11538C1CO1.467 | N/A | | 1 | 0.634 |
| 2413 | 1762C1CO1.345 | N/A | | 1 | 0.634 |
| 2414 | 11309C1CO1.490 | N/A | | 1 | 0.635 |
| 2415 | 2660C1CO1.629 | N/A | | 1 | 0.636 |
| 2416 | 1790C1CO1.837 | N/A | | 1 | 0.638 |
| 2417 | 6096C1CO1.273 | N/A | | 1 | 0.638 |
| 2418 | 2867C1CO1.125 | N/A | | 1 | 0.639 |
| 2419 | 6499C1CO1.383 | N/A | | 1 | 0.639 |
| 2420 | 975C1CO1.563 | N/A | | 1 | 0.639 |
| 2421 | 5298C1CO1.326 | N/A | | 1 | 0.642 |
| 2422 | 2471C2CO1.231 | N/A | | 1 | 0.643 |
| 2423 | 774C2CO1.225 | N/A | | 1 | 0.643 |
| 2424 | 604C1CO1.553 | N/A | | 1 | 0.645 |
| 2425 | 3582C1CO1.230 | N/A | | 1 | 0.649 |
| 2426 | 3850C1CO1.202 | N/A | | 1 | 0.649 |
| 2427 | 1023C3CO1.190 | N/A | | 1 | 0.65 |
| 2428 | 2812C1CO1.221 | N/A | | 1 | 0.65 |
| 2429 | 2938C2CO1.423 | N/A | | 1 | 0.651 |
| 2430 | 4204C1CO1.304 | N/A | | 1 | 0.651 |
| 2431 | 8355C2CO1.421 | N/A | | 1 | 0.651 |
| 2432 | 8946C1CO1.375 | N/A | | 1 | 0.651 |
| 2433 | 5486C1CO1.166 | N/A | | 1 | 0.654 |
| 2434 | 655C2CO1.66 | N/A | | 1 | 0.654 |
| 2435 | 6697C1CO1.442 | N/A | | 1 | 0.654 |
| 2436 | 7427C1CO1.631 | N/A | | 1 | 0.654 |
| 2437 | 1855C1CO1.229 | N/A | | 1 | 0.657 |
| 2438 | 344C1CO1.575 | N/A | | 1 | 0.657 |
| 2439 | 1473C1CO1.206 | N/A | | 1 | 0.658 |
| 2440 | 6142C1CO1.86 | N/A | | 1 | 0.659 |
| 2441 | 4321C1CO1.310 | N/A | | 1 | 0.66 |
| 2442 | 1649C4CO1.695 | N/A | | 1 | 0.662 |
| 2443 | 2128C1CO1.1544 | N/A | | 1 | 0.662 |
| 2444 | 1310C1CO1.527 | N/A | | 1 | 0.664 |
| 2445 | 2474C1CO1.259 | N/A | | 1 | 0.667 |
| 2446 | 1202C1CO1.669 | N/A | | 1 | 0.668 |
| 2447 | 399C4CO1.275 | N/A | | 1 | 0.668 |
| 2448 | 4463C2CO1.474 | N/A | | 1 | 0.668 |
| 2449 | 7615C1CO1.648 | N/A | | 1 | 0.669 |
| 2450 | 568C2CO1.756 | N/A | | 1 | 0.67 |
| 2451 | 10614C1CO1.447 | N/A | | 1 | 0.671 |
| 2452 | 4815C1CO1.410 | N/A | | 1 | 0.672 |
| 2453 | 2113C1CO2.603 | N/A | | 1 | 0.673 |
| 2454 | 1125C1CO1.756 | N/A | | 1 | 0.675 |
| 2455 | 1608C1CO1.160 | N/A | | 1 | 0.675 |
| 2456 | 4319C1CO1.345 | N/A | | 1 | 0.675 |
| 2457 | 1746C4CO1.122 | N/A | | 1 | 0.678 |
| 2458 | 3165C1CO1.203 | N/A | | 1 | 0.678 |
| 2459 | 759C1CO1.276 | N/A | | 1 | 0.678 |
| 2460 | 860C1CO1.98 | N/A | | 1 | 0.678 |
| 2461 | 1645C1CO1.450 | N/A | | 1 | 0.679 |
| 2462 | 1051C1CO1.254 | N/A | | 1 | 0.681 |
| 2463 | 1092C2CO1.850 | N/A | | 1 | 0.682 |
| 2464 | 41C1CO1.512 | N/A | | 1 | 0.683 |
| 2465 | 4886C1CO1.510 | N/A | | 1 | 0.683 |
| 2466 | 7530C1CO1.265 | N/A | | 1 | 0.684 |
| 2467 | 3864C1CO1.555 | N/A | | 1 | 0.687 |
| 2468 | 4584C1CO1.409 | N/A | | 1 | 0.687 |
| 2469 | 5268C1CO1.214 | N/A | | 1 | 0.687 |
| 2470 | 392C1CO1.296 | N/A | | 1 | 0.689 |
| 2471 | 5382C1CO1.358 | N/A | | 1 | 0.689 |
| 2472 | 2036C1CO1.80 | N/A | | 1 | 0.69 |
| 2473 | 711C2CO1.2214 | N/A | | 1 | 0.691 |
| 2474 | 1803C1CO1.377 | N/A | | 1 | 0.694 |
| 2475 | 2405C2CO1.427 | N/A | | 1 | 0.7 |
| 2476 | 2023C1CO1.417 | N/A | | 1 | 0.703 |
| 2477 | 2368C1CO1.350 | N/A | | 1 | 0.704 |
| 2478 | 1974C1CO1.75 | N/A | | 1 | 0.708 |
| 2479 | 4709C1CO1.286 | N/A | | 1 | 0.708 |
| 2480 | 4226C1CO1.216 | N/A | | 1 | 0.709 |
| 2481 | 2325C2CO1.127 | N/A | | 1 | 0.71 |
| 2482 | 204C2CO1.348 | N/A | | 1 | 0.711 |
| 2483 | 3327C1CO1.194 | N/A | | 1 | 0.711 |
| 2484 | 1848C1CO1.464 | N/A | | 1 | 0.712 |
| 2485 | 5927C1CO1.199 | N/A | | 1 | 0.712 |
| 2486 | 7111C1CO1.456 | N/A | | 1 | 0.713 |
| 2487 | 518C1CO1.355 | N/A | | 1 | 0.714 |
| 2488 | 2091C2CO1.675 | N/A | | 1 | 0.715 |
| 2489 | 869C1CO1.706 | N/A | | 1 | 0.715 |
| 2490 | 5628C1CO1.452 | N/A | | 1 | 0.719 |
| 2491 | 2408C1CO1.590 | N/A | | 1 | 0.721 |
| 2492 | 1374C1CO1.114 | N/A | | 1 | 0.722 |
| 2493 | 3057C1CO1.784 | N/A | | 1 | 0.728 |
| 2494 | 635C1CO1.1153 | N/A | | 1 | 0.728 |
| 2495 | 114C1CO1.747 | N/A | | 1 | 0.729 |
| 2496 | 269C1CO1.511 | N/A | | 1 | 0.73 |
| 2497 | 1741C1CO1.93 | N/A | | 1 | 0.736 |
| 2498 | 9851C1CO1.401 | N/A | | 1 | 0.736 |
| 2499 | 2709C2CO1.183 | N/A | | 1 | 0.737 |
| 2500 | 5916C1CO1.276 | N/A | | 1 | 0.737 |
| 2501 | 6145C1CO1.131 | N/A | | 1 | 0.738 |
| 2502 | 7485C1CO1.680 | N/A | | 1 | 0.738 |
| 2503 | 2945C1CO1.480 | N/A | | 1 | 0.74 |
| 2504 | 1163C1CO1.1547 | N/A | | 1 | 0.743 |
| 2505 | 1295C1CO1.462 | N/A | | 1 | 0.744 |
| 2506 | 3877C1CO1.147 | N/A | | 1 | 0.744 |
| 2507 | 6299C1CO1.179 | N/A | | 1 | 0.745 |
| 2508 | 398C1CO1.211 | N/A | | 1 | 0.747 |
| 2509 | 183C1CO1.190 | N/A | | 1 | 0.748 |
| 2510 | 2696C1CO1.195 | N/A | | 1 | 0.749 |
| 2511 | 2902C2CO1.193 | N/A | | 1 | 0.749 |
| 2512 | 1310C3CO1.258 | N/A | | 1 | 0.751 |
| 2513 | 1185C1CO1.202 | N/A | | 1 | 0.756 |
| 2514 | 1356C1CO1.749 | N/A | | 1 | 0.756 |
| 2515 | 227C1CO1.166 | N/A | | 1 | 0.759 |
| 2516 | 7086C1CO1.286 | N/A | | 1 | 0.759 |
| 2517 | 5474C1CO1.179 | N/A | | 1 | 0.76 |
| 2518 | 6356C1CO1.108 | N/A | | 1 | 0.76 |
| 2519 | 5049C1CO1.746 | N/A | | 1 | 0.761 |
| 2520 | 3382C1CO1.638 | N/A | | 1 | 0.764 |
| 2521 | 3602C1CO1.637 | N/A | | 1 | 0.766 |
| 2522 | 1685C1CO1.634 | N/A | | 1 | 0.768 |
| 2523 | 3570C1CO1.104 | N/A | | 1 | 0.769 |
| 2524 | 1340C1CO1.518 | N/A | | 1 | 0.771 |
| 2525 | 1382C1CO1.158 | N/A | | 1 | 0.772 |
| 2526 | 1983C1CO1.739 | N/A | | 1 | 0.772 |
| 2527 | 2476C1CO1.494 | N/A | | 1 | 0.773 |
| 2528 | 5684C1CO1.551 | N/A | | 1 | 0.776 |
| 2529 | 10772C1CO1.194 | N/A | | 1 | 0.778 |
| 2530 | 8439C1CO1.276 | N/A | | 1 | 0.778 |
| 2531 | 8644C1CO1.221 | N/A | | 1 | 0.778 |
| 2532 | 1204C1CO1.172 | N/A | | 1 | 0.78 |
| 2533 | 1278C1CO1.241 | N/A | | 1 | 0.78 |
| 2534 | 3183C1CO1.863 | N/A | | 1 | 0.78 |
| 2535 | 5089C1CO1.354 | N/A | | 1 | 0.78 |
| 2536 | 1017C1CO1.853 | N/A | | 1 | 0.781 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2537 | 7578C1CO1.258 | N/A |  | 1 | 0.783 |
| 2538 | 1452C3CO1.252 | N/A |  | 1 | 0.786 |
| 2539 | 3560C1CO1.488 | N/A |  | 1 | 0.786 |
| 2540 | 9770C1CO1.292 | N/A |  | 1 | 0.787 |
| 2541 | 5634C1CO1.765 | N/A |  | 1 | 0.788 |
| 2542 | 3696C1CO1.2520 | N/A |  | 1 | 0.79 |
| 2543 | 4325C1CO1.90 | N/A |  | 1 | 0.79 |
| 2544 | 4806C1CO1.619 | N/A |  | 1 | 0.79 |
| 2545 | 11275C1CO1.112 | N/A |  | 1 | 0.792 |
| 2546 | 720C1CO1.363 | N/A |  | 1 | 0.792 |
| 2547 | 3425C1CO1.94 | N/A |  | 1 | 0.795 |
| 2548 | 4843C1CO1.267 | N/A |  | 1 | 0.795 |
| 2549 | 3079C1CO1.221 | N/A |  | 1 | 0.796 |
| 2550 | 4754C1CO1.553 | N/A |  | 1 | 0.798 |
| 2551 | 2311C1CO1.535 | N/A | V | 1 | 0.802 |
| 2552 | 7812C1CO1.458 | N/A |  | 1 | 0.802 |
| 2553 | 1057C1CO1.398 | N/A | V | 1 | 0.805 |
| 2554 | 708C1CO1.481 | N/A |  | 1 | 0.805 |
| 2555 | 2523C1CO1.622 | N/A |  | 1 | 0.806 |
| 2556 | 4827C2CO1.825 | N/A |  | 1 | 0.806 |
| 2557 | 468C3CO1.568 | N/A |  | 1 | 0.81 |
| 2558 | 185C1CO1.495 | N/A |  | 1 | 0.811 |
| 2559 | 914C1CO1.186 | N/A |  | 1 | 0.811 |
| 2560 | 157C2CO1.345 | N/A |  | 1 | 0.812 |
| 2561 | 730C1CO1.507 | N/A |  | 1 | 0.813 |
| 2562 | 8021C1CO1.575 | N/A |  | 1 | 0.813 |
| 2563 | 5375C2CO1.158 | N/A |  | 1 | 0.815 |
| 2564 | 129C2CO1.693 | N/A |  | 1 | 0.816 |
| 2565 | 2648C1CO1.268 | N/A |  | 1 | 0.817 |
| 2566 | 271C1CO1.182 | N/A |  | 1 | 0.817 |
| 2567 | 4635C1CO1.843 | N/A |  | 1 | 0.817 |
| 2568 | 8158C1CO1.389 | N/A |  | 1 | 0.817 |
| 2569 | 10074C1CO1.284 | N/A |  | 1 | 0.818 |
| 2570 | 4234C2CO1.544 | N/A |  | 1 | 0.818 |
| 2571 | 5636C1CO1.388 | N/A |  | 1 | 0.818 |
| 2572 | 1555C1CO1.204 | N/A |  | 1 | 0.819 |
| 2573 | 2300C1CO1.890 | N/A |  | 1 | 0.819 |
| 2574 | 5544C1CO1.586 | N/A |  | 1 | 0.819 |
| 2575 | 4510C1CO1.604 | N/A |  | 1 | 0.821 |
| 2576 | 8374C1CO1.567 | N/A |  | 1 | 0.822 |
| 2577 | 154C2CO1.200 | N/A |  | 1 | 0.824 |
| 2578 | 8125C1CO1.384 | N/A |  | 1 | 0.825 |
| 2579 | 2881C2CO1.607 | N/A |  | 1 | 0.826 |
| 2580 | 6497C1CO1.90 | N/A |  | 1 | 0.826 |
| 2581 | 6960C1CO1.121 | N/A |  | 1 | 0.827 |
| 2582 | 7947C1CO1.351 | N/A |  | 1 | 0.828 |
| 2583 | 8277C2CO1.543 | N/A |  | 1 | 0.83 |
| 2584 | 7278C1CO1.1238 | N/A |  | 1 | 0.833 |
| 2585 | 1993C1CO1.715 | N/A |  | 1 | 0.837 |
| 2586 | 2007C1CO1.619 | N/A |  | 1 | 0.837 |
| 2587 | 5350C1CO1.73 | N/A |  | 1 | 0.837 |
| 2588 | 3245C1CO1.731 | N/A |  | 1 | 0.838 |
| 2589 | 374C7CO1.270 | N/A |  | 1 | 0.84 |
| 2590 | 2293C1CO1.106 | N/A |  | 1 | 0.843 |
| 2591 | 7301C1CO1.297 | N/A |  | 1 | 0.843 |
| 2592 | 9758C1CO1.514 | N/A |  | 1 | 0.848 |
| 2593 | 7365C2CO1.331 | N/A |  | 1 | 0.849 |
| 2594 | 1413C1CO1.626 | N/A |  | 1 | 0.853 |
| 2595 | 4555C1CO1.103 | N/A |  | 1 | 0.853 |
| 2596 | 680C2CO1.90 | N/A |  | 1 | 0.853 |
| 2597 | 3340C1CO1.444 | N/A |  | 1 | 0.855 |
| 2598 | 8753C1CO1.717 | N/A |  | 1 | 0.856 |
| 2599 | 2843C1CO1.620 | N/A |  | 1 | 0.857 |
| 2600 | 1544C1CO1.719 | N/A |  | 1 | 0.86 |
| 2601 | 664C3CO1.499 | N/A |  | 1 | 0.86 |
| 2602 | 1824C1CO1.610 | N/A |  | 1 | 0.861 |
| 2603 | 5303C1CO1.105 | N/A |  | 1 | 0.861 |
| 2604 | 5341C1CO1.552 | N/A |  | 1 | 0.862 |
| 2605 | 1257C1CO1.484 | N/A |  | 1 | 0.863 |
| 2606 | 7285C1CO1.75 | N/A |  | 1 | 0.865 |
| 2607 | 3197C3CO1.245 | N/A |  | 1 | 0.866 |
| 2608 | 3319C1CO1.618 | N/A |  | 1 | 0.866 |
| 2609 | 6969C3CO1.706 | N/A |  | 1 | 0.867 |
| 2610 | 1746C2CO1.348 | N/A |  | 1 | 0.869 |
| 2611 | 4905C1CO1.228 | N/A |  | 1 | 0.869 |
| 2612 | 2568C2CO1.540 | N/A |  | 1 | 0.87 |
| 2613 | 270C1CO1.314 | N/A |  | 1 | 0.87 |
| 2614 | 4284C1CO1.645 | N/A |  | 1 | 0.87 |
| 2615 | 478C1CO1.918 | N/A |  | 1 | 0.87 |
| 2616 | 7287C1CO1.407 | N/A |  | 1 | 0.871 |
| 2617 | 7457C1CO1.324 | N/A |  | 1 | 0.872 |
| 2618 | 1367C1CO1.720 | N/A |  | 1 | 0.873 |
| 2619 | 2825C1CO1.193 | N/A |  | 1 | 0.873 |
| 2620 | 3711C1CO1.125 | N/A |  | 1 | 0.873 |
| 2621 | 1182C1CO1.629 | N/A |  | 1 | 0.874 |
| 2622 | 1327C1CO1.696 | N/A |  | 1 | 0.874 |
| 2623 | 3011C1CO1.539 | N/A |  | 1 | 0.874 |
| 2624 | 6605C2CO1.158 | N/A |  | 1 | 0.874 |
| 2625 | 967C1CO1.417 | N/A |  | 1 | 0.874 |
| 2626 | 399C3CO1.593 | N/A |  | 1 | 0.875 |
| 2627 | 5009C1CO1.158 | N/A |  | 1 | 0.875 |
| 2628 | 5911C1CO1.447 | N/A | V | 1 | 0.875 |
| 2629 | 9837C1CO1.353 | N/A |  | 1 | 0.875 |
| 2630 | 1494C1CO1.367 | N/A |  | 1 | 0.876 |
| 2631 | 8270C2CO1.386 | N/A |  | 1 | 0.876 |
| 2632 | 1258C1CO1.752 | N/A |  | 1 | 0.877 |
| 2633 | 1497C1CO1.625 | N/A |  | 1 | 0.877 |
| 2634 | 374C4CO1.754 | N/A |  | 1 | 0.877 |
| 2635 | 7183C1CO1.452 | N/A |  | 1 | 0.877 |
| 2636 | 591C2CO1.159 | N/A |  | 1 | 0.878 |
| 2637 | 2753C1CO1.698 | N/A |  | 1 | 0.879 |
| 2638 | 3539C1CO1.288 | N/A |  | 1 | 0.879 |
| 2639 | 252C1CO1.104 | N/A |  | 1 | 0.881 |
| 2640 | 5977C2CO1.98 | N/A |  | 1 | 0.881 |
| 2641 | 5760C1CO1.568 | N/A |  | 1 | 0.882 |
| 2642 | 6560C1CO1.479 | N/A |  | 1 | 0.882 |
| 2643 | 192C1CO1.309 | N/A |  | 1 | 0.883 |
| 2644 | 3194C1CO1.722 | N/A |  | 1 | 0.883 |
| 2645 | 3657C2CO1.241 | N/A |  | 1 | 0.883 |
| 2646 | 385C1CO1.91 | N/A |  | 1 | 0.883 |
| 2647 | 6178C1CO1.615 | N/A |  | 1 | 0.884 |
| 2648 | 3502C2CO1.106 | N/A |  | 1 | 0.886 |
| 2649 | 10034C1CO1.483 | N/A |  | 1 | 0.887 |
| 2650 | 3227C1CO1.424 | N/A |  | 1 | 0.887 |
| 2651 | 4559C1CO1.346 | N/A |  | 1 | 0.888 |
| 2652 | 5600C1CO1.584 | N/A |  | 1 | 0.888 |
| 2653 | 7428C1CO1.336 | N/A |  | 1 | 0.888 |
| 2654 | 856C1CO1.244 | N/A |  | 1 | 0.888 |
| 2655 | 2984C1CO1.486 | N/A |  | 1 | 0.891 |
| 2656 | 5005C1CO1.557 | N/A |  | 1 | 0.891 |
| 2657 | 554C2CO1.400 | N/A |  | 1 | 0.892 |
| 2658 | 7948C1CO1.671 | N/A |  | 1 | 0.892 |
| 2659 | 3265C1CO1.937 | N/A |  | 1 | 0.893 |
| 2660 | 3172C1CO1.337 | N/A |  | 1 | 0.895 |
| 2661 | 5617C1CO1.233 | N/A |  | 1 | 0.895 |
| 2662 | 1259C2CO1.949 | N/A |  | 1 | 0.896 |
| 2663 | 3025C1CO1.250 | N/A |  | 1 | 0.896 |
| 2664 | 413C1CO1.171 | N/A |  | 1 | 0.897 |
| 2665 | 1781C1CO1.165 | N/A |  | 1 | 0.898 |
| 2666 | 4403C1CO1.462 | N/A |  | 1 | 0.899 |
| 2667 | 4727C1CO1.65 | N/A |  | 1 | 0.899 |
| 2668 | 6048C1CO1.259 | N/A |  | 1 | 0.899 |
| 2669 | 5805C1CO1.190 | N/A |  | 1 | 0.9 |
| 2670 | 1746C9CO1.400 | N/A |  | 1 | 0.902 |
| 2671 | 432C1CO1.66 | N/A |  | 1 | 0.902 |
| 2672 | 737C2CO1.129 | N/A |  | 1 | 0.903 |
| 2673 | 1737C1CO1.118 | N/A |  | 1 | 0.904 |
| 2674 | 334C1CO1.411 | N/A | V | 1 | 0.905 |
| 2675 | 4826C1CO1.494 | N/A |  | 1 | 0.905 |
| 2676 | 7134C4CO1.167 | N/A |  | 1 | 0.905 |
| 2677 | 5279C2CO1.498 | N/A | V | 1 | 0.906 |
| 2678 | 4366C1CO1.69 | N/A |  | 1 | 0.907 |
| 2679 | 8378C1CO1.210 | N/A |  | 1 | 0.908 |
| 2680 | 1353C1CO1.580 | N/A |  | 1 | 0.909 |
| 2681 | 4140C1CO1.544 | N/A |  | 1 | 0.909 |
| 2682 | 9250C3CO1.200 | N/A |  | 1 | 0.91 |
| 2683 | 1828C1CO1.69 | N/A |  | 1 | 0.911 |
| 2684 | 3911C1CO1.598 | N/A |  | 1 | 0.911 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2685 | 3065C1CO1.184 | N/A |   | 1 | 0.913 |
| 2686 | 155C1CO1.193 | N/A | V | 1 | 0.914 |
| 2687 | 1041C1CO1.117 | N/A |   | 1 | 0.915 |
| 2688 | 5681C1CO1.227 | N/A | V | 1 | 0.915 |
| 2689 | 10186C1CO1.325 | N/A |   | 2 | 0.99 |
| 2690 | 1056C1CO2.564 | N/A |   | 2 | 0.97 |
| 2691 | 1075C2CO1.825 | N/A |   | 2 | 0.92 |
| 2692 | 1077C4CO1.661 | N/A |   | 2 | 0.98 |
| 2693 | 10964C1CO1.541 | N/A |   | 2 | 0.93 |
| 2694 | 11404C1CO1.448 | N/A |   | 2 | 0.99 |
| 2695 | 1173C3CO1.821 | N/A |   | 2 | 0.96 |
| 2696 | 11840C1CO1.335 | N/A |   | 2 | 0.93 |
| 2697 | 1188C1CO1.173 | N/A |   | 2 | 0.95 |
| 2698 | 1250C1CO1.652 | N/A |   | 2 | 0.98 |
| 2699 | 1282C1CO1.701 | N/A |   | 2 | 0.94 |
| 2700 | 1329C1CO1.626 | N/A |   | 2 | 0.95 |
| 2701 | 1352C1CO1.530 | N/A |   | 2 | 0.97 |
| 2702 | 1463C1CO1.658 | N/A |   | 2 | 0.94 |
| 2703 | 1607C1CO1.626 | N/A |   | 2 | 0.96 |
| 2704 | 1635C2CO1.135 | N/A |   | 2 | 0.99 |
| 2705 | 1664C1CO1.415 | N/A |   | 2 | 0.98 |
| 2706 | 1674C2CO1.244 | N/A |   | 2 | 0.94 |
| 2707 | 1674C4CO1.209 | N/A |   | 2 | 0.97 |
| 2708 | 176C1CO1.400 | N/A |   | 2 | 0.98 |
| 2709 | 1895C2CO1.189 | N/A |   | 2 | 0.98 |
| 2710 | 191C1CO1.719 | N/A |   | 2 | 0.97 |
| 2711 | 1937C1CO1.648 | N/A |   | 2 | 0.94 |
| 2712 | 2017C1CO1.551 | N/A |   | 2 | 0.97 |
| 2713 | 2044C1CO1.707 | N/A |   | 2 | 0.92 |
| 2714 | 2094C1CO1.230 | N/A |   | 2 | 0.94 |
| 2715 | 2109C1CO1.350 | N/A |   | 2 | 0.96 |
| 2716 | 2117C1CO1.204 | N/A |   | 2 | 0.95 |
| 2717 | 2174C1CO1.592 | N/A |   | 2 | 0.94 |
| 2718 | 224C1CO1.1503 | N/A |   | 2 | 1 |
| 2719 | 2365C2CO1.372 | N/A |   | 2 | 1 |
| 2720 | 2401C1CO1.279 | N/A |   | 2 | 0.94 |
| 2721 | 2465C1CO1.220 | N/A |   | 2 | 0.97 |
| 2722 | 2496C1CO1.195 | N/A |   | 2 | 0.95 |
| 2723 | 2534C1CO1.216 | N/A |   | 2 | 0.92 |
| 2724 | 2545C2CO1.427 | N/A |   | 2 | 0.99 |
| 2725 | 2655C1CO2.620 | N/A |   | 2 | 0.98 |
| 2726 | 2717C1CO1.618 | N/A |   | 2 | 0.93 |
| 2727 | 275C6CO1.178 | N/A |   | 2 | 0.95 |
| 2728 | 2776C2CO1.470 | N/A |   | 2 | 0.94 |
| 2729 | 2778C2CO1.623 | N/A |   | 2 | 0.94 |
| 2730 | 2813C1CO1.153 | N/A |   | 2 | 0.95 |
| 2731 | 2869C1CO1.157 | N/A |   | 2 | 0.95 |
| 2732 | 2908C1CO1.367 | N/A |   | 2 | 0.96 |
| 2733 | 2947C1CO1.267 | N/A |   | 2 | 0.93 |
| 2734 | 2959C1CO1.138 | N/A |   | 2 | 0.97 |
| 2735 | 3054C1CO1.400 | N/A |   | 2 | 0.97 |
| 2736 | 305C1CO1.448 | N/A |   | 2 | 0.93 |
| 2737 | 3142C1CO1.828 | N/A |   | 2 | 0.93 |
| 2738 | 3228C1CO1.298 | N/A |   | 2 | 0.97 |
| 2739 | 3241C1CO1.506 | N/A |   | 2 | 0.93 |
| 2740 | 3243C1CO1.585 | N/A |   | 2 | 1 |
| 2741 | 3251C2CO1.342 | N/A |   | 2 | 0.98 |
| 2742 | 3342C1CO1.133 | N/A |   | 2 | 0.98 |
| 2743 | 3343C2CO1.592 | N/A |   | 2 | 0.95 |
| 2744 | 3387C1CO1.362 | N/A |   | 2 | 0.97 |
| 2745 | 33C1CO1.662 | N/A |   | 2 | 0.93 |
| 2746 | 3427C1CO1.336 | N/A |   | 2 | 0.92 |
| 2747 | 3491C1CO1.144 | N/A |   | 2 | 0.99 |
| 2748 | 3601C1CO1.533 | N/A |   | 2 | 0.97 |
| 2749 | 3642C1CO1.505 | N/A |   | 2 | 0.92 |
| 2750 | 3674C1CO1.154 | N/A |   | 2 | 0.94 |
| 2751 | 367C1CO1.110 | N/A |   | 2 | 0.96 |
| 2752 | 3689C1CO1.314 | N/A |   | 2 | 0.94 |
| 2753 | 3744C1CO1.304 | N/A |   | 2 | 0.96 |
| 2754 | 3754C1CO1.818 | N/A |   | 2 | 0.93 |
| 2755 | 3918C1CO1.516 | N/A |   | 2 | 0.96 |
| 2756 | 410C1CO1.197 | N/A |   | 2 | 0.97 |
| 2757 | 4209C1CO1.572 | N/A |   | 2 | 0.95 |
| 2758 | 4338C1CO1.352 | N/A |   | 2 | 0.98 |
| 2759 | 4526C1CO1.533 | N/A |   | 2 | 0.94 |
| 2760 | 4548C1CO1.595 | N/A |   | 2 | 0.94 |
| 2761 | 4558C1CO1.72 | N/A |   | 2 | 0.94 |
| 2762 | 4574C1CO1.241 | N/A |   | 2 | 0.93 |
| 2763 | 4599C1CO1.497 | N/A |   | 2 | 0.94 |
| 2764 | 4625C1CO1.478 | N/A |   | 2 | 0.94 |
| 2765 | 463C2CO1.350 | N/A |   | 2 | 0.98 |
| 2766 | 4737C1CO1.570 | N/A |   | 2 | 0.93 |
| 2767 | 4838C1CO1.110 | N/A |   | 2 | 0.97 |
| 2768 | 4987C1CO1.159 | N/A |   | 2 | 0.95 |
| 2769 | 4990C1CO1.448 | N/A |   | 2 | 0.94 |
| 2770 | 5037C1CO1.400 | N/A |   | 2 | 0.94 |
| 2771 | 5065C1CO1.1120 | N/A |   | 2 | 0.92 |
| 2772 | 5192C2CO1.487 | N/A |   | 2 | 0.94 |
| 2773 | 5237C1CO1.579 | N/A |   | 2 | 0.99 |
| 2774 | 5262C1CO1.630 | N/A |   | 2 | 0.96 |
| 2775 | 5338C1CO1.309 | N/A |   | 2 | 0.96 |
| 2776 | 552C2CO1.103 | N/A |   | 2 | 0.98 |
| 2777 | 5584C1CO1.275 | N/A |   | 2 | 0.93 |
| 2778 | 5632C1CO1.454 | N/A |   | 2 | 0.97 |
| 2779 | 5731C1CO1.382 | N/A |   | 2 | 0.99 |
| 2780 | 5737C1CO1.296 | N/A |   | 2 | 0.92 |
| 2781 | 5780C1CO1.363 | N/A |   | 2 | 0.94 |
| 2782 | 5788C1CO1.63 | N/A |   | 2 | 0.97 |
| 2783 | 6001C1CO1.100 | N/A |   | 2 | 0.93 |
| 2784 | 6163C1CO1.467 | N/A |   | 2 | 0.99 |
| 2785 | 6226C1CO1.600 | N/A |   | 2 | 0.94 |
| 2786 | 6270C1CO1.474 | N/A |   | 2 | 0.97 |
| 2787 | 6274C1CO1.406 | N/A |   | 2 | 0.93 |
| 2788 | 6290C1CO1.647 | N/A |   | 2 | 0.93 |
| 2789 | 6395C1CO1.212 | N/A |   | 2 | 0.96 |
| 2790 | 6481C1CO1.371 | N/A |   | 2 | 0.95 |
| 2791 | 6521C1CO1.246 | N/A |   | 2 | 0.98 |
| 2792 | 6638C1CO1.607 | N/A |   | 2 | 0.97 |
| 2793 | 6690C2CO1.719 | N/A |   | 2 | 0.94 |
| 2794 | 6750C1CO1.261 | N/A |   | 2 | 0.95 |
| 2795 | 6775C1CO1.425 | N/A |   | 2 | 0.96 |
| 2796 | 6779C1CO1.517 | N/A |   | 2 | 0.97 |
| 2797 | 6884C1CO1.451 | N/A |   | 2 | 0.92 |
| 2798 | 7016C1CO1.439 | N/A |   | 2 | 0.98 |
| 2799 | 7046C2CO1.461 | N/A |   | 2 | 0.99 |
| 2800 | 7196C1CO1.547 | N/A |   | 2 | 0.92 |
| 2801 | 725C1CO1.113 | N/A |   | 2 | 0.97 |
| 2802 | 7329C1CO1.675 | N/A |   | 2 | 0.92 |
| 2803 | 735C1CO1.72 | N/A |   | 2 | 0.96 |
| 2804 | 738C1CO1.676 | N/A |   | 2 | 0.94 |
| 2805 | 750C1CO1.195 | N/A |   | 2 | 0.92 |
| 2806 | 7550C1CO1.284 | N/A |   | 2 | 0.96 |
| 2807 | 7760C1CO1.463 | N/A |   | 2 | 0.99 |
| 2808 | 7842C1CO1.547 | N/A |   | 2 | 0.98 |
| 2809 | 7861C1CO1.223 | N/A |   | 2 | 0.94 |
| 2810 | 7991C1CO1.1011 | N/A |   | 2 | 0.95 |
| 2811 | 7C1CO1.239 | N/A |   | 2 | 0.98 |
| 2812 | 8122C1CO1.105 | N/A |   | 2 | 0.93 |
| 2813 | 8245C1CO1.622 | N/A |   | 2 | 0.94 |
| 2814 | 833C1CO1.77 | N/A |   | 2 | 0.97 |
| 2815 | 8620C1CO1.717 | N/A |   | 2 | 0.95 |
| 2816 | 8648C1CO1.494 | N/A |   | 2 | 0.94 |
| 2817 | 8732C1CO1.246 | N/A |   | 2 | 0.94 |
| 2818 | 879C3CO1.1643 | N/A |   | 2 | 0.97 |
| 2819 | 882C2CO1.496 | N/A |   | 2 | 0.99 |
| 2820 | 900C2CO1.178 | N/A |   | 2 | 0.94 |
| 2821 | 9018C1CO1.386 | N/A |   | 2 | 0.92 |
| 2822 | 9229C2CO1.536 | N/A |   | 2 | 0.99 |
| 2823 | 9301C1CO1.183 | N/A |   | 2 | 0.92 |
| 2824 | 9519C1CO1.358 | N/A |   | 2 | 0.93 |
| 2825 | 969C1CO1.498 | N/A |   | 2 | 0.94 |
| 2826 | 9798C1CO1.854 | N/A |   | 2 | 0.97 |
| 2827 | 9910C1CO1.377 | N/A |   | 2 | 0.98 |
| 2828 | 999C1CO1.146 | N/A |   | 2 | 0.95 |
| 2829 | 118C1CO1.496 | N/A |   | 2 | 0.9 |
| 2830 | 1565C1CO1.430 | N/A |   | 2 | 0.94 |
| 2831 | 1806C1CO1.488 | N/A |   | 2 | 0.53 |
| 2832 | 2226C1CO1.292 | N/A |   | 2 | 1 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2833 | 2629C1CO1.190 | N/A | | 2 | 1 |
| 2834 | 3643C1CO1.139 | N/A | | 2 | 0.73 |
| 2835 | 3811C1CO1.336 | N/A | | 2 | 0.92 |
| 2836 | 4017C1CO1.643 | N/A | | 2 | 0.79 |
| 2837 | 4425C1CO1.1015 | N/A | | 2 | 0.59 |
| 2838 | 5177C1CO1.326 | N/A | | 2 | 0.78 |
| 2839 | 6441C1CO1.586 | N/A | | 2 | 0.94 |
| 2840 | 8256C1CO1.126 | N/A | | 2 | 0.91 |
| 2841 | 8549C2CO1.636 | N/A | | 2 | 0.98 |
| 2842 | 8771C1CO1.438 | N/A | | 2 | 0.89 |
| 2843 | 1140C1CO1.1634 | N/A | | 2 | 0.95 |
| 2844 | 1556C1CO1.146 | N/A | | 2 | 0.7 |
| 2845 | 2218C1CO1.268 | N/A | | 2 | 0.94 |
| 2846 | 2818C1CO1.432 | N/A | | 2 | 0.91 |
| 2847 | 2968C1CO1.276 | N/A | | 2 | 0.98 |
| 2848 | 3384C1CO1.95 | N/A | | 2 | 0.98 |
| 2849 | 3778C1CO1.290 | N/A | | 2 | 0.99 |
| 2850 | 4420C1CO1.321 | N/A | | 2 | 0.89 |
| 2851 | 4925C1CO1.341 | N/A | | 2 | 0.77 |
| 2852 | 5037C1CO1.339 | N/A | | 2 | 0.99 |
| 2853 | 607C3CO1.388 | N/A | | 2 | 0.92 |
| 2854 | 6649C2CO1.145 | N/A | | 2 | 0.96 |
| 2855 | 8021C1CO1.642 | N/A | | 2 | 0.97 |
| 2856 | 8622C1CO1.395 | N/A | | 2 | 0.75 |
| 2857 | 943C2CO1.598 | N/A | | 2 | 0.97 |
| 2858 | 947C3CO1.337 | N/A | | 2 | 0.98 |
| 2859 | 1092C2CO1.590 | N/A | | 2 | 0.93 |
| 2860 | 114C1CO1.553 | N/A | | 2 | 0.92 |
| 2861 | 11538C1CO1.256 | N/A | | 2 | 0.86 |
| 2862 | 1185C1CO1.588 | N/A | | 2 | 0.94 |
| 2863 | 1269C1CO1.518 | N/A | | 2 | 0.96 |
| 2864 | 1310C1CO1.170 | N/A | | 2 | 0.75 |
| 2865 | 1468C2CO1.142 | N/A | | 2 | 0.76 |
| 2866 | 1473C1CO1.321 | N/A | | 2 | 0.87 |
| 2867 | 1486C2CO1.280 | N/A | | 2 | 0.77 |
| 2868 | 1544C1CO1.650 | N/A | | 2 | 0.87 |
| 2869 | 1746C2CO1.463 | N/A | | 2 | 0.99 |
| 2870 | 1828C1CO1.331 | N/A | | 2 | 0.97 |
| 2871 | 1998C1CO1.377 | N/A | | 2 | 0.88 |
| 2872 | 2007C1CO1.139 | N/A | | 2 | 0.99 |
| 2873 | 2128C1CO1.1392 | N/A | | 2 | 0.86 |
| 2874 | 2162C2CO1.537 | N/A | | 2 | 0.78 |
| 2875 | 2201C1CO1.217 | N/A | | 2 | 0.83 |
| 2876 | 2368C1CO1.142 | N/A | | 2 | 0.87 |
| 2877 | 2591C3CO1.735 | N/A | | 2 | 0.93 |
| 2878 | 2696C1CO1.271 | N/A | | 2 | 0.83 |
| 2879 | 269C1CO1.137 | N/A | | 2 | 0.95 |
| 2880 | 269C2CO1.122 | N/A | | 2 | 0.97 |
| 2881 | 270C1CO1.247 | N/A | | 2 | 0.94 |
| 2882 | 2867C1CO1.209 | N/A | | 2 | 0.98 |
| 2883 | 2905C1CO1.706 | N/A | | 2 | 0.98 |
| 2884 | 3382C1CO1.104 | N/A | | 2 | 0.92 |
| 2885 | 3425C1CO1.652 | N/A | | 2 | 0.95 |
| 2886 | 3623C1CO1.327 | N/A | | 2 | 0.86 |
| 2887 | 374C4CO1.425 | N/A | | 2 | 0.9 |
| 2888 | 4463C2CO1.215 | N/A | | 2 | 0.83 |
| 2889 | 4709C1CO1.498 | N/A | | 2 | 0.81 |
| 2890 | 4819C1CO1.575 | N/A | | 2 | 0.85 |
| 2891 | 4886C1CO1.418 | N/A | | 2 | 0.87 |
| 2892 | 5032C1CO1.693 | N/A | | 2 | 0.7 |
| 2893 | 561C1CO1.550 | N/A | | 2 | 0.96 |
| 2894 | 59C1CO1.347 | N/A | | 2 | 0.85 |
| 2895 | 708C1CO1.696 | N/A | | 2 | 0.84 |
| 2896 | 711C2CO1.2054 | N/A | | 2 | 0.83 |
| 2897 | 7134C4CO1.245 | N/A | | 2 | 0.98 |
| 2898 | 7301C1CO1.520 | N/A | | 2 | 0.84 |
| 2899 | 7365C2CO1.672 | N/A | | 2 | 0.86 |
| 2900 | 7457C1CO1.225 | N/A | | 2 | 0.93 |
| 2901 | 7532C1CO1.349 | N/A | | 2 | 0.85 |
| 2902 | 7552C1CO1.441 | N/A | | 2 | 0.68 |
| 2903 | 763C1CO1.711 | N/A | | 2 | 0.71 |
| 2904 | 809C1CO1.248 | N/A | | 2 | 0.89 |
| 2905 | 8246C1CO1.187 | N/A | | 2 | 0.9 |
| 2906 | 8277C2CO1.480 | N/A | | 2 | 0.91 |
| 2907 | 8478C1CO1.416 | N/A | | 2 | 0.92 |
| 2908 | 8632C1CO1.372 | N/A | | 2 | 0.71 |
| 2909 | 10554C1CO1.686 | N/A | | 2 | 0.92 |
| 2910 | 1055C2CO1.119 | N/A | | 2 | 0.97 |
| 2911 | 1111C2CO1.358 | N/A | | 2 | 0.76 |
| 2912 | 1145C2CO1.609 | N/A | | 2 | 0.75 |
| 2913 | 1148C2CO1.723 | N/A | | 2 | 0.46 |
| 2914 | 1170C1CO1.616 | N/A | | 2 | 0.51 |
| 2915 | 1184C2CO1.455 | N/A | | 2 | 0.55 |
| 2916 | 1209C2CO1.126 | N/A | | 2 | 0.56 |
| 2917 | 121C1CO1.435 | N/A | | 2 | 0.89 |
| 2918 | 1239C2CO1.137 | N/A | | 2 | 0.56 |
| 2919 | 1443C1CO1.536 | N/A | | 2 | 0.77 |
| 2920 | 1513C1CO1.145 | N/A | | 2 | 0.53 |
| 2921 | 1583C1CO1.1144 | N/A | | 2 | 0.63 |
| 2922 | 1584C2CO1.930 | N/A | | 2 | 0.66 |
| 2923 | 1618C1CO1.604 | N/A | | 2 | 0.66 |
| 2924 | 1676C1CO1.203 | N/A | | 2 | 0.72 |
| 2925 | 1713C1CO1.242 | N/A | | 2 | 0.98 |
| 2926 | 1724C1CO1.359 | N/A | | 2 | 0.96 |
| 2927 | 1777C1CO1.407 | N/A | | 2 | 0.98 |
| 2928 | 1785C1CO1.142 | N/A | | 2 | 0.92 |
| 2929 | 1802C1CO1.534 | N/A | | 2 | 0.59 |
| 2930 | 1805C2CO1.439 | N/A | | 2 | 0.82 |
| 2931 | 2015C1CO1.978 | N/A | | 2 | 0.92 |
| 2932 | 2024C1CO1.166 | N/A | | 2 | 0.93 |
| 2933 | 2047C1CO1.709 | N/A | | 2 | 0.9 |
| 2934 | 2141C1CO1.572 | N/A | | 2 | 0.54 |
| 2935 | 220C1CO1.187 | N/A | | 2 | 0.62 |
| 2936 | 2216C1CO1.663 | N/A | | 2 | 0.89 |
| 2937 | 2218C1CO1.365 | N/A | | 2 | 0.64 |
| 2938 | 2241C1CO1.577 | N/A | | 2 | 1 |
| 2939 | 2536C1CO1.417 | N/A | | 2 | 0.5 |
| 2940 | 2573C1CO1.228 | N/A | | 2 | 0.67 |
| 2941 | 2593C2CO1.978 | N/A | | 2 | 0.71 |
| 2942 | 2644C1CO1.1224 | N/A | | 2 | 0.6 |
| 2943 | 2662C1CO1.154 | N/A | | 2 | 0.93 |
| 2944 | 2722C1CO1.237 | N/A | | 2 | 0.75 |
| 2945 | 2929C1CO1.283 | N/A | | 2 | 0.69 |
| 2946 | 2950C1CO1.528 | N/A | | 2 | 0.93 |
| 2947 | 299C1CO1.121 | N/A | | 2 | 0.84 |
| 2948 | 3176C2CO1.474 | N/A | | 2 | 0.67 |
| 2949 | 3218C1CO1.147 | N/A | | 2 | 0.89 |
| 2950 | 3370C1CO1.425 | N/A | | 2 | 0.86 |
| 2951 | 3542C1CO1.300 | N/A | | 2 | 0.89 |
| 2952 | 3577C2CO1.478 | N/A | | 2 | 0.94 |
| 2953 | 3585C1CO1.245 | N/A | | 2 | 0.8 |
| 2954 | 3639C1CO1.338 | N/A | | 2 | 0.9 |
| 2955 | 3756C1CO1.662 | N/A | | 2 | 0.91 |
| 2956 | 3920C1CO1.634 | N/A | | 2 | 0.72 |
| 2957 | 4151C1CO1.497 | N/A | | 2 | 0.62 |
| 2958 | 4275C1CO1.389 | N/A | | 2 | 0.83 |
| 2959 | 439C1CO1.357 | N/A | | 2 | 0.94 |
| 2960 | 4563C1CO1.291 | N/A | | 2 | 0.91 |
| 2961 | 4636C2CO1.554 | N/A | | 2 | 0.64 |
| 2962 | 4647C1CO1.284 | N/A | | 2 | 0.46 |
| 2963 | 46C1CO1.153 | N/A | | 2 | 0.67 |
| 2964 | 4713C1CO1.105 | N/A | | 2 | 0.92 |
| 2965 | 475C1CO1.1020 | N/A | | 2 | 0.98 |
| 2966 | 4867C1CO1.582 | N/A | | 2 | 0.8 |
| 2967 | 500C1CO1.578 | N/A | | 2 | 0.88 |
| 2968 | 510C2CO1.533 | N/A | | 2 | 0.96 |
| 2969 | 516C2CO1.895 | N/A | | 2 | 0.82 |
| 2970 | 521C1CO1.230 | N/A | | 2 | 0.49 |
| 2971 | 5267C1CO1.309 | N/A | | 2 | 0.93 |
| 2972 | 5358C1CO1.666 | N/A | | 2 | 0.55 |
| 2973 | 5482C1CO1.125 | N/A | | 2 | 0.83 |
| 2974 | 5559C1CO1.303 | N/A | | 2 | 0.99 |
| 2975 | 56C1CO1.88 | N/A | | 2 | 0.89 |
| 2976 | 5822C1CO1.910 | N/A | | 2 | 0.99 |
| 2977 | 6078C1CO1.647 | N/A | | 2 | 0.93 |
| 2978 | 6374C1CO1.774 | N/A | | 2 | 0.69 |
| 2979 | 6821C1CO1.448 | N/A | | 2 | 0.77 |
| 2980 | 6883C1CO1.110 | N/A | | 2 | 0.96 |

TABLE 6-continued

Identification of SEQ ID NOS. for 3,072 SNPs including 1620 validated SNPs (P = panel; V = Validated). Each SNP is located at nucleotide position 61 in the corresponding SEQ ID NO.

| SEQ ID NO | SNP_Name | New name | V | P | Score |
|---|---|---|---|---|---|
| 2981 | 693C2CO1.328 | N/A |  | 2 | 0.91 |
| 2982 | 6996C1CO1.63 | N/A |  | 2 | 0.7 |
| 2983 | 7378C1CO1.1029 | N/A |  | 2 | 0.62 |
| 2984 | 7411C1CO1.620 | N/A |  | 2 | 0.71 |
| 2985 | 7440C1CO1.559 | N/A |  | 2 | 0.54 |
| 2986 | 7944C1CO1.65 | N/A |  | 2 | 0.55 |
| 2987 | 809C2CO1.690 | N/A |  | 2 | 0.62 |
| 2988 | 8168C1CO1.470 | N/A |  | 2 | 0.88 |
| 2989 | 8176C1CO1.481 | N/A |  | 2 | 0.86 |
| 2990 | 850C1CO1.175 | N/A |  | 2 | 0.45 |
| 2991 | 8622C1CO1.330 | N/A |  | 2 | 0.74 |
| 2992 | 8623C1CO1.457 | N/A |  | 2 | 0.69 |
| 2993 | 8782C1CO1.129 | N/A |  | 2 | 0.76 |
| 2994 | 903C1CO1.499 | N/A |  | 2 | 0.7 |
| 2995 | 960C1CO1.283 | N/A |  | 2 | 0.5 |
| 2996 | 966C1CO1.483 | N/A |  | 2 | 0.97 |
| 2997 | 1754C1CO1.114 | N/A |  | 2 | 0.79 |
| 2998 | 1766C2CO1.142 | N/A |  | 2 | 0.66 |
| 2999 | 2535C1CO1.382 | N/A |  | 2 | 0.98 |
| 3000 | 2646C1CO1.1188 | N/A |  | 2 | 0.87 |
| 3001 | 2724C1CO1.751 | N/A |  | 2 | 0.92 |
| 3002 | 3030C1CO1.828 | N/A |  | 2 | 0.95 |
| 3003 | 3452C4CO1.163 | N/A |  | 2 | 0.96 |
| 3004 | 372C3CO1.122 | N/A |  | 2 | 0.87 |
| 3005 | 3768C2CO1.397 | N/A |  | 2 | 0.8 |
| 3006 | 446C1CO1.620 | N/A |  | 2 | 0.7 |
| 3007 | 513C1CO1.428 | N/A |  | 2 | 0.95 |
| 3008 | 5924C1CO1.433 | N/A |  | 2 | 0.91 |
| 3009 | 6523C1CO1.142 | N/A |  | 2 | 0.97 |
| 3010 | 6859C1CO1.525 | N/A |  | 2 | 0.89 |
| 3011 | 7335C1CO1.491 | N/A |  | 2 | 0.82 |
| 3012 | 7875C1CO1.456 | N/A |  | 2 | 0.89 |
| 3013 | 8319C1CO1.195 | N/A |  | 2 | 0.9 |
| 3014 | 834C1CO1.596 | N/A |  | 2 | 0.9 |
| 3015 | 8760C1CO1.212 | N/A |  | 2 | 0.82 |
| 3016 | 9148C1CO1.474 | N/A |  | 2 | 0.93 |
| 3017 | 1158C1CO1.154 | N/A |  | 2 | 0.9 |
| 3018 | 118C1CO1.417 | N/A |  | 2 | 0.88 |
| 3019 | 1213C1CO1.480 | N/A |  | 2 | 0.98 |
| 3020 | 1504C1CO1.463 | N/A |  | 2 | 0.97 |
| 3021 | 1712C1CO1.425 | N/A |  | 2 | 0.68 |
| 3022 | 2040C2CO1.620 | N/A |  | 2 | 0.91 |
| 3023 | 2758C1CO1.251 | N/A |  | 2 | 1 |
| 3024 | 2778C2CO1.476 | N/A |  | 2 | 0.97 |
| 3025 | 2781C3CO1.451 | N/A |  | 2 | 0.86 |
| 3026 | 33C2CO1.1119 | N/A |  | 2 | 0.98 |
| 3027 | 373C1CO1.72 | N/A |  | 2 | 0.98 |
| 3028 | 3871C1CO1.560 | N/A |  | 2 | 0.74 |
| 3029 | 3927C2CO1.806 | N/A |  | 2 | 0.76 |
| 3030 | 4206C1CO1.250 | N/A |  | 2 | 0.89 |
| 3031 | 4309C1CO1.125 | N/A |  | 2 | 0.94 |
| 3032 | 4463C2CO1.594 | N/A |  | 2 | 0.69 |
| 3033 | 4749C1CO1.85 | N/A |  | 2 | 0.93 |
| 3034 | 4810C1CO1.246 | N/A |  | 2 | 0.98 |
| 3035 | 4886C1CO1.585 | N/A |  | 2 | 0.95 |
| 3036 | 4925C1CO1.129 | N/A |  | 2 | 0.96 |
| 3037 | 5289C1CO1.203 | N/A |  | 2 | 0.74 |
| 3038 | 607C3CO1.168 | N/A |  | 2 | 0.96 |
| 3039 | 6160C1CO1.512 | N/A |  | 2 | 0.89 |
| 3040 | 672C2CO1.487 | N/A |  | 2 | 0.71 |
| 3041 | 6866C1CO1.628 | N/A |  | 2 | 0.66 |
| 3042 | 6932C1CO1.241 | N/A |  | 2 | 0.97 |
| 3043 | 6943C2CO1.80 | N/A |  | 2 | 0.92 |
| 3044 | 6953C1CO1.157 | N/A |  | 2 | 0.9 |
| 3045 | 757C1CO1.694 | N/A |  | 2 | 0.97 |
| 3046 | 809C1CO1.316 | N/A |  | 2 | 0.9 |
| 3047 | 827C1CO1.559 | N/A |  | 2 | 0.98 |
| 3048 | 850C1CO1.519 | N/A |  | 2 | 0.6 |
| 3049 | 886C1CO1.459 | N/A |  | 2 | 0.99 |
| 3050 | 9151C1CO1.237 | N/A |  | 2 | 0.82 |
| 3051 | 9225C1CO1.159 | N/A |  | 2 | 0.9 |
| 3052 | 9826C1CO1.163 | N/A |  | 2 | 0.91 |
| 3053 | all_v2.1.C5.417 | N/A |  | 2 | 0.855 |
| 3054 | all_v2.10285.C1.226 | N/A |  | 2 | 0.847 |
| 3055 | all_v2.132.C4.158 | N/A |  | 2 | 0.74 |
| 3056 | all_v2.1431.C1.739 | N/A |  | 2 | 0.738 |
| 3057 | all_v2.3533.C1.297 | N/A |  | 2 | 0.987 |
| 3058 | all_v2.2060.C2.434 | N/A |  | 2 | 0.679 |
| 3059 | all_v2.2189.C1.1126 | N/A |  | 2 | 0.987 |
| 3060 | all_v2.2351.C1.309 | N/A |  | 2 | 0.73 |
| 3061 | all_v2.2859.C1.172 | N/A |  | 2 | 0.854 |
| 3062 | all_v2.3448.C4.464 | N/A |  | 2 | 0.919 |
| 3063 | all_v2.4063.C1.644 | N/A |  | 2 | 0.908 |
| 3064 | all_v2.459.C4.508 | N/A |  | 2 | 0.837 |
| 3065 | all_v2.5160.C1.361 | N/A |  | 2 | 0.898 |
| 3066 | all_v2.5180.C1.186 | N/A |  | 2 | 0.848 |
| 3067 | all_v2.638.C1.140 | N/A |  | 2 | 0.26 |
| 3068 | all_v2.796.C2.594 | N/A |  | 2 | 0.842 |
| 3069 | 1beta501 | N/A |  | 2 | 0.308 |
| 3070 | 2beta877 | N/A |  | 2 | 0.828 |
| 3071 | 3beta51 | N/A |  | 2 | 0.756 |
| 3072 | 3beta607 | N/A |  | 2 | 0.309 |

TABLE 7

Identification of SEQ ID NOS: for Table 1 SNPs

| SEQ ID NO: | Contig SNP ID | SNP Nucleotide Position | Table 6 SNP_Name | Table 6 New Name |
|---|---|---|---|---|
| 1549 | PP_1060.c1 | 61 | 2628C1CO1.274 | cgpGmo-S401 |
| 3073 | PP_1062.c1 | 338 | | |
| 2482 | PP_1063.c1 | 61 | 204C2CO1.348 | |
| 1559 | PP_1072.C1 | 61 | 2698C1CO1.464 | cgpGmo-S409 |
| 1318 | PP_1092.C1 | 61 | 360C1CO1.520 | cgpGmo-S2273 |
| 3074 | PP_1108.C1 | 649 | | |
| 3075 | PP_1120.C1 | 514 | | |
| 2380 | PP_1159.C1 | 61 | 4715C1CO1.311 | |
| 108 | PP_1164.C1 | 61 | 95C1CO1.158 | cgpGmo-S1087a |
| 849 | PP_1206.C1 | 61 | 3350C1CO1.531 | cgpGmo-S1845 |
| 3076 | PP_127.C1 | 440 | | |
| 3077 | PP_1301.C1 | 112 | | |
| 3078 | PP_134.C1 | 709 | | |
| 3079 | PP_147.C1 | 333 | | |
| 935 | PP_1480.C3 | 61 | 4185C1CO1.502 | cgpGmo-S1923 |

TABLE 7-continued

Identification of SEQ ID NOS: for Table 1 SNPs

| SEQ ID NO: | Contig SNP ID | SNP Nucleotide Position | Table 6 SNP_Name | Table 6 New Name |
|---|---|---|---|---|
| 2643 | PP_161.C1 | 61 | 192C1CO1.309 | |
| 937 | PP_1657.C1 | 61 | 4203C1CO1.217 | cgpGmo-S1925 |
| 3080 | PTA_018.C2 | 330 | | |
| 3081 | PTA_028.c1 | 178 | | |
| 3082 | PTA_056.c1 | 594 | | |
| 3083 | PTA_079.C1 | 491 | | |
| 1493 | PTA_1090.c1 | 61 | 386C1CO1.1015 | cgpGmo-S35a |
| 2482 | PTA_1153.c1 | 61 | 204C2CO1.348 | |
| 3084 | PTA_1435.C1 | 325 | | |
| 3085 | PTA_1473.c1 | 269 | | |
| 3086 | PTA_1522.c1 | 211 | | |
| 3087 | PTA_153.c1 | 521 | | |
| 895 | PTA_1641.c1 | 61 | 3761C2CO1.570 | cgpGmo-S1887 |
| 1117 | PTA_1764.c1 | 61 | 643C1CO1.353 | cgpGmo-S2083 |
| 3088 | PTA_179.c1 | 204 | | |
| 3089 | PTA_1803.c1 | 322 | | |
| 3090 | PTA_2083.c2 | 798 | | |
| 3091 | PTA_233.C1 | 485 | | |
| 3092 | PTA_263.C1 | 666 | | |
| 760 | PTA_2675.c1 | 61 | 2399C1CO1.352 | cgpGmo-S1769 |
| 3093 | PTA_275.c2 | 165 | | |
| 691 | PTA_276.c1 | 61 | 1625C1CO1.549 | cgpGmo-S1706 |
| 1709 | PTA_286.c1 | 61 | 3552C1CO1.717 | cgpGmo-S537 |
| 3094 | PTA_423.c1 | 402 | | |
| 1549 | PTA_449.c1 | 61 | 2628C1CO1.274 | cgpGmo-S401 |
| 3095 | PTA_463.c2 | 507 | | |
| 3096 | PTA_624.C1 | 185 | | |
| 3097 | PTA_657.c2 | 314 | | |
| 1299 | PTA_685.c1 | 61 | 1554C1CO1.295 | cgpGmo-S2258 |
| 3098 | PTA_703.C2 | 308 | | |
| 3099 | PTA_854.c1 | 553 | | |
| 2556 | PTA_912.c1 | 61 | 4827C2CO1.825 | |

TABLE 8

Description of samples genotyped in Example 2

| Description | Breeding program | No. of samples | Purpose |
|---|---|---|---|
| Cape Sable, Canada | NB YC1 | 23 | Population analysis |
| Bay Bulls, Canada | NL YC2 | 23 | Population analysis |
| Georges Bank Canada | NB YC2 | 23 | Population analysis |
| Smith Sound, Canada | NL YC3 | 23 | Population analysis |
| Akureyri, Iceland | | 26 | Population analysis |
| Barents Sea, Norway | | 26 | Population analysis |
| Galway Bay, Ireland | | 15 | Population analysis |
| Family 33 | | 2 parents, 91 progeny | Segregation analysis Linkage mapping |
| Family 87 | | 2 parents, 91 progeny | Segregation analysis Linkage mapping |

TABLE 9

Analysis of types of base substitution for both predicted and validated SNPs in Example 2. Selected SNPs represent those included for testing on the two Illumina panels, validated SNPs represent those that were identified as polymorphic upon testing using samples from four Canadian populations.

| Base Substitution | Selected SNPs | Validated Polymorphic SNPs |
|---|---|---|
| A/G | 853 | 430 |
| C/T | 807 | 422 |
| A/C | 397 | 211 |
| A/T | 416 | 241 |
| C/G | 211 | 100 |
| G/T | 388 | 216 |
| Total | 3072 | 1620 |

TABLE 10

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 1 | cgpGmo-S1438 | CGPIA1 | 0 |
| 2 | cgpGmo-S78 | CGPIA1 | 4.058 |
| 3 | cgpGmo-S564 | CGPIA1 | 4.488 |
| 4 | cgpGmo-S105 | CGPIA1 | 5.038 |
| 5 | cgpGmo-S940 | CGPIA1 | 5.998 |
| 6 | cgpGmo-S2254 | CGPIA1 | 6.019 |
| 7 | cgpGmo-S512 | CGPIA1 | 6.93 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 8 | cgpGmo-S1471 | CGPIA1 | 6.959 |
| 9 | cgpGmo-S35a | CGPIA1 | 7.229 |
| 10 | cgpGmo-S1393b | CGPIA1 | 7.305 |
| 11 | cgpGmo-S1426 | CGPIA1 | 7.437 |
| 12 | cgpGmo-S1823 | CGPIA1 | 7.608 |
| 13 | cgpGmo-S1666 | CGPIA1 | 7.823 |
| 14 | cgpGmo-S387a | CGPIA1 | 8.005 |
| 15 | cgpGmo-S2068 | CGPIA1 | 8.277 |
| 16 | cgpGmo-S1840 | CGPIA1 | 8.733 |
| 17 | cgpGmo-S1393a | CGPIA1 | 8.924 |
| 18 | cgpGmo-S1239 | CGPIA1 | 9.383 |
| 19 | cgpGmo-S1369 | CGPIA1 | 9.674 |
| 20 | cgpGmo-S1954 | CGPIA1 | 9.993 |
| 21 | cgpGmo-S1817 | CGPIA1 | 10.78 |
| 22 | cgpGmo-S1336 | CGPIA1 | 10.956 |
| 23 | cgpGmo-S686a | CGPIA1 | 12.899 |
| 24 | cgpGmo-S686b | CGPIA1 | 12.899 |
| 25 | cgpGmo-S896 | CGPIA1 | 13.208 |
| 26 | cgpGmo-S807 | CGPIA1 | 13.736 |
| 27 | cgpGmo-S1407 | CGPIA1 | 14.055 |
| 28 | cgpGmo-S1788 | CGPIA1 | 14.333 |
| 29 | cgpGmo-S1181 | CGPIA1 | 15.316 |
| 30 | cgpGmo-S1167 | CGPIA1 | 15.522 |
| 31 | cgpGmo-S334 | CGPIA1 | 15.765 |
| 32 | cgpGmo-S787 | CGPIA1 | 15.765 |
| 33 | cgpGmo-S968 | CGPIA1 | 16.064 |
| 34 | cgpGmo-S283 | CGPIA1 | 16.181 |
| 35 | cgpGmo-S760 | CGPIA1 | 16.214 |
| 36 | cgpGmo-S844 | CGPIA1 | 16.887 |
| 37 | cgpGmo-S985 | CGPIA1 | 18.262 |
| 38 | cgpGmo-S270 | CGPIA1 | 18.309 |
| 39 | cgpGmo-S1703 | CGPIA1 | 18.604 |
| 40 | cgpGmo-S1196b | CGPIA1 | 18.717 |
| 41 | cgpGmo-S694 | CGPIA1 | 18.922 |
| 42 | cgpGmo-S875b | CGPIA1 | 20.514 |
| 43 | cgpGmo-S876 | CGPIA1 | 20.514 |
| 44 | cgpGmo-S1268 | CGPIA1 | 21.625 |
| 45 | cgpGmo-S1842 | CGPIA1 | 22.295 |
| 46 | cgpGmo-S2021 | CGPIA1 | 23.377 |
| 47 | cgpGmo-S1806 | CGPIA1 | 24.287 |
| 48 | cgpGmo-S1365a | CGPIA1 | 24.338 |
| 49 | cgpGmo-S291 | CGPIA1 | 27.737 |
| 50 | cgpGmo-S1579 | CGPIA1 | 27.89 |
| 51 | cgpGmo-S773 | CGPIA1 | 30.113 |
| 52 | cgpGmo-S83 | CGPIA1 | 31.123 |
| 53 | cgpGmo-S605 | CGPIA1 | 31.415 |
| 54 | cgpGmo-S852 | CGPIA1 | 31.565 |
| 55 | cgpGmo-S536 | CGPIA1 | 32.29 |
| 56 | cgpGmo-S1107 | CGPIA1 | 33.521 |
| 57 | cgpGmo-S1749 | CGPIA1 | 34.985 |
| 58 | cgpGmo-S523 | CGPIA1 | 36.323 |
| 59 | cgpGmo-S254 | CGPIA1 | 37.486 |
| 60 | cgpGmo-S1801 | CGPIA1 | 37.986 |
| 61 | cgpGmo-S1982 | CGPIA1 | 38.189 |
| 62 | cgpGmo-S1683 | CGPIA1 | 38.807 |
| 63 | cgpGmo-S2082 | CGPIA1 | 38.807 |
| 64 | cgpGmo-S339 | CGPIA1 | 40.613 |
| 65 | cgpGmo-S603 | CGPIA1 | 40.619 |
| 66 | cgpGmo-S1038 | CGPIA1 | 41.568 |
| 67 | cgpGmo-S360 | CGPIA1 | 41.58 |
| 68 | cgpGmo-S828 | CGPIA1 | 42.165 |
| 69 | cgpGmo-S1845 | CGPIA1 | 43.054 |
| 70 | cgpGmo-S2025 | CGPIA1 | 43.612 |
| 71 | cgpGmo-S1224 | CGPIA1 | 44.261 |
| 72 | cgpGmo-S292b | CGPIA1 | 44.914 |
| 73 | cgpGmo-S1969 | CGPIA1 | 45.138 |
| 74 | cgpGmo-S407 | CGPIA1 | 46.095 |
| 75 | cgpGmo-S1087b | CGPIA1 | 51.659 |
| 76 | cgpGmo-S1212 | CGPIA1 | 57.927 |
| 77 | cgpGmo-S868 | CGPIA2 | 0 |
| 78 | cgpGmo-S749a | CGPIA2 | 0.117 |
| 79 | cgpGmo-S754 | CGPIA2 | 0.235 |
| 80 | cgpGmo-S749b | CGPIA2 | 1.434 |
| 81 | cgpGmo-S1338 | CGPIA2 | 1.788 |
| 82 | cgpGmo-S305 | CGPIA2 | 3.426 |
| 83 | cgpGmo-S1274 | CGPIA2 | 3.818 |
| 84 | cgpGmo-S2070 | CGPIA2 | 4.704 |
| 85 | cgpGmo-S535b | CGPIA2 | 5.012 |
| 86 | cgpGmo-S1662 | CGPIA2 | 5.563 |
| 87 | cgpGmo-S535a | CGPIA2 | 7.002 |
| 88 | cgpGmo-S1163 | CGPIA2 | 7.376 |
| 89 | cgpGmo-S2157 | CGPIA2 | 7.898 |
| 90 | cgpGmo-S604 | CGPIA2 | 9.164 |
| 91 | cgpGmo-S1235 | CGPIA2 | 9.496 |
| 92 | cgpGmo-S2264 | CGPIA2 | 9.734 |
| 93 | cgpGmo-S2052 | CGPIA2 | 10.53 |
| 94 | cgpGmo-S1677 | CGPIA2 | 11.013 |
| 95 | cgpGmo-S1879 | CGPIA2 | 11.813 |
| 96 | cgpGmo-S1997 | CGPIA2 | 12.1 |
| 97 | cgpGmo-S1999 | CGPIA2 | 12.949 |
| 98 | cgpGmo-S16a | CGPIA2 | 13.288 |
| 99 | cgpGmo-S1563c | CGPIA2 | 13.368 |
| 100 | cgpGmo-S1910 | CGPIA2 | 13.762 |
| 101 | cgpGmo-S1743 | CGPIA2 | 13.889 |
| 102 | cgpGmo-S1916 | CGPIA2 | 13.889 |
| 103 | cgpGmo-S951b | CGPIA2 | 14.387 |
| 104 | cgpGmo-S77 | CGPIA2 | 15.022 |
| 105 | cgpGmo-S338b | CGPIA2 | 15.676 |
| 106 | cgpGmo-S946 | CGPIA2 | 15.915 |
| 107 | cgpGmo-S185 | CGPIA2 | 16.245 |
| 108 | cgpGmo-S155 | CGPIA2 | 16.543 |
| 109 | cgpGmo-S1047 | CGPIA2 | 16.881 |
| 110 | cgpGmo-S1825 | CGPIA2 | 20.029 |
| 111 | cgpGmo-S590 | CGPIA2 | 22.045 |
| 112 | cgpGmo-S1230a | CGPIA2 | 24.762 |
| 113 | cgpGmo-S1620 | CGPIA2 | 26.063 |
| 114 | cgpGmo-S728 | CGPIA2 | 29.603 |
| 115 | cgpGmo-S1221a | CGPIA2 | 32.8 |
| 116 | cgpGmo-S1113 | CGPIA2 | 36.469 |
| 117 | cgpGmo-S1112 | CGPIA2 | 36.469 |
| 118 | cgpGmo-S1693 | CGPIA2 | 37.571 |
| 119 | cgpGmo-S1111 | CGPIA2 | 38.88 |
| 120 | cgpGmo-S2266 | CGPIA2 | 39.88 |
| 121 | cgpGmo-S40 | CGPIA2 | 40.497 |
| 122 | cgpGmo-S318 | CGPIA2 | 42.248 |
| 123 | cgpGmo-S1231 | CGPIA2 | 43.533 |
| 124 | cgpGmo-S810 | CGPIA2 | 44.84 |
| 125 | cgpGmo-S1354 | CGPIA2 | 45.026 |
| 126 | cgpGmo-S400 | CGPIA2 | 47.431 |
| 127 | cgpGmo-S2001 | CGPIA2 | 48.601 |
| 128 | cgpGmo-S1216a | CGPIA2 | 49.675 |
| 129 | cgpGmo-S1522 | CGPIA2 | 49.683 |
| 130 | cgpGmo-S333 | CGPIA2 | 49.931 |
| 131 | cgpGmo-S1284 | CGPIA2 | 50.473 |
| 132 | cgpGmo-S1217 | CGPIA2 | 51.137 |
| 133 | cgpGmo-S1216b | CGPIA2 | 51.359 |
| 134 | cgpGmo-S548 | CGPIA2 | 51.486 |
| 135 | cgpGmo-S68 | CGPIA2 | 55.472 |
| 136 | cgpGmo-S973 | CGPIA2 | 56.189 |
| 137 | cgpGmo-S1908 | CGPIA2 | 56.22 |
| 138 | cgpGmo-S2112 | CGPIA2 | 56.256 |
| 139 | cgpGmo-S1026 | CGPIA2 | 56.661 |
| 140 | cgpGmo-S1205 | CGPIA2 | 56.739 |
| 141 | cgpGmo-S454 | CGPIA2 | 56.78 |
| 142 | cgpGmo-S532 | CGPIA2 | 56.835 |
| 143 | cgpGmo-S1068 | CGPIA2 | 56.835 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr  | Locus        | Group  | Position |
|-----|--------------|--------|----------|
| 144 | cgpGmo-S1101a | CGPIA2 | 56.835   |
| 145 | cgpGmo-S1456 | CGPIA2 | 56.835   |
| 146 | cgpGmo-S1022 | CGPIA2 | 57.035   |
| 147 | cgpGmo-S174  | CGPIA2 | 57.04    |
| 148 | cgpGmo-S184  | CGPIA2 | 57.04    |
| 149 | cgpGmo-S1751 | CGPIA2 | 57.296   |
| 150 | cgpGmo-S1907 | CGPIA2 | 57.574   |
| 151 | cgpGmo-S182  | CGPIA2 | 57.574   |
| 152 | cgpGmo-S2146 | CGPIA2 | 58.037   |
| 153 | cgpGmo-S489  | CGPIA2 | 58.44    |
| 154 | cgpGmo-S780  | CGPIA2 | 60.286   |
| 155 | cgpGmo-S444  | CGPIA3 | 0        |
| 156 | cgpGmo-S1652 | CGPIA3 | 6.237    |
| 157 | cgpGmo-S81   | CGPIA3 | 7.433    |
| 158 | cgpGmo-S514  | CGPIA3 | 9.709    |
| 159 | cgpGmo-S1296 | CGPIA3 | 10.053   |
| 160 | cgpGmo-S666  | CGPIA3 | 11.139   |
| 161 | cgpGmo-S466  | CGPIA3 | 11.95    |
| 162 | cgpGmo-S32   | CGPIA3 | 12.509   |
| 163 | cgpGmo-S2229 | CGPIA3 | 12.929   |
| 164 | cgpGmo-S1070 | CGPIA3 | 13.059   |
| 165 | cgpGmo-S2185 | CGPIA3 | 13.974   |
| 166 | cgpGmo-S646  | CGPIA3 | 16.28    |
| 167 | cgpGmo-S1808 | CGPIA3 | 18.827   |
| 168 | cgpGmo-S453  | CGPIA3 | 19.415   |
| 169 | cgpGmo-S526  | CGPIA3 | 23.411   |
| 170 | cgpGmo-S171  | CGPIA3 | 23.435   |
| 171 | cgpGmo-S491  | CGPIA3 | 23.741   |
| 172 | cgpGmo-S872a | CGPIA3 | 24.459   |
| 173 | cgpGmo-S172  | CGPIA3 | 24.893   |
| 174 | cgpGmo-S1504 | CGPIA3 | 26.797   |
| 175 | cgpGmo-S872b | CGPIA3 | 26.938   |
| 176 | cgpGmo-S199  | CGPIA3 | 27.464   |
| 177 | cgpGmo-S1007 | CGPIA3 | 27.464   |
| 178 | cgpGmo-S408  | CGPIA3 | 27.714   |
| 179 | cgpGmo-S301  | CGPIA3 | 28.939   |
| 180 | cgpGmo-S2049 | CGPIA3 | 29.346   |
| 181 | cgpGmo-S923  | CGPIA3 | 29.543   |
| 182 | cgpGmo-S769  | CGPIA3 | 29.564   |
| 183 | cgpGmo-S1757 | CGPIA3 | 31.246   |
| 184 | cgpGmo-S1263 | CGPIA3 | 31.342   |
| 185 | cgpGmo-S716  | CGPIA3 | 32.884   |
| 186 | cgpGmo-S689  | CGPIA3 | 33.765   |
| 187 | cgpGmo-S643b | CGPIA3 | 35.835   |
| 188 | cgpGmo-S398  | CGPIA3 | 37.675   |
| 189 | cgpGmo-S755  | CGPIA3 | 39.034   |
| 190 | cgpGmo-S1927 | CGPIA3 | 39.187   |
| 191 | cgpGmo-S478  | CGPIA3 | 41.41    |
| 192 | cgpGmo-S643a | CGPIA3 | 41.734   |
| 193 | cgpGmo-S1789 | CGPIA3 | 41.845   |
| 194 | cgpGmo-S759  | CGPIA3 | 42.416   |
| 195 | cgpGmo-S718a | CGPIA3 | 43.345   |
| 196 | cgpGmo-S801  | CGPIA3 | 43.345   |
| 197 | cgpGmo-S1469 | CGPIA3 | 43.644   |
| 198 | cgpGmo-S718b | CGPIA3 | 43.656   |
| 199 | cgpGmo-S1598b | CGPIA3 | 45.42   |
| 200 | cgpGmo-S377  | CGPIA3 | 46.202   |
| 201 | cgpGmo-S22b  | CGPIA3 | 47.762   |
| 202 | cgpGmo-S1967 | CGPIA3 | 48.597   |
| 203 | cgpGmo-S771  | CGPIA3 | 49.41    |
| 204 | cgpGmo-S1656 | CGPIA3 | 51.471   |
| 205 | cgpGmo-S1131 | CGPIA3 | 52.512   |
| 206 | cgpGmo-S223  | CGPIA3 | 52.915   |
| 207 | cgpGmo-S1978 | CGPIA3 | 54.812   |
| 208 | cgpGmo-S644  | CGPIA3 | 55.382   |
| 209 | cgpGmo-S1328 | CGPIA3 | 56.35    |
| 210 | cgpGmo-S1218 | CGPIA3 | 56.601   |
| 211 | cgpGmo-S1890 | CGPIA3 | 57.246   |
| 212 | cgpGmo-S2255 | CGPIA3 | 57.284   |
| 213 | cgpGmo-S99   | CGPIA3 | 60.85    |
| 214 | cgpGmo-S799  | CGPIA3 | 61.887   |
| 215 | cgpGmo-S734  | CGPIA3 | 62.921   |
| 216 | cgpGmo-S1984 | CGPIA4 | 0        |
| 217 | cgpGmo-S204  | CGPIA4 | 1.475    |
| 218 | cgpGmo-S552  | CGPIA4 | 1.754    |
| 219 | cgpGmo-S1739 | CGPIA4 | 3.262    |
| 220 | cgpGmo-S1730 | CGPIA4 | 3.314    |
| 221 | cgpGmo-S657a | CGPIA4 | 4.099    |
| 222 | cgpGmo-S2155 | CGPIA4 | 6.468    |
| 223 | cgpGmo-S2156 | CGPIA4 | 6.468    |
| 224 | cgpGmo-S1491b | CGPIA4 | 7.914   |
| 225 | cgpGmo-S1491a | CGPIA4 | 9.37    |
| 226 | cgpGmo-S1197a | CGPIA4 | 10.894  |
| 227 | cgpGmo-S126a | CGPIA4 | 11.728   |
| 228 | cgpGmo-S1091 | CGPIA4 | 13.252   |
| 229 | cgpGmo-S1833 | CGPIA4 | 13.811   |
| 230 | cgpGmo-S126b | CGPIA4 | 15.458   |
| 231 | cgpGmo-S837  | CGPIA4 | 15.809   |
| 232 | cgpGmo-S395  | CGPIA4 | 17.036   |
| 233 | cgpGmo-S267  | CGPIA4 | 17.615   |
| 234 | cgpGmo-S1445 | CGPIA4 | 19.063   |
| 235 | cgpGmo-S1079 | CGPIA4 | 22.07    |
| 236 | cgpGmo-S1841 | CGPIA4 | 24.678   |
| 237 | cgpGmo-S2279 | CGPIA4 | 25.633   |
| 238 | cgpGmo-S1360a | CGPIA4 | 25.693  |
| 239 | cgpGmo-S791  | CGPIA4 | 25.693   |
| 240 | cgpGmo-S1360b | CGPIA4 | 26.136  |
| 241 | 5279C2CO1.498 | CGPIA4 | 26.322  |
| 242 | cgpGmo-S819b | CGPIA4 | 26.979   |
| 243 | cgpGmo-S250  | CGPIA4 | 26.992   |
| 244 | cgpGmo-S1979 | CGPIA4 | 28.626   |
| 245 | cgpGmo-S2056 | CGPIA4 | 29.8     |
| 246 | cgpGmo-S792  | CGPIA4 | 30.051   |
| 247 | cgpGmo-S205  | CGPIA4 | 31.162   |
| 248 | cgpGmo-S434b | CGPIA4 | 32.113   |
| 249 | cgpGmo-S434a | CGPIA4 | 32.16    |
| 250 | cgpGmo-S1865 | CGPIA4 | 33.942   |
| 251 | cgpGmo-S850  | CGPIA4 | 34.174   |
| 252 | cgpGmo-S1558 | CGPIA4 | 34.408   |
| 253 | cgpGmo-S1768 | CGPIA4 | 34.661   |
| 254 | cgpGmo-S2079 | CGPIA4 | 34.876   |
| 255 | cgpGmo-S701  | CGPIA4 | 35.114   |
| 256 | cgpGmo-S720  | CGPIA4 | 35.663   |
| 257 | cgpGmo-S306a | CGPIA4 | 35.748   |
| 258 | cgpGmo-S1010 | CGPIA4 | 35.985   |
| 259 | cgpGmo-S306b | CGPIA4 | 36.057   |
| 260 | cgpGmo-S93   | CGPIA4 | 36.846   |
| 261 | cgpGmo-S354  | CGPIA4 | 37.098   |
| 262 | cgpGmo-S615  | CGPIA4 | 37.125   |
| 263 | cgpGmo-S543  | CGPIA4 | 37.616   |
| 264 | cgpGmo-S420  | CGPIA4 | 37.616   |
| 265 | cgpGmo-S1301 | CGPIA4 | 37.866   |
| 266 | cgpGmo-S818a | CGPIA4 | 37.972   |
| 267 | cgpGmo-S1856 | CGPIA4 | 38.872   |
| 268 | cgpGmo-S134  | CGPIA4 | 39.317   |
| 269 | cgpGmo-S1744 | CGPIA4 | 39.468   |
| 270 | cgpGmo-S2015 | CGPIA4 | 39.916   |
| 271 | cgpGmo-S167  | CGPIA4 | 45.729   |
| 272 | cgpGmo-S1698 | CGPIA4 | 59.88    |
| 273 | cgpGmo-S2132 | CGPIA4 | 70.722   |
| 274 | cgpGmo-S938  | CGPIA5 | 0        |
| 275 | cgpGmo-S2044 | CGPIA5 | 0.872    |
| 276 | cgpGmo-S937  | CGPIA5 | 1.675    |
| 277 | cgpGmo-S58b  | CGPIA5 | 2.844    |
| 278 | cgpGmo-S129  | CGPIA5 | 3.287    |
| 279 | cgpGmo-S2136 | CGPIA5 | 3.409    |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 280 | cgpGmo-S2115 | CGPIA5 | 3.57 |
| 281 | cgpGmo-S1745 | CGPIA5 | 4.848 |
| 282 | cgpGmo-S1162 | CGPIA5 | 4.865 |
| 283 | cgpGmo-S1241 | CGPIA5 | 5.046 |
| 284 | cgpGmo-S496 | CGPIA5 | 6.768 |
| 285 | cgpGmo-S1924 | CGPIA5 | 7.038 |
| 286 | cgpGmo-S2235 | CGPIA5 | 9.6 |
| 287 | cgpGmo-S894 | CGPIA5 | 10.205 |
| 288 | cgpGmo-S2042 | CGPIA5 | 11.241 |
| 289 | cgpGmo-S990 | CGPIA5 | 11.923 |
| 290 | cgpGmo-S2069 | CGPIA5 | 12.113 |
| 291 | cgpGmo-S2196 | CGPIA5 | 12.122 |
| 292 | cgpGmo-S1771 | CGPIA5 | 12.288 |
| 293 | cgpGmo-S991a | CGPIA5 | 12.726 |
| 294 | cgpGmo-S228 | CGPIA5 | 13.115 |
| 295 | cgpGmo-S2083 | CGPIA5 | 13.39 |
| 296 | cgpGmo-S1169 | CGPIA5 | 13.392 |
| 297 | cgpGmo-S310 | CGPIA5 | 13.394 |
| 298 | cgpGmo-S162 | CGPIA5 | 14.023 |
| 299 | cgpGmo-S991b | CGPIA5 | 14.227 |
| 300 | cgpGmo-S1232 | CGPIA5 | 16 |
| 301 | cgpGmo-S977 | CGPIA5 | 26.336 |
| 302 | cgpGmo-S239a | CGPIA5 | 26.336 |
| 303 | cgpGmo-S1519 | CGPIA5 | 29.305 |
| 304 | cgpGmo-S1634 | CGPIA5 | 29.382 |
| 305 | cgpGmo-S1588b | CGPIA5 | 29.919 |
| 306 | cgpGmo-S1588a | CGPIA5 | 30.015 |
| 307 | cgpGmo-S1787 | CGPIA5 | 30.546 |
| 308 | cgpGmo-S893 | CGPIA5 | 30.665 |
| 309 | cgpGmo-S640b | CGPIA5 | 30.741 |
| 310 | cgpGmo-S137 | CGPIA5 | 31.141 |
| 311 | cgpGmo-S82 | CGPIA5 | 31.141 |
| 312 | GP_2_3 | CGPIA5 | 31.778 |
| 313 | GP_2_1 | CGPIA5 | 31.778 |
| 314 | cgpGmo-S715 | CGPIA5 | 33.509 |
| 315 | cgpGmo-S239b | CGPIA5 | 34.351 |
| 316 | cgpGmo-S1942 | CGPIA5 | 35.493 |
| 317 | cgpGmo-S774 | CGPIA5 | 37.607 |
| 318 | cgpGmo-S61 | CGPIA5 | 37.992 |
| 319 | cgpGmo-S2189 | CGPIA5 | 38.06 |
| 320 | cgpGmo-S1158 | CGPIA5 | 38.533 |
| 321 | cgpGmo-S2111 | CGPIA5 | 39.324 |
| 322 | cgpGmo-S2123 | CGPIA5 | 39.769 |
| 323 | cgpGmo-S2087 | CGPIA5 | 40.073 |
| 324 | cgpGmo-S158b | CGPIA5 | 40.244 |
| 325 | cgpGmo-S1816 | CGPIA5 | 40.666 |
| 326 | cgpGmo-S158a | CGPIA5 | 40.75 |
| 327 | cgpGmo-S1607 | CGPIA5 | 41.075 |
| 328 | cgpGmo-S1672 | CGPIA5 | 41.927 |
| 329 | cgpGmo-S1985 | CGPIA5 | 45.067 |
| 330 | cgpGmo-S725 | CGPIA5 | 49.237 |
| 331 | cgpGmo-S404a | CGPIA5 | 51.757 |
| 332 | cgpGmo-S1452 | CGPIA5 | 51.801 |
| 333 | cgpGmo-S1902 | CGPIA5 | 52.335 |
| 334 | cgpGmo-S1540 | CGPIA5 | 52.52 |
| 335 | cgpGmo-S1078 | CGPIA5 | 52.626 |
| 336 | cgpGmo-S800 | CGPIA5 | 53.602 |
| 337 | cgpGmo-S122 | CGPIA5 | 54.637 |
| 338 | cgpGmo-S1993 | CGPIA6 | −2.956 |
| 339 | cgpGmo-S1538b | CGPIA6 | −2.257 |
| 340 | cgpGmo-S347 | CGPIA6 | 0 |
| 341 | cgpGmo-S1359 | CGPIA6 | 0.612 |
| 342 | cgpGmo-S119b | CGPIA6 | 1.143 |
| 343 | cgpGmo-S119a | CGPIA6 | 1.484 |
| 344 | cgpGmo-S2165 | CGPIA6 | 3.206 |
| 345 | cgpGmo-S848 | CGPIA6 | 3.382 |
| 346 | cgpGmo-S2172 | CGPIA6 | 4.153 |
| 347 | cgpGmo-S1473 | CGPIA6 | 6.957 |
| 348 | cgpGmo-S1538a | CGPIA6 | 10.524 |
| 349 | cgpGmo-S2154 | CGPIA6 | 13.687 |
| 350 | cgpGmo-S1258a | CGPIA6 | 14.915 |
| 351 | cgpGmo-S764 | CGPIA6 | 16.651 |
| 352 | cgpGmo-S88b | CGPIA6 | 17.003 |
| 353 | cgpGmo-S1258b | CGPIA6 | 17.86 |
| 354 | cgpGmo-S530a | CGPIA6 | 21.781 |
| 355 | cgpGmo-S1887 | CGPIA6 | 24.875 |
| 356 | cgpGmo-S1086 | CGPIA6 | 29.114 |
| 357 | cgpGmo-S1510 | CGPIA6 | 30.62 |
| 358 | cgpGmo-S1252 | CGPIA6 | 31.23 |
| 359 | cgpGmo-S1256b | CGPIA6 | 32.691 |
| 360 | cgpGmo-S1256a | CGPIA6 | 32.693 |
| 361 | cgpGmo-S1332 | CGPIA6 | 33.153 |
| 362 | cgpGmo-S2065 | CGPIA6 | 33.34 |
| 363 | cgpGmo-S2200 | CGPIA6 | 33.353 |
| 364 | cgpGmo-S1062 | CGPIA6 | 33.67 |
| 365 | cgpGmo-S365b | CGPIA6 | 33.755 |
| 366 | cgpGmo-S389 | CGPIA6 | 33.755 |
| 367 | cgpGmo-S628 | CGPIA6 | 34.105 |
| 368 | cgpGmo-S321 | CGPIA6 | 34.105 |
| 369 | cgpGmo-S1940 | CGPIA6 | 34.166 |
| 370 | cgpGmo-S714a | CGPIA6 | 34.222 |
| 371 | cgpGmo-S630 | CGPIA6 | 34.478 |
| 372 | cgpGmo-S2124 | CGPIA6 | 34.484 |
| 373 | cgpGmo-S2081 | CGPIA6 | 35.4 |
| 374 | cgpGmo-S537 | CGPIA6 | 35.697 |
| 375 | cgpGmo-S203 | CGPIA6 | 36.426 |
| 376 | cgpGmo-S930 | CGPIA6 | 37.787 |
| 377 | cgpGmo-S785b | CGPIA6 | 37.787 |
| 378 | cgpGmo-S1872 | CGPIA6 | 37.858 |
| 379 | cgpGmo-S470 | CGPIA6 | 38.885 |
| 380 | cgpGmo-S60 | CGPIA6 | 40.601 |
| 381 | cgpGmo-S72 | CGPIA6 | 40.617 |
| 382 | cgpGmo-S1075 | CGPIA6 | 40.617 |
| 383 | cgpGmo-S2207 | CGPIA6 | 40.869 |
| 384 | cgpGmo-S312 | CGPIA6 | 41.914 |
| 385 | cgpGmo-S768 | CGPIA6 | 42.051 |
| 386 | cgpGmo-S277 | CGPIA6 | 42.989 |
| 387 | cgpGmo-S1687 | CGPIA6 | 44.596 |
| 388 | cgpGmo-S672 | CGPIA6 | 45.18 |
| 389 | cgpGmo-S1629 | CGPIA6 | 45.77 |
| 390 | cgpGmo-S2176 | CGPIA6 | 45.77 |
| 391 | cgpGmo-S638a | CGPIA6 | 47.169 |
| 392 | cgpGmo-S1813 | CGPIA6 | 47.169 |
| 393 | cgpGmo-S1777 | CGPIA6 | 48.924 |
| 394 | cgpGmo-S173 | CGPIA6 | 49.927 |
| 395 | cgpGmo-S121 | CGPIA6 | 50.726 |
| 396 | cgpGmo-S1721 | CGPIA6 | 50.863 |
| 397 | cgpGmo-S638b | CGPIA6 | 50.895 |
| 398 | cgpGmo-S212 | CGPIA6 | 52.168 |
| 399 | cgpGmo-S1463b | CGPIA6 | 52.985 |
| 400 | cgpGmo-S1826 | CGPIA6 | 55.268 |
| 401 | cgpGmo-S2119 | CGPIA6 | 60.953 |
| 402 | cgpGmo-S2100 | CGPIA7 | 0 |
| 403 | cgpGmo-S26 | CGPIA7 | 1.823 |
| 404 | cgpGmo-S1935 | CGPIA7 | 3.476 |
| 405 | cgpGmo-S1763 | CGPIA7 | 4.153 |
| 406 | cgpGmo-S393 | CGPIA7 | 4.557 |
| 407 | cgpGmo-S1906 | CGPIA7 | 4.572 |
| 408 | Pgrmc_1_1 | CGPIA7 | 4.619 |
| 409 | cgpGmo-S282 | CGPIA7 | 4.62 |
| 410 | cgpGmo-S255 | CGPIA7 | 4.793 |
| 411 | cgpGmo-S976b | CGPIA7 | 5.643 |
| 412 | cgpGmo-S833 | CGPIA7 | 5.704 |
| 413 | cgpGmo-S895 | CGPIA7 | 5.864 |
| 414 | cgpGmo-S1692 | CGPIA7 | 5.947 |
| 415 | cgpGmo-S834 | CGPIA7 | 6.228 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 416 | cgpGmo-S1867 | CGPIA7 | 6.436 |
| 417 | cgpGmo-S1399b | CGPIA7 | 6.455 |
| 418 | cgpGmo-S1859 | CGPIA7 | 6.724 |
| 419 | cgpGmo-S1497 | CGPIA7 | 7.43 |
| 420 | cgpGmo-S674 | CGPIA7 | 7.46 |
| 421 | cgpGmo-S1399a | CGPIA7 | 8.142 |
| 422 | cgpGmo-S1279 | CGPIA7 | 8.168 |
| 423 | cgpGmo-S1200 | CGPIA7 | 9.272 |
| 424 | cgpGmo-S877 | CGPIA7 | 10.283 |
| 425 | cgpGmo-S741 | CGPIA7 | 15.235 |
| 426 | cgpGmo-S2277 | CGPIA7 | 16.154 |
| 427 | cgpGmo-S2019 | CGPIA7 | 17.391 |
| 428 | cgpGmo-S917 | CGPIA7 | 18.267 |
| 429 | cgpGmo-S268 | CGPIA7 | 19.147 |
| 430 | cgpGmo-S1183 | CGPIA7 | 19.147 |
| 431 | cgpGmo-S1991 | CGPIA7 | 19.147 |
| 432 | cgpGmo-S2158 | CGPIA7 | 19.147 |
| 433 | cgpGmo-S1039b | CGPIA7 | 19.147 |
| 434 | cgpGmo-S1830 | CGPIA7 | 19.147 |
| 435 | cgpGmo-S157 | CGPIA7 | 19.147 |
| 436 | cgpGmo-S870 | CGPIA7 | 19.147 |
| 437 | cgpGmo-S982a | CGPIA7 | 19.147 |
| 438 | cgpGmo-S419 | CGPIA7 | 19.147 |
| 439 | cgpGmo-S352 | CGPIA7 | 19.147 |
| 440 | cgpGmo-S920 | CGPIA7 | 19.147 |
| 441 | cgpGmo-S152 | CGPIA7 | 19.147 |
| 442 | cgpGmo-S1089 | CGPIA7 | 19.147 |
| 443 | cgpGmo-S183 | CGPIA7 | 19.147 |
| 444 | cgpGmo-S1039a | CGPIA7 | 19.147 |
| 445 | cgpGmo-S814a | CGPIA7 | 19.147 |
| 446 | cgpGmo-S1425 | CGPIA7 | 19.147 |
| 447 | cgpGmo-S673 | CGPIA7 | 19.147 |
| 448 | cgpGmo-S1810 | CGPIA7 | 19.147 |
| 449 | cgpGmo-S739 | CGPIA7 | 19.147 |
| 450 | cgpGmo-S260a | CGPIA7 | 20.06 |
| 451 | cgpGmo-S426 | CGPIA7 | 20.392 |
| 452 | cgpGmo-S1644 | CGPIA7 | 22.341 |
| 453 | cgpGmo-S1065 | CGPIA7 | 24.377 |
| 454 | cgpGmo-S207 | CGPIA7 | 26.97 |
| 455 | cgpGmo-S62 | CGPIA7 | 27.261 |
| 456 | cgpGmo-S244 | CGPIA7 | 27.975 |
| 457 | cgpGmo-S209 | CGPIA7 | 28.015 |
| 458 | cgpGmo-S669 | CGPIA7 | 28.342 |
| 459 | cgpGmo-S889b | CGPIA7 | 28.361 |
| 460 | cgpGmo-S992 | CGPIA7 | 28.64 |
| 461 | cgpGmo-S63 | CGPIA7 | 28.791 |
| 462 | cgpGmo-S2026 | CGPIA7 | 28.837 |
| 463 | cgpGmo-S1668 | CGPIA7 | 29.63 |
| 464 | cgpGmo-S869 | CGPIA7 | 32.242 |
| 465 | cgpGmo-S2202 | CGPIA7 | 32.307 |
| 466 | cgpGmo-S1858 | CGPIA7 | 34.979 |
| 467 | cgpGmo-S584 | CGPIA7 | 34.991 |
| 468 | cgpGmo-S422 | CGPIA7 | 35 |
| 469 | cgpGmo-S831 | CGPIA7 | 35.583 |
| 470 | cgpGmo-S385a | CGPIA7 | 38.005 |
| 471 | cgpGmo-S189 | CGPIA7 | 38.23 |
| 472 | cgpGmo-S830 | CGPIA7 | 38.685 |
| 473 | cgpGmo-S2193 | CGPIA7 | 38.877 |
| 474 | cgpGmo-S1058 | CGPIA7 | 39.066 |
| 475 | cgpGmo-S110 | CGPIA7 | 40.658 |
| 476 | cgpGmo-S999 | CGPIA7 | 40.658 |
| 477 | cgpGmo-S1782 | CGPIA7 | 41.095 |
| 478 | cgpGmo-S2134 | CGPIA7 | 42.716 |
| 479 | cgpGmo-S452 | CGPIA7 | 44.739 |
| 480 | cgpGmo-S595 | CGPIA8 | 0 |
| 481 | cgpGmo-S1358 | CGPIA8 | 0.031 |
| 482 | cgpGmo-S1050 | CGPIA8 | 0.551 |
| 483 | cgpGmo-S1030 | CGPIA8 | 2.041 |
| 484 | cgpGmo-S232b | CGPIA8 | 3.145 |
| 485 | cgpGmo-S232a | CGPIA8 | 4.257 |
| 486 | cgpGmo-S52 | CGPIA8 | 5.173 |
| 487 | cgpGmo-S1287 | CGPIA8 | 6.491 |
| 488 | cgpGmo-S1747 | CGPIA8 | 7.262 |
| 489 | cgpGmo-S412 | CGPIA8 | 8.235 |
| 490 | cgpGmo-S748 | CGPIA8 | 9.413 |
| 491 | cgpGmo-S776a | CGPIA8 | 11.039 |
| 492 | cgpGmo-S776b | CGPIA8 | 11.088 |
| 493 | cgpGmo-S2191 | CGPIA8 | 11.801 |
| 494 | cgpGmo-S1785 | CGPIA8 | 12.304 |
| 495 | cgpGmo-S1018a | CGPIA8 | 13.355 |
| 496 | cgpGmo-S597 | CGPIA8 | 13.683 |
| 497 | cgpGmo-S1820 | CGPIA8 | 13.794 |
| 498 | cgpGmo-S2002 | CGPIA8 | 14.001 |
| 499 | cgpGmo-S1430a | CGPIA8 | 14.054 |
| 500 | cgpGmo-S786 | CGPIA8 | 14.226 |
| 501 | cgpGmo-S421 | CGPIA8 | 14.226 |
| 502 | cgpGmo-S362 | CGPIA8 | 14.51 |
| 503 | cgpGmo-S1018b | CGPIA8 | 14.824 |
| 504 | cgpGmo-S332a | CGPIA8 | 16.007 |
| 505 | cgpGmo-S857 | CGPIA8 | 16.084 |
| 506 | cgpGmo-S332b | CGPIA8 | 17.992 |
| 507 | cgpGmo-S1898 | CGPIA8 | 21.791 |
| 508 | cgpGmo-S1430b | CGPIA8 | 21.848 |
| 509 | cgpGmo-S556 | CGPIA8 | 22.503 |
| 510 | cgpGmo-S562 | CGPIA8 | 22.807 |
| 511 | cgpGmo-S438 | CGPIA8 | 24.379 |
| 512 | cgpGmo-S511b | CGPIA8 | 24.609 |
| 513 | cgpGmo-S1814 | CGPIA8 | 25.025 |
| 514 | cgpGmo-S943 | CGPIA8 | 25.705 |
| 515 | cgpGmo-S1714 | CGPIA8 | 27.497 |
| 516 | cgpGmo-S891 | CGPIA8 | 29.387 |
| 517 | cgpGmo-S396 | CGPIA8 | 30.044 |
| 518 | cgpGmo-S1242 | CGPIA8 | 31.708 |
| 519 | cgpGmo-S2059 | CGPIA8 | 31.817 |
| 520 | cgpGmo-S1085b | CGPIA8 | 32.884 |
| 521 | cgpGmo-S1122 | CGPIA8 | 33.503 |
| 522 | cgpGmo-S756a | CGPIA8 | 34.303 |
| 523 | cgpGmo-S550 | CGPIA8 | 34.63 |
| 524 | cgpGmo-S509 | CGPIA8 | 35.495 |
| 525 | cgpGmo-S311b | CGPIA8 | 36.696 |
| 526 | cgpGmo-S1891 | CGPIA8 | 38.924 |
| 527 | cgpGmo-S1179 | CGPIA8 | 39.572 |
| 528 | cgpGmo-S2089 | CGPIA8 | 40.427 |
| 529 | cgpGmo-S1085a | CGPIA8 | 40.441 |
| 530 | cgpGmo-S284 | CGPIA8 | 40.441 |
| 531 | cgpGmo-S2222 | CGPIA8 | 42.779 |
| 532 | cgpGmo-S1553a | CGPIA8 | 43.633 |
| 533 | cgpGmo-S45 | CGPIA8 | 46.025 |
| 534 | cgpGmo-S751 | CGPIA8 | 47.099 |
| 535 | cgpGmo-S1370 | CGPIA8 | 47.158 |
| 536 | cgpGmo-S1708 | CGPIA8 | 48.478 |
| 537 | cgpGmo-S1276a | CGPIA8 | 49.201 |
| 538 | cgpGmo-S1748 | CGPIA8 | 49.941 |
| 539 | cgpGmo-S2054 | CGPIA8 | 50.585 |
| 540 | cgpGmo-S1779 | CGPIA8 | 50.585 |
| 541 | cgpGmo-S1713 | CGPIA8 | 51.467 |
| 542 | cgpGmo-S2104 | CGPIA8 | 51.507 |
| 543 | cgpGmo-S383 | CGPIA8 | 51.719 |
| 544 | cgpGmo-S1341 | CGPIA8 | 52.455 |
| 545 | cgpGmo-S2144 | CGPIA8 | 55.333 |
| 546 | cgpGmo-S779 | CGPIA9 | −0.005 |
| 547 | cgpGmo-S882a | CGPIA9 | 0 |
| 548 | cgpGmo-S1572 | CGPIA9 | 3.389 |
| 549 | cgpGmo-S553 | CGPIA9 | 4.01 |
| 550 | cgpGmo-S2180 | CGPIA9 | 4.366 |
| 551 | cgpGmo-S1735 | CGPIA9 | 4.537 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 552 | cgpGmo-S201 | CGPIA9 | 4.784 |
| 553 | cgpGmo-S1237 | CGPIA9 | 4.862 |
| 554 | cgpGmo-S658 | CGPIA9 | 5.99 |
| 555 | cgpGmo-S127 | CGPIA9 | 6.843 |
| 556 | cgpGmo-S998 | CGPIA9 | 7.716 |
| 557 | cgpGmo-S953 | CGPIA9 | 9.231 |
| 558 | cgpGmo-S1123 | CGPIA9 | 10.347 |
| 559 | cgpGmo-S341 | CGPIA9 | 12.632 |
| 560 | cgpGmo-S1704 | CGPIA9 | 15.357 |
| 561 | cgpGmo-S114 | CGPIA9 | 16.028 |
| 562 | cgpGmo-S259 | CGPIA9 | 16.996 |
| 563 | cgpGmo-S429 | CGPIA9 | 18.997 |
| 564 | cgpGmo-S447 | CGPIA9 | 23.648 |
| 565 | cgpGmo-S770 | CGPIA9 | 25.076 |
| 566 | cgpGmo-S1507 | CGPIA9 | 30.912 |
| 567 | cgpGmo-S30 | CGPIA9 | 32.371 |
| 568 | cgpGmo-S18 | CGPIA9 | 32.447 |
| 569 | cgpGmo-S361 | CGPIA9 | 33.337 |
| 570 | cgpGmo-S413 | CGPIA9 | 33.909 |
| 571 | cgpGmo-S1013 | CGPIA9 | 35.184 |
| 572 | cgpGmo-S1442 | CGPIA9 | 36.487 |
| 573 | cgpGmo-S572 | CGPIA9 | 36.982 |
| 574 | cgpGmo-S578 | CGPIA9 | 37.664 |
| 575 | cgpGmo-S89a | CGPIA9 | 40.149 |
| 576 | cgpGmo-S2173 | CGPIA9 | 40.304 |
| 577 | cgpGmo-S159 | CGPIA9 | 41.031 |
| 578 | cgpGmo-S1017 | CGPIA9 | 41.665 |
| 579 | cgpGmo-S1965 | CGPIA9 | 43.25 |
| 580 | cgpGmo-S1001 | CGPIA9 | 44.355 |
| 581 | cgpGmo-S682 | CGPIA9 | 44.643 |
| 582 | cgpGmo-S376 | CGPIA9 | 45.248 |
| 583 | cgpGmo-S449b | CGPIA9 | 45.601 |
| 584 | cgpGmo-S410 | CGPIA9 | 45.714 |
| 585 | cgpGmo-S544 | CGPIA9 | 46.355 |
| 586 | cgpGmo-S1031 | CGPIA9 | 46.581 |
| 587 | cgpGmo-S2016 | CGPIA9 | 46.854 |
| 588 | cgpGmo-S703 | CGPIA9 | 47.187 |
| 589 | cgpGmo-S435 | CGPIA9 | 47.49 |
| 590 | cgpGmo-S609 | CGPIA9 | 47.756 |
| 591 | cgpGmo-S309 | CGPIA9 | 49.342 |
| 592 | cgpGmo-S948 | CGPIA9 | 49.731 |
| 593 | cgpGmo-S730 | CGPIA9 | 49.962 |
| 594 | cgpGmo-S719 | CGPIA9 | 50.072 |
| 595 | cgpGmo-S1412 | CGPIA9 | 50.166 |
| 596 | cgpGmo-S1045 | CGPIA9 | 50.166 |
| 597 | cgpGmo-S1178 | CGPIA9 | 50.62 |
| 598 | cgpGmo-S1839 | CGPIA9 | 50.744 |
| 599 | cgpGmo-S874 | CGPIA9 | 52.05 |
| 600 | cgpGmo-S1377 | CGPIA9 | 52.123 |
| 601 | cgpGmo-S1092a | CGPIA9 | 53.451 |
| 602 | cgpGmo-S342 | CGPIA9 | 55.199 |
| 603 | cgpGmo-S546 | CGPIA9 | 55.295 |
| 604 | cgpGmo-S986 | CGPIA9 | 56.559 |
| 605 | cgpGmo-S1157 | CGPIA9 | 56.561 |
| 606 | cgpGmo-S1011a | CGPIA9 | 57.431 |
| 607 | cgpGmo-S1011b | CGPIA9 | 57.431 |
| 608 | cgpGmo-S1513 | CGPIA9 | 61.195 |
| 609 | cgpGmo-S746 | CGPIA9 | 63.072 |
| 610 | cgpGmo-S802 | CGPIA10 | 0 |
| 611 | cgpGmo-S1832 | CGPIA10 | 1.5 |
| 612 | cgpGmo-S115 | CGPIA10 | 2.829 |
| 613 | cgpGmo-S135 | CGPIA10 | 5.041 |
| 614 | cgpGmo-S1076a | CGPIA10 | 7.425 |
| 615 | cgpGmo-S2182 | CGPIA10 | 7.816 |
| 616 | cgpGmo-S1943 | CGPIA10 | 8.36 |
| 617 | cgpGmo-S864 | CGPIA10 | 8.477 |
| 618 | cgpGmo-S425 | CGPIA10 | 8.904 |
| 619 | cgpGmo-S1929 | CGPIA10 | 8.952 |
| 620 | cgpGmo-S1034 | CGPIA10 | 9.187 |
| 621 | cgpGmo-S516 | CGPIA10 | 9.354 |
| 622 | cgpGmo-S942 | CGPIA10 | 9.47 |
| 623 | cgpGmo-S1344 | CGPIA10 | 9.777 |
| 624 | cgpGmo-S668 | CGPIA10 | 10.113 |
| 625 | cgpGmo-S1654 | CGPIA10 | 10.179 |
| 626 | cgpGmo-S1025 | CGPIA10 | 10.336 |
| 627 | cgpGmo-S1869 | CGPIA10 | 11.874 |
| 628 | cgpGmo-S778 | CGPIA10 | 13.246 |
| 629 | cgpGmo-S2012 | CGPIA10 | 14.223 |
| 630 | cgpGmo-S37b | CGPIA10 | 16.423 |
| 631 | cgpGmo-S37a | CGPIA10 | 16.539 |
| 632 | cgpGmo-S327 | CGPIA10 | 16.744 |
| 633 | cgpGmo-S2107 | CGPIA10 | 17.336 |
| 634 | cgpGmo-S1556 | CGPIA10 | 17.362 |
| 635 | cgpGmo-S775 | CGPIA10 | 17.696 |
| 636 | cgpGmo-S479 | CGPIA10 | 17.821 |
| 637 | cgpGmo-S921 | CGPIA10 | 18.14 |
| 638 | cgpGmo-S25 | CGPIA10 | 18.485 |
| 639 | cgpGmo-S575 | CGPIA10 | 22.589 |
| 640 | cgpGmo-S448 | CGPIA10 | 23.205 |
| 641 | cgpGmo-S1273 | CGPIA10 | 23.337 |
| 642 | cgpGmo-S367 | CGPIA10 | 24.096 |
| 643 | cgpGmo-S336 | CGPIA10 | 24.31 |
| 644 | cgpGmo-S215 | CGPIA10 | 24.95 |
| 645 | cgpGmo-S1304b | CGPIA10 | 25.379 |
| 646 | cgpGmo-S1900 | CGPIA10 | 26.066 |
| 647 | cgpGmo-S1836 | CGPIA10 | 26.368 |
| 648 | cgpGmo-S313 | CGPIA10 | 26.489 |
| 649 | cgpGmo-S153a | CGPIA10 | 26.539 |
| 650 | cgpGmo-S1304a | CGPIA10 | 26.814 |
| 651 | cgpGmo-S1778 | CGPIA10 | 27.496 |
| 652 | cgpGmo-S1327a | CGPIA10 | 27.766 |
| 653 | cgpGmo-S471 | CGPIA10 | 28.152 |
| 654 | cgpGmo-S1334 | CGPIA10 | 28.175 |
| 655 | cgpGmo-S1410 | CGPIA10 | 28.763 |
| 656 | cgpGmo-S371 | CGPIA10 | 29.08 |
| 657 | cgpGmo-S49 | CGPIA10 | 30.238 |
| 658 | cgpGmo-S1490 | CGPIA10 | 30.604 |
| 659 | cgpGmo-S2153 | CGPIA10 | 30.9 |
| 660 | cgpGmo-S1098 | CGPIA10 | 31.66 |
| 661 | cgpGmo-S1866 | CGPIA10 | 32.181 |
| 662 | cgpGmo-S513 | CGPIA10 | 33.648 |
| 663 | cgpGmo-S1104 | CGPIA10 | 33.773 |
| 664 | cgpGmo-S363 | CGPIA10 | 33.773 |
| 665 | cgpGmo-S1455 | CGPIA10 | 33.773 |
| 666 | cgpGmo-S94 | CGPIA10 | 33.918 |
| 667 | cgpGmo-S1024 | CGPIA11 | 0 |
| 668 | cgpGmo-S390b | CGPIA11 | 4.557 |
| 669 | cgpGmo-S945a | CGPIA11 | 7.333 |
| 670 | cgpGmo-S245a | CGPIA11 | 8.436 |
| 671 | cgpGmo-S1009 | CGPIA11 | 8.821 |
| 672 | cgpGmo-S667 | CGPIA11 | 8.821 |
| 673 | cgpGmo-S670 | CGPIA11 | 8.983 |
| 674 | cgpGmo-S1609a | CGPIA11 | 9.87 |
| 675 | cgpGmo-S681a | CGPIA11 | 10.354 |
| 676 | cgpGmo-S245b | CGPIA11 | 10.401 |
| 677 | cgpGmo-S403 | CGPIA11 | 13.622 |
| 678 | cgpGmo-S1272 | CGPIA11 | 14.007 |
| 679 | cgpGmo-S967b | CGPIA11 | 14.008 |
| 680 | cgpGmo-S967a | CGPIA11 | 14.35 |
| 681 | cgpGmo-S1948 | CGPIA11 | 17.854 |
| 682 | cgpGmo-S1733 | CGPIA11 | 19.914 |
| 683 | cgpGmo-S455 | CGPIA11 | 22.94 |
| 684 | cgpGmo-S1484 | CGPIA11 | 26.928 |
| 685 | cgpGmo-S2232 | CGPIA11 | 29.509 |
| 686 | cgpGmo-S1548 | CGPIA11 | 32.063 |
| 687 | cgpGmo-S1541a | CGPIA11 | 32.424 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 688 | cgpGmo-S424 | CGPIA11 | 34.805 |
| 689 | cgpGmo-S618 | CGPIA11 | 35.645 |
| 690 | cgpGmo-S1802 | CGPIA11 | 35.728 |
| 691 | cgpGmo-S1925 | CGPIA11 | 36.082 |
| 692 | cgpGmo-S1222 | CGPIA11 | 39.616 |
| 693 | cgpGmo-S939 | CGPIA11 | 39.945 |
| 694 | cgpGmo-S1094 | CGPIA11 | 41.584 |
| 695 | cgpGmo-S154 | CGPIA11 | 41.584 |
| 696 | cgpGmo-S613b | CGPIA11 | 42.416 |
| 697 | cgpGmo-S691 | CGPIA11 | 43.149 |
| 698 | cgpGmo-S1063 | CGPIA11 | 43.208 |
| 699 | cgpGmo-S867 | CGPIA11 | 43.975 |
| 700 | cgpGmo-S1647 | CGPIA11 | 45.507 |
| 701 | cgpGmo-S811a | CGPIA11 | 45.925 |
| 702 | cgpGmo-S634 | CGPIA11 | 47.196 |
| 703 | cgpGmo-S1658 | CGPIA11 | 47.277 |
| 704 | cgpGmo-S4 | CGPIA11 | 47.581 |
| 705 | cgpGmo-S1108 | CGPIA11 | 48.242 |
| 706 | cgpGmo-S2179 | CGPIA11 | 50.418 |
| 707 | cgpGmo-S150 | CGPIA11 | 50.669 |
| 708 | cgpGmo-S2113 | CGPIA11 | 50.849 |
| 709 | cgpGmo-S717 | CGPIA11 | 51.155 |
| 710 | cgpGmo-S1998 | CGPIA11 | 51.75 |
| 711 | cgpGmo-S79 | CGPIA11 | 52.806 |
| 712 | cgpGmo-S1767 | CGPIA11 | 53.144 |
| 713 | cgpGmo-S1712 | CGPIA11 | 53.218 |
| 714 | cgpGmo-S1431a | CGPIA11 | 53.378 |
| 715 | cgpGmo-S2159 | CGPIA11 | 53.882 |
| 716 | cgpGmo-S788 | CGPIA11 | 54.257 |
| 717 | cgpGmo-S2017 | CGPIA11 | 54.705 |
| 718 | cgpGmo-S2211 | CGPIA11 | 54.709 |
| 719 | cgpGmo-S607 | CGPIA11 | 54.809 |
| 720 | cgpGmo-S707 | CGPIA11 | 55.13 |
| 721 | cgpGmo-S1090 | CGPIA11 | 55.193 |
| 722 | cgpGmo-S2102 | CGPIA11 | 55.357 |
| 723 | cgpGmo-S1843 | CGPIA11 | 55.756 |
| 724 | cgpGmo-S587 | CGPIA11 | 55.84 |
| 725 | cgpGmo-S386 | CGPIA11 | 56.086 |
| 726 | cgpGmo-S2005 | CGPIA11 | 56.419 |
| 727 | cgpGmo-S138 | CGPIA11 | 56.518 |
| 728 | cgpGmo-S488 | CGPIA11 | 56.917 |
| 729 | cgpGmo-S922 | CGPIA11 | 57.057 |
| 730 | cgpGmo-S44 | CGPIA11 | 57.633 |
| 731 | cgpGmo-S416b | CGPIA11 | 59.389 |
| 732 | cgpGmo-S416a | CGPIA11 | 60.308 |
| 733 | cgpGmo-S581 | CGPIA11 | 60.435 |
| 734 | cgpGmo-S580 | CGPIA11 | 60.85 |
| 735 | cgpGmo-S1384 | CGPIA11 | 67.066 |
| 736 | cgpGmo-S594 | CGPIA12 | −2.022 |
| 737 | cgpGmo-S1846 | CGPIA12 | −1.583 |
| 738 | cgpGmo-S521b | CGPIA12 | −0.385 |
| 739 | cgpGmo-S1956 | CGPIA12 | 0 |
| 740 | cgpGmo-S1995 | CGPIA12 | 1.166 |
| 741 | cgpGmo-S476 | CGPIA12 | 2.1 |
| 742 | cgpGmo-S439 | CGPIA12 | 3.326 |
| 743 | cgpGmo-S1225 | CGPIA12 | 3.842 |
| 744 | cgpGmo-S1226 | CGPIA12 | 6.532 |
| 745 | cgpGmo-S275 | CGPIA12 | 6.635 |
| 746 | cgpGmo-S936 | CGPIA12 | 7.653 |
| 747 | cgpGmo-S582 | CGPIA12 | 8.435 |
| 748 | cgpGmo-S2209 | CGPIA12 | 12.952 |
| 749 | cgpGmo-S624 | CGPIA12 | 13.754 |
| 750 | cgpGmo-S251 | CGPIA12 | 14.796 |
| 751 | cgpGmo-S248a | CGPIA12 | 15.582 |
| 752 | cgpGmo-S57 | CGPIA12 | 16.59 |
| 753 | cgpGmo-S866 | CGPIA12 | 16.674 |
| 754 | cgpGmo-S1312 | CGPIA12 | 16.674 |
| 755 | cgpGmo-S1689 | CGPIA12 | 17.322 |
| 756 | cgpGmo-S1882 | CGPIA12 | 17.322 |
| 757 | cgpGmo-S2032 | CGPIA12 | 17.327 |
| 758 | cgpGmo-S914 | CGPIA12 | 17.582 |
| 759 | cgpGmo-S596 | CGPIA12 | 17.647 |
| 760 | cgpGmo-S688 | CGPIA12 | 17.687 |
| 761 | cgpGmo-S1543 | CGPIA12 | 18.327 |
| 762 | cgpGmo-S180b | CGPIA12 | 18.327 |
| 763 | cgpGmo-S816a | CGPIA12 | 18.327 |
| 764 | cgpGmo-S372a | CGPIA12 | 18.327 |
| 765 | cgpGmo-S1260 | CGPIA12 | 18.327 |
| 766 | cgpGmo-S486 | CGPIA12 | 18.327 |
| 767 | cgpGmo-S314 | CGPIA12 | 18.496 |
| 768 | cgpGmo-S116 | CGPIA12 | 18.552 |
| 769 | cgpGmo-S417 | CGPIA12 | 18.685 |
| 770 | cgpGmo-S510 | CGPIA12 | 18.726 |
| 771 | cgpGmo-S493 | CGPIA12 | 18.952 |
| 772 | cgpGmo-S1696 | CGPIA12 | 19.081 |
| 773 | cgpGmo-S229 | CGPIA12 | 19.149 |
| 774 | cgpGmo-S1737 | CGPIA12 | 19.69 |
| 775 | cgpGmo-S636 | CGPIA12 | 19.814 |
| 776 | cgpGmo-S233 | CGPIA12 | 20.055 |
| 777 | cgpGmo-S2034 | CGPIA12 | 20.328 |
| 778 | cgpGmo-S190 | CGPIA12 | 20.489 |
| 779 | cgpGmo-S1046 | CGPIA12 | 20.994 |
| 780 | cgpGmo-S502 | CGPIA12 | 21.31 |
| 781 | cgpGmo-S256 | CGPIA12 | 22.468 |
| 782 | cgpGmo-S1769 | CGPIA12 | 22.837 |
| 783 | cgpGmo-S1193 | CGPIA12 | 23.505 |
| 784 | cgpGmo-S316 | CGPIA12 | 24.168 |
| 785 | cgpGmo-S2101 | CGPIA12 | 34.413 |
| 786 | cgpGmo-S742a | CGPIA12 | 41.271 |
| 787 | cgpGmo-S348 | CGPIA13 | −8.884 |
| 788 | cgpGmo-S1653 | CGPIA13 | −4.445 |
| 789 | cgpGmo-S2177 | CGPIA13 | −0.97 |
| 790 | cgpGmo-S1695 | CGPIA13 | 0 |
| 791 | cgpGmo-S191 | CGPIA13 | 0.304 |
| 792 | cgpGmo-S294 | CGPIA13 | 1.45 |
| 793 | cgpGmo-S1483 | CGPIA13 | 1.697 |
| 794 | cgpGmo-S1206 | CGPIA13 | 2.255 |
| 795 | cgpGmo-S2215 | CGPIA13 | 2.578 |
| 796 | cgpGmo-S820 | CGPIA13 | 3.022 |
| 797 | cgpGmo-S652 | CGPIA13 | 3.351 |
| 798 | cgpGmo-S692a | CGPIA13 | 3.832 |
| 799 | cgpGmo-S2067 | CGPIA13 | 4.113 |
| 800 | cgpGmo-S576 | CGPIA13 | 4.62 |
| 801 | cgpGmo-S2262 | CGPIA13 | 5.769 |
| 802 | cgpGmo-S949a | CGPIA13 | 9.341 |
| 803 | cgpGmo-S1097 | CGPIA13 | 15.857 |
| 804 | cgpGmo-S980 | CGPIA13 | 18.498 |
| 805 | cgpGmo-S1069 | CGPIA13 | 18.498 |
| 806 | cgpGmo-S1889 | CGPIA13 | 18.778 |
| 807 | cgpGmo-S281 | CGPIA13 | 23.265 |
| 808 | cgpGmo-S1961 | CGPIA13 | 25.95 |
| 809 | cgpGmo-S752b | CGPIA13 | 25.968 |
| 810 | cgpGmo-S1390a | CGPIA13 | 26.716 |
| 811 | cgpGmo-S752a | CGPIA13 | 29.901 |
| 812 | cgpGmo-S399 | CGPIA13 | 33.224 |
| 813 | cgpGmo-S1990 | CGPIA13 | 33.832 |
| 814 | cgpGmo-S29 | CGPIA13 | 35.922 |
| 815 | cgpGmo-S36a | CGPIA13 | 36.561 |
| 816 | cgpGmo-S36b | CGPIA13 | 36.575 |
| 817 | cgpGmo-S906 | CGPIA13 | 37.213 |
| 818 | cgpGmo-S2013 | CGPIA13 | 37.513 |
| 819 | cgpGmo-S2018 | CGPIA13 | 37.599 |
| 820 | cgpGmo-S350 | CGPIA13 | 39.978 |
| 821 | cgpGmo-S1981 | CGPIA13 | 40.993 |
| 822 | cgpGmo-S1563 | CGPIA13 | 41.908 |
| 823 | cgpGmo-S1959 | CGPIA13 | 42.508 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 824 | cgpGmo-S487 | CGPIA13 | 42.546 |
| 825 | cgpGmo-S1209 | CGPIA13 | 43.105 |
| 826 | cgpGmo-S614b | CGPIA13 | 43.37 |
| 827 | cgpGmo-S2281 | CGPIA13 | 43.541 |
| 828 | cgpGmo-S765 | CGPIA13 | 43.727 |
| 829 | cgpGmo-S1762 | CGPIA13 | 43.735 |
| 830 | cgpGmo-S881 | CGPIA13 | 43.897 |
| 831 | cgpGmo-S1639 | CGPIA13 | 44.062 |
| 832 | cgpGmo-S905 | CGPIA13 | 44.062 |
| 833 | cgpGmo-S614a | CGPIA13 | 44.46 |
| 834 | cgpGmo-S793a | CGPIA13 | 44.905 |
| 835 | cgpGmo-S2160 | CGPIA13 | 44.913 |
| 836 | cgpGmo-S2039 | CGPIA13 | 45.393 |
| 837 | cgpGmo-S220 | CGPIA13 | 45.687 |
| 838 | cgpGmo-S2028 | CGPIA13 | 45.731 |
| 839 | cgpGmo-S107 | CGPIA13 | 45.76 |
| 840 | cgpGmo-S241 | CGPIA13 | 47.516 |
| 841 | cgpGmo-S1720 | CGPIA13 | 49.028 |
| 842 | cgpGmo-S888 | CGPIA13 | 49.39 |
| 843 | cgpGmo-S217a | CGPIA13 | 52.994 |
| 844 | cgpGmo-S1977 | CGPIA13 | 53.859 |
| 845 | cgpGmo-S1219c | CGPIA14 | 0 |
| 846 | cgpGmo-S1219b | CGPIA14 | 0.025 |
| 847 | cgpGmo-S1219a | CGPIA14 | 0.025 |
| 848 | cgpGmo-S1665 | CGPIA14 | 1.25 |
| 849 | cgpGmo-S1530 | CGPIA14 | 3.15 |
| 850 | cgpGmo-S1725 | CGPIA14 | 7.134 |
| 851 | cgpGmo-S505 | CGPIA14 | 7.783 |
| 852 | cgpGmo-S1760 | CGPIA14 | 8.372 |
| 853 | cgpGmo-S1844 | CGPIA14 | 8.778 |
| 854 | cgpGmo-S252 | CGPIA14 | 9.333 |
| 855 | cgpGmo-S988 | CGPIA14 | 11.355 |
| 856 | cgpGmo-S2110 | CGPIA14 | 12.673 |
| 857 | cgpGmo-S963 | CGPIA14 | 12.822 |
| 858 | cgpGmo-S631 | CGPIA14 | 13.242 |
| 859 | cgpGmo-S577 | CGPIA14 | 13.376 |
| 860 | cgpGmo-S841 | CGPIA14 | 13.87 |
| 861 | cgpGmo-S796 | CGPIA14 | 14.022 |
| 862 | cgpGmo-S1922 | CGPIA14 | 14.09 |
| 863 | cgpGmo-S1697 | CGPIA14 | 14.197 |
| 864 | cgpGmo-S462 | CGPIA14 | 19.181 |
| 865 | cgpGmo-S427 | CGPIA14 | 19.551 |
| 866 | cgpGmo-S617 | CGPIA14 | 21.131 |
| 867 | cgpGmo-S1467 | CGPIA14 | 21.42 |
| 868 | cgpGmo-S1466b | CGPIA14 | 21.627 |
| 869 | cgpGmo-S1466a | CGPIA14 | 21.627 |
| 870 | cgpGmo-S1803 | CGPIA14 | 24.353 |
| 871 | cgpGmo-S932b | CGPIA14 | 24.805 |
| 872 | cgpGmo-S1914 | CGPIA14 | 25.094 |
| 873 | cgpGmo-S1049 | CGPIA14 | 29.476 |
| 874 | cgpGmo-S1792 | CGPIA14 | 30.507 |
| 875 | cgpGmo-S1701 | CGPIA14 | 30.96 |
| 876 | Aroma_2_1 | CGPIA14 | 32.373 |
| 877 | Aroma_1_1 | CGPIA14 | 32.388 |
| 878 | cgpGmo-S1234 | CGPIA14 | 33.594 |
| 879 | cgpGmo-S302 | CGPIA14 | 33.872 |
| 880 | Aroma_1_9 | CGPIA14 | 34.006 |
| 881 | cgpGmo-S240 | CGPIA14 | 34.123 |
| 882 | cgpGmo-S1821 | CGPIA14 | 34.921 |
| 883 | cgpGmo-S1888 | CGPIA14 | 35.323 |
| 884 | cgpGmo-S1988 | CGPIA14 | 36.018 |
| 885 | cgpGmo-S520 | CGPIA14 | 36.056 |
| 886 | cgpGmo-S1424b | CGPIA14 | 36.474 |
| 887 | cgpGmo-S1968 | CGPIA14 | 36.573 |
| 888 | cgpGmo-S411 | CGPIA14 | 36.8 |
| 889 | cgpGmo-S2078 | CGPIA14 | 36.922 |
| 890 | cgpGmo-S70 | CGPIA14 | 37.423 |
| 891 | cgpGmo-S827 | CGPIA14 | 37.903 |
| 892 | cgpGmo-S1080 | CGPIA14 | 39.732 |
| 893 | cgpGmo-S226 | CGPIA14 | 39.967 |
| 894 | cgpGmo-S1394a | CGPIA14 | 42.56 |
| 895 | cgpGmo-S1280 | CGPIA14 | 43.692 |
| 896 | 1057C1CO1.398 | CGPIA14 | 44.092 |
| 897 | cgpGmo-S1186 | CGPIA14 | 44.159 |
| 898 | cgpGmo-S965 | CGPIA14 | 44.317 |
| 899 | cgpGmo-S824 | CGPIA14 | 52.754 |
| 900 | cgpGmo-S142 | CGPIA14 | 53.824 |
| 901 | cgpGmo-S711b | CGPIA14 | 54.095 |
| 902 | cgpGmo-S503 | CGPIA14 | 55.34 |
| 903 | cgpGmo-S249 | CGPIA14 | 61.013 |
| 904 | cgpGmo-S583 | CGPIA14 | 62.095 |
| 905 | cgpGmo-S551 | CGPIA14 | 63.269 |
| 906 | cgpGmo-S1783 | CGPIA14 | 63.361 |
| 907 | FshB_1_1 | CGPIA14 | 67.201 |
| 908 | cgpGmo-S92 | CGPIA15 | 0 |
| 909 | HSD_2_1 | CGPIA15 | 10.41 |
| 910 | cgpGmo-S1048 | CGPIA15 | 15.284 |
| 911 | cgpGmo-S1752 | CGPIA15 | 20.943 |
| 912 | cgpGmo-S1905 | CGPIA15 | 21.78 |
| 913 | cgpGmo-S2093 | CGPIA15 | 24.461 |
| 914 | cgpGmo-S1770 | CGPIA15 | 24.461 |
| 915 | cgpGmo-S677 | CGPIA15 | 27.108 |
| 916 | cgpGmo-S676 | CGPIA15 | 28.475 |
| 917 | cgpGmo-S608 | CGPIA15 | 28.788 |
| 918 | cgpGmo-S1621 | CGPIA15 | 29.322 |
| 919 | cgpGmo-S298 | CGPIA15 | 29.717 |
| 920 | cgpGmo-S591 | CGPIA15 | 32.334 |
| 921 | cgpGmo-S1781 | CGPIA15 | 33.806 |
| 922 | cgpGmo-S1728 | CGPIA15 | 35.152 |
| 923 | cgpGmo-S1577 | CGPIA15 | 36.43 |
| 924 | cgpGmo-S1899 | CGPIA15 | 37.159 |
| 925 | cgpGmo-S629 | CGPIA15 | 37.173 |
| 926 | cgpGmo-S1896 | CGPIA15 | 38.025 |
| 927 | cgpGmo-S1773 | CGPIA15 | 39.18 |
| 928 | cgpGmo-S1784 | CGPIA15 | 39.771 |
| 929 | cgpGmo-S909 | CGPIA15 | 42.239 |
| 930 | cgpGmo-S238 | CGPIA15 | 42.397 |
| 931 | cgpGmo-S1920 | CGPIA15 | 42.535 |
| 932 | cgpGmo-S1707 | CGPIA15 | 43.61 |
| 933 | cgpGmo-S296 | CGPIA15 | 45.183 |
| 934 | cgpGmo-S1201 | CGPIA15 | 45.228 |
| 935 | cgpGmo-S2142 | CGPIA15 | 46.618 |
| 936 | cgpGmo-S2178 | CGPIA15 | 47.391 |
| 937 | cgpGmo-S687 | CGPIA15 | 48.153 |
| 938 | cgpGmo-S1755 | CGPIA15 | 48.215 |
| 939 | cgpGmo-S1077b | CGPIA15 | 48.647 |
| 940 | cgpGmo-S1650 | CGPIA15 | 49.878 |
| 941 | cgpGmo-S726 | CGPIA15 | 51.839 |
| 942 | cgpGmo-S46a | CGPIA15 | 58.665 |
| 943 | cgpGmo-S1082 | CGPIA15 | 60.22 |
| 944 | cgpGmo-S696 | CGPIA15 | 62.392 |
| 945 | cgpGmo-S602 | CGPIA15 | 63.507 |
| 946 | cgpGmo-S1057a | CGPIA15 | 63.863 |
| 947 | cgpGmo-S1938 | CGPIA15 | 64.068 |
| 948 | cgpGmo-S1035 | CGPIA15 | 64.599 |
| 949 | cgpGmo-S542 | CGPIA15 | 65.308 |
| 950 | cgpGmo-S1649 | CGPIA15 | 67.501 |
| 951 | cgpGmo-S46b | CGPIA15 | 71.949 |
| 952 | cgpGmo-S972 | CGPIA16 | 0 |
| 953 | cgpGmo-S2166 | CGPIA16 | 0.303 |
| 954 | cgpGmo-S1350 | CGPIA16 | 2.678 |
| 955 | cgpGmo-S2085 | CGPIA16 | 4.777 |
| 956 | cgpGmo-S111b | CGPIA16 | 6.3 |
| 957 | cgpGmo-S111a | CGPIA16 | 6.3 |
| 958 | cgpGmo-S464 | CGPIA16 | 6.329 |
| 959 | cgpGmo-S2224 | CGPIA16 | 10.638 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 960 | cgpGmo-S109 | CGPIA16 | 11.333 |
| 961 | cgpGmo-S1339 | CGPIA16 | 11.622 |
| 962 | cgpGmo-S1032 | CGPIA16 | 13.163 |
| 963 | cgpGmo-S195 | CGPIA16 | 18.386 |
| 964 | SL_2_1 | CGPIA16 | 20.41 |
| 965 | cgpGmo-S2287 | CGPIA16 | 22.321 |
| 966 | cgpGmo-S1797 | CGPIA16 | 22.831 |
| 967 | cgpGmo-S497 | CGPIA16 | 23.681 |
| 968 | cgpGmo-S1761 | CGPIA16 | 26.779 |
| 969 | cgpGmo-S1941 | CGPIA16 | 27.456 |
| 970 | cgpGmo-S1608 | CGPIA16 | 28.367 |
| 971 | cgpGmo-S113 | CGPIA16 | 30.156 |
| 972 | cgpGmo-S2126 | CGPIA16 | 32.081 |
| 973 | cgpGmo-S533b | CGPIA16 | 32.095 |
| 974 | cgpGmo-S1664 | CGPIA16 | 32.309 |
| 975 | cgpGmo-S1347 | CGPIA16 | 32.418 |
| 976 | cgpGmo-S1281 | CGPIA16 | 32.488 |
| 977 | cgpGmo-S842 | CGPIA16 | 32.488 |
| 978 | cgpGmo-S1188 | CGPIA16 | 32.637 |
| 979 | cgpGmo-S944 | CGPIA16 | 33.803 |
| 980 | cgpGmo-S2106 | CGPIA16 | 34.909 |
| 981 | cgpGmo-S1243b | CGPIA16 | 36.685 |
| 982 | cgpGmo-S600 | CGPIA16 | 36.685 |
| 983 | cgpGmo-S1243a | CGPIA16 | 36.685 |
| 984 | cgpGmo-S213 | CGPIA16 | 39.835 |
| 985 | cgpGmo-S1947 | CGPIA16 | 42.392 |
| 986 | cgpGmo-S1140 | CGPIA16 | 42.479 |
| 987 | cgpGmo-S392 | CGPIA16 | 43.582 |
| 988 | cgpGmo-S2174 | CGPIA16 | 44.961 |
| 989 | cgpGmo-S508 | CGPIA16 | 44.962 |
| 990 | cgpGmo-S504 | CGPIA16 | 44.964 |
| 991 | cgpGmo-S515 | CGPIA16 | 45.708 |
| 992 | cgpGmo-S1042a | CGPIA16 | 47.38 |
| 993 | cgpGmo-S1290 | CGPIA16 | 48.108 |
| 994 | cgpGmo-S401 | CGPIA16 | 48.548 |
| 995 | cgpGmo-S1042b | CGPIA16 | 48.667 |
| 996 | cgpGmo-S415 | CGPIA16 | 48.715 |
| 997 | cgpGmo-S287a | CGPIA16 | 49.034 |
| 998 | cgpGmo-S1073 | CGPIA16 | 49.051 |
| 999 | cgpGmo-S627 | CGPIA16 | 49.394 |
| 1000 | cgpGmo-S2164 | CGPIA16 | 50.165 |
| 1001 | cgpGmo-S287b | CGPIA16 | 50.901 |
| 1002 | cgpGmo-S2263 | CGPIA16 | 51.414 |
| 1003 | cgpGmo-S2138 | CGPIA16 | 53.067 |
| 1004 | cgpGmo-S1457 | CGPIA16 | 53.208 |
| 1005 | cgpGmo-S463b | CGPIA16 | 54.433 |
| 1006 | cgpGmo-S300 | CGPIA16 | 56.582 |
| 1007 | cgpGmo-S437 | CGPIA16 | 64.659 |
| 1008 | cgpGmo-S1265b | CGPIA17 | 0 |
| 1009 | cgpGmo-S561 | CGPIA17 | 1.627 |
| 1010 | cgpGmo-S1172 | CGPIA17 | 1.779 |
| 1011 | cgpGmo-S777 | CGPIA17 | 3.72 |
| 1012 | cgpGmo-S285 | CGPIA17 | 3.998 |
| 1013 | cgpGmo-S1617 | CGPIA17 | 4.221 |
| 1014 | cgpGmo-S1265c | CGPIA17 | 5.986 |
| 1015 | cgpGmo-S104 | CGPIA17 | 6.382 |
| 1016 | cgpGmo-S904 | CGPIA17 | 8.895 |
| 1017 | cgpGmo-S276b | CGPIA17 | 11.798 |
| 1018 | cgpGmo-S2220 | CGPIA17 | 13.247 |
| 1019 | cgpGmo-S541b | CGPIA17 | 13.71 |
| 1020 | cgpGmo-S541a | CGPIA17 | 14.938 |
| 1021 | cgpGmo-S727 | CGPIA17 | 15.001 |
| 1022 | cgpGmo-S2184 | CGPIA17 | 17.777 |
| 1023 | cgpGmo-S879 | CGPIA17 | 18.331 |
| 1024 | cgpGmo-S2169 | CGPIA17 | 19.486 |
| 1025 | cgpGmo-S1974 | CGPIA17 | 20.882 |
| 1026 | cgpGmo-S566 | CGPIA17 | 20.941 |
| 1027 | cgpGmo-S565 | CGPIA17 | 20.995 |
| 1028 | cgpGmo-S1006 | CGPIA17 | 24.562 |
| 1029 | cgpGmo-S1041 | CGPIA17 | 27.147 |
| 1030 | cgpGmo-S878 | CGPIA17 | 28.572 |
| 1031 | cgpGmo-S1780 | CGPIA17 | 37.043 |
| 1032 | cgpGmo-S2212 | CGPIA17 | 37.354 |
| 1033 | cgpGmo-S1056 | CGPIA17 | 37.727 |
| 1034 | cgpGmo-S1655 | CGPIA17 | 38.284 |
| 1035 | cgpGmo-S1738 | CGPIA17 | 38.959 |
| 1036 | cgpGmo-S955 | CGPIA17 | 38.969 |
| 1037 | cgpGmo-S381 | CGPIA17 | 43.977 |
| 1038 | 334C1CO1.411 | CGPIA17 | 46.969 |
| 1039 | cgpGmo-S1864 | CGPIA17 | 46.969 |
| 1040 | cgpGmo-S616 | CGPIA17 | 48.124 |
| 1041 | cgpGmo-S650b | CGPIA17 | 56.539 |
| 1042 | cgpGmo-S2041 | CGPIA18 | 0 |
| 1043 | cgpGmo-S9b | CGPIA18 | 0.875 |
| 1044 | cgpGmo-S2162 | CGPIA18 | 1.044 |
| 1045 | cgpGmo-S813 | CGPIA18 | 1.573 |
| 1046 | cgpGmo-S1474 | CGPIA18 | 2.2 |
| 1047 | cgpGmo-S1323 | CGPIA18 | 2.222 |
| 1048 | cgpGmo-S2139 | CGPIA18 | 3.65 |
| 1049 | cgpGmo-S1294 | CGPIA18 | 5.795 |
| 1050 | cgpGmo-S2175 | CGPIA18 | 11.354 |
| 1051 | cgpGmo-S84 | CGPIA18 | 13.122 |
| 1052 | cgpGmo-S958 | CGPIA18 | 13.909 |
| 1053 | cgpGmo-S706 | CGPIA18 | 14.289 |
| 1054 | cgpGmo-S1774 | CGPIA18 | 15.899 |
| 1055 | cgpGmo-S861 | CGPIA18 | 16.776 |
| 1056 | cgpGmo-S2259 | CGPIA18 | 19.295 |
| 1057 | cgpGmo-S2027 | CGPIA18 | 20.186 |
| 1058 | cgpGmo-S1300a | CGPIA18 | 21.768 |
| 1059 | cgpGmo-S197a | CGPIA18 | 25.357 |
| 1060 | cgpGmo-S601 | CGPIA18 | 26.346 |
| 1061 | cgpGmo-S2077 | CGPIA18 | 27.663 |
| 1062 | cgpGmo-S1441 | CGPIA18 | 29.273 |
| 1063 | cgpGmo-S331b | CGPIA18 | 29.676 |
| 1064 | cgpGmo-S1055a | CGPIA18 | 31.219 |
| 1065 | cgpGmo-S1918 | CGPIA18 | 31.219 |
| 1066 | cgpGmo-S1435 | CGPIA18 | 31.27 |
| 1067 | cgpGmo-S330 | CGPIA18 | 31.776 |
| 1068 | cgpGmo-S1115 | CGPIA18 | 32.176 |
| 1069 | cgpGmo-S1117 | CGPIA18 | 32.336 |
| 1070 | cgpGmo-S1710 | CGPIA18 | 32.464 |
| 1071 | cgpGmo-S442a | CGPIA18 | 32.467 |
| 1072 | cgpGmo-S1095 | CGPIA18 | 33.189 |
| 1073 | cgpGmo-S1379 | CGPIA18 | 34.778 |
| 1074 | cgpGmo-S391 | CGPIA18 | 35.855 |
| 1075 | cgpGmo-S1340 | CGPIA18 | 38.158 |
| 1076 | cgpGmo-S1992 | CGPIA18 | 39.202 |
| 1077 | cgpGmo-S916 | CGPIA18 | 39.529 |
| 1078 | cgpGmo-S97 | CGPIA18 | 40.002 |
| 1079 | cgpGmo-S684 | CGPIA18 | 40.123 |
| 1080 | cgpGmo-S1818 | CGPIA18 | 42.196 |
| 1081 | cgpGmo-S1520 | CGPIA18 | 42.201 |
| 1082 | cgpGmo-S900 | CGPIA18 | 44.65 |
| 1083 | cgpGmo-S975b | CGPIA18 | 46.292 |
| 1084 | cgpGmo-S975a | CGPIA18 | 48.44 |
| 1085 | cgpGmo-S1083 | CGPIA18 | 49.174 |
| 1086 | cgpGmo-S2187 | CGPIA19 | 0 |
| 1087 | cgpGmo-S557 | CGPIA19 | 0.053 |
| 1088 | cgpGmo-S108 | CGPIA19 | 1.707 |
| 1089 | cgpGmo-S1408 | CGPIA19 | 5.157 |
| 1090 | cgpGmo-S1834 | CGPIA19 | 11.603 |
| 1091 | cgpGmo-S247 | CGPIA19 | 13.05 |
| 1092 | cgpGmo-S1837 | CGPIA19 | 15.633 |
| 1093 | cgpGmo-S918 | CGPIA19 | 16.422 |
| 1094 | cgpGmo-S1740 | CGPIA19 | 17.604 |
| 1095 | cgpGmo-S649a | CGPIA19 | 21.388 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 1096 | cgpGmo-S665 | CGPIA19 | 23.427 |
| 1097 | cgpGmo-S495 | CGPIA19 | 24.147 |
| 1098 | cgpGmo-S649b | CGPIA19 | 26.271 |
| 1099 | cgpGmo-S621 | CGPIA19 | 28.113 |
| 1100 | cgpGmo-S2120 | CGPIA19 | 29.31 |
| 1101 | cgpGmo-S1385a | CGPIA19 | 29.483 |
| 1102 | cgpGmo-S1385b | CGPIA19 | 29.793 |
| 1103 | cgpGmo-S586 | CGPIA19 | 34.172 |
| 1104 | cgpGmo-S1944 | CGPIA19 | 35.093 |
| 1105 | cgpGmo-S1105 | CGPIA19 | 35.205 |
| 1106 | cgpGmo-S374 | CGPIA19 | 37.04 |
| 1107 | cgpGmo-S328 | CGPIA19 | 38.165 |
| 1108 | cgpGmo-S329 | CGPIA19 | 38.165 |
| 1109 | cgpGmo-S911 | CGPIA19 | 39.153 |
| 1110 | cgpGmo-S2143 | CGPIA19 | 39.59 |
| 1111 | cgpGmo-S633 | CGPIA19 | 41.345 |
| 1112 | cgpGmo-S1005 | CGPIA19 | 41.366 |
| 1113 | cgpGmo-S436 | CGPIA19 | 41.98 |
| 1114 | cgpGmo-S1528a | CGPIA19 | 43.698 |
| 1115 | cgpGmo-S642 | CGPIA19 | 44.72 |
| 1116 | cgpGmo-S1489 | CGPIA19 | 44.72 |
| 1117 | cgpGmo-S443 | CGPIA19 | 45.652 |
| 1118 | cgpGmo-S1775 | CGPIA19 | 48.839 |
| 1119 | cgpGmo-S366 | CGPIA19 | 50.409 |
| 1120 | cgpGmo-S271 | CGPIA19 | 50.773 |
| 1121 | cgpGmo-S767 | CGPIA19 | 54.661 |
| 1122 | cgpGmo-S2130 | CGPIA19 | 54.96 |
| 1123 | cgpGmo-S297 | CGPIA19 | 55.085 |
| 1124 | cgpGmo-S1461a | CGPIA19 | 56.108 |
| 1125 | cgpGmo-S1014b | CGPIA19 | 56.211 |
| 1126 | cgpGmo-S193 | CGPIA19 | 56.329 |
| 1127 | cgpGmo-S1700 | CGPIA19 | 56.378 |
| 1128 | cgpGmo-S1028 | CGPIA19 | 56.652 |
| 1129 | cgpGmo-S124 | CGPIA19 | 56.723 |
| 1130 | cgpGmo-S1461b | CGPIA19 | 57.424 |
| 1131 | cgpGmo-S2161 | CGPIA20 | 0 |
| 1132 | cgpGmo-S995b | CGPIA20 | 1.045 |
| 1133 | cgpGmo-S1204 | CGPIA20 | 2.274 |
| 1134 | cgpGmo-S2114 | CGPIA20 | 2.274 |
| 1135 | cgpGmo-S1297a | CGPIA20 | 6.04 |
| 1136 | cgpGmo-S1348 | CGPIA20 | 6.231 |
| 1137 | cgpGmo-S2269 | CGPIA20 | 6.634 |
| 1138 | cgpGmo-S854b | CGPIA20 | 6.724 |
| 1139 | cgpGmo-S501 | CGPIA20 | 8.184 |
| 1140 | cgpGmo-S559 | CGPIA20 | 9.114 |
| 1141 | cgpGmo-S149 | CGPIA20 | 9.796 |
| 1142 | cgpGmo-S995a | CGPIA20 | 9.958 |
| 1143 | cgpGmo-S1423a | CGPIA20 | 11.497 |
| 1144 | cgpGmo-S1392 | CGPIA20 | 13.154 |
| 1145 | cgpGmo-S661b | CGPIA20 | 14.136 |
| 1146 | cgpGmo-S661a | CGPIA20 | 14.136 |
| 1147 | cgpGmo-S1742 | CGPIA20 | 14.162 |
| 1148 | cgpGmo-S1667 | CGPIA20 | 14.671 |
| 1149 | cgpGmo-S1857 | CGPIA20 | 15.955 |
| 1150 | cgpGmo-S599 | CGPIA20 | 16.217 |
| 1151 | cgpGmo-S632a | CGPIA20 | 17.033 |
| 1152 | cgpGmo-S1945 | CGPIA20 | 17.062 |
| 1153 | cgpGmo-S632b | CGPIA20 | 17.168 |
| 1154 | cgpGmo-S693 | CGPIA20 | 17.353 |
| 1155 | cgpGmo-S1391 | CGPIA20 | 19.17 |
| 1156 | cgpGmo-S637 | CGPIA20 | 21.711 |
| 1157 | cgpGmo-S1454 | CGPIA20 | 27.868 |
| 1158 | cgpGmo-S1184 | CGPIA20 | 32.098 |
| 1159 | cgpGmo-S357 | CGPIA20 | 33.925 |
| 1160 | cgpGmo-S1362 | CGPIA20 | 33.98 |
| 1161 | cgpGmo-S695 | CGPIA20 | 34.521 |
| 1162 | cgpGmo-S143 | CGPIA20 | 34.566 |
| 1163 | cgpGmo-S635 | CGPIA20 | 36.107 |
| 1164 | cgpGmo-S1503 | CGPIA20 | 36.639 |
| 1165 | cgpGmo-S196 | CGPIA20 | 38.981 |
| 1166 | cgpGmo-S525 | CGPIA20 | 41.002 |
| 1167 | cgpGmo-S2201 | CGPIA20 | 41.03 |
| 1168 | cgpGmo-S431 | CGPIA20 | 41.104 |
| 1169 | cgpGmo-S1401 | CGPIA20 | 49.716 |
| 1170 | cgpGmo-S1482 | CGPIA20 | 51.903 |
| 1171 | cgpGmo-S218 | CGPIA20 | 51.933 |
| 1172 | cgpGmo-S2198 | CGPIA20 | 54.177 |
| 1173 | cgpGmo-S1807 | CGPIA20 | 55.581 |
| 1174 | cgpGmo-S1093 | CGPIA21 | 0 |
| 1175 | cgpGmo-S1573 | CGPIA21 | 0.934 |
| 1176 | cgpGmo-S772 | CGPIA21 | 1.23 |
| 1177 | cgpGmo-S1794 | CGPIA21 | 1.779 |
| 1178 | cgpGmo-S225a | CGPIA21 | 2.934 |
| 1179 | cgpGmo-S2283 | CGPIA21 | 3.655 |
| 1180 | cgpGmo-S315 | CGPIA21 | 3.993 |
| 1181 | cgpGmo-S1706 | CGPIA21 | 6.054 |
| 1182 | cgpGmo-S130 | CGPIA21 | 6.247 |
| 1183 | cgpGmo-S225b | CGPIA21 | 6.392 |
| 1184 | cgpGmo-S1084 | CGPIA21 | 6.417 |
| 1185 | cgpGmo-S794 | CGPIA21 | 7.995 |
| 1186 | cgpGmo-S1316 | CGPIA21 | 8.771 |
| 1187 | cgpGmo-S925 | CGPIA21 | 9.125 |
| 1188 | cgpGmo-S2097 | CGPIA21 | 9.261 |
| 1189 | cgpGmo-S2171 | CGPIA21 | 10.156 |
| 1190 | cgpGmo-S858 | CGPIA21 | 11.297 |
| 1191 | cgpGmo-S698 | CGPIA21 | 11.433 |
| 1192 | cgpGmo-S1741 | CGPIA21 | 12.138 |
| 1193 | cgpGmo-S91 | CGPIA21 | 12.756 |
| 1194 | cgpGmo-S853 | CGPIA21 | 14.259 |
| 1195 | Hsp90 | CGPIA21 | 15.65 |
| 1196 | cgpGmo-S2055 | CGPIA21 | 16.574 |
| 1197 | cgpGmo-S1465 | CGPIA21 | 18.629 |
| 1198 | cgpGmo-S1646 | CGPIA21 | 19.653 |
| 1199 | cgpGmo-S954 | CGPIA21 | 20.57 |
| 1200 | cgpGmo-S120 | CGPIA21 | 20.958 |
| 1201 | cgpGmo-S1255b | CGPIA21 | 22.052 |
| 1202 | cgpGmo-S1926 | CGPIA21 | 22.525 |
| 1203 | cgpGmo-S947 | CGPIA21 | 22.69 |
| 1204 | cgpGmo-S1255a | CGPIA21 | 22.967 |
| 1205 | cgpGmo-S1972 | CGPIA21 | 24.019 |
| 1206 | cgpGmo-S224 | CGPIA21 | 24.079 |
| 1207 | cgpGmo-S1342 | CGPIA21 | 24.219 |
| 1208 | cgpGmo-S697 | CGPIA21 | 25.675 |
| 1209 | cgpGmo-S907 | CGPIA21 | 26.917 |
| 1210 | cgpGmo-S675a | CGPIA21 | 28.335 |
| 1211 | cgpGmo-S2063 | CGPIA21 | 31.746 |
| 1212 | cgpGmo-S423 | CGPIA21 | 32.505 |
| 1213 | cgpGmo-S459 | CGPIA21 | 41.011 |
| 1214 | cgpGmo-S808 | CGPIA21 | 41.279 |
| 1215 | cgpGmo-S579 | CGPIA21 | 41.493 |
| 1216 | cgpGmo-S1702 | CGPIA21 | 41.539 |
| 1217 | cgpGmo-S549 | CGPIA21 | 42.157 |
| 1218 | cgpGmo-S1003 | CGPIA21 | 44.071 |
| 1219 | cgpGmo-S679 | CGPIA21 | 45.185 |
| 1220 | cgpGmo-S2183 | CGPIA22 | 0 |
| 1221 | cgpGmo-S740 | CGPIA22 | 0.894 |
| 1222 | cgpGmo-S1705 | CGPIA22 | 2.974 |
| 1223 | cgpGmo-S1552b | CGPIA22 | 4.344 |
| 1224 | cgpGmo-S1552a | CGPIA22 | 4.379 |
| 1225 | cgpGmo-S1799 | CGPIA22 | 4.807 |
| 1226 | cgpGmo-S1919 | CGPIA22 | 4.866 |
| 1227 | cgpGmo-S1852 | CGPIA22 | 7.229 |
| 1228 | cgpGmo-S20 | CGPIA22 | 7.87 |
| 1229 | cgpGmo-S2121 | CGPIA22 | 8.356 |
| 1230 | cgpGmo-S1691 | CGPIA22 | 9.014 |
| 1231 | cgpGmo-S1417 | CGPIA22 | 13.602 |

TABLE 10-continued

SNP Linkage Map Linkage groups for second generation genetic linkage map to be used for QTL analysis. This map contains all the markers that it has been possible to place on the map, has been generated using three families, B30, B33 and B87, and JoinMap ® 4 has been allowed to force the maximum number of markers into each linkage group. Markers with the prefix cgpGmo have been developed by the CGP and are novel; markers with alternative nomenclature have been provided by other groups, or have been published previously (e.g. 2311C1CO1.535).

| Nr | Locus | Group | Position |
|---|---|---|---|
| 1232 | cgpGmo-S997b | CGPIA22 | 13.917 |
| 1233 | cgpGmo-S206 | CGPIA22 | 15.369 |
| 1234 | cgpGmo-S1909 | CGPIA22 | 15.853 |
| 1235 | cgpGmo-S382 | CGPIA22 | 17.351 |
| 1236 | cgpGmo-S2125 | CGPIA22 | 17.566 |
| 1237 | cgpGmo-S1335 | CGPIA22 | 18.541 |
| 1238 | cgpGmo-S2105 | CGPIA22 | 18.672 |
| 1239 | cgpGmo-S1106 | CGPIA22 | 18.966 |
| 1240 | cgpGmo-S1643 | CGPIA22 | 22.843 |
| 1241 | cgpGmo-S13b | CGPIA22 | 23.068 |
| 1242 | cgpGmo-S996 | CGPIA22 | 23.939 |
| 1243 | 155C1CO1.193 | CGPIA22 | 24.01 |
| 1244 | cgpGmo-S2242 | CGPIA22 | 25.091 |
| 1245 | cgpGmo-S1904 | CGPIA22 | 25.305 |
| 1246 | cgpGmo-S1578 | CGPIA22 | 25.305 |
| 1247 | cgpGmo-S258 | CGPIA22 | 26.054 |
| 1248 | cgpGmo-S1659 | CGPIA22 | 27.523 |
| 1249 | cgpGmo-S2288 | CGPIA22 | 33.444 |
| 1250 | cgpGmo-S2186 | CGPIA22 | 34.653 |
| 1251 | cgpGmo-S2108 | CGPIA22 | 34.909 |
| 1252 | cgpGmo-S822a | CGPIA22 | 36.419 |
| 1253 | cgpGmo-S1382 | CGPIA22 | 36.896 |
| 1254 | cgpGmo-S1308 | CGPIA22 | 37.333 |
| 1255 | cgpGmo-S263 | CGPIA22 | 37.333 |
| 1256 | cgpGmo-S1957 | CGPIA22 | 38.172 |
| 1257 | 5681C1CO1.227 | CGPIA22 | 39.997 |
| 1258 | cgpGmo-S1657 | CGPIA22 | 40.184 |
| 1259 | cgpGmo-S1718 | CGPIA22 | 40.477 |
| 1260 | cgpGmo-S962b | CGPIA22 | 41.857 |
| 1261 | cgpGmo-S1310 | CGPIA22 | 46.161 |
| 1262 | cgpGmo-S28 | CGPIA22 | 59.459 |
| 1263 | cgpGmo-S805 | CGPIA22 | 59.459 |
| 1264 | cgpGmo-S1804 | CGPIA22 | 69.959 |
| 1265 | cgpGmo-S1008 | CGPIA23 | 0 |
| 1266 | cgpGmo-S418 | CGPIA23 | 0.802 |
| 1267 | cgpGmo-S1596a | CGPIA23 | 1.273 |
| 1268 | cgpGmo-S1766 | CGPIA23 | 2.647 |
| 1269 | cgpGmo-S1071a | CGPIA23 | 4.577 |
| 1270 | cgpGmo-S335 | CGPIA23 | 4.779 |
| 1271 | cgpGmo-S1622 | CGPIA23 | 5.906 |
| 1272 | cgpGmo-S227 | CGPIA23 | 6.682 |
| 1273 | cgpGmo-S626a | CGPIA23 | 6.752 |
| 1274 | cgpGmo-S626b | CGPIA23 | 7.065 |
| 1275 | 5911C1CO1.447 | CGPIA23 | 7.758 |
| 1276 | cgpGmo-S2218 | CGPIA23 | 16.686 |
| 1277 | cgpGmo-S529 | CGPIA23 | 18.251 |
| 1278 | cgpGmo-S897 | CGPIA23 | 18.251 |
| 1279 | cgpGmo-S1202 | CGPIA23 | 19.399 |
| 1280 | cgpGmo-S623 | CGPIA23 | 20.777 |
| 1281 | cgpGmo-S838a | CGPIA23 | 22.042 |
| 1282 | cgpGmo-S528 | CGPIA23 | 22.84 |
| 1283 | cgpGmo-S458a | CGPIA23 | 22.988 |
| 1284 | cgpGmo-S849 | CGPIA23 | 23.314 |
| 1285 | cgpGmo-S1250 | CGPIA23 | 23.479 |
| 1286 | cgpGmo-S351 | CGPIA23 | 23.983 |
| 1287 | cgpGmo-S1903 | CGPIA23 | 25.086 |
| 1288 | cgpGmo-S606a | CGPIA23 | 25.086 |
| 1289 | cgpGmo-S722 | CGPIA23 | 25.086 |
| 1290 | cgpGmo-S1506 | CGPIA23 | 25.405 |
| 1291 | cgpGmo-S606b | CGPIA23 | 25.423 |
| 1292 | cgpGmo-S1475 | CGPIA23 | 26.35 |
| 1293 | cgpGmo-S2086 | CGPIA23 | 27.898 |
| 1294 | 2311C1CO1.535 | CGPIA23 | 28.516 |
| 1295 | cgpGmo-S272 | CGPIA23 | 31.582 |
| 1296 | cgpGmo-S994 | CGPIA23 | 31.644 |
| 1297 | cgpGmo-S2035 | CGPIA23 | 32.016 |
| 1298 | cgpGmo-S1320 | CGPIA23 | 39.83 |

TABLE 11

SNPs that that are monomorphic from Eastern Atlantic cod populations tested (Iceland, Ireland and Norway) and polymorphic in Western Atlantic cod populations.

| SNP_name | New name | SNP_name | New name |
|---|---|---|---|
| 5909C1CO1.1049 | cgpGmo-S807 | 3987C1CO1.739 | cgpGmo-S1903 |
| 5643C1CO1.151 | cgpGmo-S2029 | 3beta670 | cgpGmo-S1117 |
| 5279C1CO1.392 | cgpGmo-S2279 | 4016C1CO1.62 | cgpGmo-S1905 |
| 4823C1CO1.458 | cgpGmo-S694 | 4048C1CO1.570 | cgpGmo-S1394b |
| 2332C1CO1.139 | cgpGmo-S357 | 4109C1CO1.558 | cgpGmo-S613b |
| 10377C1CO1.101 | cgpGmo-S1653 | 412C2CO1.581 | cgpGmo-S614b |
| 10590C1CO1.513 | cgpGmo-S1660 | 414C1CO1.432 | cgpGmo-S1919 |
| 1125C1CO1.153 | cgpGmo-S1178 | 4427C1CO1.243 | cgpGmo-S1945 |
| 11916C1CO1.209 | cgpGmo-S1673 | 4517C1CO1.551 | cgpGmo-S1952 |
| 1215C1CO1.327 | cgpGmo-S180a | 4649C1CO1.962 | cgpGmo-S1962 |
| 1414C1CO1.566 | cgpGmo-S1689 | 4748C1CO1.393 | cgpGmo-S1435 |
| 1428C2CO1.182 | cgpGmo-S217a | 4863C1CO1.276 | cgpGmo-S1977 |
| 1497C1CO1.102 | cgpGmo-S1209 | 4888C1CO1.932 | cgpGmo-S1445 |
| 1557C1CO1.255 | cgpGmo-S1213c | 5209C1CO1.196 | cgpGmo-S2003 |
| 1630C3CO1.531 | cgpGmo-S1707 | 5275C1CO1.461 | cgpGmo-S2008 |
| 1733C1CO1.202 | cgpGmo-S1714 | 5322C1CO1.297 | cgpGmo-S1461b |
| 1754C2CO1.245 | cgpGmo-S1716 | 5325C2CO1.319 | cgpGmo-S2011 |
| 1898C1CO1.530 | cgpGmo-S1242 | 5370C1CO1.568 | cgpGmo-S752b |
| 2052C1CO1.474 | cgpGmo-S1736 | 5375C1CO2.398 | cgpGmo-S1466b |
| 2075C1CO1.706 | cgpGmo-S1737 | 5655C1CO1.488 | cgpGmo-S2031 |
| 2107C2CO1.110 | cgpGmo-S1255b | 5854C1CO1.475 | cgpGmo-S1489 |
| 2118C1CO1.434 | cgpGmo-S1741 | 5886C1CO1.527 | cgpGmo-S2047 |
| 2143C1CO1.182 | cgpGmo-S1258a | 5895C1CO1.188 | cgpGmo-S2049 |
| 2177C1CO1.202 | cgpGmo-S338a | 6314C1CO1.109 | cgpGmo-S2074 |

TABLE 11-continued

SNPs that that are monomorphic from Eastern Atlantic cod populations tested (Iceland, Ireland and Norway) and polymorphic in Western Atlantic cod populations.

| SNP_name | New name | SNP_name | New name |
|---|---|---|---|
| 2220C1CO1.459 | cgpGmo-S59a | 6558C1CO1.582 | cgpGmo-S2091 |
| 2306C2CO1.268 | cgpGmo-S1764 | 6675C1CO1.512 | cgpGmo-S2097 |
| 2337C1CO1.284 | cgpGmo-S1273 | 6704C1CO1.367 | cgpGmo-S2098 |
| 2361C1CO1.632 | cgpGmo-S1767 | 6728C1CO1.428 | cgpGmo-S882a |
| 2539C1CO1.218 | cgpGmo-S385b | 6746C2CO1.793 | cgpGmo-S2099 |
| 262C1CO1.163 | cgpGmo-S1291 | 677C1CO1.540 | cgpGmo-S890b |
| 2756C4CO1.469 | cgpGmo-S1302 | 679C1CO1.356 | cgpGmo-S2102 |
| 2779C1CO1.229 | cgpGmo-S1795 | 6903C1CO1.213 | cgpGmo-S1543 |
| 2814C1CO1.108 | cgpGmo-S430a | 724C1CO1.555 | cgpGmo-S1553b |
| 2917C2CO1.452 | cgpGmo-S1809 | 7288C1CO1.182 | cgpGmo-S1556 |
| 2929C1CO1.64 | cgpGmo-S1315 | 7333C1CO1.612 | cgpGmo-S2130 |
| 2957C1CO1.841 | cgpGmo-S1813 | 7421C1CO1.345 | cgpGmo-S2136 |
| 2968C1CO1.121 | cgpGmo-S458a | 7468C1CO1.284 | cgpGmo-S2140 |
| 2993C1CO1.495 | cgpGmo-S1320 | 7565C1CO1.470 | cgpGmo-S2145 |
| 3002C1CO1.472 | cgpGmo-S463b | 8332C1CO1.229 | cgpGmo-S1014a |
| 336C1CO1.89 | cgpGmo-S1847 | 846C1CO1.541 | cgpGmo-S1608 |
| 3411C1CO1.411 | cgpGmo-S1346 | 8672C1CO1.556 | cgpGmo-S2183 |
| 346C1CO1.463 | cgpGmo-S1858 | 9176C1CO1.128 | cgpGmo-S2199 |
| 3539C1CO1.797 | cgpGmo-S1354 | 9323C1CO1.439 | cgpGmo-S46b |
| 3590C1CO1.517 | cgpGmo-S1868 | 9456C1CO1.448 | cgpGmo-S2208 |
| all_v2.1182.C3.404 | cgpGmo-S1121 | 4404C1CO1.224 | cgpGmo-S644 |
| all_v2.4.C42.1238 | cgpGmo-S1142 | 4664C2CO1.271 | cgpGmo-S672 |
| 10078C1CO1.320 | cgpGmo-S124 | 466C1CO1.619 | cgpGmo-S673 |
| 10330C1CO1.584 | cgpGmo-S134 | 466C2CO1.340 | cgpGmo-S674 |
| 10580C1CO1.134 | cgpGmo-S142 | 4773C1CO1.458 | cgpGmo-S688 |
| 1073C1CO1.202 | cgpGmo-S147 | 4866C1CO1.262 | cgpGmo-S699b |
| 1215C1CO1.596 | cgpGmo-S180b | 4936C1CO1.161 | cgpGmo-S706 |
| 132C1CO1.1121 | cgpGmo-S207 | 4961C2CO1.220 | cgpGmo-S710 |
| 1347C2CO1.580 | cgpGmo-S210 | 528C1CO1.1038 | cgpGmo-S94 |
| 1470C1CO1.120 | cgpGmo-S221a | 5431C1CO1.324 | cgpGmo-S757 |
| 1673C2CO1.405 | cgpGmo-S261a | 5472C1CO1.337 | cgpGmo-S758 |
| 1742C1CO1.369 | cgpGmo-S275 | 5645C1CO1.1566 | cgpGmo-S779 |
| 1780C1CO1.581 | cgpGmo-S281 | 6003C1CO1.427 | cgpGmo-S821 |
| 1851C2CO1.600 | cgpGmo-S289 | 6156C1CO1.442 | cgpGmo-S835 |
| 1878C1CO1.634 | cgpGmo-S291 | 638C1CO1.415 | cgpGmo-S853 |
| 193C2CO1.193 | cgpGmo-S302 | 6511C1CO1.374 | cgpGmo-S865 |
| 2040C2CO1.850 | cgpGmo-S322 | 666C1CO1.341 | cgpGmo-S878 |
| 2048C1CO1.312 | cgpGmo-S324 | 672C2CO1.309 | cgpGmo-S883 |
| 2126C1CO1.342 | cgpGmo-S334 | 7158C1CO1.350 | cgpGmo-S927 |
| 2153C2CO1.693 | cgpGmo-S57 | 7201C1CO1.450 | cgpGmo-S930 |
| 2185C1CO1.519 | cgpGmo-S339 | 727C1CO1.856 | cgpGmo-S103 |
| 2244C1CO1.338 | cgpGmo-S1265a | 7456C1CO1.351 | cgpGmo-S951b |
| 2296C6CO1.459 | cgpGmo-S351 | 7514C1CO1.267 | cgpGmo-S107 |
| 2308C2CO1.226 | cgpGmo-S352 | 7537C1CO1.337 | cgpGmo-S958 |
| 2545C1CO1.366 | cgpGmo-S388 | 7696C1CO1.426 | cgpGmo-S110 |
| 2617C2CO1.465 | cgpGmo-S399 | 781C1CO1.305 | cgpGmo-S982a |
| 270C2CO1.126 | cgpGmo-S411 | 7852C1CO1.926 | cgpGmo-S984 |
| 2805C1CO1.1000 | cgpGmo-S428 | 8083C1CO1.458 | cgpGmo-S997a |
| 2826C1CO1.252 | cgpGmo-S433 | 8195C2CO1.467 | cgpGmo-S1598a |
| 2895C1CO1.348 | cgpGmo-S444 | 829C1CO1.716 | cgpGmo-S1011b |
| 2906C1CO1.115 | cgpGmo-S68 | 8355C1CO1.403 | cgpGmo-S1016 |
| 290C1CO1.627 | cgpGmo-S446 | 8428C1CO1.521 | cgpGmo-S115 |
| 3097C1CO1.589 | cgpGmo-S475 | 8518C1CO1.523 | cgpGmo-S6 |
| 3129C1CO1.316 | cgpGmo-S478 | 8590C1CO1.487 | cgpGmo-S1032 |
| 3157C1CO1.686 | cgpGmo-S481 | 85C1CO1.261 | cgpGmo-S1034 |
| 3238C1CO1.625 | cgpGmo-S490 | 8831C1CO1.119 | cgpGmo-S1044 |
| 325C1CO1.835 | cgpGmo-S493 | 8852C2CO1.180 | cgpGmo-S1045 |
| 3330C1CO1.353 | cgpGmo-S504 | 8876C1CO1.97 | cgpGmo-S1049 |
| 3384C1CO1.157 | cgpGmo-S513 | 8898C1CO1.316 | cgpGmo-S1050 |
| 3530C1CO1.317 | cgpGmo-S536 | 9008C1CO1.522 | cgpGmo-S1056 |
| 3569C1CO1.391 | cgpGmo-S541b | 913C2CO1.505 | cgpGmo-S1062 |
| 3700C1CO1.185 | cgpGmo-S556 | 95C1CO1.548 | cgpGmo-S1087b |
| 373C1CO1.221 | cgpGmo-S560 | 9682C1CO1.765 | cgpGmo-S1093 |
| 3753C2CO1.291 | cgpGmo-S563 | 968C1CO1.536 | cgpGmo-S1095 |
| 3863C1CO1.284 | cgpGmo-S577 | 9732C1CO1.311 | cgpGmo-S1097 |
| 3899C1CO1.483 | cgpGmo-S584 | | |
| 3912C1CO1.393 | cgpGmo-S588 | | |
| 3965C2CO1.185 | cgpGmo-S593 | | |
| 412C2CO1.446 | cgpGmo-S614a | | |
| 4345C1CO1.634 | cgpGmo-S638b | | |
| 437C1CO1.241 | cgpGmo-S642 | | |

TABLE 12

Set of associated genotypes (21 SNPs identified on 20 contigs) that distinguish Southern
[South (Ire, Ireland)] and Northern [North (Nor, Norway - Barents Sea)] populations.

| Population | SNP_Name | | | | | | | | | | | | | | |
|---|---|---|---|---|---|---|---|---|---|---|---|---|---|---|---|
| | cgpGmo-S152 | cgpGmo-S157 | cgpGmo-S183 | cgpGmo-S268 | cgpGmo-S352 | cgpGmo-S419 | cgpGmo-S673 | cgpGmo-S739 | cgpGmo-S814a | cgpGmo-S870 | cgpGmo-S920 | cgpGmo-S982a | cgpGmo-S1039b | cgpGmo-S1089 | cgpGmo-S1183 |
| SOUTH(Ire) | C | C | A | A | G | G | C | T | C | T | A | A | T | T | G |
| SOUTH (Ice) | C | C | A | A | G | G | C | T | C | T | A | A | T | T | G |
| SOUTH (GB) | C | C | A | A | G | G | C | T | C | *T/C* | A | A | T | T | G |
| SOUTH (CS) | C | C | A | A | G | G | C | T | C | *T/C* | A | A | T | T | G |
| NORTH(Nor) | T | T | *A/G* | T | G | A | C | C | T | C | C | A | G | C | A |
| NORTH (Ice) | T | T | *A/G* | T | G | A | C | C | T | C | C | A | G | C | A |
| NORTH (GB) | T | T | *A/G* | T | *C/G* | A | *A/C* | C | T | C | C | *A/G* | G | C | A |
| NORTH (CS) | T | T | *A/G* | T | *C/G* | A | C | C | T | C | C | A | G | C | A |
| NORTH (NL_YC2) | T | T | *A/G* | T | *C/G* | A | *A/C* | C | T | C | C | *A/G* | G | C | A |
| NORTH (NL_YC3) | T | T | *A/G* | T | *C/G* | A | *A/C* | C | T | C | C | *A/G* | G | C | A |
| SNP sequence | [T/C] | [T/C] | [A/G] | [A/T] | [C/G] | [A/G] | [A/C] | [T/C] | [T/C] | [A/C] | [A/G] | [T/G] | [T/C] | [A/G] |

| Population | SNP_Name | | | | | | Number of individuals homozygous for major S or N genotype | Total number of individuals tested for that population |
|---|---|---|---|---|---|---|---|---|
| | cgpGmo-S1810 | cgpGmo-S1830 | cgpGmo-S1425 | cgpGmo-S1991 | cgpGmo-S2158 | cgpGmo-S1039a | | |
| SOUTH(Ire) | T | A | G | G | G | G | 14 | 15 |
| SOUTH (Ice) | T | A | G | G | G | G | 7 | 26 |
| SOUTH (GB) | T | A | G | G | G | G | 7 | 23 |
| SOUTH (CS) | T | A | G | G | G | G | 12 | 23 |
| NORTH(Nor) | G | G | *T/G* | *T/G* | A | A | 26 | 26 |
| NORTH (Ice) | G | G | *T/G* | *T/G* | A | A | 8 | 26 |
| NORTH (GB) | G | G | *T/G* | *T/G* | A | A | 6 | 23 |
| NORTH (CS) | G | G | *T/G* | *T/G* | A | A | 2 | 23 |
| NORTH (NL_YC2) | G | G | *T/G* | *T/G* | A | A | 23 | 23 |
| NORTH (NL_YC3) | G | G | *T/G* | *T/G* | A | A | 23 | 23 |
| SNP sequence | [T/G] | [A/G] | [T/G] | [T/G] | [A/G] | [A/G] | | |

Several populations (Ire, Ireland; Ice, Iceland; GB, Georges Bank; CS, Cape Sable; NL_YC2, fish from Newfoundland Bay Bulls population that were also used to generate Newfoundland breeding program second year class progeny; NL_YC3, fish from Newfoundland Smith Sound population that were also used to generate Newfoundland breeding program third year class progeny) were genotyped to determine which set or sets of associated genotypes were present. Where results were variable for given populations, genotypes for the populations are listed under both South (Ire, Ireland) and North (Nor, Norway Barents Sea) sets of associated genotypes. The SNP substitution originally detected in the sequence data is provided at the bottom of the table. Data in italics demonstrate where optional bases were found for specific SNPs in certain populations. It should be noted that for SNP cgpGmo-S870, T to C transition substitutions were only found in 2 of 7 homozygous individuals from GB, and in 1 of 12 in individuals from CS. SNP names where the SNPs are from the same contig are marked with bold font.

TABLE 13

SNPs that overlap with those described in Moen et al. (2008).

| CGP_SNP_Name | New name | SNP name from Moen et al. 2008 | SNP panel |
|---|---|---|---|
| 1057C1CO1.398 | #N/A | Gm1001_0189 | Panel 1 |
| 155C1CO1.193 | #N/A | Gm0986_0621 | Panel 1 |
| 2311C1CO1.535 | #N/A | Gm1205_0365 | Panel 1 |
| 334C1CO1.411 | #N/A | Gm0399_0241 | Panel 1 |
| 5279C2CO1.498 | #N/A | Gm0766_0315 | Panel 1 |
| 5681C1CO1.227 | #N/A | Gm370_0380 | Panel 1 |
| 5911C1CO1.447 | #N/A | Gm159_0228 | Panel 1 |
| 1534C1CO1.626 | cgpGmo-S232b | Gm0685_0303 | Panel 2 |
| 1959C2CO1.349 | cgpGmo-S1730 | Gm1174_0311 | Panel 2 |
| 4440C1CO1.1126 | cgpGmo-S649b | Gm328_0124 | Panel 2 |

TABLE 14

Properties of SNPs used for experimental testing of family assignment panel. SNPs selected for parental assignment are shown, with their chromosomal position (Cm), and minor allele frequency (MAF) as determined by Illumina GoldenGate genotyping of multiple Atlantic cod populations. Two map positions are provided, the first from the initial version of the genetic map that was created using two family crosses (See Example 2; FIG. 5), and the second (New) genetic map from an updated map generated after adding an additional family (Table 10).

| SNP name | Linkage group | Position (Cm) | Position (Cm) New | MAF |
|---|---|---|---|---|
| cgpGmo_s305 | 2 | | 3.426 | 0.4588 |
| cgpGmo_s1743 | 2 | 12.52 | 13.889 | 0.4323 |
| cgpGmo_s1217 | 2 | 51.914 | 51.137 | 0.4236 |
| cgpGmo_s646 | 3 | | 16.28 | 0.4892 |
| cgpGmo_s1979 | 4 | 33.693 | 28.626 | 0.4269 |
| cgpGmo_s205 | 4 | 39.111 | 31.162 | 0.4219 |
| cgpGmo_s1698 | 4 | | 59.88 | 0.488 |
| cgpGmo_s2069 | 5 | 17.797 | 12.113 | 0.4258 |
| cgpGmo_s977 | 5 | 29.694 | 26.336 | 0.4555 |
| cgpGmo_s1787 | 5 | 35.082 | 30.546 | 0.44 |
| cgpGmo_s774 | 5 | 45.796 | 37.607 | 0.4967 |
| cgpGmo_s60 | 6 | 42.927 | 40.601 | 0.449 |
| cgpGmo_s1820 | 8 | 13.99 | 13.794 | 0.4716 |

TABLE 14-continued

Properties of SNPs used for experimental testing of family assignment panel. SNPs selected for parental assignment are shown, with their chromosomal position (Cm), and minor allele frequency (MAF) as determined by Illumina GoldenGate genotyping of multiple Atlantic cod populations. Two map positions are provided, the first from the initial version of the genetic map that was created using two family crosses (See Example 2; FIG. 5), and the second (New) genetic map from an updated map generated after adding an additional family (Table 10).

| SNP name | Linkage group | Position (Cm) | Position (Cm) New | MAF |
|---|---|---|---|---|
| cgpGmo_s362 | 8 | 13.946 | 14.51 | 0.4154 |
| cgpGmo_s2089 | 8 | 41.027 | 40.427 | 0.4629 |
| cgpGmo_s2222 | 8 |  | 42.779 | 0.4945 |
| cgpGmo_s1965 | 9 | 55.179 | 43.25 | 0.4334 |
| cgpGmo_s1001 | 9 | 57.131 | 44.355 | 0.4902 |
| cgpGmo_s410 | 9 | 56.294 | 45.714 | 0.4132 |
| cgpGmo_s1098 | 10 | 50.784 | 31.66 | 0.4458 |
| cgpGmo_s403 | 11 | 9.547 | 13.622 | 0.4534 |
| cgpGmo_s154 | 11 |  | 41.584 | 0.4382 |
| cgpGmo_s488 | 11 | 51.537 | 56.917 | 0.4306 |
| cgpGmo_s1225 | 12 |  | 3.842 | 0.4334 |
| cgpGmo_s251 | 12 |  | 14.796 | 0.4111 |
| cgpGmo_s866 | 12 | 33.657 | 16.674 | 0.4371 |
| cgpGmo_s233 | 12 | 33.772 | 20.055 | 0.4848 |
| cgpGmo_s932 | 14 | 30.36 | 24.805 | 0.461 |
| cgpGmo_s909 | 15 | 42.264 | 42.239 | 0.4067 |
| cgpGmo_s1032 | 16 |  | 13.163 | 0.4631 |
| cgpGmo_s1265 | 17 | 8.163 | 0 | 0.4334 |
| cgpGmo_s727 | 17 | 24.154 | 15.001 | 0.4403 |
| cgpGmo_s1864 | 17 |  | 46.969 | 0.4323 |
| cgpGmo_s900 | 18 | 52.06 | 44.65 | 0.4718 |
| cgpGmo_s2187 | 19 | 1.019 | 0 | 0.4345 |
| cgpGmo_s247 | 19 | 10.512 | 13.05 | 0.4642 |
| cgpGmo_s1385 | 19 | 23.833 | 29.483 | 0.4563 |
| cgpGmo_s328 | 19 |  | 38.165 | 0.4479 |
| cgpGmo_s767 | 19 | 54.792 | 54.661 | 0.4664 |
| cgpGmo_s193 | 19 | 54.274 | 56.329 | 0.4469 |
| cgpGmo_s661 | 20 | 11.711 | 14.136 | 0.4837 |
| cgpGmo_s1659 | 22 | 28.547 | 27.523 | 0.4563 |
| cgpGmo_s1168 |  |  |  | 0.4727 |
| cgpGmo_s1440 |  |  |  | 0.417 |
| cgpGmo_s1498 |  |  |  | 0.4127 |
| cgpGmo_s1593 |  |  |  | 0.4793 |
| cgpGmo_s1606 |  |  |  | 0.4094 |
| cgpGmo_s1631 |  |  |  | 0.4869 |

TABLE 15

Genotyping errors associated with SNPs after experimental testing. SNP S1001 generated a large percentage of total errors, and is highlighted in grey.

| SNP name | Number of errors | Percentage of total |
|---|---|---|
| cgpGmo_s205 | 9 | 15.8 |
| cgpGmo_s1743 | 1 | 1.8 |
| cgpGmo_s362 | 3 | 5.3 |
| cgp_Gmo_s403 | 1 | 1.8 |
| cgpGmo_s1965 | 1 | 1.8 |
| cgpGmo_s767 | 1 | 1.8 |
| cgpGmo_s909 | 8 | 14.0 |
| cgpGmo_s977 | 6 | 10.5 |
| cgpGmo_s1001 | 23 | 40.4 |
| cgpGmo_s1032 | 1 | 1.8 |
| cgpGmo_s1631 | 2 | 3.5 |
| cgpGmo_s1168 | 1 | 1.8 |
| Total | 57 | 100.0 |

TABLE 16

Genotyping errors generated per family. The dams and sires giving rise to each family cross are shown. All family crosses were generated as part of the NB selective breeding program. Sire M1330 and dam F182 were associated with a large percentage of total genotyping errors and are highlighted in grey.

| Family | Dam | Sire | Number of errors | Percentage of total errors |
|---|---|---|---|---|
| B03 | F181 | M1082 | 6 | 10.5 |
| B04 | F177 | M1171 | 2 | 3.5 |
| B06 | F177 | M1186 | 1 | 1.8 |
| B09 | F180 | M1186 | 0 | 0.0 |
| B13 | F180 | M1157 | 2 | 3.5 |
| B16 | F329 | M1324 | 2 | 3.5 |
| B21 | F49 | M1330 | 10 | 17.5 |
| B22 | F49 | M1035 | 1 | 1.8 |
| B23 | F182 | M1082 | 9 | 15.8 |
| B24 | F182 | M1330 | 6 | 10.5 |
| B28 | F49 | M1126 | 4 | 7.0 |
| B33 | F2 | M1013 | 2 | 3.5 |
| B34 | F2 | M1023 | 0 | 0.0 |
| B35 | F395 | M1013 | 4 | 7.0 |
| B37 | F275 | M1278 | 3 | 5.3 |
| B51 | F163 | M1108 | 5 | 8.8 |
| Total |  |  | 57 | 100 |

TABLE 17

Determining the minimal SNP set required for correct parental assignment. SNPs were sequentially removed from the panel, with the reduced SNP set tested for its ability to correctly assign parents.

| Number of SNPs in panel | Correct assignment (%) | Ambiguous assignment (%) | Incorrect assignment (%) |
|---|---|---|---|
| 48 | 100 |  |  |
| 36 | 100 |  |  |
| 30 | 100 |  |  |
| 24 | 98.9 | 1.1 |  |
| 20 | 94.6 | 4.3 | 1.1 |
| 16 | 84.9 | 12.9 | 2.2 |

TABLE 18

SNPs and alleles associated with nodavirus resistance in codfish

| SNP | linkage group | Preferred Allele | p-value | FDR p-value | Position (cM) |
|---|---|---|---|---|---|
| cgpGmo-S557 | 19 | C | 0.0003 | 0.01538 | 0.053 |
| cgpGmo-S943 | 8 | T | 0.0011 | 0.06983 | 25.705 |
| cgpGmo-1596a | 23 | A | 0.0043 | 0.08600 | 1.273 |
| cgpGmo-S1071a | 23 | T | 0.0057 | 0.08600 | 4.577 |

TABLE 19

Descriptive statistics for SL (cm), Wt (g), BledWt (g), GonadWt (g), LiverWt (g), HOGWt (g), SOnFWt (g), SOffFWt (g) measurements taken at harvest.

| Trait | Mean | Min | Max | Std |
|---|---|---|---|---|
| SL | 44.4 | 29.5 | 52.2 | 4.0 |
| Wt | 1504.5 | 325.0 | 2543.0 | 465.9 |
| BledWt | 1479.3 | 310.0 | 2511.4 | 456.9 |
| GonadWt | 97.0 | 0.5 | 316.6 | 53.8 |
| LiverWt | 172.2 | 12.6 | 335.9 | 73.3 |
| HOGWt | 1155.7 | 280.1 | 1953.2 | 341.1 |
| SOnWt | 598.0 | 120.2 | 1088.0 | 197.5 |
| SOffWt | 522.3 | 98.0 | 962.0 | 179.6 |

TABLE 20

SNPs associated with measures of weight. Preferred alleles are associated with increased weight

| Linkage Group | Preferred Allele | FDR p-value | Position (cM) | Locus Name | Trait |
|---|---|---|---|---|---|
| 7 | C | 0.04229 | 5.704 | cgpGmo-S833 | Wt, |
|   |   | 0.0481 |   |   | BledWt |
| 7 | C | 0.04229 | 6.228 | cgpGmo-S834 | Wt, |
|   |   | 0.0481 |   |   | BledWt |
| 7 | A | 0.04229 | 19.147 | cgpGmo-S268 | Wt, |
|   |   | 0.0481 |   |   | BledWt, |
|   |   | 0.00398 |   |   | HOGWt |
| 7 | G | 0.04229 | 19.147 | cgpGmo-S1183 | Wt, |
|   |   | 0.0481 |   |   | BledWt, |
|   |   | 0.00398 |   |   | HOGWt |
| 7 | G | 0.04229 | 19.147 | cgpGmo-S2158 | Wt, |
|   |   | 0.0481 |   |   | BledWt |
|   |   | 0.00398 |   |   | HOGWt |
| 7 | T | 0.04229 | 19.147 | cgpGmo-S1039b | Wt, |
|   |   | 0.0481 |   |   | BledWt, |
|   |   | 0.00398 |   |   | HOGWt |
| 7 | A | 0.04229 | 19.147 | cgpGmo-S1830 | Wt, |
|   |   | 0.0481 |   |   | BledWt, |
|   |   | 0.00398 |   |   | HOGWt |
| 7 | C | 0.04229 | 19.147 | cgpGmo-S157 | Wt, |
|   |   | 0.0481 |   |   | BledWt |
|   |   | 0.00398 |   |   | HOGWt |
| 7 | T | 0.0192 | 19.147 | cgpGmo-S870 | HOGWt |
| 7 | G | 0.04229 | 19.147 | cgpGmo-S419 | Wt, |
|   |   | 0.0481 |   |   | BledWt |
|   |   | 0.00398 |   |   | HOGWt |
| 7 | G | 0.02525 | 19.147 | cgpGmo-S352 | HOGWt |
| 7 | A | 0.04229 | 19.147 | cgpGmo-S920 | Wt, |
|   |   | 0.0481 |   |   | BledWt |
|   |   | 0.00398 |   |   | HOGWt |
| 7 | C | 0.04229 | 19.147 | cgpGmo-S152 | Wt, |
|   |   | 0.0481 |   |   | BledWt |
|   |   | 0.00398 |   |   | HOGWt |
| 7 | T | 0.04229 | 19.147 | cgpGmo-S1089 | Wt, |
|   |   | 0.0481 |   |   | BledWt |
|   |   | 0.00398 |   |   | HOGWt |
| 7 | G | 0.0444 | 19.147 | cgpGmo-S1039a | Wt |
|   |   | 0.00398 |   |   | HOGWt |
| 7 | C | 0.04229 | 19.147 | cgpGmo-S814a | Wt, |
|   |   | 0.0481 |   |   | BledWt |
|   |   | 0.00398 |   |   | HOGWt |
| 7 | G | 0.02497 | 19.147 | cgpGmo-S1425 | HOGWt |
| 7 | T | 0.04229 | 19.147 | cgpGmo-S1810 | Wt, |
|   |   | 0.0481 |   |   | BledWt |
|   |   | 0.00398 |   |   | HOGWt |
| 7 | C | 0.01057 | 22.341 | cgpGmo-S1644 | HOGWt |

TABLE 21

List of SNPs not on linkage group 7 with significant associations.

| linkage group | Preferred Allele | FDR p-value | Position (cM) | Locus Name | Trait |
|---|---|---|---|---|---|
| 11 | T | 0.0325 | 45.925 | cgpGmo-S811a | SOnWt |
|   |   | 0.0260 |   |   | SOffWt |
| 23 | C | 0.0093 | 5.906 | cgpGmo-S1622 | SOnWt |
|   |   | 0.0372 |   |   | SOffWt |
| 18 | A (−) | 0.0430 | 35.855 | cgpGmo-S391 | GonadWt |
| 22 | G (−) | 0.0126 | 33.444 | cgpGmo-S2288 | GonadWt |
| 1 | A (−) | 0.0280 | 27.89 | cgpGmo-S1579 | LiverWt |
| 23 | A (−) | 0.0403 | 23.314 | cgpGmo-S849 | LiverWt |

(−) indicates a preferred allele associated with a reduction in weight

TABLE 22

List of 21 single nucleotide polymorphisms associated with gender: linkage group, F value, false discovery rate p value, position of SNP in linkage group, locus name.

| Linkage Group | F | FDR p-value | Position (cM) | Locus Name |
|---|---|---|---|---|
| 11 | 5.96 | 0.01138 | 13.622 | cgpGmo-S403 |
| 11 | 12.77 | 0.00006 | 35.645 | cgpGmo-S618 |
| 11 | 4.95 | 0.026 | 35.728 | cgpGmo-S1802 |
| 11 | 31.91 | 0 | 41.584 | cgpGmo-S154 |
| 11 | 15.32 | 0.00001 | 43.149 | cgpGmo-S691 |
| 11 | 8.26 | 0.00177 | 43.208 | cgpGmo-S1063 |
| 11 | 19.58 | 0 | 43.975 | cgpGmo-S867 |
| 11 | 8.11 | 0.01797 | 45.507 | cgpGmo-S1647 |
| 11 | 7.11 | 0.0045 | 47.196 | cgpGmo-S634 |
| 11 | 9.79 | 0.00068 | 47.277 | cgpGmo-S1658 |
| 11 | 4.66 | 0.03282 | 47.581 | cgpGmo-S4 |
| 11 | 11.67 | 0.00379 | 53.144 | cgpGmo-S1767 |
| 11 | 10.28 | 0.0005 | 54.705 | cgpGmo-S2017 |
| 11 | 9.55 | 0.00072 | 54.709 | cgpGmo-S2211 |
| 11 | 9.32 | 0.00072 | 55.193 | cgpGmo-S1090 |
| 11 | 6.02 | 0.01138 | 56.419 | cgpGmo-S2005 |
| 11 | 10.83 | 0.00511 | 56.518 | cgpGmo-S138 |
| 11 | 8.18 | 0.00177 | 56.917 | cgpGmo-S488 |
| 11 | 25 | 0 | 57.633 | cgpGmo-S44 |
| 11 | 5.25 | 0.02058 | 59.389 | cgpGmo-S416b |
| 15 | 6.83 | 0.0492 | 48.153 | cgpGmo-S687 |

TABLE 23

Summary statistics for Z Score, Mean Cortisol, Resting Cortisol, Mean Weight (g) for association analysis in Example 7.

| Trait | Mean | Min | Max | Std |
|---|---|---|---|---|
| Zt Score | 0.11 | −1.05 | 1.70 | 0.73 |
| Mean Cortisol | 108.61 | 18.08 | 264.86 | 58.73 |
| Resting Cortisol | 42.87 | 0.10 | 426.50 | 69.48 |
| Mean Weight | 155.37 | 38.40 | 362.39 | 64.59 |

TABLE 24

List of SNPs associated with change in cortisol level and the alleles associated with a smaller change in cortisol level, false discovery rate p value, and position of SNP in linkage group.

| linkage group | Preferred Allele | fdr_p | Position (cM) | Locus Name |
|---|---|---|---|---|
| 6 | A | 0.0174 | 3.382 | cgpGmo-S848 |
| 13 | C | 0.00002 | 42.546 | cgpGmo-S487 |
| 18 | T | 0.0287 | 48.440 | cgpGmo-S975a |
| 20 | T | 0.0369 | 41.030 | cgpGmo-S525 |

REFERENCES

Altschul S F, Gish W, Miller W, Myers E W, J. LD: Basic local alignment search tool. *Journal of Molecular Biology* 1990, 5:403-410.

Anderson, E. C., Garza, J. C., 2006. The power of single-nucleotide polymorphisms for large-scale parentage inference. Genetics. 172, 2567-2582.

Baruch, E., Weller, J. I., 2008. Estimation of the number of SNP genetic markers required for parentage verification. Anim Genet. 39, 474-479.

Benjamini, Y. and Y. Hochberg. 1995. Controlling the false discovery rate: a practical and powerful approach to multiple testing. J. R. Stat. Soc. Ser. B., 57:289-300.

Bonaldo M F, Lennon G, Soares M B: Normalization and subtraction: two approaches to facilitate gene discovery. *Genome Research* 1996, 6:791-806.

Bowman, S., Higgins, B., Stone, C., Kozera, C., Curtis, B. A., Tarrant Bussey, J., Kimball, J., Verheul, H., Johnson, S. C., 2007. Generation of genomics resources for Atlantic cod (*Gadus morhua*): progress and plans. Bulletin of the Aquaculture Association of Canada. 105, 24-30.

Bricknell, I. R., J. E. Bron and T. J. Bowden. 2006. Diseases of gadoid fish in cultivation: a review. ICES Journal of Marine Science, 63:253-266.

Brown, J. A., Minkoff, G., Puvanendran, V., 2003. Larviculture of Atlantic cod (*Gadus morhua*): progress, protocols and problems. Aquaculture. 227, 357-372.

Campbell, N. R., Overturf, K., Narum, S. R., 2009. Characterization of 22 novel single nucleotide polymorphism markers in steelhead and rainbow trout. Molecular Ecology Resources. 9, 318-322.

Cenadelli, S., Maran, V., Bongioni, G., Fusetti, L., Parma, P., Aleandri, R., 2007. Identification of nuclear SNPs in gilthead seabream. Journal of Fish Biology. 70, 399-405.

Christie, M. R., 2009. Parentage in natural populations: novel methods to detect parent-offspring pairs in large data sets. Molecular Ecology Resources.

Danzmann, R. G., 1997. PROBMAX: a computer program for assigning unknown parentage in pedigree analysis from known genotypic pools of parents and progeny. Journal of Heredity. 88, 333.

Delghandi, M., Mortensen, A., Westgaard, J. I., 2003. Simultaneous analysis of six microsatellite markers in Atlantic cod (*Gadus morhua*): a novel multiplex assay system for use in selective breeding studies. Marine Biotechnology. 5, 141-148.

Delghandi M, Wesmajervi M S, Mennen S, Nilsen F: Development of twenty sequence-tagged microsatellites for the Atlantic cod (*Gadus morhua* L.). *Conservation Genetics* 2008, 9(5):1395-1398.

Delghandi M, Wesmajervi M S, Tafese T, Nilsen F: Twenty-three novel microsatellite markers developed from Atlantic cod (*Gadus morhua* L.) expressed sequence tags. *Journal of Fish Biology* 2008, 73(2):444-449.

Devlin, R. H., Nagahama, Y., 2002. Sex determination and sex differentiation in fish: an overview of genetic, physiological, and environmental influences. Aquaculture. 208, 191-364.

Fan Z, Fox D P: Robertsonian polymorphism in plaice, *Pleuronectes platessa* L., and cod, *Gadus morhua* L. (Pisces Pleuronectiformes and Gadiformes). *Journal of Fish Biology* 1991, 38:635-640.

Feng C Y, Johnson S C, Hori T, Rise M, Hall J R, Gamperl A K, Hubert S, Kimball J, Bowman S, Rise M L: Identification and analysis of differentially expressed genes in immune tissues of Atlantic cod stimulated with formalin-killed atypical *Aeromonas salmonicida*. *Physiological Genomics* 2009.

Garber, A. F., S. E. Fordham, J. E. Symonds, E. A. Trippel and D. L. Berlinsky. 2009. Hormone-induced ovulation and spermiation in Atlantic cod (*Gadus morhua*). Aquaculture, 296:179-183.

Gjedrem, T., 2000. Genetic improvement of coldwater fish species. Aquaculture Research. 31, 25-33.

Glaubitz, J. C., Rhodes, E., Dewoody, A., 2003. Prospects for inferring pairwise relationships with single nucleotide polymorphisms. Molecular Ecology. 12, 1039-1047.

Gorbach, D. M., Hu, Z.-L., Du, Z.-Q., Rothschild, M. F., 2008. SNP discovery in Litopenaeus vannamei with a new computational pipeline. Anim Genet. 40, 106-109.

Guryev V, Koudijs M J, Berezikov E, Johnson S L, Plasterk R H, van Eeden F J, Cuppen E: Genetic variation in the zebrafish. *Genome Research* 2006, 16(4):491-497.

Guryev V, Berezikov E, Malik R, Plasterk R H, Cuppen E: Single nucleotide polymorphisms associated with rat expressed sequences. *Genome Res* 2004, 14(7):1438-1443.

Hayes, B., Sonesson, A. K., Gjerde, B., 2005. Evaluation of three strategies using DNA markers for traceability in aquaculture species. Aquaculture. 250, 70-81.

Hayes, B., Laerdahl, J. K., Lien, S., Moen, T., Berg, P., Hindar, K., Davidson, W. S., Koop, B. F., Adzhubei, A., Hoyheim, B., 2007. An extensive resource of single nucleotide polymorphism markers associated with Atlantic salmon (*Salmo salar*) expressed sequences. Aquaculture. 265, 82-90.

He C, Chen L, Simmons M, Li P, Kim S, Liu Z J: Putative SNP discovery in interspecific hybrids of catfish by comparative EST analysis. *Anim Genet* 2003, 34(6):445-448.

Heaton, M. P., Harhay, G. P., Bennett, G. L., Stone, R. T., Grosse, W. M., Casas, E., Keele, J. W., Smith, T. P., Chitko-McKown, C. G., Laegreid, W. W., 2002. Selection and use of SNP markers for animal identification and paternity analysis in U.S. beef cattle. Mamm Genome. 13, 272-281.

Herlin, M., Taggart, J. B., McAndrew, B. J., Penman, D. J., 2007. Parentage allocation in a complex situation: A large commercial Atlantic cod (*Gadus morhua*) mass spawning tank. Aquaculture. 272S1, S195-S203.

Herlin, M., Delghandi, M., Wesmajervi, M., Taggart, J. B., McAndrew, B. J., Penman, D. J., 2008. Analysis of the parental contribution to a group of fry from a single day of spawning from a commercial Atlantic cod (*Gadus morhua*) breeding tank. Aquaculture. 274, 218-224.

Herlin, M. C. G., 2007. Genetic management of Atlantic cod (*Gadus morhua* L.) hatchery populations, Institute of Aquaculture. University of Stirling, Stirling, pp. 222.

Hill, W. G., Salisbury, B. A., Webb, A. J., 2008. Parentage identification using single nucleotide polymorphism genotypes: Application to product tracing. Journal of Animal Science. 86, 2508-2517.

Higgins B, Hubert S, Simpson G, Stone C, Bowman S: Characterization of 155 EST-derived microsatellites and validation for linkage mapping. *Molecular Ecology Resources* 2009, 9(3):733-737.

Hubert S, Tarrant Bussey J, Higgins B, Curtis B A, Bowman S: Development of single nucleotide polymorphism markers for Atlantic cod (*Gadus morhua*) using expressed sequences. *Aquaculture* 2009, 296(1-2):7-14.

Hubert S, Higgins, B, Borza T and Bowman S. 2010. Development of a SNP resource and a genetic linkage map for Atlantic cod (*Gadus morhua*). BMC Genomics 11:191.

Jakobsdottir, K. B., Jorundsdottir, O. D., Skirnisdottir, S., Hjorleifsdottir, S., Hreggviosson, G. O., Danielsdottir, A. K., Pampoulie, C., 2006. Nine new polymorphic microsatellite loci for the amplification of archived otolith DNA of Atlantic cod, *Gadus morhua* L. Molecular Ecology Notes. 6, 337-339.

Johansen, S. D., Coucheron, D. H., Andreassen, M., Karlsen, B. O., Furmanek, T., Jorgensen, T. E., Emblem, A., Breines, R., Nordeide, J. T., Moum, T., Nederbragt, A. J., Stenseth, N. C., Jakobsen, K. S., 2009. Large-scale sequence analyses of Atlantic cod. New Biotechnol, 25, 263-271.

Jones, B., Walsh, D., Werner, L., Fiumera, A., 2009. Using blocks of linked single nucleotide polymorphisms as highly polymorphic genetic markers for parentage linkage. Molecular Ecology Resources. 9, 487-497.

Kijas, J. W., Townley, D., Dalrymple, B. P., Heaton, M. P., Maddox, J. F., McGrath, A., Wilson, P., Ingersoll, R. G., McCulloch, R., McWilliam, S., Tang, D., McEwan, J., Cockett, N., Oddy, V. H., Nicholas, F. W., Raadsma, H., 2009. A genome wide survey of SNP variation reveals the genetic structure of sheep breeds. PLoS One. 4, e4668.

Koski L B, Gray M W, Lang B F, Burger G: AutoFACT: an automatic functional annotation and classification tool. *BMC Bioinformatics* 2005, 6:151.

Kim H, Schmidt C J, Decker K S, Emara M G: A double-screening method to identify reliable candidate non-synonymous SNPs from chicken EST data. *Anim Genet* 2003, 34(4):249-254.

Krawczak, M., 1999. Informativity assessment for biallelic single nucleotide polymorphisms. Electrophoresis. 20, 1676-1681.

Matson, S. E., Camara, M., Eichert, W., Banks, M. A., 2008. P-LOCI: a computer program for chosing the most efficient set of loci for parentage assignment. Molecular Ecology Resources. 8, 765-768.

Matukumalli, L. K., Lawley, C. T., Schnabel, R. D., Taylor, J. F., Allan, M. F., Heaton, M. P., O'Connell, J., Moore, S. S., Smith, T. P., Sonstegard, T. S., Van Tassell, C. P., 2009. Development and characterization of a high density SNP genotyping assay for cattle. PLoS One. 4, e5350.

Miller, K. M., Le, K. D., Beacham, T. D., 2000. Development of tri- and tetranucleotide repeat microsatellite loci in Altantic cod (*Gadus morhua*). Molecular Ecology. 9, 238-239.

Moen, T., Hayes, B., Nilsen, F., Delghandi, M., Fjalestad, K. T., Fevolden, S. E., Berg, P. R., Lien, S., 2008. Identification and characterisation of novel SNP markers in Atlantic cod: evidence for directional selection. BMC Genet. 9, 18.

Moen T, Delghandi M, Wesmajervi M S, Westgaard J I, Fjalestad K T: A SNP/microsatellite genetic linkage map of the Atlantic cod (*Gadus morhua*). *Anim Genet* 2009.

Nickerson D A, Tobe V O, Taylor S L: PolyPhred: automating the detection and genotyping of single nucleotide substitutions using fluorescence-based resequencing. *Nucleic Acids Res* 1997, 25(14):2745-2751.

Ødegård, J., A.-I. Sommer and A. K. Praebel. 2010. Heritability of resistance to viral nervous necrosis in Atlantic cod (*Gadus morhua* L.). Aquaculture, 300:59-64.

O'Reilly, P. T., Canino, M. F., Bailey, K. M., Bentzen, P., 2000. Isolation of twenty low stutter di- and tetranucleotide microsatellites for population analyses of walleye pollock and other gadoids. Journal of Fish Biology. 56, 1074-1086.

Palermo M, Marazzi M G, Hughes B A, Stewart P M, Clayton P T, Shackleton C H L: Human delta4-3-oxosteroid 5beta-reductase (AKR1D1) deficiency and steroid metabolism. *Steroids* 2008, 73:417-423.

Peichel, C. L., Ross, J. A., Matson, C. K., Dickson, M., Grimwood, J., Schmutz, J., Myers, R. M., Mori, S., Schluter, D., Kingsley, D. M., 2004. The Master Sex-Determination Locus in Threespine Sticklebacks is on a Nascent Y Chromosome. Curr Biol. 14, 1416-1424.

Penman, D. J., Piferrer, F., 2008. Fish Gonadogenesis. Part 1: Genetic and Environmental Mechanisms of Sex Determination. Rev. Fish. Sci. 16:1, 16-34.

Pogson G H, Mesa K A, Boutilier R G: Genetic population structure and gene flow in the Atlantic cod *Gadus morhua*: a comparison of allozyme and nuclear RFLP loci. Genetics 1995, 139:375-385.

Quilang, J., Wang, S., Li, P., Abernathy, J., Peatman, E., Wang, Y., Wang, L., Shi, Y., Wallace, R., Guo, X., Liu, Z., 2007. Generation and analysis of ESTs from the eastern oyster, Crassostrea virginia Gmelin and identification of microsatellite and SNP markers. BMC Genomics. 8.

Rengmark, A. H., Slettan, A., Skaala, O., Lie, O., Lingaas, F., 2006. Genetic variability in wild and farmed Atlantic slamon (*Salmo salar*) strains estimated by SNP and microsatellites. Aquaculture. 253, 229-237.

Rise M L, Hall J, Rise M, Hori T, Gamperl A K, Kimball J, Hubert S, Bowman S, Johnson S C: Functional genomic analysis of the response of Atlantic cod (*Gadus morhua*) spleen to the viral mimic polyriboinosinic polyribocytidylic acid (pIC). *Dev Comp Immunol* 2008, 32(8):916-931.

Rohrer, G. A., Freking, B. A., Normeman, D., 2007. Single nucleotide polymorphisms for pig identification and parentage exclusion. Animal Genetics. 38.

Rose G A: Cod: The ecological history of the North Atlantic fisheries: Breakwater Books, St. John's, Newfoundland; 2007

Rosenlund, G., Skretting, M., 2006. Worldwide status and perspective on gadoid aquaculture. ICES Journal of Marine Science. 63, 194-197.

Rousset F: GenePop '007: a complete reimplementation of the GenePop software for windows and Linux. *Molecular Ecology Notes* 2008, 8:103-106.

Ruzzante D E, Taggart C T, Cook D, Goddard S: Genetic differentiation between inshore and offshore Atlantic cod (*Gadus morhua*) off Newfoundland: Microsatellite DNA variation and antifreeze level. *Canadian Journal of Fisheries and Aquatic Sciences* 1996, 53:634-645.

Ryynanen H J, Primmer C R: Single nucleotide polymorphism (SNP) discovery in duplicated genomes: intron-primed exon-crossing (IPEC) as a strategy for avoiding amplification of duplicated loci in Atlantic salmon (*Salmo salar*) and other salmonid fishes. *BMC Genomics* 2006, 7:192

Simoes M, Bahia D, Zerlotini A, Torres K, Artiguenave F, Neshich G, Kuser P, Oliveira G: Single nucleotide polymorphisms identification in expressed genes of *Schistosoma mansoni*. *Mol Biochem Parasitol* 2007, 154(2):134-140.

Smith C T, Elfstrom C M, Seeb L W, Seeb J E: Use of sequence data from rainbow trout and Atlantic salmon for SNP detection in Pacific salmon. *Molecular Ecology* 2005, 14:4193-4203.

Snelling, W. M., Casas, E., Stone, R. T., Keele, J. W., Harhay, G. P., Bennett, G. L., Smith, T. P., 2005. Linkage mapping bovine EST-based SNP. BMC Genomics. 6, 74.

Spigler R B, Lewers K S, Main D S, Ashman T-L: Genetic mapping of sex determination in a wild strawberry, *Fragaria virginiana*, reveals earliest form of sex chromosome. *Heredity* 2008, 101:507-517.

Stickney H L, Schmutz J, Woods I G, Holtzer C C, Dickson M C, Kelly P D, Myers R M, Talbot W S: Rapid mapping of zebrafish mutations with SNPs and oligonucleotide microarrays. *Genome Res* 2002, 12(12):1929-1934.

Symonds, J., Garber, A., Puvanendran, V., Robinson, A., Neil, S., Trippel, E., Walker, S., Boyce, D., Gamperl, K., Lush, L., Nardi, G., Powell, F., Walsh, A., Bowman, S., 2007. Family-based Atlantic cod (*Gadus morhua*) broodstock development. Bulletin of the Aquaculture Association of Canada. 105, 39-46.

Tani N, Takahashi T, Iwata H, Mukai Y, Ujino-Ihara T, Matsumoto A, Yoshimura K, Yoshimaru H, Murai M, Nagasaka K et al: A consensus linkage map for Sugi (*Cryptomeria japonica*) from two pedigrees, based on microsatellites and expressed sequence tags. *Genetics* 2003, 165:1551-1568.

Van Ooijen J W: JoinMap 4, Software for the calculation of genetic linkage maps in experimental populations. In.: Kyazma, B. V. Wageningen, Netherlands; 2006.

Wang, S., Sha, Z., Sonstegard, T. S., Liu, H., Xu, P., Somridhivej, B., Peatman, E., Kucuktas, H., Liu, Z., 2008. Quality assessment parameters for EST-derived SNPs from catfish. BMC Genomics. 9, 450.

Weller, J. I. 2001. Quantitative Trait Loci Analysis in Animals. CABI Publishing, New York.

Werner, F. A. O., Durstewitz, G., Habermann, F. A., Thaller, G., Kramer, W., Kollers, S., Buitkamp, J., Georges, M., Brem, G., Mosner, J., Fries, R., 2004. Detection and characterization of SNPs used for identity control and parentage testing in major European dairy breeds. Anim Genet. 35, 44-49.

Wesmajervi M, Delghandi M, Westgaard J I, Stenvik J, Fjalestad K T: Genotyping of Atlantic cod (*Gadus morhua* L.) using five microsatellite markers and a population specific single nucleotide polymorphism. *Aquaculture* 2007, 272S1:S317-S318.

Wondji C S, Hemingway J, Ranson H: Identification and analysis of single nucleotide polymorphisms (SNPs) in the mosquito *Anopheles funestus*, malaria vector. *BMC Genomics* 2007, 8:5.

Zhulidov P A, Bogdanova E A, Schcheglov A S, Vagner L L, Khaspekov G L, Kozhemyako V B, Matz M V, Meleshkevitch E, Moroz L L, Lukyanov S A et al: Simple cDNA normalization using kamchatcka crab duplex-specific nuclease. *Nucleic Acids Res* 2004, 32(3):e37.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08597887B2). An electronic copy of the "Sequence Listing" will also be available from the USPTO upon request and payment of the fee set forth in 37 CFR 1.19(b)(3).

The invention claimed is:

1. A method of forming a stock of Western Atlantic codfish with a quantitative trait locus (QTL) for a desirable growth production trait from a population of Western Atlantic codfish, the method comprising:

a) genotyping the population of Western Atlantic codfish for one or more of the following single nucleotide polymorphisms (SNPs):

SNP marker cgpGMO_S833, wherein presence of at least one C allele indicates the presence of a QTL for increased weight;

SNP marker cgpGMO_S834, wherein presence of at least one C allele indicates the presence of a QTL for increased weight;

SNP marker cgpGMO_S268, wherein the presence of at least one A allele indicates the presence of a QTL for increased weight;

SNP marker cgpGMO_S1183, wherein the presence of at least one G allele indicates the presence of a QTL for increased weight;

SNP marker cgpGMO_S2158, wherein the presence of at least one G allele indicates the presence of a QTL for increased weight;

SNP marker cgpGMO_S1039b, wherein the presence of at least one T allele indicates the presence of a QTL for increased weight;

SNP marker cgpGMO_S1830, wherein the presence of at least one A allele indicates the presence of a QTL for increased weight;

SNP marker cgpGMO_S157, wherein the presence of at least one C allele indicates the presence of a QTL for increased weight;

SNP marker cgpGMO_S870, wherein the presence of at least one T allele indicates the presence of a QTL for increased weight;

SNP marker cgpGMO_S419, wherein the presence of at least one G allele indicates the presence of a QTL for increased weight;

SNP marker cgpGMO_S352, wherein the presence of at least one G allele indicates the presence of a QTL for increased weight;

SNP marker cgpGMO_S920, wherein the presence of at least one A allele indicates the presence of a QTL for increased weight;

SNP marker cgpGMO_S152, wherein the presence of at least one C alleles indicates the presence of a QTL for increased weight;

SNP marker cgpGMO_S1089, wherein the presence of at least one T allele indicates the presence of a QTL for increased weight;

SNP marker cgpGMO_S1039a, wherein the presence of at least one G allele indicates the presence of a QTL for increased weight;

SNP marker cgpGMO_S814a, wherein the presence of at least one C allele indicates the presence of a QTL for increased weight;

SNP marker cgpGMO_S1425, wherein the presence of at least one G allele indicates the presence of a QTL for increased weight;

SNP marker cgpGMO_S1810, wherein the presence of at least one T alleles indicates the presence of a QTL for increased weight;

SNP marker cgpGmo-S1644, wherein the presence of at least one C allele indicates the presence of a QTL for increased weight;

SNP marker cgpGmo-S811a, wherein the presence of at least one T allele indicates the presence of a QTL for increased weight;

SNP marker cgpGmo-S1622, wherein the presence of at least one C alleles indicates the presence of a QTL for increased weight;

SNP marker cgpGmo-S391, wherein the presence of at least one A allele indicates the presence of a QTL for decreased gonad weight;

SNP marker cgpGmo-S2288, wherein the presence of at least one G alleles indicates the presence of a QTL for decreased gonad weight;

SNP marker cgpGmo-S1579, wherein the presence of at least one A allele indicates the presence of a QTL for decreased liver weight; or SNP marker cgpGmo-S849, wherein the presence of at least one A allele indicates the presence of a QTL for decreased liver weight; and b) separating codfish with at least one allele that indicates the presence of the QTL for increased weight, decreased liver weight or decreased gonad weight from the population of Western Atlantic codfish to form the stock of Western Atlantic codfish with the QTL for the desirable growth production trait.

2. The method of claim 1, wherein the presence of homozygous alleles at the SNP marker indicates the presence of the desirable growth production trait QTL.

3. The method of claim 1, further comprising using the stock of Western Atlantic codfish for breeding stock or aquaculture.

4. The method of claim 1, wherein the SNP markers are on linkage group 7 and codfish with the QTL for increased weight have increased weight, bled weight or gutted weight compared to codfish without the QTL.

5. The method of claim 1, wherein the SNP markers are on linkage group 11 and codfish with the QTL for increased weight have increased skin-on-fillet weight or skin-off-fillet weight compared to codfish without the QTL.

6. The method of claim 1, wherein the SNP markers are on linkage group 23 and codfish with the QTL for increased weight have increased skin on fillet weight or skin off fillet weight compared to codfish without the QTL.

7. The method of claim 1, further comprising obtaining a sample from a codfish in the population of Western Atlantic codfish and extracting DNA prior to genotyping the codfish.

8. The method of claim 7, wherein the sample is a piece of fin.

9. The method of claim 1, wherein genotyping the population of Western Atlantic codfish for one or more SNPs comprises detecting:
  an isolated nucleic acid molecule comprising SEQ ID NO: 2075 wherein the SNP marker is cgpGMO_S833;
  an isolated nucleic acid molecule comprising SEQ ID NO: 2076 wherein the SNP marker is cgpGMO_S834;
  an isolated nucleic acid molecule comprising SEQ ID NO: 1386 wherein the SNP marker is cgpGMO_S268;
  an isolated nucleic acid molecule comprising SEQ ID NO: 210 wherein the SNP marker is cgpGMO_S1183;
  an isolated nucleic acid molecule comprising SEQ ID NO: 1200 wherein the SNP marker is cgpGMO_S2158;
  an isolated nucleic acid molecule comprising SEQ ID NO: 49 wherein the SNP marker is cgpGMO_S1039b;
  an isolated nucleic acid molecule comprising SEQ ID NO: 833 wherein the SNP marker is cgpGMO_S1830;
  an isolated nucleic acid molecule comprising SEQ ID NO: 560 wherein the SNP marker is cgpGMO_S157;
  an isolated nucleic acid molecule comprising SEQ ID NO: 2120 wherein the SNP marker is cgpGMO_S870;
  an isolated nucleic acid molecule comprising SEQ ID NO: 1571 wherein the SNP marker is cgpGMO_S419;
  an isolated nucleic acid molecule comprising SEQ ID NO: 1485 wherein the SNP marker is cgpGMO_S352;
  an isolated nucleic acid molecule comprising SEQ ID NO: 2186 wherein the SNP marker is cgpGMO_S920;
  an isolated nucleic acid molecule comprising SEQ ID NO: 514 wherein the SNP marker is cgpGMO_S152;
  an isolated nucleic acid molecule comprising SEQ ID NO: 111 wherein the SNP marker is cgpGMO_S1089;
  an isolated nucleic acid molecule comprising SEQ ID NO: 48 wherein the SNP marker is cgpGMO_S1039a;
  an isolated nucleic acid molecule comprising SEQ ID NO: 2049 wherein the SNP marker is cgpGMO_S814a;
  an isolated nucleic acid molecule comprising SEQ ID NO: 434 wherein the SNP marker is cgpGMO_S1425;
  an isolated nucleic acid molecule comprising SEQ ID NO: 811 wherein the SNP marker is cgpGMO_S1810;
  an isolated nucleic acid molecule comprising SEQ ID NO: 622 wherein the SNP marker is cgpGmo-S1644;
  an isolated nucleic acid molecule comprising SEQ ID NO: 2045 wherein the SNP marker is cgpGmo-S811a;
  an isolated nucleic acid molecule comprising SEQ ID NO: 606 wherein the SNP marker is cgpGmo-S1622;
  an isolated nucleic acid molecule comprising SEQ ID NO: 1537 wherein the SNP marker cgpGmo-S391;
  an isolated nucleic acid molecule comprising SEQ ID NO: 1334 wherein the SNP marker is cgpGmo-S2288;
  an isolated nucleic acid molecule comprising SEQ ID NO: 568 wherein the SNP marker is cgpGmo-S1579; or
  an isolated nucleic acid molecule comprising SEQ ID NO: 2095 wherein the SNP marker is cgpGmo-S849.

10. The method of claim 1, wherein genotyping the population of Western Atlantic codfish for one or more SNPs comprises amplifying an isolated nucleic acid molecule comprising the SNP using a polymerase chain reaction (PCR).

11. The method of claim 10, wherein the isolated nucleic acid molecule comprising the SNP comprises a nucleic acid sequence selected from the group consisting of SEQ ID NOS: 2075, 2076, 1386, 210, 1200, 49, 833, 560, 2120, 1571, 1485, 2186, 514, 111, 48, 2049, 434, 811, 622, 2045, 606, 1537, 1334, 568, and 2095.

12. The method of claim 1, further comprising identifying Western Atlantic codfish resistant to nodavirus infection in the stock of Western Atlantic codfish with the QTL for the desirable growth production trait, the method comprising:
  a) genotyping the codfish for one or more of the following SNPs:
    SNP marker cgpGMO_S557, wherein the presence of at least one C allele indicates resistance to nodavirus infection;
    SNP marker cgpGMO_S943, wherein the presence of at least one T allele indicates resistance to nodavirus infection;
    SNP marker cgpGMO_S1596a, wherein the presence of at least one A allele indicates resistance to nodavirus infection; or
    SNP marker cgpGMO_S1071a, wherein the presence of at least one T allele indicates resistance to nodavirus infection.

13. The method of claim 12, wherein the presence of homozygous alleles at the SNP marker indicates resistance to nodavirus infection.

14. The method of claim 12, further comprising selecting Western Atlantic codfish identified as resistant to nodavirus infection for breeding stock or aquaculture.

15. The method of claim 1 further comprising identifying Western Atlantic codfish with a quantitative trait locus (QTL) for resistance to handling stress in the stock of Western Atlantic codfish with the QTL for the desirable growth production trait, the method comprising:
  a) genotyping the codfish for one or more of the following SNPs:
    SNP marker cgpGmo-S848, wherein the presence of at least one A allele indicates resistance to handling stress;
    SNP marker cgpGmo-S487, wherein the presence at least one C allele indicates resistance to handling stress;
    SNP marker cgpGmo-S975a, wherein the presence of at least one T allele indicates resistance to handling stress; or SNP marker cgpGmo-S525, wherein the presence of at least one T allele indicates resistance to handling stress.

16. The method of claim 15, wherein the presence of homozygous alleles at the SNP marker indicates improved resistance to handling stress.

17. The method of claim 15, wherein Western Atlantic codfish with the QTL for improved resistance to handling stress have reduced cortisol levels in response to handling stress compared to Western Atlantic codfish without the QTL.

* * * * *